(12) United States Patent
Jenkins et al.

(10) Patent No.: US 10,028,945 B2
(45) Date of Patent: *Jul. 24, 2018

(54) COMPOSITIONS COMPRISING ENZYME-CLEAVABLE KETONE-MODIFIED OPIOID PRODRUGS AND OPTIONAL INHIBITORS THEREOF

(71) Applicant: Signature Therapeutics, Inc., Palo Alto, CA (US)

(72) Inventors: Thomas E. Jenkins, Half Moon Bay, CA (US); Craig O. Husfeld, San Mateo, CA (US); Julie D. Seroogy, San Carlos, CA (US); Jonathan W. Wray, San Francisco, CA (US)

(73) Assignee: Signature Therapeutics, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/285,818

(22) Filed: Oct. 5, 2016

(65) Prior Publication Data

US 2017/0119754 A1    May 4, 2017

Related U.S. Application Data

(63) Continuation of application No. 13/393,470, filed as application No. PCT/US2010/031956 on Apr. 21, 2010, now Pat. No. 9,493,477.

(60) Provisional application No. 61/240,611, filed on Sep. 8, 2009, provisional application No. 61/288,148, filed on Dec. 18, 2009.

(51) Int. Cl.
| | | |
|---|---|---|
| *A01N 43/42* | (2006.01) | |
| *A61K 31/44* | (2006.01) | |
| *A61K 31/485* | (2006.01) | |
| *A61K 31/495* | (2006.01) | |
| *A61K 31/445* | (2006.01) | |
| *A61K 38/05* | (2006.01) | |
| *A61K 47/48* | (2006.01) | |

(52) U.S. Cl.
CPC .......... *A61K 31/485* (2013.01); *A61K 31/445* (2013.01); *A61K 31/495* (2013.01); *A61K 38/05* (2013.01); *A61K 47/48023* (2013.01); *A61K 47/48038* (2013.01)

(58) Field of Classification Search
CPC .. A61K 31/445; A61K 31/485; A61K 31/495; A61K 38/05; A61K 47/48023; A61K 47/48038
See application file for complete search history.

(56) References Cited

U.S. PATENT DOCUMENTS

| | | |
|---|---|---|
| 4,454,338 A | 6/1984 | Fujii et al. |
| 4,532,255 A | 7/1985 | Fujii et al. |
| 5,109,118 A | 4/1992 | Mizushima et al. |
| 5,352,704 A | 10/1994 | Okuyama et al. |
| 6,388,122 B1 | 5/2002 | Kido et al. |
| 6,586,196 B1 | 7/2003 | Bronstein et al. |
| 7,060,290 B1 | 6/2006 | Morimoto et al. |
| 7,189,414 B2 | 3/2007 | Rubinstein et al. |
| 7,893,105 B2 | 2/2011 | Xiang et al. |
| 8,163,701 B2 | 4/2012 | Jenkins et al. |
| 8,497,237 B2 | 7/2013 | Jenkins et al. |
| 8,569,228 B2 | 10/2013 | Jenkins et al. |
| 8,685,916 B2 | 4/2014 | Jenkins et al. |
| 8,802,681 B2 | 8/2014 | Jenkins et al. |
| 8,962,547 B2 | 2/2015 | Jenkins et al. |
| 9,023,860 B2 | 5/2015 | Jenkins et al. |
| 9,040,032 B2 | 5/2015 | Jenkins et al. |
| 9,095,627 B2 | 8/2015 | Jenkins et al. |
| 9,139,612 B2 | 9/2015 | Jenkins et al. |
| 9,493,477 B2 * | 11/2016 | Jenkins ............... C07D 489/02 |
| 9,499,581 B2 * | 11/2016 | Jenkins ............... A61K 31/485 |
| 2003/0180352 A1 | 9/2003 | Patel et al. |
| 2004/0063628 A1 | 4/2004 | Piccariello et al. |
| 2005/0176644 A1 | 8/2005 | Mickle et al. |
| 2005/0176645 A1 | 8/2005 | Mickle et al. |

(Continued)

FOREIGN PATENT DOCUMENTS

| | | |
|---|---|---|
| WO | WO 2002043767 | 6/2002 |
| WO | WO 2005032474 | 4/2005 |

(Continued)

OTHER PUBLICATIONS

Berkop-Schnurch (1998) "The use of inhibitory agents to overcome the enzymatic barrier to perorally administered therapeutic peptides and proteins" *J Control Release* 50(1-2):1-16.
Birk et al. (1976) "Trypsin and chymotrypsin inhibitors from soybeans" *Methods in Enzymology* 45:700-707.
Database Internet [Online]Apr. 5, 2005 (Apr. 5, 2005), XP002350634 retrieved from Internet accession No. http://onlineethics.org/reseth/helsinki.html.
Geratz et al. (1976) "Novel bis(benzamidine) compounds with an aromatic central link. Inhibitors of thrombin, pancreatic kallikrein, trypsin, and complement" *J. Med. Chem.* 19:634-639.
Göke et al. (1984) "Effect of a Specific Serine Protease Inhibitor on the Rat Pancreas: Systemic Administration of Camostate and Exocrine" *Digestion* 30:171-178.

(Continued)

*Primary Examiner* — Marcela M Cordero Garcia
(74) *Attorney, Agent, or Firm* — Khin K. Chin; Bozicevic, Field & Francis LLP

(57) ABSTRACT

A method of providing a patient with controlled release of ketone-containing opioid using a prodrug capable, upon enzymatic activation and intramolecular cyclization, of releasing the ketone-containing opioid is disclosed. The disclosure also provides such prodrug compounds and pharmaceutical compositions comprising such compounds. Such pharmaceutical compositions can optionally include an enzyme inhibitor that interacts with the enzyme(s) to mediate the enzymatically-controlled release of the ketone-containing opioid from the prodrug so as to modify enzymatic cleavage of the prodrug. Also included are methods to use such compounds and pharmaceutical compositions.

20 Claims, 21 Drawing Sheets

(56) References Cited

U.S. PATENT DOCUMENTS

| | | |
|---|---|---|
| 2007/0082929 A1 | 4/2007 | Gant et al. |
| 2007/0123468 A1 | 5/2007 | Jenkins et al. |
| 2007/0203055 A1 | 8/2007 | Mickle et al. |
| 2009/0136980 A1 | 5/2009 | Bebbington et al. |
| 2009/0137618 A1 | 5/2009 | Jenkins et al. |
| 2009/0192093 A1 | 7/2009 | Mickle et al. |
| 2009/0209569 A1 | 8/2009 | Arnelle et al. |
| 2010/0035826 A1 | 2/2010 | Jenkins et al. |
| 2010/0080797 A1 | 4/2010 | Yeomans et al. |
| 2010/0092562 A1 | 4/2010 | Hollenbeck et al. |
| 2010/0286186 A1 | 11/2010 | Franklin et al. |
| 2011/0040072 A1* | 2/2011 | Mickle ............ A61K 9/0019 530/330 |
| 2011/0262355 A1 | 10/2011 | Jenkins et al. |
| 2011/0262360 A1 | 10/2011 | Jenkins et al. |
| 2012/0178772 A1 | 7/2012 | Jenkins et al. |
| 2012/0178773 A1 | 7/2012 | Jenkins et al. |
| 2012/0270847 A1 | 10/2012 | Franklin et al. |
| 2014/0121152 A1 | 5/2014 | Jenkins et al. |

FOREIGN PATENT DOCUMENTS

| | | |
|---|---|---|
| WO | WO 2005042772 | 5/2005 |
| WO | WO 20070120864 | 10/2007 |
| WO | WO 2007140272 | 12/2007 |
| WO | WO 20070120648 | 7/2008 |
| WO | WO 2008101187 | 8/2008 |
| WO | WO 2008101202 | 8/2008 |
| WO | WO 2009080030 | 7/2009 |
| WO | WO 2009092073 | 7/2009 |
| WO | WO 2009136392 | 11/2009 |
| WO | WO 2010045599 | 4/2010 |
| WO | WO 2011133346 | 4/2011 |

OTHER PUBLICATIONS

Gomes et al. (2007) "Cyclization-activated prodrugs" *Molecules* 12:2484-2506.

Hansch et al. (1990) "Comprehensive Medicinal Chemistry, vol. 5 Biopharmaceutics" *Rational Design, Mechanistic Study and Therapeutic Application of Chemical Compounds, Oxford, Pergamon Press* 5:251-278.

Hijikata-Okunomiya et al. (2000) "Selective Inhibition of Trypsin by (2R,4R)-4-Phenyl-1-[$N^\alpha$-(7-methoxy-2-naphthalenesulfonyl)-L-arginyl]-2-piperidinecarboxylic Acid" *J. Biochem.* 275:18995-18999.

Katragadda et al. (2006) "Simultaneous Modulation of Transport and Metabolism of Acyclovir Prodrugs across Rabbit Cornea: An approach Involving Enzyme Inhibitors" *Int J Pharm* 320(1-2):104-113.

Kunze et al. (1983) "Effects of the serine protease inhibitors FOY and FOY 305 on phospholipase A I (EC 3.1.1.32) activity in rat-liver lysosomes" *Pharm. Research Com.* 15: 451-459.

Lin et al. (1993) "The 0.25-nm X-ray structure of the Bowman-Birk type inhibitor from mung bean in ternary complex with porcine trypsin" *Eur. J. Biochem.* 212:549-555.

Markwardt et al. (1968) "Comparative studies on the inhibition of trypsin, plasmin, and thrombin by derivatives of benzylamine and benzylamidine" *Eur. J. Biochem*, 6:502-506.

Ozawa et al. (1966) "The reactive site of trypsin inhibitors" *J. Biol. Chem.* 241:3955-3961.

Pauletti, Giovanni et al. (1997) "Esterase-Sensitive Cyclic Prodrugs of Peptides: Evaluation of a Phenylpropionic Acid Promoiety in a Model Hexapeptide" *Pharm Res* 14(1):11-17.

Ramjee et al. (2000) "The Kinetic and Structural Characterization of the Reaction of Nafamostat with Bovine Pancreatic Trypsin" *Thrmb Res.* 98(6):559-569.

Renatus et al. (1998) "Structural and Functional Analyses of Benzamidine-Based Inhibitors in Complex with Trypsin: Implications for the Inhibition of Factor Xa, tPA, and Urokinase" *J. Med. Chem.* 41(27):5445-5456.

Song, Xiaoping et al. (2002) "Synthesis of a Novel Cyclic Prodrug of RGD Peptidomimetic to Improve Its Cell Membrane Permeation" *Bioorg Chem* 30(4):285-301.

Tanizawa et al. (1987) "Inverse Substrates for Trypsin and Tryspin-like Enzymes" *Acc. Chem. Res.* 20:337-343.

Testa et al. (2003) "Hydrolysis in Drug and Prodrug Metabolism" Verlag Helvetica Chimica Acta, Postfach, CH-8042, Switzerland, pp. 420-534.

Tirkkonen et al. (2004) "Drug interactions with the potential to prevent prodrug activation as a common source of irrational prescribing in hospital inpatients" *Clinical Pharmacology and Therapeutics* 76(6):639-647.

Umezawa (1976) "Structure and activities of protease inhibitors of microbial origin" *Methods in Enzymology* 45:678-695.

* cited by examiner

COMPOSITIONS COMPRISING ENZYME-CLEAVABLE KETONE-MODIFIED OPIOID PRODRUGS AND OPTIONAL INHIBITORS THEREOF

CROSS REFERENCE TO RELATED APPLICATIONS

This application is a continuation of U.S. patent application Ser. No. 13/393,470 filed on May 14, 2012, now U.S. Pat. No. 9,493,477, which is a 371 National Phase Filing of International Patent Application Serial No. PCT/US2010/031956 filed Apr. 21, 2010 which claims the benefit of priority to U.S. Provisional Application Nos. 61/240,611, filed Sep. 8, 2009 and 61/288,148, filed Dec. 18, 2009.

INTRODUCTION

Ketone-containing opioids are susceptible to misuse, abuse, or overdose. Use of and access to these drugs therefore needs to be controlled. The control of access to the drugs is expensive to administer and can result in denial of treatment for patients that are not able to present themselves for dosing. For example, patients suffering from acute pain may be denied treatment with an opioid unless they have been admitted to a hospital. Furthermore, control of use is often ineffective, leading to substantial morbidity and deleterious social consequences.

SUMMARY

The embodiments include compositions comprising a ketone-modified opioid prodrug, wherein the ketone-modified opioid prodrug comprises a ketone-containing opioid covalently bound to a promoiety comprising a trypsin-cleavable moiety, wherein cleavage of the trypsin-cleavable moiety by trypsin mediates release of the ketone-containing opioid; and a trypsin inhibitor that interacts with the trypsin that mediates enzymatically-controlled release of the ketone-containing opioid from the ketone-modified opioid prodrug following ingestion of the composition. Such cleavage can initiate, contribute to or effect ketone-containing opioid release.

The embodiments include dose units comprising compositions comprising a ketone-modified opioid prodrug and a trypsin inhibitor, where the ketone-modified opioid prodrug and trypsin inhibitor are present in the dose unit in an amount effective to provide for a pre-selected pharmacokinetic (PK) profile following ingestion. In further embodiments, the pre-selected PK profile comprises at least one PK parameter value that is less than the PK parameter value of ketone-containing opioid released following ingestion of an equivalent dosage of ketone-modified opioid prodrug in the absence of inhibitor. In further embodiments, the PK parameter value is selected from a ketone-containing opioid Cmax value, a ketone-containing opioid exposure value, and a (1/ketone-containing opioid Tmax) value.

In certain embodiments, the dose unit provides for a pre-selected PK profile following ingestion of at least two dose units. In related embodiments, the pre-selected PK profile of such dose units is modified relative to the PK profile following ingestion of an equivalent dosage of ketone-modified opioid prodrug without inhibitor. In related embodiments, such a dose unit provides that ingestion of an increasing number of the dose units provides for a linear PK profile.

In related embodiments, such a dose unit provides that ingestion of an increasing number of the dose units provides for a nonlinear PK profile. In related embodiments, the PK parameter value of the PK profile of such a dose units is selected from a ketone-containing opioid Cmax value, a (1/ketone-containing opioid Tmax) value, and a ketone-containing opioid exposure value.

The embodiments include compositions comprising a container suitable for containing a composition for administration to a patient; and a dose unit as described herein disposed within the container.

The embodiments include dose units of a ketone-modified opioid prodrug and a trypsin inhibitor wherein the dose unit has a total weight of from 1 microgram to 2 grams. The embodiments include pharmaceutical compositions of a ketone-modified opioid prodrug and a trypsin inhibitor wherein the combined weight of ketone-modified opioid prodrug and trypsin inhibitor is from 0.1% to 99% per gram of the composition.

The embodiments include compositions and dose units wherein the ketone-modified opioid prodrug is a compound of formula KC-(Ia):

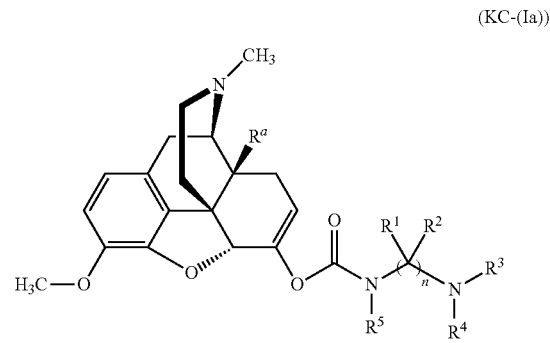

wherein:
$R^a$ is hydrogen or hydroxyl;
$R^5$ is selected from alkyl, substituted alkyl, arylalkyl, substituted arylalkyl, aryl and substituted aryl;
each $R^1$ is independently selected from hydrogen, alkyl, substituted alkyl, aryl, substituted aryl, acyl, and aminoacyl;
each $R^2$ is independently selected from hydrogen, alkyl, substituted alkyl, aryl, substituted aryl, acyl, and aminoacyl;
or $R^1$ and $R^2$ together with the carbon to which they are attached form a cycloalkyl, substituted cycloalkyl, aryl, or substituted aryl group, or two $R^1$ or $R^2$ groups on adjacent carbon atoms, together with the carbon atoms to which they are attached, form a cycloalkyl, substituted cycloalkyl, aryl, or substituted aryl group;
n is an integer from 2 to 4;
$R^3$ is hydrogen;
$R^4$ is

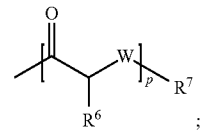

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently $-NR^8-$, $-O-$ or $-S-$;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The embodiments include compositions and dose units wherein the ketone-modified opioid prodrug is a compound of formula KC-(Ib):

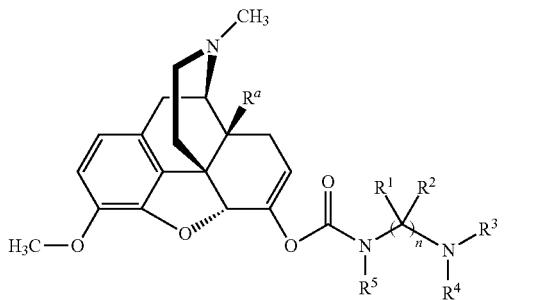

(KC-(Ib))

wherein:

$R^a$ is hydrogen or hydroxyl;

$R^5$ is selected from alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl or substituted cycloalkyl group, or two $R^1$ or $R^2$ groups on adjacent carbon atoms, together with the carbon atoms to which they are attached, form a cycloalkyl or substituted cycloalkyl group;

n is an integer from 2 to 4;

$R^3$ is hydrogen;

$R^4$ is

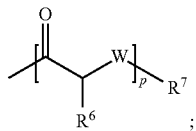

;

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently $-NR^8-$, $-O-$ or $-S-$;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The embodiments include compositions and dose units wherein the ketone-modified opioid prodrug is a compound of formula KC-(II):

(KC-(II))

wherein:

$R^a$ is hydrogen or hydroxyl;

$R^5$ is selected from (1-6C)alkyl, (1-6C) substituted alkyl, $-(CH_2)_q(C_6H_4)-COOH$, $-(CH_2)_q(C_6H_4)-COOCH_3$, and $-(CH_2)_q(C_6H_4)-COOCH_2CH_3$, where q is an integer from one to 10;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl or substituted cycloalkyl group, or two $R^1$ or $R^2$ groups on adjacent carbon atoms, together with the carbon atoms to which they are attached, form a cycloalkyl or substituted cycloalkyl group;

n is 2 or 3;

$R^3$ is hydrogen;

$R^4$ is a residue of an L-amino acid selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine, or a residue of an N-acyl derivative of any of said amino acids; or a residue of a peptide composed of at least two L-amino acid residues selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine or a residue of an N-acyl derivative thereof.

The embodiments include compositions and dose units wherein the ketone-modified opioid prodrug is a compound of formula KC-(IIIa):

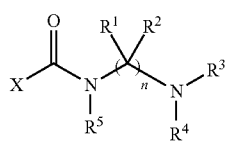
(KC-(IIIa))

wherein:

X represents a residue of a ketone-containing opioid, wherein the hydrogen atom of the corresponding enolic group of the ketone is replaced by a covalent bond to —C(O)—NR$^5$—(C(R$^1$)(R$^2$))$_n$—NR$^3$R$^4$;

R$^5$ is selected from alkyl, substituted alkyl, arylalkyl, substituted arylalkyl, aryl and substituted aryl;

each R$^1$ is independently selected from hydrogen, alkyl, substituted alkyl, aryl, substituted aryl, acyl, and aminoacyl;

each R$^2$ is independently selected from hydrogen, alkyl, substituted alkyl, aryl, substituted aryl, acyl, and aminoacyl;

or R$^1$ and R$^2$ together with the carbon to which they are attached form a cycloalkyl, substituted cycloalkyl, aryl, or substituted aryl group, or two R$^2$ or R$^3$ groups on adjacent carbon atoms, together with the carbon atoms to which they are attached, form a cycloalkyl, substituted cycloalkyl, aryl, or substituted aryl group;

n is an integer from 2 to 4;

R$^3$ is hydrogen;

R$^4$ is

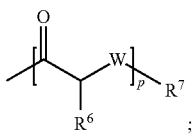

each R$^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, R$^6$ and R$^7$ together with the atoms to which they are bonded form a cycloheteroalkyl or substituted cycloheteroalkyl ring;

each W is independently —NR$^8$—, —O— or —S—;

each R$^8$ is independently selected from hydrogen, alkyl, substituted alkyl, aryl and substituted aryl, or optionally, each R$^6$ and R$^8$ independently together with the atoms to which they are bonded form a cycloheteroalkyl or substituted cycloheteroalkyl ring;

p is an integer from one to 100; and

R$^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The embodiments include compositions and dose units wherein the ketone-modified opioid prodrug is a compound of formula KC-(IIIb):

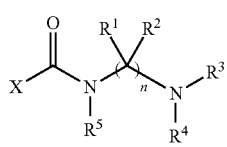
(KC-(IIIb))

wherein:

X represents a residue of a ketone-containing opioid, wherein the hydrogen atom of the corresponding enolic group of the ketone is replaced by a covalent bond to —C(O)—NR$^5$—(C(R$^1$)(R$^2$))$_n$—NR$^3$R$^4$;

R$^5$ is selected from alkyl, substituted alkyl, arylalkyl, substituted arylalkyl, aryl and substituted aryl;

each R$^1$ is independently selected from hydrogen, alkyl, substituted alkyl, aryl, substituted aryl, acyl, and aminoacyl;

each R$^2$ is independently selected from hydrogen, alkyl, substituted alkyl, aryl, substituted aryl, acyl, and aminoacyl;

or R$^1$ and R$^2$ together with the carbon to which they are attached form a cycloalkyl or substituted cycloalkyl group, or two R$^1$ or R$^2$ groups on adjacent carbon atoms, together with the carbon atoms to which they are attached, form a cycloalkyl or substituted cycloalkyl group;

n is an integer from 2 to 4;

R$^3$ is hydrogen;

R$^4$ is

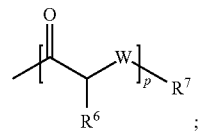

each R$^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, R$^6$ and R$^7$ together with the atoms to which they are bonded form a cycloheteroalkyl or substituted cycloheteroalkyl ring;

each W is independently —NR$^8$—, —O— or —S—;

each R$^8$ is independently selected from hydrogen, alkyl, substituted alkyl, aryl and substituted aryl, or optionally, each R$^6$ and R$^8$ independently together with the atoms to which they are bonded form a cycloheteroalkyl or substituted cycloheteroalkyl ring;

p is an integer from one to 100; and

R$^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The embodiments include compositions and dose units wherein the ketone-modified opioid prodrug is a compound of formula KC-(IV):

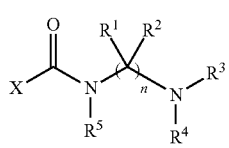
(KC-(IV))

wherein:

X represents a residue of a ketone-containing opioid, wherein the hydrogen atom of the corresponding enolic group of the ketone is replaced by a covalent bond to —C(O)—NR$^5$—(C(R$^1$)(R$^2$))$_n$—NR$^3$R$^4$;

R$^5$ is selected from (1-6C)alkyl, (1-6C) substituted alkyl, —(CH$_2$)$_q$(C$_6$H$_4$)—COOH, —(CH$_2$)$_q$(C$_6$H$_4$)—COOCH$_3$, and —(CH$_2$)$_q$(C$_6$H$_4$)—COOCH$_2$CH$_3$, where q is an integer from one to 10;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl or substituted cycloalkyl group, or two $R^1$ or $R^2$ groups on adjacent carbon atoms, together with the carbon atoms to which they are attached, form a cycloalkyl or substituted cycloalkyl group;

n is 2 or 3;

$R^3$ is hydrogen;

$R^4$ is a residue of an L-amino acid selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine, or a residue of an N-acyl derivative of any of said amino acids; or a residue of a peptide composed of at least two L-amino acid residues selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine or a residue of an N-acyl derivative thereof;

or a salt, hydrate or solvate thereof.

The embodiments include compositions and dose units wherein the ketone-modified opioid prodrug is a compound of formula KC-(V):

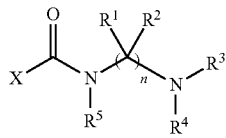

(KC-(V))

wherein:

X represents a residue of a ketone-containing opioid, wherein the hydrogen atom of the corresponding enolic group of the ketone is replaced by a covalent bond to —C(O)—NR$^5$—(C(R$^1$)(R$^2$))$_n$—NR$^3$R$^4$;

$R^5$ is selected from alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl, substituted cycloalkyl, aryl, or substituted aryl group, or two $R^1$ or $R^2$ groups on adjacent carbon atoms, together with the carbon atoms to which they are attached, form a cycloalkyl, substituted cycloalkyl, aryl, or substituted aryl group;

n is an integer from 2 to 4;

$R^3$ is hydrogen;

$R^4$ is a trypsin-cleavable moiety;

or a salt, hydrate or solvate thereof.

The embodiments include methods for treating a patient comprising administering any of the compositions or dose units described herein to a patient in need thereof. The embodiments include methods to reduce side effects of a therapy comprising administering any of the compositions or dose units described herein to a patient in need thereof. The embodiments include methods of improving patient compliance with a therapy prescribed by a clinician comprising directing administration of any of the compositions or dose units described herein to a patient in need thereof. Such embodiments can provide for improved patient compliance with a prescribed therapy as compared to patient compliance with a prescribed therapy using drug and/or using prodrug without inhibitor as compared to prodrug with inhibitor.

The embodiments include methods of reducing risk of unintended overdose of a ketone-containing opioid comprising directing administration of any of the pharmaceutical compositions or dose units described herein to a patient in need of treatment.

The embodiments include methods of making a dose unit comprising combining a ketone-modified opioid prodrug and a trypsin inhibitor in a dose unit, wherein the ketone-modified opioid prodrug and trypsin inhibitor are present in the dose unit in an amount effective to attenuate release of the ketone-containing opioid from the ketone-modified opioid prodrug.

The embodiments include methods of deterring misuse or abuse of multiple dose units of a ketone-modified opioid prodrug comprising combining a ketone-modified opioid prodrug and a trypsin inhibitor in a dose unit, wherein the ketone-modified opioid prodrug and trypsin inhibitor are present in the dose unit in an amount effective to attenuate release of the ketone-containing opioid from the ketone-modified opioid prodrug such that ingestion of multiples of dose units by a patient does not provide a proportional release of ketone-containing opioid. In further embodiments, release of drug is decreased compared to release of drug by an equivalent dosage of prodrug in the absence of inhibitor.

One embodiment is a method for identifying a prodrug and a GI enzyme inhibitor suitable for formulation in a dose unit. Such a method can be conducted as, for example, an in vitro assay, an in vivo assay, or an ex vivo assay.

The embodiments include methods for identifying a ketone-modified opioid prodrug and a trypsin inhibitor suitable for formulation in a dose unit comprising combining a ketone-modified opioid prodrug, a trypsin inhibitor, and trypsin in a reaction mixture, and detecting ketone-modified opioid prodrug conversion, wherein a decrease in ketone-modified opioid prodrug conversion in the presence of the trypsin inhibitor as compared to ketone-modified opioid prodrug conversion in the absence of the trypsin inhibitor indicates the ketone-modified opioid prodrug and trypsin inhibitor are suitable for formulation in a dose unit.

The embodiments include methods for identifying a ketone-modified opioid prodrug and a trypsin inhibitor suitable for formulation in a dose unit comprising administering to an animal a ketone-modified opioid prodrug and a trypsin inhibitor and detecting ketone-modified opioid prodrug conversion, wherein a decrease in ketone-containing opioid conversion in the presence of the trypsin inhibitor as compared to ketone-containing opioid conversion in the absence of the trypsin inhibitor indicates the ketone-modified opioid prodrug and trypsin inhibitor are suitable for formulation in a dose unit. In certain embodiments, administering comprises administering to the animal increasing doses of inhibitor co-dosed with a selected fixed dose of ketone-modified opioid prodrug. Detecting prodrug conversion can facilitate identification of a dose of inhibitor and a dose of ketone-modified opioid prodrug that provides for a pre-selected pharmacokinetic (PK) profile. Such methods can be conducted as, for example, an in vivo assay or an ex vivo assay.

The embodiments include methods for identifying a ketone-modified opioid prodrug and a trypsin inhibitor suitable for formulation in a dose unit comprising administering to an animal tissue a ketone-modified opioid prodrug and a trypsin inhibitor and detecting ketone-modified opioid prodrug conversion, wherein a decrease in ketone-modified opioid prodrug conversion in the presence of the trypsin inhibitor as compared to ketone-modified opioid prodrug conversion in the absence of the trypsin inhibitor indicates the ketone-modified opioid prodrug and trypsin inhibitor are suitable for formulation in a dose unit.

DEFINITIONS

Figure 1:
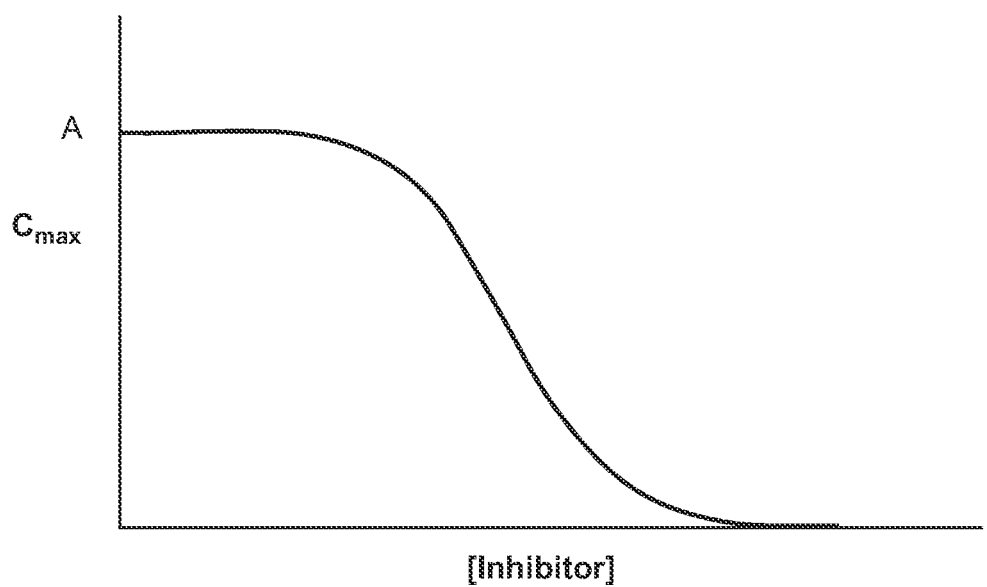
FIG. 1 is a schematic representing the effect of increasing the level of a GI enzyme inhibitor ("inhibitor", X axis) on a PK parameter (e.g., drug Cmax) (Y axis) for a fixed dose of prodrug. The effect of inhibitor upon a prodrug PK parameter can range from undetectable, to moderate, to complete inhibition (i.e., no detectable drug release).

The following terms have the following meaning unless otherwise indicated. Any undefined terms have their art recognized meanings.

As used herein, the term "alkyl" by itself or as part of another substituent refers to a saturated branched or straight-chain monovalent hydrocarbon radical derived by the removal of one hydrogen atom from a single carbon atom of a parent alkane. Typical alkyl groups include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group comprises from 1 to 20 carbon atoms. In other embodiments, an alkyl group comprises from 1 to 10 carbon atoms. In still other embodiments, an alkyl group comprises from 1 to 6 carbon atoms, such as from 1 to 4 carbon atoms.

"Alkanyl" by itself or as part of another substituent refers to a saturated branched, straight-chain or cyclic alkyl radical derived by the removal of one hydrogen atom from a single carbon atom of an alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkylene" refers to a branched or unbranched saturated hydrocarbon chain, usually having from 1 to 40 carbon atoms, more usually 1 to 10 carbon atoms and even more usually 1 to 6 carbon atoms. This term is exemplified by groups such as methylene ($-CH_2-$), ethylene ($-CH_2CH_2-$), the propylene isomers (e.g., $-CH_2CH_2CH_2-$ and $-CH(CH_3)CH_2-$) and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of an alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of an alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —C(O)R$^{30}$, where R$^{30}$ is hydrogen, alkyl, cycloalkyl, cycloheteroalkyl, aryl, arylalkyl, heteroalkyl, heteroaryl, heteroarylalkyl as defined herein and substituted versions thereof. Representative examples include, but are not limited to formyl, acetyl, cyclohexylcarbonyl, cyclohexylmethylcarbonyl, benzoyl, benzylcarbonyl, piperonyl, succinyl, and malonyl, and the like.

The term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Alkoxy" by itself or as part of another substituent refers to a radical —OR$^{31}$ where R$^{31}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent refers to a radical —C(O)OR$^{3}$ where R$^{31}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Aryl" by itself or as part of another substituent refers to a monovalent aromatic hydrocarbon radical derived by the removal of one hydrogen atom from a single carbon atom of an aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group comprises from 6 to 20 carbon atoms. In certain embodiments, an aryl group comprises from 6 to 12 carbon atoms. Examples of an aryl group are phenyl and naphthyl.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In certain embodiments, an arylalkyl group is ($C_7$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$). In certain embodiments, an arylalkyl group is ($C_7$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Arylaryl" by itself or as part of another substituent, refers to a monovalent hydrocarbon group derived by the removal of one hydrogen atom from a single carbon atom of a ring system in which two or more identical or non-identical aromatic ring systems are joined directly together by a single bond, where the number of such direct ring junctions is one less than the number of aromatic ring systems involved. Typical arylaryl groups include, but are not limited to, biphenyl, triphenyl, phenyl-napthyl, binaphthyl, biphenyl-napthyl, and the like. When the number of carbon atoms in an arylaryl group are specified, the numbers refer to the carbon atoms comprising each aromatic ring. For example, ($C_5$-$C_{14}$) arylaryl is an arylaryl group in which each aromatic ring comprises from 5 to 14 carbons, e.g., biphenyl, triphenyl, binaphthyl, phenylnapthyl, etc. In certain embodiments, each aromatic ring system of an arylaryl group is independently a ($C_5$-$C_{14}$) aromatic. In certain embodiments, each aromatic ring system of an arylaryl group is independently a ($C_5$-$C_{10}$) aromatic. In certain embodiments, each aromatic ring system is identical, e.g., biphenyl, triphenyl, binaphthyl, trinaphthyl, etc.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. In certain embodiments, the cycloalkyl group is ($C_3$-$C_{10}$) cycloalkyl. In certain embodiments, the cycloalkyl group is ($C_3$-$C_7$) cycloalkyl.

"Cycloheteroalkyl" or "heterocyclyl" by itself or as part of another substituent, refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —S—S—, —O—S—, —NR$^{37}$R$^{38}$—, =N—N=, —N=N—, —N=N—NR$^{39}$R$^{40}$, —PR$^{41}$—, —P(O)$_2$—, —POR$^{42}$—, —O—P(O)$_2$—, —S—O—, —S—(O)—, —SO$_2$—, —SnR$^{43}$R$^{44}$— and the like, where R$^{37}$, R$^{38}$, R$^{39}$, R$^{40}$, R$^{41}$, R$^{42}$, R$^{43}$ and R$^{44}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a heteroaromatic ring system. Typical heteroaryl groups include, but are not limited to, groups derived from acridine, arsindole, carbazole, 3-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent, refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. In certain embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In certain embodiments, the heteroarylalkyl group is 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Aromatic Ring System" by itself or as part of another substituent, refers to an unsaturated cyclic or polycyclic ring system having a conjugated π electron system. Specifically included within the definition of "aromatic ring system" are fused ring systems in which one or more of the rings are aromatic and one or more of the rings are saturated or unsaturated, such as, for example, fluorene, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Heteroaromatic Ring System" by itself or as part of another substituent, refers to an aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical heteroaromatic ring systems include, but are not limited to, arsindole, carbazole, 3-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Substituted" refers to a group in which one or more hydrogen atoms are independently replaced with the same or different substituent(s). Typical substituents include, but are not limited to, alkylenedioxy (such as methylenedioxy), -M, —R$^{60}$, —O$^-$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{60}$, —OS(O)$_2$O, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O—, —C(S)OR$^{60}$, —NR$^{62}$C(O)NR$^{60}$R$^{61}$, —NR$^{62}$C(S)NR$^{60}$R$^{61}$, —NR$^{62}$C(NR$^{63}$)NR$^{60}$R$^{61}$ and —C(NR$^{62}$)NR$^{60}$R$^{61}$ where M is halogen; R$^{60}$, R$^{61}$, R$^{62}$ and R$^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally R$^{60}$ and R$^{61}$ together with the nitrogen atom to which they are bonded form a cycloheteroalkyl or substituted cycloheteroalkyl ring; and R$^{64}$ and R$^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally R$^{64}$ and R$^{65}$ together with the nitrogen atom to which they are bonded form a cycloheteroalkyl or substituted cycloheteroalkyl ring. In certain embodiments, substituents include -M, —R$^{60}$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$R$^{60}$, —OS(O)$_2$O$^-$, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —NR$^{62}$C(O)NR$^{60}$R$^{61}$. In certain embodiments, substituents include -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —P(O)(OR$^{60}$)(O$^-$), —OP(O)(OR$^{60}$)(OR$^{61}$), —C(O)R$^{60}$, —C(O)OR$^{60}$, —C(O)NR$^{60}$R$^{61}$, —C(O)O$^-$. In certain embodiments, substituents include -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —OP(O)(OR$^{60}$)(OR$^{61}$), —C(O)R$^{60}$, —C(O)OR$^{60}$, —C(O)O$^-$, where R$^{60}$, R$^{61}$ and R$^{62}$ are as defined above. For example, a substituted group may bear a methylenedioxy substituent or one, two, or three substituents selected from a halogen atom, a (1-4C)alkyl group and a (1-4C)alkoxy group.

"Dose unit" as used herein refers to a combination of a GI enzyme-cleavable prodrug (e.g., trypsin-cleavable prodrug) and a GI enzyme inhibitor (e.g., a trypsin inhibitor). A "single dose unit" is a single unit of a combination of a GI enzyme-cleavable prodrug (e.g., trypsin-cleavable prodrug) and a GI enzyme inhibitor (e.g., trypsin inhibitor), where the single dose unit provide a therapeutically effective amount of drug (i.e., a sufficient amount of drug to effect a therapeutic effect, e.g., a dose within the respective drug's therapeutic window, or therapeutic range). "Multiple dose units" or "multiples of a dose unit" or a "multiple of a dose unit" refers to at least two single dose units.

"PK profile" refers to a profile of drug concentration in blood or plasma. Such a profile can be a relationship of drug concentration over time (i.e., a "concentration-time PK profile") or a relationship of drug concentration versus number of doses ingested (i.e., a "concentration-dose PK profile"). A PK profile is characterized by PK parameters.

"PK parameter" refers to a measure of drug concentration in blood or plasma, such as: 1) "drug Cmax", the maximum concentration of drug achieved in blood or plasma; 2) "drug Tmax", the time elapsed following ingestion to achieve Cmax; and 3) "drug exposure", the total concentration of drug present in blood or plasma over a selected period of time, which can be measured using the area under the curve (AUC) of a time course of drug release over a selected period of time (t). Modification of one or more PK parameters provides for a modified PK profile.

"Pharmacodynamic (PD) profile" refers to a profile of the efficacy of a drug in a patient (or subject or user), which is characterized by PD parameters. "PD parameters" include "drug Emax" (the maximum drug efficacy), "drug EC50" (the concentration of drug at 50% of the Emax) and side effects.

"Gastrointestinal enzyme" or "GI enzyme" refers to an enzyme located in the gastrointestinal (GI) tract, which encompasses the anatomical sites from mouth to anus. Trypsin is an example of a GI enzyme.

"Gastrointestinal enzyme-cleavable moiety" or "GI enzyme-cleavable moiety" refers to a group comprising a site susceptible to cleavage by a GI enzyme. For example, a "trypsin-cleavable moiety" refers to a group comprising a site susceptible to cleavage by trypsin.

"Gastrointestinal enzyme inhibitor" or "GI enzyme inhibitor" refers to any agent capable of inhibiting the action of a gastrointestinal enzyme on a substrate. The term also encompasses salts of gastrointestinal enzyme inhibitors. For example, a "trypsin inhibitor" refers to any agent capable of inhibiting the action of trypsin on a substrate.

"Pharmaceutical composition" refers to at least one compound and can further comprise a pharmaceutically acceptable carrier, with which the compound is administered to a patient.

"Pharmaceutically acceptable salt" refers to a salt of a compound, which possesses the desired pharmacological activity of the compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

The term "solvate" as used herein refers to a complex or aggregate formed by one or more molecules of a solute, e.g. a prodrug or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

"Pharmaceutically acceptable carrier" refers to a diluent, adjuvant, excipient or vehicle with, or in which a compound is administered.

"Preventing" or "prevention" or "prophylaxis" refers to a reduction in risk of occurrence of a condition, such as pain.

"Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent.

"Promoiety" refers to a form of protecting group that when used to mask a functional group within an active agent converts the active agent into a prodrug. Typically, the promoiety will be attached to the drug via bond(s) that are cleaved by enzymatic or non-enzymatic means in vivo.

"Treating" or "treatment" of any condition, such as pain, refers, in certain embodiments, to ameliorating the condition (i.e., arresting or reducing the development of the condition). In certain embodiments "treating" or "treatment" refers to ameliorating at least one physical parameter, which may not be discernible by the patient. In certain embodiments, "treating" or "treatment" refers to inhibiting the condition, either physically, (e.g., stabilization of a discernible symptom), physiologically, (e.g., stabilization of a physical parameter), or both. In certain embodiments, "treating" or "treatment" refers to delaying the onset of the condition.

"Therapeutically effective amount" means the amount of a compound (e.g., prodrug) that, when administered to a patient for preventing or treating a condition such as pain, is sufficient to effect such treatment. The "therapeutically effective amount" will vary depending on the compound, the condition and its severity and the age, weight, etc., of the patient.

DETAILED DESCRIPTION

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It should be understood that as used herein, the term "a" entity or "an" entity refers to one or more of that entity. For example, a compound refers to one or more compounds. As such, the terms "a", "an", "one or more" and "at least one" can be used interchangeably. Similarly the terms "comprising", "including" and "having" can be used interchangeably.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

The nomenclature used herein to name the subject compounds is illustrated in the Examples herein. When possible, this nomenclature has generally been derived using the commercially-available AutoNom software (MDL, San Leandro, Calif.).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the compounds of the present disclosure, it may be necessary and/or desirable to protect sensitive or reactive groups on any of the molecules concerned. This can be achieved by means of conventional protecting groups as described in standard works, such as T. W. Greene and P. G. M. Wuts, "Protective Groups in Organic Synthesis", Fourth edition, Wiley, New York 2006. The protecting groups can be removed at a convenient subsequent stage using methods known from the art.

The compounds described herein can contain one or more chiral centers and/or double bonds and therefore, can exist as stereoisomers, such as double-bond isomers (i.e., geometric isomers), enantiomers or diastereomers. Accordingly, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^2$H, $^3$H, $^{11}$C, $^{13}$C, $^{14}$C, $^{15}$N, $^{18}$O, $^{17}$O, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

Representative Embodiments

Reference will now be made in detail to various embodiments. It will be understood that the invention is not limited to these embodiments. To the contrary, it is intended to cover alternatives, modifications, and equivalents as may be included within the spirit and scope of the allowed claims.

The present disclosure provides pharmaceutical compositions, and their methods of use, where the pharmaceutical compositions comprise a ketone-modified opioid prodrug that provides enzymatically-controlled release of a ketone-containing opioid and an optional enzyme inhibitor that interacts with the enzyme(s) that mediates the enzymatically-controlled release of the ketone-containing opioid from the prodrug so as to attenuate enzymatic cleavage of the prodrug.

The disclosure provides pharmaceutical compositions which comprise an optional trypsin inhibitor and a ketone-modified opioid prodrug that contains a trypsin-cleavable moiety that, when cleaved, facilitates release of ketone-containing opioid.

According to one aspect, the embodiments include pharmaceutical compositions, which comprise a trypsin-cleavable ketone-modified opioid prodrug and an optional trypsin inhibitor.

Examples of ketone-modified opioid prodrugs and trypsin inhibitors are described below.

Ketone-Containing Opioids

An "opioid" refers to a chemical substance that exerts its pharmacological action by interaction at an opioid receptor. An opioid can be an isolated natural product, a synthetic compound or a semi-synthetic compound. "Ketone-containing opioid" refers to a subset of the opioids that contain a ketone group. As used herein, a ketone-containing opioid is an opioid containing an enolizable ketone group. A ketone-containing opioid is a compound with a pharmacophore that presents to the opioid receptor an aromatic group and an aliphatic amine group in an architecturally discrete way. See, for example, Foye's Principles of Medicinal Chemistry, Sixth Edition, ed. T. L. Lemke and D. A. Williams, Lippincott Williams & Wilkins, 2008, particularly Chapter 24, pages 653-678.

For example, ketone-containing opioids include, but are not limited to, acetylmorphone, hydrocodone, hydromorphone, ketobemidone, methadone, naloxone, N-methylnaloxone, naltrexone, N-methylnaltrexone, oxycodone, oxymorphone, and pentamorphone.

In certain embodiments, the ketone-containing opioid is hydrocodone or oxycodone.

It is contemplated that opioids bearing at least some of the functionalities described herein will be developed; such opioids are included as part of the scope of this disclosure.

Ketone-Modified Opioid Prodrugs

The disclosure provides a ketone-modified opioid prodrug which provides enzymatically-controlled release of a ketone-containing opioid. In a ketone-modified opioid prodrug, a promoiety is attached to the ketone-containing opioid through the enolic oxygen atom of the ketone moiety. In a ketone-modified opioid prodrug, the hydrogen atom of the corresponding enolic group of the ketone-containing opioid is replaced by a covalent bond to a promoiety.

As disclosed herein, a trypsin-cleavable ketone-modified opioid prodrug is a ketone-modified opioid prodrug that comprises a promoiety comprising a trypsin-cleavable moiety, i.e., a moiety having a site susceptible to cleavage by trypsin. Such a prodrug comprises a ketone-containing opioid covalently bound to a promoiety comprising a trypsin-cleavable moiety, wherein cleavage of the trypsin-cleavable moiety by trypsin mediates release of the drug. Cleavage can initiate, contribute to or effect drug release.

Ketone-Modified Opioid Prodrugs with Promoiety Comprising Cyclizable Spacer Leaving Group and Cleavable Moiety According to certain embodiments, there is provided a ketone-modified opioid prodrug which provides enzymatically-controlled release of a ketone-containing opioid. The disclosure provides for a ketone-modified opioid in which the promoiety comprises a cyclizable spacer leaving group and a cleavable moiety. In certain embodiments, the ketone-containing opioid is a corresponding compound in which the enolic oxygen atom has a substituent which is a spacer leaving group bearing a nitrogen nucleophile that is protected with an enzymatically-cleavable moiety, the configuration of the spacer leaving group and nitrogen nucleophile being such that, upon enzymatic cleavage of the cleavable moiety, the nitrogen nucleophile is capable of forming a cyclic urea, liberating the compound from the spacer leaving group so as to provide a ketone-containing opioid.

The corresponding prodrug provides post administration-activated, controlled release of the ketone-containing opioid. The prodrug requires enzymatic cleavage to initiate release of the ketone-containing opioid and thus the rate of release of the ketone-containing opioid depends upon both the rate of enzymatic cleavage and the rate of cyclization. Accordingly, the prodrug has reduced susceptibility to accidental overdosing or abuse, whether by deliberate overdosing, administration through an inappropriate route, such as by injection, or by chemical modification using readily available household chemicals. The prodrug is configured so that it will not provide excessively high plasma levels of the active drug if it is administered inappropriately, and cannot readily be decomposed to afford the active drug other than by enzymatic cleavage followed by controlled cyclization.

The enzyme-cleavable moiety linked to the nitrogen nucleophile through an amide bond can be, for example, a residue of an amino acid or a peptide, or an (alpha)N-acyl derivative of an amino acid or peptide (for example an N-acyl derivative of a pharmaceutically acceptable carboxylic acid). The peptide can contain, for example, up to about 100 amino acid residues.

Each amino acid can advantageously be a naturally occurring amino acid, such as an L-amino acid. Examples of naturally occurring amino acids are alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine. Accordingly, examples of enzyme-cleavable moieties include residues of the L-amino acids listed hereinabove and N-acyl derivatives thereof, and peptides formed from at least two of the L-amino acids listed hereinabove, and the N-acyl derivatives thereof.

The cyclic group formed when the ketone-containing opioid is released is conveniently pharmaceutically acceptable, in particular a pharmaceutically acceptable cyclic urea. It will be appreciated that cyclic ureas are generally very stable and have low toxicity.

Formulae KC-(I) and KC-(II)

The compositions of the present disclosure include compounds of formulae KC-(I) and KC-(II) shown below. Compounds of formulae KC-(I) and KC-(II) are prodrugs of oxycodone and hydrocodone. Pharmaceutical compositions and methods of the present disclosure also contemplate compounds of formulae KC-(I) and KC-(II).

Formula KC-(I)

In one of its composition aspects, the present embodiments provide a compound of formula KC-(Ia):

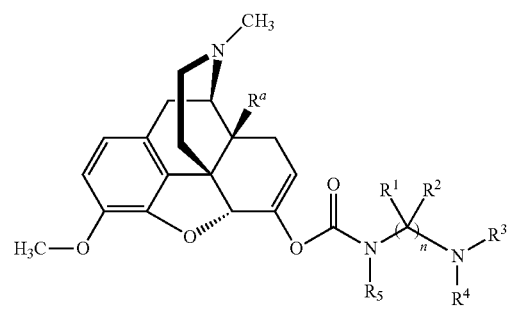

(KC-(Ia))

wherein:
$R^a$ is hydrogen or hydroxyl;
$R^5$ is selected from alkyl, substituted alkyl, arylalkyl, substituted arylalkyl, aryl and substituted aryl;
each $R^1$ is independently selected from hydrogen, alkyl, substituted alkyl, aryl, substituted aryl, acyl, and aminoacyl;
each $R^2$ is independently selected from hydrogen, alkyl, substituted alkyl, aryl, substituted aryl, acyl, and aminoacyl;
or $R^1$ and $R^2$ together with the carbon to which they are attached form a cycloalkyl, substituted cycloalkyl, aryl, or substituted aryl group, or two $R^1$ or $R^2$ groups on adjacent carbon atoms, together with the carbon atoms to which they are attached, form a cycloalkyl, substituted cycloalkyl, aryl, or substituted aryl group;
n is an integer from 2 to 4;
$R^3$ is hydrogen;
$R^4$ is

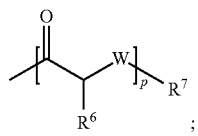

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;
each W is independently —$NR^8$—, —O— or —S—;
each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;
p is an integer from one to 100; and
$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;
or a salt, hydrate or solvate thereof.

In one of its composition aspects, the present embodiments provide a compound of formula KC-(Ib):

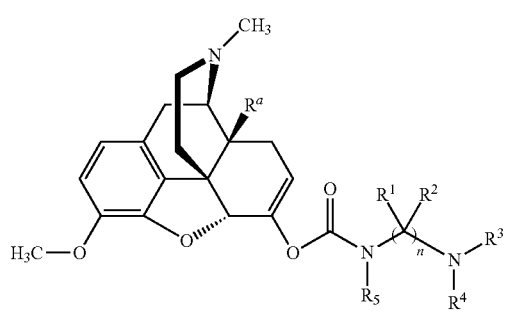

(KC-(Ib))

wherein:
$R^a$ is hydrogen or hydroxyl;
$R^5$ is selected from alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;
each $R^2$ is independently selected from hydrogen, alkyl, substituted alkyl, aryl, substituted aryl, acyl, and aminoacyl;
or $R^1$ and $R^2$ together with the carbon to which they are attached form a cycloalkyl or substituted cycloalkyl group, or two $R^1$ or $R^2$ groups on adjacent carbon atoms, together with the carbon atoms to which they are attached, form a cycloalkyl or substituted cycloalkyl group;
n is an integer from 2 to 4;
$R^3$ is hydrogen;
$R^4$ is

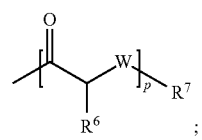

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;
each W is independently —$NR^8$—, —O— or —S—;
each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;
p is an integer from one to 100; and
$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;
or a salt, hydrate or solvate thereof.

Reference to formula KC-(I) is meant to include compounds of formula KC-(Ia) and KC-(Ib).

In formula KC-(I), $R^a$ can be hydrogen or hydroxyl. In certain instances, $R^a$ is hydrogen. In other instances, $R^a$ is hydroxyl.

In formula KC-(I), $R^5$ can be selected from alkyl, substituted alkyl, arylalkyl, substituted arylalkyl, aryl and substituted aryl. In certain instances, $R^5$ is (1-6C)alkyl. In other instances, $R^5$ is (1-4C)alkyl. In other instances, $R^5$ is methyl or ethyl. In other instances, $R^5$ is methyl. In certain instances, $R^5$ is ethyl.

In certain instances, $R^5$ is substituted alkyl. In certain instances, $R^5$ is an alkyl group substituted with a carboxylic group such as a carboxylic acid, carboxylic ester or carboxylic amide. In certain instances, $R^5$ is —$(CH_2)_n$—COOH, —$(CH_2)_n$—$COOCH_3$, or —$(CH_2)_n$—$COOCH_2CH_3$, wherein n is a number form one to 10. In certain instances, $R^1$ is —$(CH_2)_5$—COOH, —$(CH_2)_5$—$COOCH_3$, or —$(CH_2)_5$—$COOCH_2CH_3$.

In certain instances, in formula KC-(I), $R^5$ is arylalkyl or substituted arylalkyl. In certain instances, in formula KC-(I), $R^5$ is arylalkyl. In certain instances, $R^5$ is substituted arylalkyl. In certain instances, $R^5$ is an arylalkyl group substituted with a carboxylic group such as a carboxylic acid, carboxylic ester or carboxylic amide. In certain instances, $R^5$ is —$(CH_2)_q(C_6H_4)$—COOH, —$(CH_2)_q(C_6H_4)$—$COOCH_3$, or —$(CH_2)_q(C_6H_4)$—$COOCH_2CH_3$, where q is an integer from one to 10. In certain instances, R⁵ is —CH₂(C₆H₄)—COOH, —CH₂(C₆H₄)—COOCH₃, or —CH₂ (C₆H₄)—COOCH₂CH₃.

In certain instances, in formula KC-(I), R⁵ is aryl. In certain instances, R⁵ is substituted aryl. In certain instances, R⁵ is an aryl group ortho, meta or para-substituted with a carboxylic group such as a carboxylic acid, carboxylic ester or carboxylic amide. In certain instances, R⁵ is —(C₆H₄)—COOH, —(C₆H₄)—COOCH₃, or —(C₆H₄)—COOCH₂CH₃.

In formula KC-(I), each R¹ can be independently selected from hydrogen, alkyl, substituted alkyl, aryl, substituted aryl, acyl, and aminoacyl. In certain instances, R¹ is hydrogen or alkyl. In certain instances, R¹ is hydrogen. In certain instances, R¹ is alkyl. In certain instances, R¹ is acyl. In certain instances, R¹ is aminoacyl.

In formula KC-(I), each R² can be independently selected from hydrogen, alkyl, substituted alkyl, aryl, substituted aryl, acyl, and aminoacyl. In certain instances, R² is hydrogen or alkyl. In certain instances, R² is hydrogen. In certain instances, R² is alkyl. In certain instances, R² is acyl. In certain instances, R² is aminoacyl.

In certain instances, R¹ and R² are hydrogen. In certain instances, R¹ and R² on the same carbon are both alkyl. In certain instances, R¹ and R² on the same carbon are methyl. In certain instances, R¹ and R² on the same carbon are ethyl.

In certain instances, R¹ and R¹ which are vicinal are both alkyl and R² and R² which are vicinal are both hydrogen. In certain instances, R¹ and R¹ which are vicinal are both ethyl and R² and R² which are vicinal are both hydrogen. In certain instances, R¹ and R¹ which are vicinal are both methyl and R² and R² which are vicinal are both hydrogen.

In certain instances, in the chain of —[C(R¹)(R²)]ₙ— in Formula KC-(I), not every carbon is substituted. In certain instances, in the chain of —[C(R¹)(R²)]ₙ—, there is a combination of different alkyl substituents, such as methyl or ethyl.

In certain instances, one of R¹ and R² is methyl, ethyl or other alkyl and R⁵ is alkyl. In certain instances, R¹ and R¹ which are vicinal are both alkyl and R² and R² which are vicinal are both hydrogen and R⁵ is alkyl. In certain instances, R¹ and R¹ which are vicinal are both ethyl and R² and R² which are vicinal are both hydrogen and R⁵ is alkyl. In certain instances, R¹ and R¹ which are vicinal are both methyl and R² and R² which are vicinal are both hydrogen and R⁵ is alkyl.

In certain instances, one of R¹ and R² is methyl, ethyl or other alkyl and R⁵ is substituted alkyl. In certain instances, one of R¹ and R² is methyl, ethyl or other alkyl and R⁵ is an alkyl group substituted with a carboxylic group such as a carboxylic acid, carboxylic ester or carboxylic amide. In certain instances, one of R¹ and R² is methyl, ethyl or other alkyl and R⁵ is —(CH₂)_q(C₆H₄)—COOH, —(CH₂)_q(C₆H₄)—COOCH₃, or —(CH₂)_q(C₆H₄)—COOCH₂CH₃, where q is an integer from one to 10. In certain instances, one of R¹ and R² is methyl, ethyl or other alkyl and R⁵ is an alkyl group substituted with carboxamide.

In formula KC-(I), R¹ and R² together with the carbon to which they are attached can form a cycloalkyl or substituted cycloalkyl group, or two R¹ or R² groups on adjacent carbon atoms, together with the carbon atoms to which they are attached, can form a cycloalkyl or substituted cycloalkyl group. In certain instances, R¹ and R² together with the carbon to which they are attached can form a cycloalkyl group. Thus, in certain instances, R¹ and R² on the same carbon form a spirocycle. In certain instances, R¹ and R² together with the carbon to which they are attached can form a substituted cycloalkyl group. In certain instances, two R¹ or R² groups on adjacent carbon atoms, together with the carbon atoms to which they are attached, can form a cycloalkyl group. In certain instances, two R¹ or R² groups on adjacent carbon atoms, together with the carbon atoms to which they are attached, can form a substituted cycloalkyl group.

In formula KC-(I), R¹ and R² together with the carbon to which they are attached can form an aryl or substituted aryl group, or two R¹ or R² groups on adjacent carbon atoms, together with the carbon atoms to which they are attached, can form an aryl or substituted aryl group. In certain instances, two R¹ or R² groups on adjacent carbon atoms, together with the carbon atoms to which they are attached, form a phenyl ring. In certain instances, two R¹ or R² groups on adjacent carbon atoms, together with the carbon atoms to which they are attached, form a substituted phenyl ring. In certain instances, two R¹ or R² groups on adjacent carbon atoms, together with the carbon atoms to which they are attached, form a naphthyl ring.

In certain instances, one of R¹ and R² is aminoacyl.

In certain instances, one or both of R¹ and R² is aminoacyl comprising phenylenediamine.

In certain instances, one of R¹ and R² is

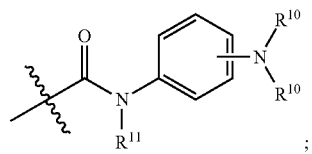

wherein each R¹ is independently selected from hydrogen, alkyl, substituted alkyl, and acyl and R¹¹ is alkyl or substituted alkyl. In certain instances, at least one of R¹⁰ is acyl. In certain instances, at least one of R¹⁰ is alkyl or substituted alkyl. In certain instances, at least one of R¹⁰ is hydrogen. In certain instances, both of R¹⁰ are hydrogen.

In certain instances, one of R¹ and R² is

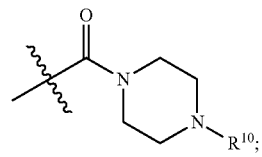

wherein R¹⁰ is hydrogen, alkyl, substituted alkyl, or acyl. In certain instances, R¹⁰ is acyl. In certain instances, R¹⁰ is alkyl or substituted alkyl. In certain instances, R¹⁰ is hydrogen.

In certain instances, one of R¹ and R² is

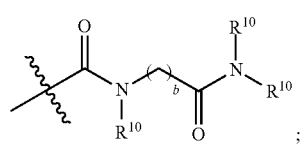

wherein each R¹⁰ is independently hydrogen, alkyl, substituted alkyl, or acyl and b is a number from one to 5. In certain instances, one of R¹ and R² is

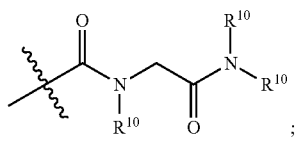

wherein each $R^{10}$ is independently hydrogen, alkyl, substituted alkyl, or acyl. In certain instances, one of $R^1$ and $R^2$ is

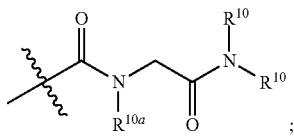

wherein $R^{10a}$ is alkyl and each $R^{10}$ is independently hydrogen, alkyl, substituted alkyl, or acyl.

In certain instances, one of $R^1$ and $R^2$ is

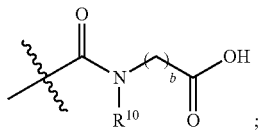

wherein $R^{10}$ is independently hydrogen, alkyl, substituted alkyl, or acyl and b is a number from one to 5. In certain instances, one of $R^1$ and $R^2$ is

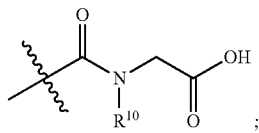

wherein $R^{10}$ is independently hydrogen, alkyl, substituted alkyl, or acyl.

In certain instances, one of $R^1$ and $R^2$ is an aminoacyl group, such as —C(O)NR$^{10a}$R$^{10b}$ wherein each $R^{10a}$ and $R^{10b}$ is independently selected from hydrogen, alkyl, substituted alkyl, and acyl. In certain instances, one of $R^1$ and $R^2$ is an aminoacyl group, such as —C(O)NR$^{10a}$R$^{10b}$ wherein $R^{10a}$ is an alkyl and $R^{10b}$ is substituted alkyl. In certain instances, one of $R^1$ and $R^2$ is an aminoacyl group, such as —C(O)NR$^{10a}$R$^{10b}$, wherein $R^{10a}$ is an alkyl and $R^{10b}$ is alkyl substituted with a carboxylic acid or carboxyl ester. In certain instances, one of $R^1$ and $R^2$ is an aminoacyl group, such as —C(O)NR$^{10a}$R$^{10b}$, wherein $R^{10a}$ is methyl and $R^{10b}$ is alkyl substituted with a carboxylic acid or carboxyl ester.

In certain instances, $R^1$ or $R^2$ can modulate a rate of intramolecular cyclization. $R^1$ or $R^2$ can speed up a rate of intramolecular cyclization, when compared to the corresponding molecule where $R^1$ and $R^2$ are both hydrogen. In certain instances, $R^1$ or $R^2$ comprise an electron-withdrawing group or an electron-donating group. In certain instances, $R^1$ or $R^2$ comprise an electron-withdrawing group. In certain instances, $R^1$ or $R^2$ comprise an electron-donating group.

Atoms and groups capable of functioning as electron withdrawing substituents are well known in the field of organic chemistry. They include electronegative atoms and groups containing electronegative atoms. Such groups function to lower the basicity or protonation state of a nucleophilic nitrogen in the beta position via inductive withdrawal of electron density. Such groups can also be positioned on other positions along the alkylene chain. Examples include halogen atoms (for example, a fluorine atom), acyl groups (for example an alkanoyl group, an aroyl group, a carboxyl group, an alkoxycarbonyl group, an aryloxycarbonyl group or an aminocarbonyl group (such as a carbamoyl, alkylaminocarbonyl, dialkylaminocarbonyl or arylaminocarbonyl group)), an oxo (=O) substituent, a nitrile group, a nitro group, ether groups (for example an alkoxy group) and phenyl groups bearing a substituent at the ortho position, the para position or both the ortho and the para positions, each substituent being selected independently from a halogen atom, a fluoroalkyl group (such as trifluoromethyl), a nitro group, a cyano group and a carboxyl group. Each of the electron withdrawing substituents can be selected independently from these.

In certain instances, —[C(R$^1$)(R$^2$)]$_n$— is selected from —CH(CH$_2$F)CH(CH$_2$F)—; —CH(CHF$_2$)CH(CHF$_2$)—; —CH(CF$_3$)CH(CF$_3$)—; —CH$_2$CH(CF$_3$)—; —CH$_2$CH(CHF$_2$)—; —CH$_2$CH(CH$_2$F)—; —CH$_2$CH(F)CH$_2$—; —CH$_2$C(F$_2$)CH$_2$—; —CH$_2$CH(C(O)NR$^{20}$R$^{21}$)—; —CH$_2$CH(C(O)OR$^{22}$)—; —CH$_2$CH(C(O)OH)—; —CH(CH$_2$F)CH$_2$CH(CH$_2$F)—; —CH(CHF$_2$)CH$_2$CH(CHF$_2$)—; —CH(CF$_3$)CH$_2$CH(CF$_3$)—; —CH$_2$CH$_2$CH(CF$_3$)—; —CH$_2$CH$_2$CH(CHF$_2$)—; —CH$_2$CH$_2$CH(CH$_2$F)—; —CH$_2$CH$_2$CH(C(O) NR$^{23}$R$^{24}$)—; —CH$_2$CH$_2$CH(C(O) OR$^{25}$)—; and —CH$_2$CH$_2$CH(C(O)OH)—, in which R$^{20}$, R$^{21}$, R$^{22}$ and R$^{23}$ each independently represents hydrogen or (1-6C)alkyl, and R$^{24}$ and R$^{25}$ each independently represents (1-6C)alkyl.

In formula KC-(I), n can be an integer from 2 to 4. In certain instances, n is two. In other instances, n is three. In other instances, n is four.

In formula KC-(I), $R^4$ can be a residue of an L-amino acid selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine, or a residue of an N-acyl derivative of any of said amino acids; or a residue of a peptide composed of at least two L-amino acid residues selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine or a residue of an N-acyl derivative thereof. Such a peptide can be from 2 to about 100 amino acids in length. Examples of N-acyl derivatives include acetyl, benzoyl, malonyl, piperonyl or succinyl derivatives.

In certain instances, $R^4$ is a residue of L-arginine or L-lysine, or a residue of an N-acyl derivative of L-arginine or L-lysine.

In certain instances, in formula KC-(I), when p is greater than one, then the $R^4$ adjacent to the nitrogen of —N(R$^3$)(R$^4$) is a residue of L-arginine or L-lysine. In certain instances, when p is greater than one, the $R^4$ adjacent to the nitrogen of —N(R$^3$)(R$^4$) is a residue of L-arginine or L-lysine and the first residue is joined to at least one additional L-amino acid residue selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine. The terminal residue of the peptide can be an N-acyl derivative of any of such L-amino acids. In certain instances R$^4$ is a dipeptide or an N-acyl derivative thereof. In certain instances R is a tripeptide or an N-acyl derivative thereof.

In formula KC-(I), R$^4$ is

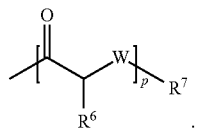

In formula KC-(I), each R$^6$ can be independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, R$^6$ and R$^7$ together with the atoms to which they are bonded form a cycloheteroalkyl or substituted cycloheteroalkyl ring.

In certain instances, in formula KC-(I), R$^6$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl. In certain instances, R$^6$ is selected from hydrogen, alkyl, substituted alkyl, arylalkyl, substituted arylalkyl, heteroarylalkyl, and substituted heteroarylalkyl. In certain instances, R$^6$ is hydrogen. In certain instances, R$^6$ is alkyl. In certain instances, R$^6$ is substituted alkyl. In certain instances, R$^6$ is arylalkyl or substituted arylalkyl. In certain instances, R$^6$ is heteroarylalkyl or substituted heteroarylalkyl.

In certain instances, R$^6$ is a side chain of an amino acid, such as alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine or valine. In certain instances, R$^6$ is a side chain of an L-amino acid, such as L-alanine, L-arginine, L-asparagine, L-aspartic acid, L-cysteine, L-glycine, L-glutamine, L-glutamic acid, L-histidine, L-isoleucine, L-leucine, L-lysine, L-methionine, L-phenylalanine, L-proline, L-serine, L-threonine, L-tryptophan, L-tyrosine or L-valine.

In certain instances, R$^6$ is —CH$_2$CH$_2$CH$_2$NH(C=NH)NH$_2$ or —CH$_2$CH$_2$CH$_2$CH$_2$NH$_2$.

In formula KC-(I), each W can be independently —NR$^8$—, —O— or —S—. In certain instances, W is —NR$^8$—. In certain instances, W is —O—. In certain instances, W is —S—.

In formula KC-(I), each R$^8$ can be independently hydrogen, alkyl, substituted alkyl, aryl or substituted aryl, or optionally, each R$^6$ and R$^8$ independently together with the atoms to which they are bonded form a cycloheteroalkyl or substituted cycloheteroalkyl ring.

In certain instances, in formula KC-(I), R$^8$ is hydrogen or alkyl. In certain instances, R$^8$ is hydrogen. In certain instances, R$^8$ is alkyl. In certain instances, R$^8$ is aryl. In certain instances, R$^6$ and R$^8$ independently together with the atoms to which they are bonded form a cycloheteroalkyl or substituted cycloheteroalkyl ring.

In formula KC-(I), p can be an integer from one to 100 and each R$^6$ can be selected independently from a side chain of any amino acid. In certain instances, p is an integer from one to 50. In certain instances, p is an integer from one to 90, 80, 70, 60, 50, 40, 30, 20, or 10. In certain instances, p is about 100. In certain instances, p is about 75. In certain instances, p is about 50. In certain instances, p is about 25.

In certain instances, p is about 20. In certain instances, p is about 15. In certain instances, p is about 10. In certain instances, p is about 9. In certain instances, p is about 8. In certain instances, p is about 7. In certain instances, p is about 6. In certain instances, p is about 5. In certain instances, p is about 4. In certain instances, p is about 3. In certain instances, p is about 2. In certain instances, p is about one.

In certain instances, the R$^6$ of R$^4$ adjacent to the nitrogen of —N(R$^3$)(R$^4$) is —CH$_2$CH$_2$CH$_2$NH(C=NH)NH$_2$ or —CH$_2$CH$_2$CH$_2$CH$_2$NH$_2$, and any additional R$^6$ can be a side chain of any amino acid independently selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine or valine.

In formula KC-(I), R$^7$ can be selected from hydrogen, alkyl, substituted alkyl, acyl, substituted acyl, alkoxycarbonyl, substituted alkoxycarbonyl, aryl, substituted aryl, arylalkyl, and substituted arylalkyl.

In certain instances, R$^7$ is hydrogen, alkyl, acyl, or substituted acyl. In certain instances, R$^7$ is hydrogen. In certain instances, R$^7$ is alkyl. In certain instances, R$^7$ is acyl or substituted acyl. In certain instances, R$^7$ is acyl. In certain instances, R$^7$ is substituted acyl. In certain instances, R$^7$ can be acetyl, benzoyl, malonyl, piperonyl or succinyl.

Formula KC-(II)

Compounds of formula KC-(II) are compounds of formula KC-(I) in which R$^5$ is selected from (1-6C) alkyl, (1-6C) substituted alkyl, —(CH$_2$)$_q$(C$_6$H$_4$)—COOH, —(CH$_2$)$_q$(C$_6$H$_4$)—COOCH$_3$, and —(CH$_2$)$_q$(C$_6$H$_4$)—COOCH$_2$CH$_3$, where q is an integer from one to 10; n is 2 or 3; R$^3$ is hydrogen; R$^4$ is an L-amino acid or peptide, where the peptide can be comprised of L-amino acids. In one of its composition aspects, the present embodiments provide a compound of formula KC-(II):

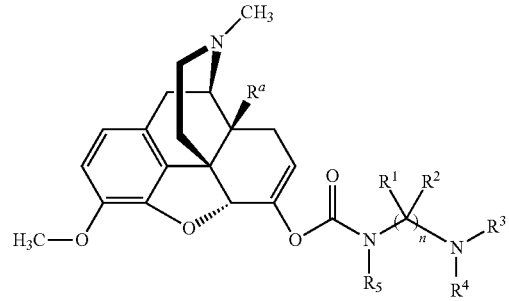

(KC-(II))

wherein:

R$^a$ is hydrogen or hydroxyl;

R$^5$ is selected from (1-6C)alkyl, (1-6C) substituted alkyl, —(CH$_2$)$_q$(C$_6$H$_4$)—COOH, —(CH$_2$)$_q$(C$_6$H$_4$)—COOCH$_3$, and —(CH$_2$)$_q$(C$_6$H$_4$)—COOCH$_2$CH$_3$, where q is an integer from one to 10;

each R$^1$ is independently selected from hydrogen, alkyl, substituted alkyl, aryl, substituted aryl, acyl, and aminoacyl;

each R$^2$ is independently selected from hydrogen, alkyl, substituted alkyl, aryl, substituted aryl, acyl, and aminoacyl;

or R$^1$ and R$^2$ together with the carbon to which they are attached form a cycloalkyl or substituted cycloalkyl group, or two R$^1$ or R$^2$ groups on adjacent carbon atoms, together with the carbon atoms to which they are attached, form a cycloalkyl or substituted cycloalkyl group;

29 n is 2 or 3;

R$^3$ is hydrogen;

R$^4$ is a residue of an L-amino acid selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine, or a residue of an N-acyl derivative of any of said amino acids; or a residue of a peptide composed of at least two L-amino acid residues selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine or a residue of an N-acyl derivative thereof.

In certain embodiments in Formula KC-(II), R$^4$ is a residue of an L-amino acid selected from arginine and lysine.

In certain instances, in formula KC-(II), when R$^4$ is a peptide comprising more than one amino acid, then the R$^4$ adjacent to the nitrogen of —N(R$^3$)(R$^4$) is a residue of L-arginine or L-lysine. In certain instances R$^4$ is a dipeptide or an N-acyl derivative thereof. In certain instances R$^4$ is a tripeptide or an N-acyl derivative thereof.

In certain embodiments in Formula KC-(II), R$^4$ is a residue of an N-acyl derivative thereof. In certain instances, R$^4$ is a residue of an N-acyl derivative thereof, where the N-acyl derivative is substituted, such as, but not limited to, malonyl and succinyl.

Formulae KC-(III) to KC-(V)

The compositions of the present disclosure include compounds of formulae KC-(III) to KC-(V) shown below. Pharmaceutical compositions and methods of the present disclosure also contemplate compounds of formulae KC-(III) to KC-(V).

Formula KC-(III)

In one of its composition aspects, the present embodiments provide a compound of formula KC-(IIIa):

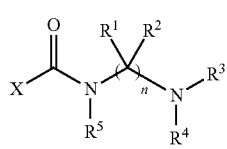

(KC-(IIIa))

wherein:

X represents a residue of a ketone-containing opioid, wherein the hydrogen atom of the corresponding enolic group of the ketone is replaced by a covalent bond to —C(O)—NR$^5$—(C(R$^1$)(R$^2$))$_n$—NR$^3$R$^4$;

R$^5$ is selected from alkyl, substituted alkyl, arylalkyl, substituted arylalkyl, aryl and substituted aryl;

each R$^1$ is independently selected from hydrogen, alkyl, substituted alkyl, aryl, substituted aryl, acyl, and aminoacyl;

each R$^2$ is independently selected from hydrogen, alkyl, substituted alkyl, aryl, substituted aryl, acyl, and aminoacyl;

or R$^1$ and R$^2$ together with the carbon to which they are attached form a cycloalkyl, substituted cycloalkyl, aryl, or substituted aryl group, or two R$^2$ or R$^3$ groups on adjacent carbon atoms, together with the carbon atoms to which they are attached, form a cycloalkyl, substituted cycloalkyl, aryl, or substituted aryl group;

n is an integer from 2 to 4;

R$^3$ is hydrogen;

30

R$^4$ is

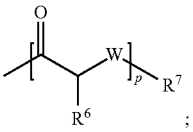

;

each R$^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, R$^6$ and R$^7$ together with the atoms to which they are bonded form a cycloheteroalkyl or substituted cycloheteroalkyl ring;

each W is independently —NR$^8$—, —O— or —S—;

each R$^8$ is independently selected from hydrogen, alkyl, substituted alkyl, aryl and substituted aryl, or optionally, each R$^6$ and R$^8$ independently together with the atoms to which they are bonded form a cycloheteroalkyl or substituted cycloheteroalkyl ring;

p is an integer from one to 100; and

R$^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

In one of its composition aspects, the present embodiments provide a compound of formula KC-(IIIb):

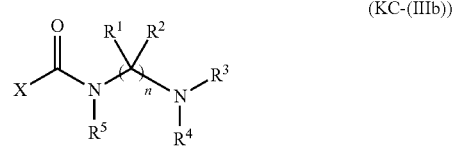

(KC-(IIIb))

wherein:

X represents a residue of a ketone-containing opioid, wherein the hydrogen atom of the corresponding enolic group of the ketone is replaced by a covalent bond to —C(O)—NR$^5$—(C(R$^1$)(R$^2$))$_n$—NR$^3$R$^4$;

R$^5$ is selected from alkyl, substituted alkyl, arylalkyl, substituted arylalkyl, aryl and substituted aryl;

each R$^1$ is independently selected from hydrogen, alkyl, substituted alkyl, aryl, substituted aryl, acyl, and aminoacyl;

each R$^2$ is independently selected from hydrogen, alkyl, substituted alkyl, aryl, substituted aryl, acyl, and aminoacyl;

or R$^1$ and R$^2$ together with the carbon to which they are attached form a cycloalkyl or substituted cycloalkyl group, or two R$^1$ or R$^2$ groups on adjacent carbon atoms, together with the carbon atoms to which they are attached, form a cycloalkyl or substituted cycloalkyl group;

n is an integer from 2 to 4;

R$^3$ is hydrogen;

R$^4$ is

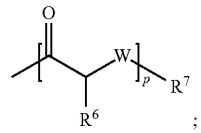

;

each R$^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently $-NR^8-$, $-O-$ or $-S-$;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

Reference to formula KC-(III) is meant to include compounds of formula KC-(IIIa) and KC-(IIIb).

In formula KC-(III), $R^5$ can be selected from alkyl, substituted alkyl, arylalkyl, substituted arylalkyl, aryl and substituted aryl. In certain instances, $R^5$ is (1-6C)alkyl. In other instances, $R^5$ is (1-4C)alkyl. In other instances, $R^5$ is methyl or ethyl. In other instances, $R^5$ is methyl. In certain instances, $R^5$ is ethyl.

In certain instances, $R^5$ is substituted alkyl. In certain instances, $R^5$ is an alkyl group substituted with a carboxylic group such as a carboxylic acid, carboxylic ester or carboxylic amide. In certain instances, $R^5$ is $-(CH_2)_n-COOH$, $-(CH_2)_n-COOCH_3$, or $-(CH_2)_n-COOCH_2CH_3$, wherein n is a number form one to 10. In certain instances, $R^1$ is $-(CH_2)_5-COOH$, $-(CH_2)_5-COOCH_3$, or $-(CH_2)_5-COOCH_2CH_3$.

In certain instances, in formula KC-(III), $R^5$ is arylalkyl or substituted arylalkyl. In certain instances, in formula KC-(III), $R^5$ is arylalkyl. In certain instances, $R^5$ is substituted arylalkyl. In certain instances, $R^5$ is an arylalkyl group substituted with a carboxylic group such as a carboxylic acid, carboxylic ester or carboxylic amide. In certain instances, $R^5$ is $-(CH_2)_q(C_6H_4)-COOH$, $-(CH_2)_q(C_6H_4)-COOCH_3$, or $-(CH_2)_q(C_6H_4)-COOCH_2CH_3$, where q is an integer from one to 10. In certain instances, $R^5$ is $-CH_2(C_6H_4)-COOH$, $-CH_2(C_6H_4)-COOCH_3$, or $-CH_2(C_6H_4)-COOCH_2CH_3$.

In certain instances, in formula KC-(III), $R^5$ is aryl. In certain instances, $R^5$ is substituted aryl. In certain instances, $R^5$ is an aryl group ortho, meta or para-substituted with a carboxylic group such as a carboxylic acid, carboxylic ester or carboxylic amide. In certain instances, $R^5$ is $-(C_6H_4)-COOH$, $-(C_6H_4)-COOCH_3$, or $-(C_6H_4)-COOCH_2CH_3$.

In formula KC-(III), each $R^1$ can be independently selected from hydrogen, alkyl, substituted alkyl, aryl, substituted aryl, acyl, and aminoacyl. In certain instances, $R^1$ is hydrogen or alkyl. In certain instances, $R^1$ is hydrogen. In certain instances, $R^1$ is alkyl. In certain instances, $R^1$ is acyl. In certain instances, $R^1$ is aminoacyl.

In formula KC-(III), each $R^2$ can be independently selected from hydrogen, alkyl, substituted alkyl, aryl, substituted aryl, acyl, and aminoacyl. In certain instances, $R^2$ is hydrogen or alkyl. In certain instances, $R^2$ is hydrogen. In certain instances, $R^2$ is alkyl. In certain instances, $R^2$ is acyl. In certain instances, $R^2$ is aminoacyl.

In certain instances, $R^1$ and $R^2$ are hydrogen. In certain instances, $R^1$ and $R^2$ on the same carbon are both alkyl. In certain instances, $R^1$ and $R^2$ on the same carbon are methyl. In certain instances, $R^1$ and $R^2$ on the same carbon are ethyl.

In certain instances, $R^1$ and $R^1$ which are vicinal are both alkyl and $R^2$ and $R^2$ which are vicinal are both hydrogen. In certain instances, $R^1$ and $R^1$ which are vicinal are both ethyl and $R^2$ and $R^2$ which are vicinal are both hydrogen. In certain instances, $R^1$ and $R^1$ which are vicinal are both methyl and $R^2$ and $R^2$ which are vicinal are both hydrogen.

In certain instances, in the chain of $-[C(R^1)(R^2)]_n-$ in Formula KC-(III), not every carbon is substituted. In certain instances, in the chain of $-[C(R^1)(R^2)]_n-$, there is a combination of different alkyl substituents, such as methyl or ethyl.

In certain instances, one of $R^1$ and $R^2$ is methyl, ethyl or other alkyl and $R^5$ is alkyl. In certain instances, $R^1$ and $R^1$ which are vicinal are both alkyl and $R^2$ and $R^2$ which are vicinal are both hydrogen and $R^5$ is alkyl. In certain instances, $R^1$ and $R^1$ which are vicinal are both ethyl and $R^2$ and $R^2$ which are vicinal are both hydrogen and $R^5$ is alkyl. In certain instances, $R^1$ and $R^1$ which are vicinal are both methyl and $R^2$ and $R^2$ which are vicinal are both hydrogen and $R^5$ is alkyl.

In certain instances, one of $R^1$ and $R^2$ is methyl, ethyl or other alkyl and $R^5$ is substituted alkyl. In certain instances, one of $R^1$ and $R^2$ is methyl, ethyl or other alkyl and $R^5$ is an alkyl group substituted with a carboxylic group such as a carboxylic acid, carboxylic ester or carboxylic amide. In certain instances, one of $R^1$ and $R^2$ is methyl, ethyl or other alkyl and $R^5$ is $-(CH_2)_q(C_6H_4)-COOH$, $-(CH_2)_q(C_6H_4)-COOCH_3$, or $-(CH_2)_q(C_6H_4)-COOCH_2CH_3$, where q is an integer from one to 10. In certain instances, one of $R^1$ and $R^2$ is methyl, ethyl or other alkyl and $R^5$ is an alkyl group substituted with carboxamide.

In formula KC-(III), $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group. In certain instances, $R^1$ and $R^2$ together with the carbon to which they are attached can form a cycloalkyl group. Thus, in certain instances, $R^1$ and $R^2$ on the same carbon form a spirocycle. In certain instances, $R^1$ and $R^2$ together with the carbon to which they are attached can form a substituted cycloalkyl group. In certain instances, two $R^1$ or $R^2$ groups on adjacent carbon atoms, together with the carbon atoms to which they are attached, can form a cycloalkyl group. In certain instances, two $R^1$ or $R^2$ groups on adjacent carbon atoms, together with the carbon atoms to which they are attached, can form a substituted cycloalkyl group.

In certain instances, $R^1$ and $R^2$ together with the carbon to which they are attached can form an aryl or substituted aryl group, or two $R^1$ or $R^2$ groups on adjacent carbon atoms, together with the carbon atoms to which they are attached, can form an aryl or substituted aryl group. In certain instances, two $R^1$ or $R^2$ groups on adjacent carbon atoms, together with the carbon atoms to which they are attached, form a phenyl ring. In certain instances, two $R^1$ or $R^2$ groups on adjacent carbon atoms, together with the carbon atoms to which they are attached, form a substituted phenyl ring. In certain instances, two $R^1$ or $R^2$ groups on adjacent carbon atoms, together with the carbon atoms to which they are attached, form a naphthyl ring.

In certain instances, one of $R^1$ and $R^2$ is aminoacyl.

In certain instances, one or both of $R^1$ and $R^2$ is aminoacyl comprising phenylenediamine.

In certain instances, one of $R^1$ and $R^2$ is

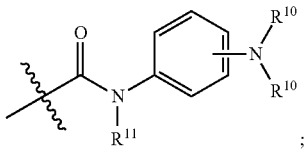

wherein each $R^{10}$ is independently selected from hydrogen, alkyl, substituted alkyl, and acyl and $R^{11}$ is alkyl or substituted alkyl. In certain instances, at least one of $R^{10}$ is acyl. In certain instances, at least one of $R^{10}$ is alkyl or substituted alkyl. In certain instances, at least one of $R^{10}$ is hydrogen. In certain instances, both of $R^{10}$ are hydrogen.

In certain instances, one of $R^1$ and $R^2$ is

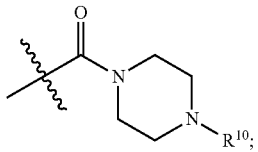

wherein $R^{10}$ is hydrogen, alkyl, substituted alkyl, or acyl. In certain instances, $R^{10}$ is acyl. In certain instances, $R^{10}$ is alkyl or substituted alkyl. In certain instances, $R^{10}$ is hydrogen.

In certain instances, one of $R^1$ and $R^2$ is

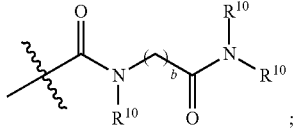

wherein each $R^{10}$ is independently hydrogen, alkyl, substituted alkyl, or acyl and b is a number from one to 5. In certain instances, one of $R^1$ and $R^2$ is

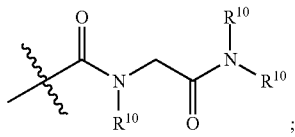

wherein each $R^{10}$ is independently hydrogen, alkyl, substituted alkyl, or acyl. In certain instances, one of $R^1$ and $R^2$ is

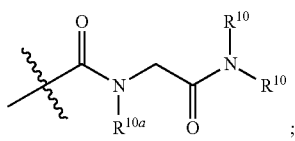

wherein $R^{10a}$ is alkyl and each $R^{10}$ is independently hydrogen, alkyl, substituted alkyl, or acyl.

In certain instances, one of $R^1$ and $R^2$ is

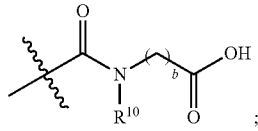

wherein $R^{10}$ is independently hydrogen, alkyl, substituted alkyl, or acyl and b is a number from one to 5. In certain instances, one of $R^1$ and $R^2$ is

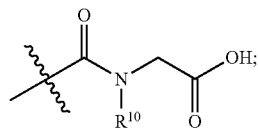

wherein $R^{10}$ is independently hydrogen, alkyl, substituted alkyl, or acyl.

In certain instances, one of $R^1$ and $R^2$ is an aminoacyl group, such as —C(O)NR$^{10a}$R$^{10b}$ wherein each $R^{10a}$ and $R^{10b}$ is independently selected from hydrogen, alkyl, substituted alkyl, and acyl. In certain instances, one of $R^1$ and $R^2$ is an aminoacyl group, such as —C(O)NR$^{10a}$R$^{10b}$ wherein $R^{10a}$ is an alkyl and $R^{10b}$ is substituted alkyl. In certain instances, one of $R^1$ and $R^2$ is an aminoacyl group, such as —C(O)NR$^{10a}$R$^{10b}$, wherein $R^{10a}$ is an alkyl and $R^{10b}$ is alkyl substituted with a carboxylic acid or carboxyl ester. In certain instances, one of $R^1$ and $R^2$ is an aminoacyl group, such as —C(O)NR$^{10a}$R$^{10b}$, wherein $R^{10a}$ is methyl and $R^{10b}$ is alkyl substituted with a carboxylic acid or carboxyl ester.

In certain instances, $R^1$ or $R^2$ can modulate a rate of intramolecular cyclization. $R^1$ or $R^2$ can speed up a rate of intramolecular cyclization, when compared to the corresponding molecule where $R^1$ and $R^2$ are both hydrogen. In certain instances, $R^1$ or $R^2$ comprise an electron-withdrawing group or an electron-donating group. In certain instances, $R^1$ or $R^2$ comprise an electron-withdrawing group. In certain instances, $R^1$ or $R^2$ comprise an electron-donating group.

Atoms and groups capable of functioning as electron withdrawing substituents are well known in the field of organic chemistry. They include electronegative atoms and groups containing electronegative atoms. Such groups function to lower the basicity or protonation state of a nucleophilic nitrogen in the beta position via inductive withdrawal of electron density. Such groups can also be positioned on other positions along the alkylene chain. Examples include halogen atoms (for example, a fluorine atom), acyl groups (for example an alkanoyl group, an aroyl group, a carboxyl group, an alkoxycarbonyl group, an aryloxycarbonyl group or an aminocarbonyl group (such as a carbamoyl, alkylaminocarbonyl, dialkylaminocarbonyl or arylaminocarbonyl group)), an oxo (=O) substituent, a nitrile group, a nitro group, ether groups (for example an alkoxy group) and phenyl groups bearing a substituent at the ortho position, the para position or both the ortho and the para positions, each substituent being selected independently from a halogen atom, a fluoroalkyl group (such as trifluoromethyl), a nitro group, a cyano group and a carboxyl group. Each of the electron withdrawing substituents can be selected independently from these.

In certain instances, —[C($R^1$)($R^2$)]$_n$— is selected from —CH(CH$_2$F)CH(CH$_2$F)—; —CH(CHF$_2$)CH(CHF$_2$)—;

—CH(CF$_3$)CH(CF$_3$)—; —CH$_2$CH(CF$_3$)—; —CH$_2$CH(CHF$_2$)—; —CH$_2$CH(CH$_2$F)—; —CH$_2$CH(F)CH$_2$—; —CH$_2$C(F$_2$)CH$_2$—; —CH$_2$CH(C(O)NR$^{20}$R$^{21}$)—; —CH$_2$CH(C(O)OR$^{22}$)—; —CH$_2$CH(C(O)OH)—; —CH(CH$_2$F)CH$_2$CH(CH$_2$F)—; —CH(CHF$_2$)CH$_2$CH(CHF$_2$)—; —CH(CF$_3$)CH$_2$CH(CF$_3$)—; —CH$_2$CH$_2$CH(CF$_3$)—; —CH$_2$CH$_2$CH(CHF$_2$)—; —CH$_2$CH$_2$CH(CH$_2$F)—; —CH$_2$CH$_2$CH(C(O) NR$^{23}$R$^{24}$)—; —CH$_2$CH$_2$CH(C(O) OR$^{25}$)—; and —CH$_2$CH$_2$CH(C(O)OH)—, in which R$^{20}$, R$^{21}$, R$^{22}$ and R$^{23}$ each independently represents hydrogen or (1-6C)alkyl, and R$^{24}$ and R$^{25}$ each independently represents (1-6C)alkyl.

In formula KC-(III), n can be an integer from 2 to 4. In certain instances, n is two. In other instances, n is three. In other instances, n is four.

In formula KC-(III), R$^4$ can be a residue of an L-amino acid selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine, or a residue of an N-acyl derivative of any of said amino acids; or a residue of a peptide composed of at least two L-amino acid residues selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine or a residue of an N-acyl derivative thereof. Such a peptide can be from 2 to about 100 amino acids in length. Examples of N-acyl derivatives include acetyl, benzoyl, malonyl, piperonyl or succinyl derivatives.

In certain instances, R$^4$ is a residue of L-arginine or L-lysine, or a residue of an N-acyl derivative of L-arginine or L-lysine.

In certain instances, in formula KC-(III), when p is greater than one, then the R$^4$ adjacent to the nitrogen of —N(R$^3$)(R$^4$) is a residue of L-arginine or L-lysine. In certain instances, when p is greater than one, the R$^4$ adjacent to the nitrogen of —N(R$^3$)(R$^4$) is a residue of L-arginine or L-lysine and the first residue is joined to at least one additional L-amino acid residue selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine. The terminal residue of the peptide can be an N-acyl derivative of any of such amino acids. In certain instances R$^4$ is a dipeptide or an N-acyl derivative thereof. In certain instances R is a tripeptide or an N-acyl derivative thereof.

In formula KC-(III), R$^4$ is

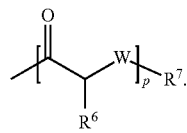

In formula KC-(III), each R$^6$ can be independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, R$^6$ and R$^7$ together with the atoms to which they are bonded form a cycloheteroalkyl or substituted cycloheteroalkyl ring.

In certain instances, in formula KC-(III), R$^6$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl. In certain instances, R$^6$ is selected from hydrogen, alkyl, substituted alkyl, arylalkyl, substituted arylalkyl, heteroarylalkyl, and substituted heteroarylalkyl. In certain instances, R$^6$ is hydrogen. In certain instances, R$^6$ is alkyl. In certain instances, R$^6$ is substituted alkyl. In certain instances, R$^6$ is arylalkyl or substituted arylalkyl. In certain instances, R$^6$ is heteroarylalkyl or substituted heteroarylalkyl.

In certain instances, R$^6$ is a side chain of an amino acid, such as alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine or valine. In certain instances, R$^6$ is a side chain of an L-amino acid, such as L-alanine, L-arginine, L-asparagine, L-aspartic acid, L-cysteine, L-glycine, L-glutamine, L-glutamic acid, L-histidine, L-isoleucine, L-leucine, L-lysine, L-methionine, L-phenylalanine, L-proline, L-serine, L-threonine, L-tryptophan, L-tyrosine or L-valine.

In certain instances, R$^6$ is —CH$_2$CH$_2$CH$_2$NH(C=NH)NH$_2$ or —CH$_2$CH$_2$CH$_2$CH$_2$NH$_2$.

In formula KC-(III), each W can be independently —NR$^8$—, —O— or —S—. In certain instances, W is —NR$^8$—. In certain instances, W is —O—. In certain instances, W is —S—.

In formula KC-(III), each R$^8$ can be independently hydrogen, alkyl, substituted alkyl, aryl or substituted aryl, or optionally, each R$^6$ and R$^8$ independently together with the atoms to which they are bonded form a cycloheteroalkyl or substituted cycloheteroalkyl ring.

In certain instances, in formula KC-(III), R$^8$ is hydrogen or alkyl. In certain instances, R$^8$ is hydrogen. In certain instances, R$^8$ is alkyl. In certain instances, R$^8$ is aryl. In certain instances, R$^6$ and R$^8$ independently together with the atoms to which they are bonded form a cycloheteroalkyl or substituted cycloheteroalkyl ring.

In formula KC-(III), p can be an integer from one to 100 and each R$^6$ can be selected independently from a side chain of any amino acid. In certain instances, p is an integer from one to 50. In certain instances, p is an integer from one to 90, 80, 70, 60, 50, 40, 30, 20, or 10. In certain instances, p is about 100. In certain instances, p is about 75. In certain instances, p is about 50. In certain instances, p is about 25. In certain instances, p is about 20. In certain instances, p is about 15. In certain instances, p is about 10. In certain instances, p is about 9. In certain instances, p is about 8. In certain instances, p is about 7. In certain instances, p is about 6. In certain instances, p is about 5. In certain instances, p is about 4. In certain instances, p is about 3. In certain instances, p is about 2. In certain instances, p is about one.

In certain instances, the R$^6$ of R$^4$ adjacent to the nitrogen of —N(R$^3$)(R$^4$) is —CH$_2$CH$_2$CH$_2$NH(C=NH)NH$_2$ or —CH$_2$CH$_2$CH$_2$CH$_2$NH$_2$, and any additional R$^6$ can be a side chain of any amino acid independently selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine or valine.

In formula KC-(III), R$^7$ can be selected from hydrogen, alkyl, substituted alkyl, acyl, substituted acyl, alkoxycarbonyl, substituted alkoxycarbonyl, aryl, substituted aryl, arylalkyl, and substituted arylalkyl.

In certain instances, $R^7$ is hydrogen, alkyl, acyl, or substituted acyl. In certain instances, $R^7$ is hydrogen. In certain instances, $R^7$ is alkyl. In certain instances, $R^7$ is acyl or substituted acyl. In certain instances, $R^7$ is acyl. In certain instances, $R^7$ is substituted acyl. In certain instances, $R^7$ can be acetyl, benzoyl, malonyl, piperonyl or succinyl.

Formula KC-(IV)

Compounds of formula KC-(IV) are compounds of formula KC-(III) in which $R^5$ is selected from (1-6C) alkyl, (1-6C) substituted alkyl, —$(CH_2)_q(C_6H_4)$—COOH, —$(CH_2)_q(C_6H_4)$—COOCH$_3$, and —$(CH_2)_q(C_6H_4)$—COOCH$_2$CH$_3$, where q is an integer from one to 10; n is 2 or 3; $R^3$ is hydrogen; $R^4$ is an L-amino acid or peptide, where the peptide can be comprised of L-amino acids. In one of its composition aspects, the present embodiments provide a compound of formula KC-(IV):

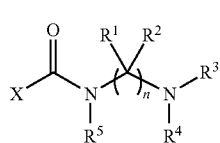

(KC-(IV))

wherein:

X represents a residue of a ketone-containing opioid, wherein the hydrogen atom of the corresponding enolic group of the ketone is replaced by a covalent bond to —C(O)—NR$^5$—(C(R$^1$)(R$^2$))$_n$—NR$^3$R$^4$;

$R^5$ is selected from (1-6C)alkyl, (1-6C) substituted alkyl, —$(CH_2)_q(C_6H_4)$—COOH, —$(CH_2)_q(C_6H_4)$—COOCH$_3$, and —$(CH_2)_q(C_6H_4)$—COOCH$_2$CH$_3$, where q is an integer from one to 10;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl or substituted cycloalkyl group, or two $R^1$ or $R^2$ groups on adjacent carbon atoms, together with the carbon atoms to which they are attached, form a cycloalkyl or substituted cycloalkyl group;

n is 2 or 3;

$R^3$ is hydrogen;

$R^4$ is a residue of an L-amino acid selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine, or a residue of an N-acyl derivative of any of said amino acids; or a residue of a peptide composed of at least two L-amino acid residues selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine or a residue of an N-acyl derivative thereof;

or a salt, hydrate or solvate thereof.

In certain embodiments in Formula KC-(IV), $R^4$ is a residue of an L-amino acid selected from arginine and lysine.

In certain instances, in formula KC-(IV), when $R^4$ is a peptide comprising more than one amino acid, then the $R^4$ adjacent to the nitrogen of —N(R$^3$)(R$^4$) is a residue of L-arginine or L-lysine. In certain instances $R^4$ is a dipeptide or an N-acyl derivative thereof. In certain instances $R^4$ is a tripeptide or an N-acyl derivative thereof.

In certain embodiments in Formula KC-(IV), $R^4$ is a residue of an N-acyl derivative thereof. In certain instances, $R^4$ is a residue of an N-acyl derivative thereof, where the N-acyl derivative is substituted, such as, but not limited to, malonyl and succinyl.

Formulae KC-(V)

Compounds of formula KC-(V) are compounds of formula KC-(III) in which $R^4$ is a trypsin-cleavable moiety.

In one of its composition aspects, the present embodiments provide a compound of formula KC-(V):

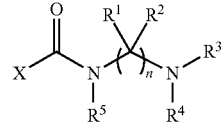

(KC-(V))

wherein:

X represents a residue of a ketone-containing opioid, wherein the hydrogen atom of the corresponding enolic group of the ketone is replaced by a covalent bond to —C(O)—NR$^5$—(C(R$^1$)(R$^2$))$_n$—NR$^3$R$^4$;

$R^5$ is selected from alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl, substituted cycloalkyl, aryl, or substituted aryl group, or two $R^1$ or $R^2$ groups on adjacent carbon atoms, together with the carbon atoms to which they are attached, form a cycloalkyl, substituted cycloalkyl, aryl, or substituted aryl group;

n is an integer from 2 to 4;

$R^3$ is hydrogen;

$R^4$ is a trypsin-cleavable moiety;

or a salt, hydrate or solvate thereof.

In formula KC-(V), $R^4$ is a trypsin-cleavable moiety. A trypsin-cleavable moiety is a structural moiety that is capable of being cleaved by trypsin. In certain instances, a trypsin-cleavable moiety comprises a charged moiety that can fit into an active site of trypsin and is able to orient the prodrug for cleavage at a scissile bond. For instance, the charged moiety can be a basic moiety that exists as a charged moiety at physiological pH.

In certain embodiments, in formula KC-(V), $R^4$ is —C(O)—CH(R$^{6a}$)—NH(R$^{7a}$), wherein $R^{6a}$ represents a side chain of an amino acid or a derivative of a side chain of an amino acid that effects $R^4$ to be a trypsin-cleavable moiety. A derivative refers to a substance that has been altered from another substance by modification, partial substitution, homologation, truncation, or a change in oxidation state.

For example, to form a trypsin-cleavable moiety, $R^{6a}$ can include, but is not limited to, a side chain of lysine (such as L-lysine), arginine (such as L-arginine), homolysine, homoarginine, and ornithine. Other values for $R^4$ include, but are not limited to, arginine mimics, arginine homologues, arginine truncates, arginine with varying oxidation states (for instance, metabolites), lysine mimics, lysine homologues, lysine truncates, and lysine with varying oxidation states (for instance, metabolites). Examples of arginine and lysine mimics include arylguanidines, arylamidines (substituted benzamidines), benzylamines, and (bicyclo [2.2.2]octan-1-yl)methanamine and derivatives thereof.

In certain instances, in formula KC-(V), $R^{6a}$ represents —$CH_2CH_2CH_2NH(C=NH)NH_2$ or —$CH_2CH_2CH_2CH_2NH_2$, the configuration of the carbon atom to which $R^4$ is attached corresponding with that in an L-amino acid.

In formula KC-(V), $R^{7a}$ is selected from hydrogen, alkyl, substituted alkyl, acyl, substituted acyl, alkoxycarbonyl, substituted alkoxycarbonyl, aryl, substituted aryl, arylalkyl, and substituted arylalkyl. In certain instances, $R^{7a}$ is an amino acid or an N-acyl derivative of an amino acid. In certain instances, $R^{7a}$ is a peptide or N-acyl derivative of such a peptide, where the peptide comprises one to 100 amino acids and where each amino acid can be selected independently. In certain instances, there are one to 50 amino acids in the peptide. In certain instances, there are one to 90, 80, 70, 60, 50, 40, 30, 20, or 10 amino acids in the peptide. In certain instances, there are about 100 amino acids in the peptide. In certain instances, there are about 75 amino acids in the peptide. In certain instances, there are about 50 amino acids in the peptide. In certain instances, there are about 25 amino acids in the peptide. In certain instances, there are about 20 amino acids in the peptide. In certain instances, there are about 15 amino acids in the peptide. In certain instances, there are about 10 amino acids in the peptide. In certain instances, there are about 9 amino acids in the peptide. In certain instances, there are about 8 amino acids in the peptide. In certain instances, there are about 7 amino acids in the peptide. In certain instances, there are about 6 amino acids in the peptide. In certain instances, there are about 5 amino acids in the peptide. In certain instances, there are about 4 amino acids in the peptide. In certain instances, there are about 3 amino acids in the peptide. In certain instances, there are about 2 amino acids in the peptide. In certain instances, there is about 1 amino acid in the peptide.

Particular compounds of interest, and salts or solvates or stereoisomers thereof, include:

oxycodone 6-(N-methyl-N-(2-N'-acetylarginylamino))ethylcarbamate

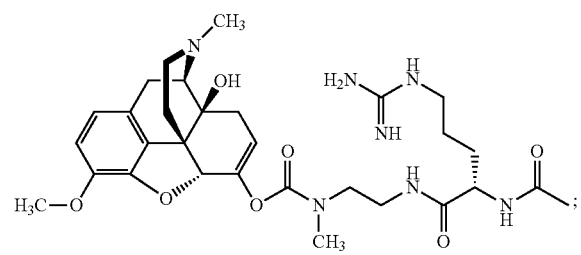

hydrocodone 6-(N-methyl-N-(2-N'-acetylarginylamino))ethylcarbamate

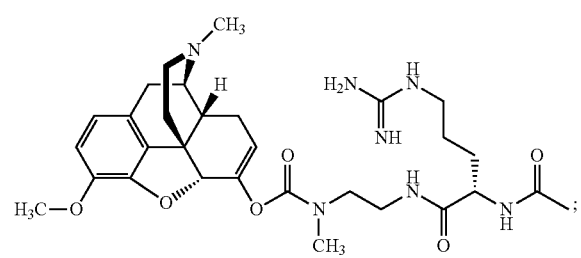

oxycodone 6-(N-methyl-N-(2-N'-malonylarginylamino))ethylcarbamate

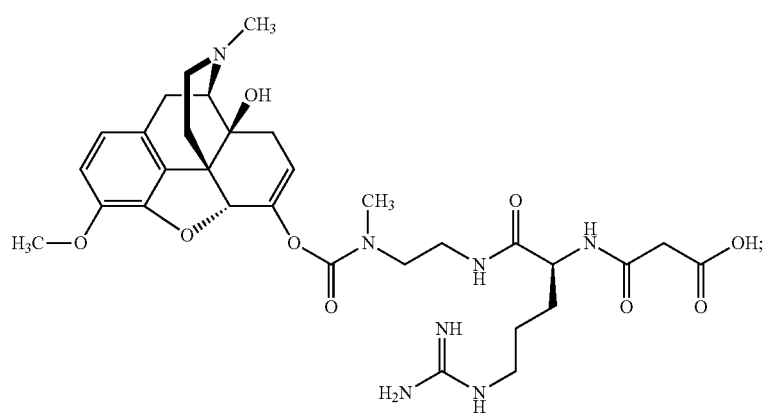

oxycodone 6-(N-5'-carboxypentyl-N-(2-N'-acetylarginylamino))ethylcarbamate

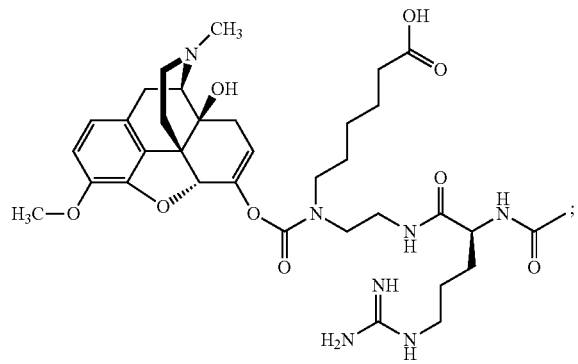

hydrocodone 6-(N-methyl-N-(2-N'-malonylarginylamino))ethylcarbamate

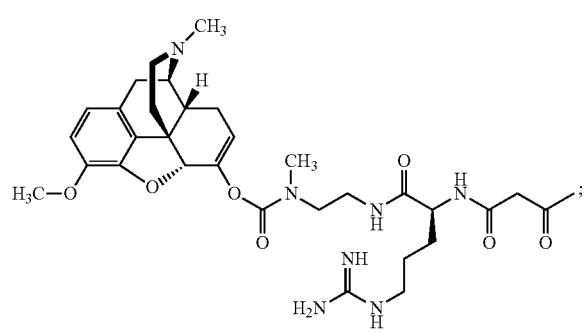

oxycodone 6-(N-methyl-N-(2-N'-acetylarginylamino-2-(N-methyl-N-carboxymethyl-acetamido))ethylcarbamate

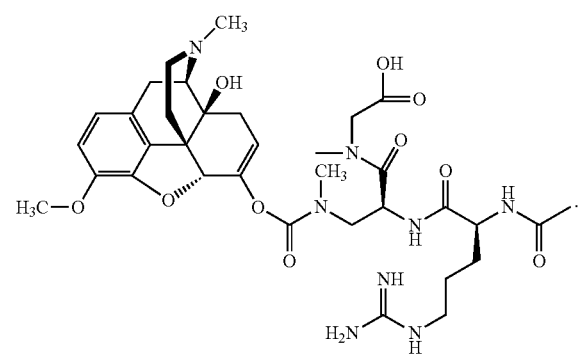

wherein the amino acid residue is of the L configuration.

The embodiments provide a pharmaceutical composition, which comprises a compound of general Formula KC-(I) to KC-(II), or a pharmaceutically acceptable salt thereof.

The embodiments provide a pharmaceutical composition, which comprises a compound of general Formulae KC-(III) to KC-(V), or a pharmaceutically acceptable salt thereof.

The embodiments provide a pharmaceutical composition, which comprises a compound disclosed herein other than a compound of general Formulae KC-(I) to KC-(II), or a pharmaceutically acceptable salt thereof.

General Synthetic Procedures for Formulae KC-(I) to KC-(VI)

A representative synthesis for compounds of Formulae KC-(I) and KC-(II) is shown in the following schemes. Compounds of Formulae KC-(III) to KC-(VI) can also be synthesized by using the disclosed methods. A representative synthesis for Compound KC203 is shown in Scheme KC-1. In Scheme KC-1, the terms $R^1$, $R^2$, $R^5$, and n are defined herein. The terms PG and $PG^2$ are amino protecting groups.

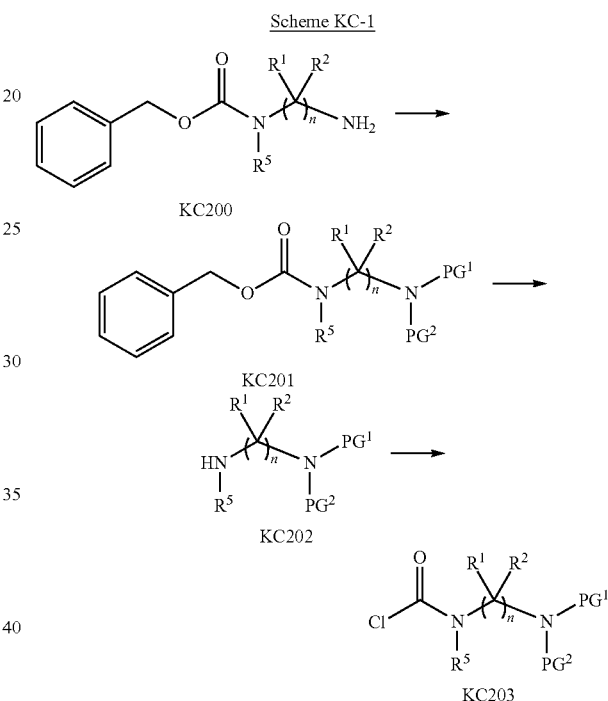

Scheme KC-1

In Scheme KC-1, Compound KC200 is a commercially available starting material. Alternatively, Compound KC200 can be synthesized via a variety of different synthetic routes using commercially available starting materials and/or starting materials prepared by conventional synthetic methods.

With continued reference to Scheme KC-1, Compound KC200 is protected at the amino group to form Compound KC201, wherein $PG^1$ and $PG^2$ are amino protecting groups. Amino protecting groups can be found in T. W. Greene and P. G. M. Wuts, "Protective Groups in Organic Synthesis", Fourth edition, Wiley, New York 2006. Representative amino-protecting groups include, but are not limited to, formyl groups; acyl groups, for example alkanoyl groups, such as acetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBS); and the like.

In certain embodiments, $PG^1$ and $PG^2$ are Boc groups. Conditions for forming Boc groups on Compound KC201 can be found in Greene and Wuts. One method is reaction of Compound KC200 with di-tert-butyl dicarbonate. The reaction can optionally be run in the presence of an activating agent, such as DMAP.

With continued reference to Scheme KC-1, the carboxybenzyl group on Compound KC201 is deprotected to form Compound KC202. Conditions to remove the carboxybenzyl group can be found in Greene and Wuts. Methods to remove the carboxybenzyl group include hydrogenolysis of Compound KC201 or treatment of Compound KC201 with HBr. One method to remove the carboxybenzyl group is reaction of Compound KC201 with hydrogen and palladium.

With continued reference to Scheme KC-1, Compound KC202 is reacted with phosgene to form Compound KC203. Reaction with phosgene forms an acyl chloride on the amino group of Compound KC202. Other reagents can act as substitutes for phosgene, such as diphosgene or triphosgene.

A representative synthesis for Compound KC302 is shown in Scheme KC-2. In Scheme 2, the terms $R^a$, $R^1$, $R^2$, $R^5$, and n are defined herein. The terms $PG^1$ and $PG^2$ are amino protecting groups.

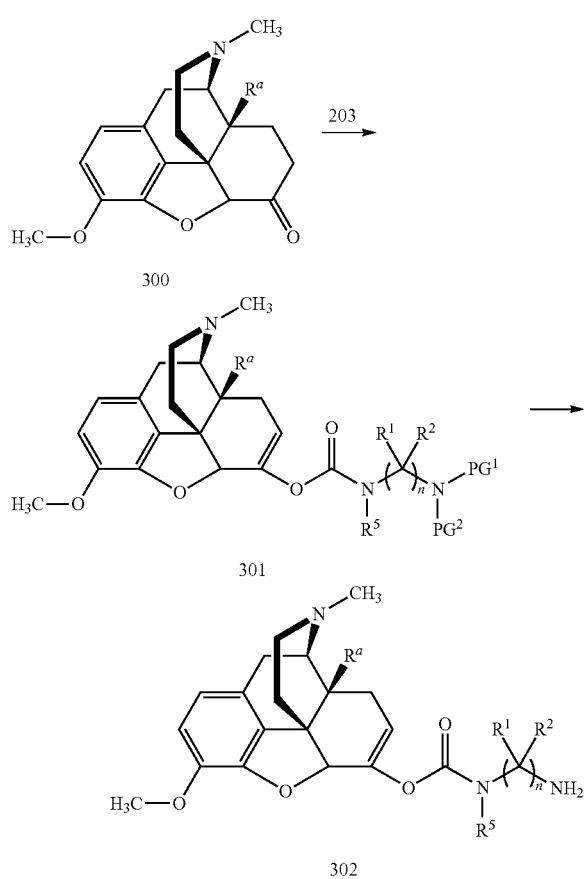

In Scheme KC-2, Compound KC300 is a commercially available starting material. Alternatively, Compound KC300 can be synthesized via a variety of different synthetic routes using commercially available starting materials and/or starting materials prepared by conventional synthetic methods.

With continued reference to Scheme KC-2, Compound KC300 is reacted with Compound KC203 to form Compound KC301. In this reaction, the enolate of Compound KC300 reacts with the acyl chloride of Compound KC203 to form a carbamate.

With continued reference to Scheme KC-2, the protecting groups $PG^1$ and $PG^2$ are removed from Compound KC301 to form Compound KC302. Conditions to remove amino groups can be found in Greene and Wuts. When $PG^1$ and $PG^2$ are Boc groups, the protecting groups can be removed with acidic conditions, such as treatment with trifluoroacetic acid.

A representative synthesis for Compound KC402 is shown in Scheme KC-3. In Scheme KC-3, the terms $R^a$, $R^1$, $R^2$, $R^5$, $R^6$, $R^7$ and n are defined herein. The term $PG^3$ is an amino protecting group.

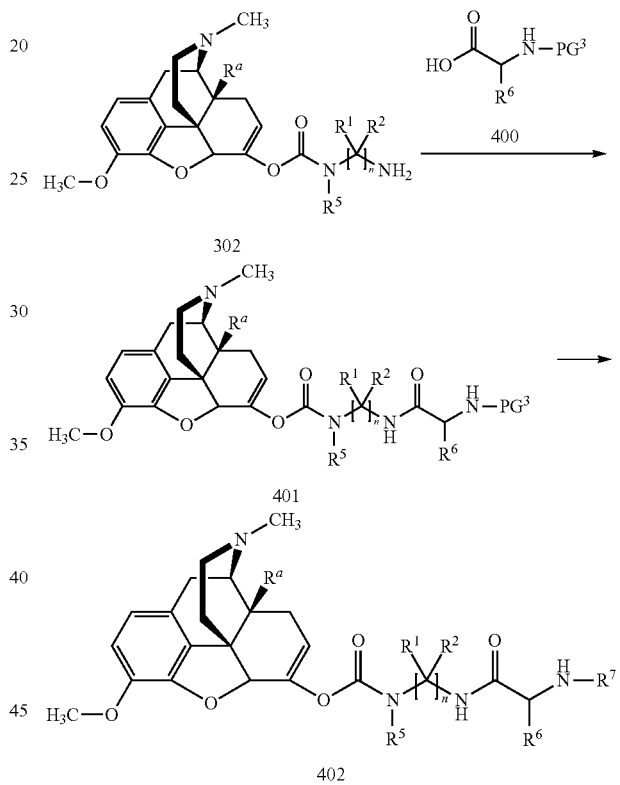

In Scheme KC-3, Compound KC400 is a commercially available starting material. Alternatively, Compound KC400 can be synthesized via a variety of different synthetic routes using commercially available starting materials and/or starting materials prepared by conventional synthetic methods.

With continued reference to Scheme KC-3, Compound KC302 reacts with Compound KC400 to form Compound KC401 in a peptide coupling reaction. A peptide coupling reaction typically employs a conventional peptide coupling reagent and is conducted under conventional coupling reaction conditions, typically in the presence of a trialkylamine, such as ethyldiisopropylamine or diisopropylethylamine (DIEA). Suitable coupling reagents for use include, by way of example, carbodiimides, such as ethyl-3-(3-dimethylamino)propylcarbodiimide (EDC), dicyclohexylcarbodiimide (DCC), diisopropylcarbodiimide (DIC) and the like, and other well-known coupling reagents, such as N,N'-carbonyldiimidazole, 2-ethoxy-1-ethoxycarbonyl-1,2-dihydroquinoline (EEDQ), benzotriazol-1-yloxy-tris(dimethylamino) phosphonium hexafluorophosphate (BOP), O-(7-azabenzotriazol-1-yl)-N,N,N,N',N'-tetramethyluronium hexafluorophosphate (HATU) and the like. Optionally, well-known coupling promoters, such N-hydroxysuccinimide, 1-hydroxybenzotriazole (HOBT), 1-hydroxy-7-azabenzotriazole (HOAT), N,N-dimethylaminopyridine (DMAP) and the like, can be employed in this reaction. Typically, this coupling reaction is conducted at a temperature ranging from about 0° C. to about 60° C. for about 1 to about 72 hours in an inert diluent, such as THF or DMF. In certain instances, Compound KC302 reacts with Compound KC400 to form Compound KC401 in the presence of HATU and DIEA in DMF.

With continued reference to Scheme KC-3, Compound KC401 is transformed into Compound KC402 with removal of the amino protecting group and addition of an $R^7$ group. In certain cases, the amino protecting group is $R^7$ and removal of the amino protecting group is optional.

As disclosed herein, representative amino-protecting groups include, but are not limited to, formyl groups; acyl groups, for example alkanoyl groups, such as acetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBS); and the like. In certain embodiments, $PG^3$ is a Boc group. When $PG^3$ is a Boc group, the protecting group can be removed with acidic conditions, such as treatment with trifluoroacetic acid.

In certain instances, the $R^7$ group is added to Compound KC401. Conditions for addition of $R^7$ depend on the identity of $R^7$ and are known to those skilled in the art. In certain instances $R^7$ is an acyl group, such as acetyl, benzoyl, malonyl, piperonyl or succinyl.

N-Acyl derivatives of the compounds of formula KC-(I) may conveniently be prepared by acylating a corresponding compound of formula KC-(I) using an appropriate acylating agent, for example an anhydride, such as acetic anhydride (to prepare an N-acetyl compound) or an acid halide. The reaction is conveniently performed in the presence of a non-reactive base, for example a tertiary amine, such as triethylamine. Convenient solvents include amides, such as dimethyl formamide. The temperature at which the reaction is performed is conveniently in the range of from 0 to 100° C., such as at ambient temperature.

With continued reference to Scheme KC-3, removal of other protecting groups can be performed if other protecting groups were used, such as protecting groups present on the $R^6$ moiety. Conditions for removal of other protecting groups depend on the identity of the protecting group and are known to those skilled in the art. The conditions can also be found in Greene and Wuts.

As described in more detail herein, the disclosure provides processes and intermediates useful for preparing compounds of the present disclosure or a salt or solvate or stereoisomer thereof. Accordingly, the present disclosure provides a process of preparing a compound of the present disclosure, the process involves:
contacting a compound of formula:

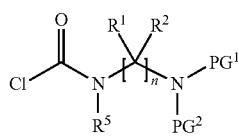

with a compound of formula

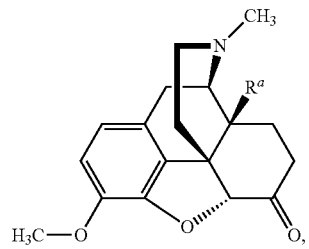

wherein $PG^1$ and $PG^2$ are amino protecting groups.

Accordingly and as described in more detail herein, the present disclosure provides a process of preparing a compound of the present disclosure, the process involves:
contacting a compound of formula:

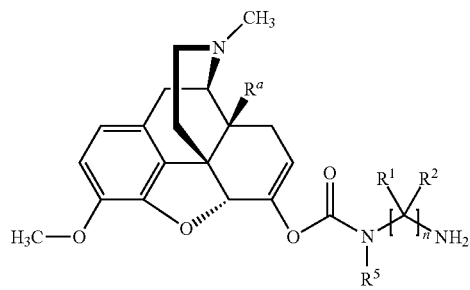

with a compound of formula

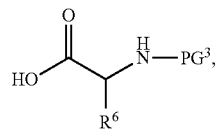

wherein $PG^3$ is an amino protecting group.

In one instance, the above process further involving the step of forming a salt of a compound of the present disclosure. Embodiments are directed to the other processes described herein; and to the product prepared by any of the processes described herein.

Trypsin Inhibitors

The enzyme capable of cleaving the enzymatically-cleavable moiety of a ketone-modified opioid prodrug can be a protease. In certain embodiments, the enzyme is an enzyme located in the gastrointestinal (GI) tract, i.e., a gastrointestinal enzyme, or a GI enzyme. The enzyme can be a digestive enzyme such as a gastric, intestinal, pancreatic or brush border enzyme or enzyme of GI microbial flora, such as those involved in peptide hydrolysis. Examples include a pepsin, such as pepsin A or pepsin B; a trypsin; a chymotrypsin; an elastase; a carboxypeptidase, such as carboxypeptidase A or carboxypeptidase B; an aminopeptidase, such as aminopeptidase N or aminopeptidase A; an endopeptidase; an exopeptidase; a dipeptidylaminopeptidase, such as dipeptidylaminopeptidase IV; a dipeptidase; a tripeptidase; or an enteropeptidase. In certain embodiments, the enzyme is a cytoplasmic protease located on or in the GI brush border. In certain embodiments, the enzyme is trypsin.

Accordingly, in certain embodiments, the corresponding composition is administered orally to the patient.

The disclosure provides for a composition comprising a GI enzyme inhibitor. Such an inhibitor can inhibit at least one of any of the GI enzymes disclosed herein. An example of a GI enzyme inhibitor is a protease inhibitor, such as a trypsin inhibitor.

As used herein, the term "trypsin inhibitor" refers to any agent capable of inhibiting the action of trypsin on a substrate. The term "trypsin inhibitor" also encompasses salts of trypsin inhibitors. The ability of an agent to inhibit trypsin can be measured using assays well known in the art. For example, in a typical assay, one unit corresponds to the amount of inhibitor that reduces the trypsin activity by one benzoyl-L-arginine ethyl ester unit (BAEE-U). One BAEE-U is the amount of enzyme that increases the absorbance at 253 nm by 0.001 per minute at pH 7.6 and 25° C. See, for example, K. Ozawa, M. Laskowski, 1966, J. Biol. Chem. 241, 3955 and Y. Birk, 1976, Meth. Enzymol. 45, 700. In certain instances, a trypsin inhibitor can interact with an active site of trypsin, such as the S1 pocket and the S3/4 pocket. The S1 pocket has an aspartate residue which has affinity for a positively charged moiety. The S3/4 pocket is a hydrophobic pocket. The disclosure provides for specific trypsin inhibitors and non-specific serine protease inhibitors.

There are many trypsin inhibitors known in the art, both those specific to trypsin and those that inhibit trypsin and other proteases such as chymotrypsin. The disclosure provides for trypsin inhibitors that are proteins, peptides, and small molecules. The disclosure provides for trypsin inhibitors that are irreversible inhibitors or reversible inhibitors. The disclosure provides for trypsin inhibitors that are competitive inhibitors, non-competitive inhibitors, or uncompetitive inhibitors. The disclosure provides for natural, synthetic or semi-synthetic trypsin inhibitors.

Trypsin inhibitors can be derived from a variety of animal or vegetable sources: for example, soybean, corn, lima and other beans, squash, sunflower, bovine and other animal pancreas and lung, chicken and turkey egg white, soy-based infant formula, and mammalian blood. Trypsin inhibitors can also be of microbial origin: for example, antipain; see, for example, H. Umezawa, 1976, Meth. Enzymol. 45, 678.

In one embodiment, the trypsin inhibitor is derived from soybean. Trypsin inhibitors derived from soybean (*Glycine max*) are readily available and are considered to be safe for human consumption. They include, but are not limited to, SBTI, which inhibits trypsin, and Bowman-Birk inhibitor, which inhibits trypsin and chymotrypsin. Such trypsin inhibitors are available, for example from Sigma-Aldrich, St. Louis, Mo., USA.

A trypsin inhibitor can be an arginine mimic or lysine mimic, either natural or synthetic compound. In certain embodiments, the trypsin inhibitor is an arginine mimic or a lysine mimic, wherein the arginine mimic or lysine mimic is a synthetic compound. As used herein, an arginine mimic or lysine mimic can include a compound capable of binding to the $P^1$ pocket of trypsin and/or interfering with trypsin active site function. The arginine or lysine mimic can be a cleavable or non-cleavable moiety.

Examples of trypsin inhibitors, which are arginine mimics and/or lysine mimics, include, but not limited to, arylguanidine, benzamidine, 3,4-dichloroisocoumarin, diisopropylfluorophosphate, gabexate mesylate, and phenylmethanesulfonyl fluoride, or substituted versions or analogs thereof. In certain embodiments, trypsin inhibitors comprise a covalently modifiable group, such as a chloroketone moiety, an aldehyde moiety, or an epoxide moiety. Other examples of trypsin inhibitors are aprotinin, camostat and pentamidine.

Other examples of trypsin inhibitors include compounds of formula:

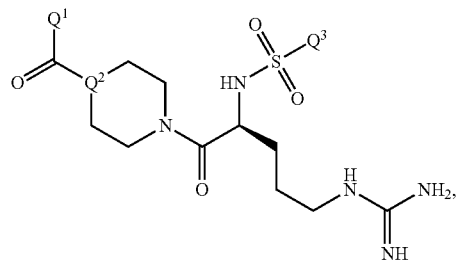

wherein:

$Q^1$ is selected from —O-$Q^4$ or -$Q^4$-COOH, where $Q^4$ is $C_1$-$C_4$ alkyl;

$Q^2$ is N or CH; and $Q^3$ is aryl or substituted aryl.

Certain trypsin inhibitors include compounds of formula:

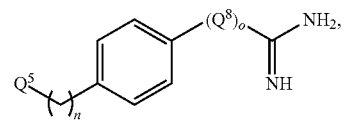

wherein:

$Q^5$ is —C(O)—COOH or —NH-$Q^6$-$Q^7$-$SO_2$—$C_6H_5$, where $Q^6$ is —$(CH_2)_p$—COOH;

$Q^7$ is —$(CH_2)_r$—$C_6H_5$;

$Q^8$ is NH;

n is a number from zero to two;

o is zero or one;

p is an integer from one to three; and r is an integer from one to three.

Certain trypsin inhibitors include compounds of formula:

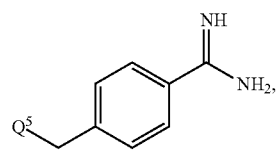

wherein:

$Q^5$ is —C(O)—COOH or —NH-$Q^6$-$Q^7$-$SO_2$—$C_6H_5$, where $Q^6$ is —$(CH_2)_p$—COOH;

$Q^7$ is —$(CH_2)_r$—$C_6H_5$; and p is an integer from one to three; and r is an integer from one to three.

Certain trypsin inhibitors include the following:

| Compound 101 | 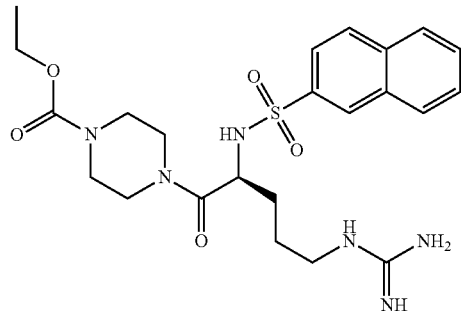 | (S)-ethyl 4-(5-guanidino-2-(naphthalene-2-sulfonamido)pentanoyl)piperazine-1-carboxylate |
| --- | --- | --- |
| Compound 102 | 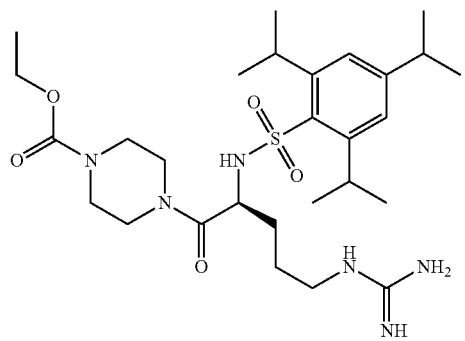 [SMILES: CCOC(=O)N1CCN(C(=O)[C@H](CCCNC(=N)N)NS(=O)(=O)c2c(C(C)C)cc(C(C)C)cc2C(C)C)CC1] | (S)-ethyl 4-(5-guanidino-2-(2,4,6-triisopropylphenylsulfonamido)pentanoyl)piperazine-1-carboxylate |
| Compound 103 | 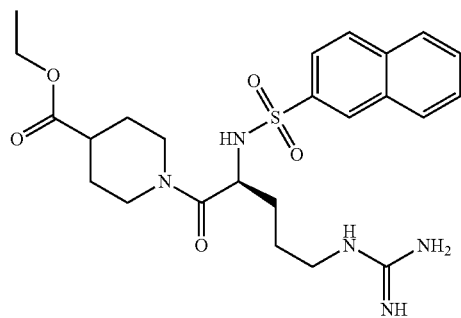 [SMILES: CCOC(=O)C1CCN(C(=O)[C@H](CCCNC(=N)N)NS(=O)(=O)c2ccc3ccccc3c2)CC1] | (S)-ethyl 1-(5-guanidino-2-(naphthalene-2-sulfonamido)pentanoyl)piperidine-4-carboxylate |
| Compound 104 | 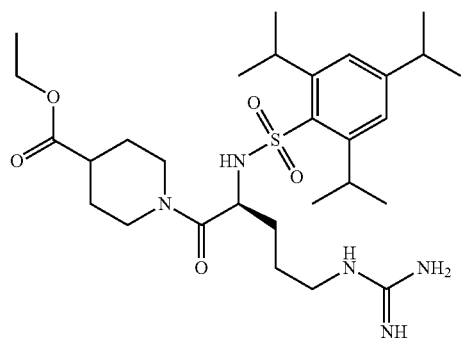 [SMILES: CCOC(=O)C1CCN(C(=O)[C@H](CCCNC(=N)N)NS(=O)(=O)c2c(C(C)C)cc(C(C)C)cc2C(C)C)CC1] | (S)-ethyl 1-(5-guanidino-2-(2,4,6-triisopropylphenylsulfonamido)pentanoyl)piperidine-4-carboxylate |

-continued

| | | |
|---|---|---|
| Compound 105 | | (S)-6-(4-(5-guanidino-2-(naphthalene-2-sulfonamido)pentanoyl)piperazin-1-yl)-6-oxohexanoic acid |
| Compound 106 | | 4-aminobenzimidamide (also 4-aminobenzamidine) |
| Compound 107 | | 3-(4-carbamimidoylphenyl)-2-oxopropanoic acid |
| Compound 108 | | (S)-5-(4-carbamimidoylbenzylamino)-5-oxo-4-((R)-4-phenyl-2-(phenylmethylsulfonamido)butanamido)pentanoic acid |
| Compound 109 | | 6-carbamimidoylnaphthalen-2-yl 4-(diaminomethyleneamino)benzoate |
| Compound 110 | | 4,4'-(pentane-1,5-diylbis(oxy))dibenzimidamide |

In certain embodiments, the trypsin inhibitor is SBTI, BBSI, Compound 101, Compound 106, Compound 108, Compound 109, or Compound 110. In certain embodiments, the trypsin inhibitor is camostat.

In certain embodiments, the trypsin inhibitor is a compound of formula T-I:

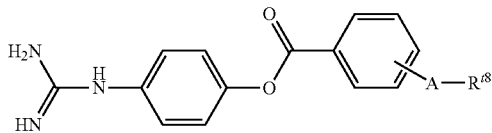

(T-I)

wherein

A represents a group of the following formula:

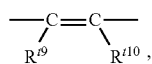

$R^{t9}$ and $R^{t10}$ each represents independently a hydrogen atom or a $C_{1-4}$ alkyl group, $R^{t8}$ represents a group selected from the following formulae:

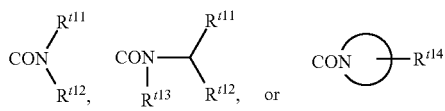

wherein $R^{t11}$, $R^{t12}$ and $R^{t13}$ each represents independently
(1) a hydrogen atom,
(2) a phenyl group,
(3) a $C_{1-4}$ alkyl group substituted by a phenyl group,
(4) a $C_{1-10}$ alkyl group,
(5) a $C_{1-10}$ alkoxyl group,
(6) a $C_{2-10}$ alkenyl group having 1 to 3 double bonds,
(7) a $C_{2-10}$ alkynyl group having 1 to 2 triple bonds,
(8) a group of formula: $R^{t15}$—C(O)$XR^{t16}$,
wherein $R^{t15}$ represents a single bond or a $C_{1-8}$ alkylene group,
X represents an oxygen atom or an NH-group, and
$R^{t16}$ represents a hydrogen atom, a $C_{1-4}$ alkyl group, a phenyl group or a $C_{1-4}$ alkyl group substituted by a phenyl group, or
(9) a $C_{3-7}$ cycloalkyl group;
the structure

represents a 4-7 membered monocyclic hetero-ring containing 1 to 2 nitrogen or oxygen atoms, $R^{t14}$ represents a hydrogen atom, a $C_{1-4}$ alkyl group substituted by a phenyl group or a group of formula: $COOR^{t17}$, wherein $R^{t17}$ represents a hydrogen atom, a $C_{1-4}$ alkyl group or a $C_{1-4}$ alkyl group substituted by a phenyl group;
provided that $R^{t11}$, $R^{t12}$ and $R^{t13}$ do not represent simultaneously hydrogen atoms;
or nontoxic salts, acid addition salts or hydrates thereof.

In certain embodiments, the trypsin inhibitor is a compound selected from the following:

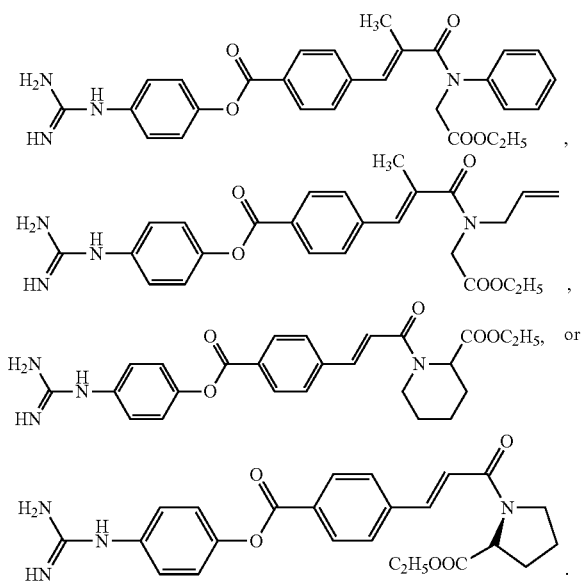

In certain embodiments, the trypsin inhibitor is a compound of formula T-II:

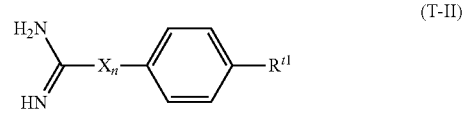

(T-II)

wherein

X is NH;

n is zero or one; and $R^{t1}$ is selected from hydrogen, halogen, nitro, alkyl, substituted alkyl, alkoxy, carboxyl, alkoxycarbonyl, acyl, aminoacyl, guanidine, amidino, carbamide, amino, substituted amino, hydroxyl, cyano and —(CH$_2$)$_m$—C(O)—O—(CH$_2$)$_m$—C(O)—N—$R^{n2}$, wherein each m is independently zero to 2; and $R^{n1}$ and $R^{n2}$ are independently selected from hydrogen and $C_{1-4}$ alkyl.

In certain embodiments, in formula T-II, $R^{t1}$ is guanidino or amidino.

In certain embodiments, in formula T-II, $R^{t1}$ is —(CH$_2$)$_m$—C(O)—O—(CH$_2$)$_m$—C(O)—N—$R^{n1}R^{n2}$, wherein m is one and $R^{n1}$ and $R^{n2}$ are methyl.

In certain embodiments, the trypsin inhibitor is a compound of formula T-III:

In certain embodiments, the trypsin inhibitor is a compound of formula T-III:

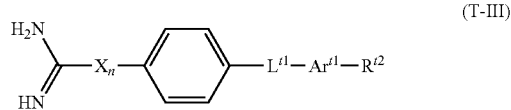

(T-III)

wherein

X is NH;

n is zero or one;

$L^{t1}$ is selected from —C(O)—O—; —O—C(O)—; —O—(CH$_2$)$_m$—O—; —OCH$_2$—Ar$^{t2}$—CH$_2$O—; —C(O)—NR$^{t3}$—; and —NR$^{t3}$—C(O)—;

$R^{t3}$ is selected from hydrogen, C$_{1-6}$ alkyl, and substituted C$_{1-6}$ alkyl;

Ar$^{t1}$ and Ar$^{t2}$ are independently a substituted or unsubstituted aryl group;

m is a number from 1 to 3; and $R^{t2}$ is selected from hydrogen, halogen, nitro, alkyl, substituted alkyl, alkoxy, carboxyl, alkoxycarbonyl, acyl, aminoacyl, guanidine, amidino, carbamide, amino, substituted amino, hydroxyl, cyano and —(CH$_2$)$_m$—C(O)—O—(CH$_2$)$_m$—C(O)—N—R$^{n2}$, wherein each m is independently zero to 2; and R$^{n1}$ and R$^{n2}$ are independently selected from hydrogen and C$_{1-4}$ alkyl.

In certain embodiments, in formula T-III, $R^{t2}$ is guanidino or amidino.

In certain embodiments, in formula T-III, $R^{t2}$ is —(CH$_2$)$_m$—C(O)—O—(CH$_2$)$_m$—C(O)—N—R$^{n1}$R$^{n2}$ wherein m is one and R$^{n1}$ and R$^{n2}$ are methyl.

In certain embodiments, the trypsin inhibitor is a compound of formula T-IV:

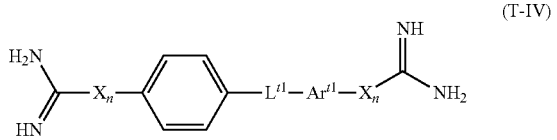

(T-IV)

wherein each X is NH;

each n is independently zero or one;

$L^{t1}$ is selected from —C(O)—O—; —O—C(O)—; —O—(CH$_2$)$_m$—O—; —OCH$_2$—Ar$^{t2}$—CH$_2$O—; —C(O)—NR$^{t3}$—; and —NR$^{t3}$—C(O)—;

$R^{t3}$ is selected from hydrogen, C$_{1-6}$ alkyl, and substituted C$_{1-6}$ alkyl;

Ar$^{t1}$ and Ar$^{t2}$ are independently a substituted or unsubstituted aryl group; and m is a number from 1 to 3.

In certain embodiments, in formula T-IV, Ar$^{t1}$ or Ar$^{t2}$ is phenyl.

In certain embodiments, in formula T-IV, Ar$^{t1}$ or Ar$^{t2}$ is naphthyl.

In certain embodiments, the trypsin inhibitor is Compound 109.

In certain embodiments, the trypsin inhibitor is

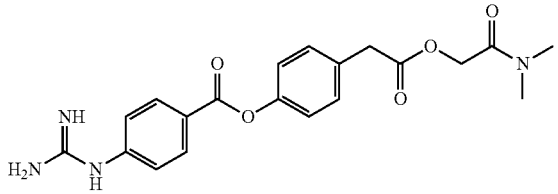 [SMILES: CN(C)C(=O)COC(=O)Cc1ccc(OC(=O)c2ccc(NC(=N)N)cc2)cc1]

In certain embodiments, the trypsin inhibitor is Compound 110 or a bis-arylamidine variant thereof; see, for example, J. D. Geratz, M. C.-F. Cheng and R. R. Tidwell (1976) J Med. Chem. 19, 634-639.

It will be appreciated that the pharmaceutical composition according to the embodiments may further comprise one or more other trypsin inhibitors.

It is to be appreciated that the invention also includes inhibitors of other enzymes involved in protein assimilation that can be used in combination with a prodrug disclosed herein comprising an amino acid of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine or variants thereof. An amino acid variant refers to an amino acid that is modified from a naturally-occurring amino acid but still comprises an activity similar to that of as the naturally-occurring amino acid.

Combinations of Prodrug and Trypsin Inhibitor

As discussed above, the present disclosure provides pharmaceutical compositions which comprise a trypsin inhibitor and a ketone-modified opioid prodrug that contains a trypsin-cleavable moiety that, when cleaved, facilitates release of ketone-containing opioid. Examples of compositions containing a ketone-modified opioid prodrug and a trypsin inhibitor are described below.

Combinations of Formulae KC-(I) to KC-(II) and Trypsin Inhibitor

The embodiments provide a pharmaceutical composition, which comprises a trypsin inhibitor and a compound of general Formulae KC-(I) to KC-(II), or a pharmaceutically acceptable salt thereof. The embodiments provide a pharmaceutical composition, which comprises a compound of Formulae T-I to T-VI and a compound of general Formulae KC-(I) to KC-(II), or a pharmaceutically acceptable salt thereof. The embodiments provide a pharmaceutical composition, which comprises Compound 109 and a compound of general Formulae KC-(I) to KC-(II), or a pharmaceutically acceptable salt thereof.

Certain embodiments provide for a combination of a compound of Formula KC-(I) and a trypsin inhibitor, in which the ketone-containing opioid of Formula KC-(I) and the trypsin inhibitor are shown in the following table. Certain embodiments provide for a combination of a compound of Formula KC-(II) and a trypsin inhibitor, in which the ketone-containing opioid of Formula KC-(II) and the trypsin inhibitor are also shown in the following table.

| Prodrug of Formula KC-(I) Having Indicated Opioid; and Trypsin Inhibitor | | Prodrug of Formula KC-(II) Having Indicated Opioid; and Trypsin Inhibitor | |
|---|---|---|---|
| Oxycodone; SBTI | Hydrocodone; SBTI | Oxycodone; SBTI | Hydrocodone; SBTI |
| Oxycodone; BBSI | Hydrocodone; BBSI | Oxycodone; BBSI | Hydrocodone; BBSI |
| Oxycodone; Compound 101 | Hydrocodone; Compound 101 | Oxycodone; Compound 101 | Hydrocodone; Compound 101 |
| Oxycodone; Compound 106 | Hydrocodone; Compound 106 | Oxycodone; Compound 106 | Hydrocodone; Compound 106 |
| Oxycodone; Compound 108 | Hydrocodone; Compound 108 | Oxycodone; Compound 108 | Hydrocodone; Compound 108 |
| Oxycodone; Compound 109 | Hydrocodone; Compound 109 | Oxycodone; Compound 109 | Hydrocodone; Compound 109 |
| Oxycodone; Compound 110 | Hydrocodone; Compound 110 | Oxycodone; Compound 110 | Hydrocodone; Compound 110 |

Combinations of Formulae KC-(III) to KC-(V) and Trypsin Inhibitor

The embodiments provide a pharmaceutical composition, which comprises a trypsin inhibitor and a compound of general Formulae KC-(III) to KC-(V), or a pharmaceutically acceptable salt thereof. The embodiments provide a pharmaceutical composition, which comprises a compound of Formulae T-I to T-VI and a compound of general Formulae KC-(III) to KC-(V), or a pharmaceutically acceptable salt thereof. The embodiments provide a pharmaceutical composition, which comprises Compound 109 and a compound of general Formulae KC-(III) to KC-(V), or a pharmaceutically acceptable salt thereof.

The embodiments provide a pharmaceutical composition, which comprises a trypsin inhibitor and a compound disclosed herein other than a compound of general Formulae KC-(I) to KC-(II), or a pharmaceutically acceptable salt thereof.

Certain embodiments provide for a combination of a compound of Formula KC-(III) and a trypsin inhibitor, in which the ketone-containing opioid of Formula KC-(III) and the trypsin inhibitor are shown in the table below. Certain embodiments provide for a combination of a compound of Formula KC-(IV) and a trypsin inhibitor, in which the non-ketone-containing opioid of Formula KC-(IV) and the trypsin inhibitor are shown in the table below. Certain embodiments provide for a combination of a compound of Formula KC-(V) and a trypsin inhibitor, in which the ketone-containing opioid of Formula KC-(V) and the trypsin inhibitor are shown in the following table.

| Prodrug of Formula KC-(III) Having Indicated Opioid; and Trypsin Inhibitor | | Prodrug of Formula KC-(IV) Having Indicated Opioid; and Trypsin Inhibitor | | Prodrug of Formula KC-(V) Having Indicated Opioid; and Trypsin Inhibitor | |
|---|---|---|---|---|---|
| Oxycodone; SBTI | Hydrocodone; SBTI | Oxycodone; SBTI | Hydrocodone; SBTI | Oxycodone; SBTI | Hydrocodone; SBTI |
| Oxycodone; BBSI | Hydrocodone; BBSI | Oxycodone; BBSI | Hydrocodone; BBSI | Oxycodone; BBSI | Hydrocodone; BBSI |
| Oxycodone; Compound 101 | Hydrocodone; Compound 101 | Oxycodone; Compound 101 | Hydrocodone; Compound 101 | Oxycodone; Compound 101 | Hydrocodone; Compound 101 |
| Oxycodone; Compound 106 | Hydrocodone; Compound 106 | Oxycodone; Compound 106 | Hydrocodone; Compound 106 | Oxycodone; Compound 106 | Hydrocodone; Compound 106 |
| Oxycodone; Compound 108 | Hydrocodone; Compound 108 | Oxycodone; Compound 108 | Hydrocodone; Compound 108 | Oxycodone; Compound 108 | Hydrocodone; Compound 108 |
| Oxycodone; Compound 109 | Hydrocodone; Compound 109 | Oxycodone; Compound 109 | Hydrocodone; Compound 109 | Oxycodone; Compound 109 | Hydrocodone; Compound 109 |
| Oxycodone; Compound 110 | Hydrocodone; Compound 110 | Oxycodone; Compound 110 | Hydrocodone; Compound 110 | Oxycodone; Compound 110 | Hydrocodone; Compound 110 |

Combinations of Compound KC-2 and Trypsin Inhibitor

Certain embodiments provide for a combination of Compound KC-2 and a trypsin inhibitor, in which the trypsin inhibitor is shown in the following table.

| Compound | Trypsin inhibitor |
|---|---|
| Compound KC-2 | SBTI |
| Compound KC-2 | BBSI |
| Compound KC-2 | Compound 101 |
| Compound KC-2 | Compound 106 |
| Compound KC-2 | Compound 108 |
| Compound KC-2 | Compound 109 |
| Compound KC-2 | Compound 110 |

Combinations of Ketone-Modified Opioid Prodrugs and Other Drugs

The disclosure provides for a ketone-modified opioid prodrug and a further prodrug or drug included in a pharmaceutical composition. Such a prodrug or drug would provide additional analgesia or other benefits. Examples include opioids, acetaminophen, non-steroidal anti-inflammatory drugs (NSAIDs) and other analgesics. In one embodiment, an opioid agonist prodrug or drug would be combined with an opioid antagonist prodrug or drug. Other examples include drugs or prodrugs that have benefits other than, or in addition to, analgesia. The embodiments provide a pharmaceutical composition, which comprises a ketone-modified opioid prodrug and acetaminophen and optionally comprises a trypsin inhibitor. Also included are pharmaceutically acceptable salts thereof.

In certain embodiments, the ketone-modified opioid prodrug is a compound of general Formulae KC-(I) to KC-(V).

In certain embodiments, the trypsin inhibitor is selected from SBTI, BBSI, Compound 101, Compound 106, Compound 108, Compound 109, and Compound 110. In certain embodiments, the trypsin inhibitor is camostat.

In certain embodiments, a pharmaceutical composition can comprise a ketone-modified opioid prodrug, a non-opioid drug and at least one opioid or opioid prodrug.

Pharmaceutical Compositions and Methods of Use

The pharmaceutical composition according to the embodiments can further comprise a pharmaceutically acceptable carrier. The composition is conveniently formulated in a form suitable for oral (including buccal and sublingual) administration, for example as a tablet, capsule, thin film, powder, suspension, solution, syrup, dispersion or emulsion. The composition can contain components conventional in pharmaceutical preparations, e.g. one or more carriers, binders, lubricants, excipients (e.g., to impart controlled release characteristics), pH modifiers, sweeteners, bulking agents, coloring agents or further active agents.

Patients can be humans, and also other mammals, such as livestock, zoo animals and companion animals, such as a cat, dog or horse.

In another aspect, the embodiments provide a pharmaceutical composition as described hereinabove for use in the treatment of pain. The pharmaceutical composition according to the embodiments is useful, for example, in the treatment of a patient suffering from, or at risk of suffering from pain. Accordingly, the present disclosure provides methods of treating or preventing pain in a subject, the methods involving administering to the subject a disclosed composition. The present disclosure provides for a disclosed composition for use in therapy or prevention or as a medicament. The present disclosure also provides the use of a disclosed composition for the manufacture of a medicament, especially for the manufacture of a medicament for the treatment or prevention of pain.

The compositions of the present disclosure can be used in the treatment or prevention of pain including, but not limited to include, acute pain, chronic pain, neuropathic pain, acute traumatic pain, arthritic pain, osteoarthritic pain, rheumatoid arthritic pain, muscular skeletal pain, post-dental surgical pain, dental pain, myofascial pain, cancer pain, visceral pain, diabetic pain, muscular pain, post-herpetic neuralgic pain, chronic pelvic pain, endometriosis pain, pelvic inflammatory pain and child birth related pain. Acute pain includes, but is not limited to, acute traumatic pain or post-surgical pain. Chronic pain includes, but is not limited to, neuropathic pain, arthritic pain, osteoarthritic pain, rheumatoid arthritic pain, muscular skeletal pain, dental pain, myofascial pain, cancer pain, diabetic pain, visceral pain, muscular pain, post-herpetic neuralgic pain, chronic pelvic pain, endometriosis pain, pelvic inflammatory pain and back pain.

The present disclosure provides use of a ketone-modified opioid prodrug and a trypsin inhibitor in the treatment of pain. The present disclosure provides use of a ketone-modified opioid prodrug and a trypsin inhibitor in the prevention of pain.

The present disclosure provides use of a ketone-modified opioid prodrug and a trypsin inhibitor in the manufacture of a medicament for treatment of pain. The present disclosure provides use of a ketone-modified opioid prodrug and a trypsin inhibitor in the manufacture of a medicament for prevention of pain.

In another aspect, the embodiments provide a method of treating pain in a patient requiring treatment, which comprises administering an effective amount of a pharmaceutical composition as described hereinabove. In another aspect, the embodiments provides method of preventing pain in a patient requiring treatment, which comprises administering an effective amount of a pharmaceutical composition as described hereinabove.

The amount of composition disclosed herein to be administered to a patient to be effective (i.e. to provide blood levels of ketone-containing opioid sufficient to be effective in the treatment or prophylaxis of pain) will depend upon the bioavailability of the particular composition, the susceptibility of the particular composition to enzyme activation in the gut, the amount and potency of trypsin inhibitor present in the composition, as well as other factors, such as the species, age, weight, sex, and condition of the patient, manner of administration and judgment of the prescribing physician. In general, the dose can be such that the ketone-modified opioid prodrug is in the range of from 0.01 milligrams per kilogram to 20 milligrams prodrug per kilogram (mg/kg) body weight. For example, a prodrug comprising a residue of oxycodone or hydrocodone can be administered at a dose equivalent to administering free oxycodone or hydrocodone in the range of from 0.02 to 0.5 mg/kg body weight or 0.01 mg/kg to 10 mg/kg body weight or 0.01 to 2 mg/kg body weight. In one embodiment wherein the composition comprises an oxycodone or hydrocodone prodrug, the composition can be administered at a dose such that the level of oxycodone or hydrocodone achieved in the blood is in the range of from 0.5 ng/ml to 10 ng/ml.

The amount of a trypsin inhibitor to be administered to the patient to be effective (i.e. to attenuate release of ketone-containing opioid when administration of a compound disclosed herein alone would lead to overexposure of the ketone-containing opioid) will depend upon the effective dose of the particular prodrug and the potency of the particular inhibitor, as well as other factors, such as the species, age, weight, sex and condition of the patient, manner of administration and judgment of the prescribing physician. In general, the dose of inhibitor can be in the range of from 0.05 mg to 50 mg per mg of prodrug disclosed herein. In a certain embodiment, the dose of inhibitor can be in the range of from 0.001 mg to 50 mg per mg of prodrug disclosed herein. In one embodiment, the dose of inhibitor can be in the range of from 0.01 nanomoles to 100 micromoles per micromole of prodrug disclosed herein.

Dose Units of Prodrug and Inhibitor Having a Desired Pharmacokinetic Profile

The present disclosure provides dose units of prodrug and inhibitor that can provide for a desired pharmacokinetic (PK) profile. Dose units can provide a modified PK profile compared to a reference PK profile as disclosed herein. It will be appreciated that a modified PK profile can provide for a modified pharmacodynamic (PD) profile. Ingestion of multiples of such a dose unit can also provide a desired PK profile.

Unless specifically stated otherwise, "dose unit" as used herein refers to a combination of a GI enzyme-cleavable prodrug (e.g., trypsin-cleavable prodrug) and a GI enzyme inhibitor (e.g., a trypsin inhibitor). A "single dose unit" is a single unit of a combination of a GI enzyme-cleavable prodrug (e.g., trypsin-cleavable prodrug) and a GI enzyme inhibitor (e.g., trypsin inhibitor), where the single dose unit provide a therapeutically effective amount of drug (i.e., a sufficient amount of drug to effect a therapeutic effect, e.g., a dose within the respective drug's therapeutic window, or therapeutic range). "Multiple dose units" or "multiples of a dose unit" or a "multiple of a dose unit" refers to at least two single dose units.

As used herein, a "PK profile" refers to a profile of drug concentration in blood or plasma. Such a profile can be a relationship of drug concentration over time (i.e., a "concentration-time PK profile") or a relationship of drug concentration versus number of doses ingested (i.e., a "concentration-dose PK profile".) A PK profile is characterized by PK parameters.

As used herein, a "PK parameter" refers to a measure of drug concentration in blood or plasma, such as: 1) "drug Cmax", the maximum concentration of drug achieved in blood or plasma; 2) "drug Tmax", the time elapsed following ingestion to achieve Cmax; and 3) "drug exposure", the total concentration of drug present in blood or plasma over a selected period of time, which can be measured using the area under the curve (AUC) of a time course of drug release over a selected period of time (t). Modification of one or more PK parameters provides for a modified PK profile.

For purposes of describing the features of dose units of the present disclosure, "PK parameter values" that define a PK profile include drug Cmax (e.g., ketone-containing opioid Cmax), total drug exposure (e.g., area under the curve) (e.g., ketone-containing opioid exposure) and 1/(drug Tmax) (such that a decreased 1/Tmax is indicative of a delay in Tmax relative to a reference Tmax) (e.g., 1/ketone-containing opioid Tmax). Thus a decrease in a PK parameter value relative to a reference PK parameter value can indicate, for example, a decrease in drug Cmax, a decrease in drug exposure, and/or a delayed Tmax.

Dose units of the present disclosure can be adapted to provide for a modified PK profile, e.g., a PK profile that is different from that achieved from dosing a given dose of prodrug in the absence of inhibitor (i.e., without inhibitor). For example, dose units can provide for at least one of decreased drug Cmax, delayed drug Tmax and/or decreased drug exposure compared to ingestion of a dose of prodrug in the same amount but in the absence of inhibitor. Such a modification is due to the inclusion of an inhibitor in the dose unit.

As used herein, "a pharmacodynamic (PD) profile" refers to a profile of the efficacy of a drug in a patient (or subject or user), which is characterized by PD parameters. "PD parameters" include "drug Emax" (the maximum drug efficacy), "drug EC50" (the concentration of drug at 50% of the Emax), and side effects.

FIG. 1 is a schematic illustrating an example of the effect of increasing inhibitor concentrations upon the PK parameter drug Cmax for a fixed dose of prodrug. At low concentrations of inhibitor, there may be no detectable effect on drug release, as illustrated by the plateau portion of the plot of drug Cmax (Y axis) versus inhibitor concentration (X axis). As inhibitor concentration increases, a concentration is reached at which drug release from prodrug is attenuated, causing a decrease in, or suppression of, drug Cmax. Thus, the effect of inhibitor upon a prodrug PK parameter for a dose unit of the present disclosure can range from undetectable, to moderate, to complete inhibition (i.e., no detectable drug release).

A dose unit can be adapted to provide for a desired PK profile (e.g., a concentration-time PK profile) following ingestion of a single dose. A dose unit can be adapted to provide for a desired PK profile (e.g., a concentration-dose PK profile) following ingestion of multiple dose units (e.g., at least 2, at least 3, at least 4 or more dose units).

Dose Units Providing Modified PK Profiles

A combination of a prodrug and an inhibitor in a dose unit can provide a desired (or "pre-selected") PK profile (e.g., a concentration-time PK profile) following ingestion of a single dose.

The PK profile of such a dose unit can be characterized by one or more of a pre-selected drug Cmax, a pre-selected drug Tmax or a pre-selected drug exposure. The PK profile of the dose unit can be modified compared to a PK profile achieved from the equivalent dosage of prodrug in the absence of inhibitor (i.e., a dose that is the same as the dose unit except that it lacks inhibitor).

A modified PK profile can have a decreased PK parameter value relative to a reference PK parameter value (e.g., a PK parameter value of a PK profile following ingestion of a dosage of prodrug that is equivalent to a dose unit except without inhibitor). For example, a dose unit can provide for a decreased drug Cmax, decreased drug exposure, and/or delayed drug Tmax.

Figure 2:
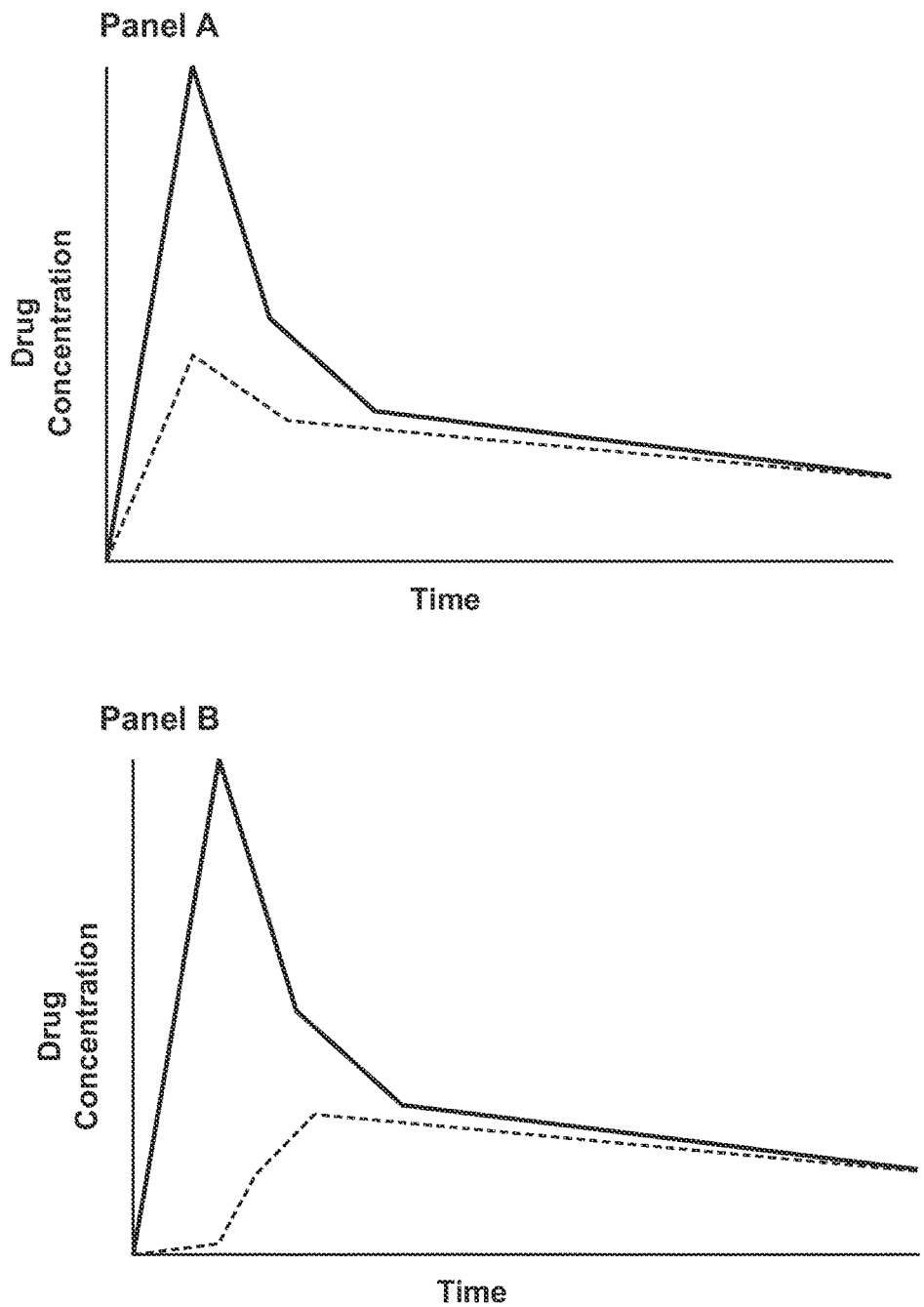
FIG. 2 provides schematics of drug concentration in plasma (Y axis) over time (X axis). Panel A is a schematic of a pharmacokinetic (PK) profile following ingestion of prodrug with a GI enzyme inhibitor (dashed line) where the drug Cmax is modified relative to that of prodrug without inhibitor (solid line). Panel B is a schematic of a PK profile following ingestion of prodrug with inhibitor (dashed line) where drug Cmax and drug Tmax are modified relative to that of prodrug without inhibitor (solid line). Panel C is a schematic of a PK profile following ingestion of prodrug with inhibitor (dashed line) where drug Tmax is modified relative to that of prodrug without inhibitor (solid line).
Figure 2:
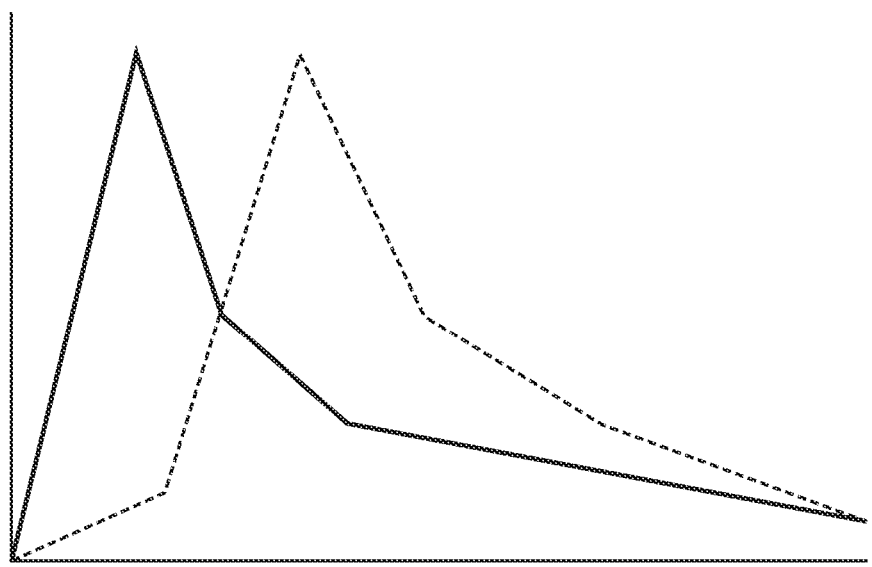

FIG. 2 presents schematic graphs showing examples of modified concentration-time PK profiles of a single dose unit. Panel A is a schematic of drug concentration in blood or plasma (Y axis) following a period of time (X axis) after ingestion of prodrug in the absence or presence of inhibitor. The solid, top line in Panel A provides an example of drug concentration following ingestion of prodrug without inhibitor. The dashed, lower line in Panel A represents drug concentration following ingestion of the same dose of prodrug with inhibitor. Ingestion of inhibitor with prodrug provides for a decreased drug Cmax relative to the drug Cmax that results from ingestion of the same amount of prodrug in the absence of inhibitor. Panel A also illustrates that the total drug exposure following ingestion of prodrug with inhibitor is also decreased relative to ingestion of the same amount of prodrug without inhibitor.

Panel B of FIG. 2 provides another example of a dose unit having a modified concentration-time PK profile. As in Panel A, the solid top line represents drug concentration over time in blood or plasma following ingestion of prodrug without inhibitor, while the dashed lower line represents drug concentration following ingestion of the same amount of prodrug with inhibitor. In this example, the dose unit provides a PK profile having a decreased drug Cmax, decreased drug exposure, and a delayed drug Tmax (i.e., decreased (1/drug Tmax) relative to ingestion of the same dose of prodrug without inhibitor.

Panel C of FIG. 2 provides another example of a dose unit having a modified concentration-time PK profile. As in Panel A, the solid line represents drug concentration over time in blood or plasma following ingestion of prodrug without inhibitor, while the dashed line represents drug concentration following ingestion of the same amount of prodrug with inhibitor. In this example, the dose unit provides a PK profile having a delayed drug Tmax (i.e., decreased (1/drug Tmax) relative to ingestion of the same dose of prodrug without inhibitor.

Dose units that provide for a modified PK profile (e.g., a decreased drug Cmax and/or delayed drug Tmax as compared to, a PK profile of drug or a PK profile of prodrug without inhibitor), find use in tailoring of drug dose according to a patient's needs (e.g., through selection of a particular dose unit and/or selection of a dosage regimen), reduction of side effects, and/or improvement in patient compliance (as compared to side effects or patient compliance associated with drug or with prodrug without inhibitor). As used herein, "patient compliance" refers to whether a patient follows the direction of a clinician (e.g., a physician) including ingestion of a dose that is neither significantly above nor significantly below that prescribed. Such dose units also reduce the risk of misuse, abuse or overdose by a patient as compared to such risk(s) associated with drug or prodrug without inhibitor. For example, dose units with a decreased drug Cmax provide less reward for ingestion than does a dose of the same amount of drug, and/or the same amount of prodrug without inhibitor.

Dose Units Providing Modified PK Profiles Upon Ingestion of Multiple Dose Units

A dose unit of the present disclosure can be adapted to provide for a desired PK profile (e.g., a concentration-time PK profile or concentration-dose PK profile) following ingestion of multiples of a dose unit (e.g., at least 2, at least 3, at least 4, or more dose units). A concentration-dose PK profile refers to the relationship between a selected PK parameter and a number of single dose units ingested. Such a profile can be dose proportional, linear (a linear PK profile) or nonlinear (a nonlinear PK profile). A modified concentration-dose PK profile can be provided by adjusting the relative amounts of prodrug and inhibitor contained in a single dose unit and/or by using a different prodrug and/or inhibitor.

Figure 3:
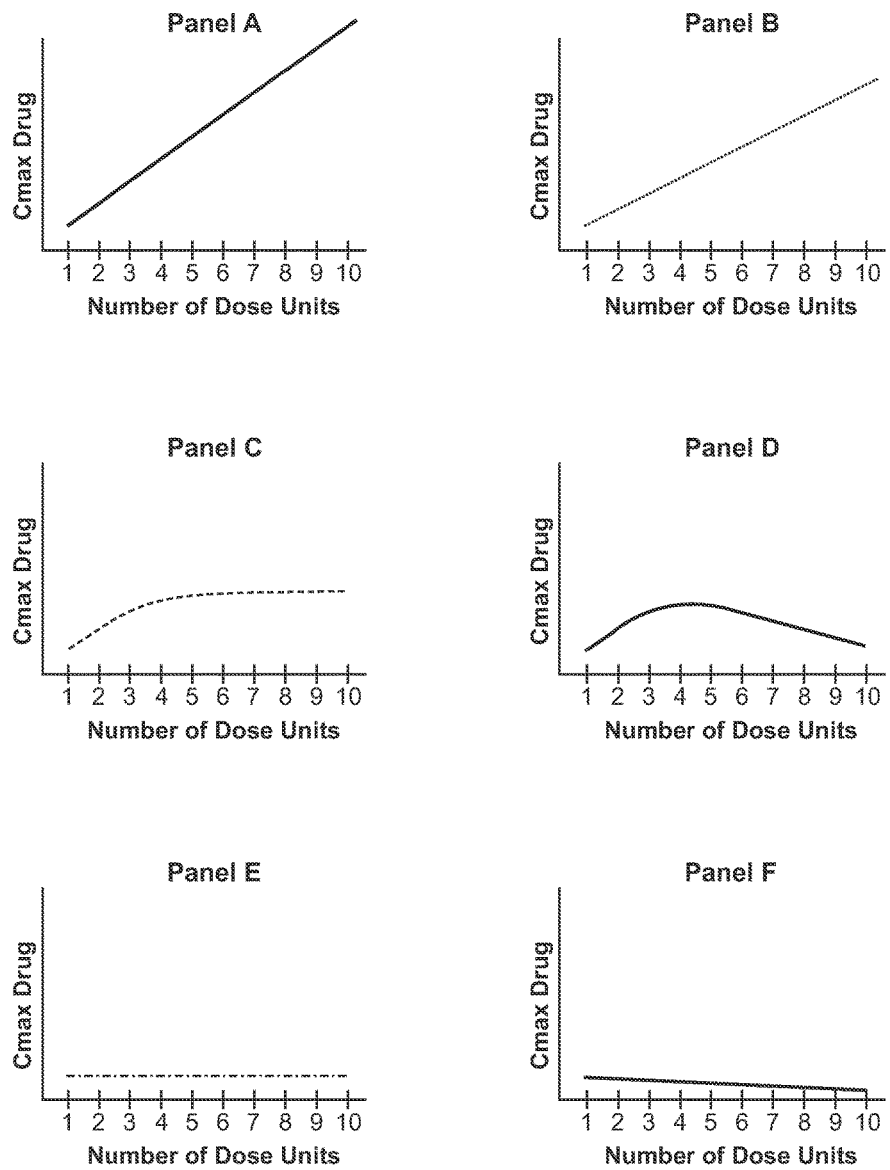
FIG. 3 provides schematics representing differential concentration-dose PK profiles that can result from the dosing of multiples of a dose unit (X axis) of the present disclosure. Different PK profiles (as exemplified herein for a representative PK parameter, drug Cmax (Y axis)) can be provided by adjusting the relative amount of prodrug and GI enzyme inhibitor contained in a single dose unit or by using a different prodrug or inhibitor in the dose unit.

FIG. 3 provides schematics of examples of concentration-dose PK profiles (exemplified by drug Cmax, Y axis) that can be provided by ingestion of multiples of a dose unit (X axis) of the present disclosure. Each profile can be compared to a concentration-dose PK profile provided by increasing doses of drug alone, where the amount of drug in the blood or plasma from one dose represents a therapeutically effective amount equivalent to the amount of drug released into the blood or plasma by one dose unit of the disclosure. Such a "drug alone" PK profile is typically dose proportional, having a forty-five degree angle positive linear slope. It is also to be appreciated that a concentration-dose PK profile resulting from ingestion of multiples of a dose unit of the disclosure can also be compared to other references, such as a concentration-dose PK profile provided by ingestion of an increasing number of doses of prodrug without inhibitor wherein the amount of drug released into the blood or plasma by a single dose of prodrug in the absence of inhibitor represents a therapeutically effective amount equivalent to the amount of drug released into the blood or plasma by one dose unit of the disclosure.

As illustrated by the relationship between prodrug and inhibitor concentration in FIG. 2, a dose unit can include inhibitor in an amount that does not detectably affect drug release following ingestion. Ingestion of multiples of such a dose unit can provide a concentration-dose PK profile such that the relationship between number of dose units ingested and PK parameter value is linear with a positive slope, which is similar to, for example, a dose proportional PK profile of increasing amounts of prodrug alone. Panel A of FIG. 3 depicts such a profile. Dose units that provide a concentration-dose PK profile having such an undetectable change in drug Cmax in vivo compared to the profile of prodrug alone can find use in thwarting enzyme conversion of prodrug from a dose unit that has sufficient inhibitor to reduce or prevent in vitro cleavage of the enzyme-cleavable prodrug by its respective enzyme.

Panel B in FIG. 3 represents a concentration-dose PK profile such that the relationship between the number of dose units ingested and a PK parameter value is linear with positive slope, where the profile exhibits a reduced slope relative to panel A. Such a dose unit provides a profile having a decreased PK parameter value (e.g., drug Cmax) relative to a reference PK parameter value exhibiting dose proportionality.

Concentration-dose PK profiles following ingestion of multiples of a dose unit can be non-linear. Panel C in FIG. 3 represents an example of a non-linear, biphasic concentration-dose PK profile. In this example, the biphasic concentration-dose PK profile contains a first phase over which the concentration-dose PK profile has a positive rise, and then a second phase over which the relationship between number of dose units ingested and a PK parameter value (e.g., drug Cmax) is relatively flat (substantially linear with zero slope). For such a dose unit, for example, drug Cmax can be increased for a selected number of dose units (e.g., 2, 3, or 4 dose units). However, ingestion of additional dose units does not provide for a significant increase in drug Cmax.

Panel D in FIG. 3 represents another example of a non-linear, biphasic concentration-dose PK profile. In this example, the biphasic concentration-dose PK profile is characterized by a first phase over which the concentration-dose PK profile has a positive rise and a second phase over which the relationship between number of dose units ingested and a PK parameter value (e.g., drug Cmax) declines. Dose units that provide this concentration-dose PK profile provide for an increase in drug Cmax for a selected number of ingested dose units (e.g., 2, 3, or 4 dose units). However, ingestion of further additional dose units does not provide for a significant increase in drug Cmax and instead provides for decreased drug Cmax.

Panel E in FIG. 3 represents a concentration-dose PK profile in which the relationship between the number of dose units ingested and a PK parameter (e.g., drug Cmax) is linear with zero slope. Such dose units do not provide for a significant increase or decrease in drug Cmax with ingestion of multiples of dose units.

Panel F in FIG. 3 represents a concentration-dose PK profile in which the relationship between number of dose units ingested and a PK parameter value (e.g., drug Cmax) is linear with a negative slope. Thus drug Cmax decreases as the number of dose units ingested increases.

Dose units that provide for concentration-dose PK profiles when multiples of a dose unit are ingested find use in tailoring of a dosage regimen to provide a therapeutic level of released drug while reducing the risk of overdose, misuse, or abuse. Such reduction in risk can be compared to a reference, e.g., to administration of drug alone or prodrug alone. In one embodiment, risk is reduced compared to administration of a drug or prodrug that provides a proportional concentration-dose PK profile. A dose unit that provides for a concentration-dose PK profile can reduce the risk of patient overdose through inadvertent ingestion of dose units above a prescribed dosage. Such a dose unit can reduce the risk of patient misuse (e.g., through self-medication). Such a dose unit can discourage abuse through deliberate ingestion of multiple dose units. For example, a dose unit that provides for a biphasic concentration-dose PK profile can allow for an increase in drug release for a limited number of dose units ingested, after which an increase in drug release with ingestion of more dose units is not realized. In another example, a dose unit that provides for a concentration-dose PK profile of zero slope can allow for retention of a similar drug release profile regardless of the number of dose units ingested.

Ingestion of multiples of a dose unit can provide for adjustment of a PK parameter value relative to that of ingestion of multiples of the same dose (either as drug alone or as a prodrug) in the absence of inhibitor such that, for example, ingestion of a selected number (e.g., 2, 3, 4 or more) of a single dose unit provides for a decrease in a PK parameter value compared to ingestion of the same number of doses in the absence of inhibitor.

Pharmaceutical compositions include those having an inhibitor to provide for protection of a therapeutic compound from degradation in the GI tract. Inhibitor can be combined with a drug (i.e., not a prodrug) to provide for protection of the drug from degradation in the GI system.

In this example, the composition of inhibitor and drug provide for a modified PK profile by increasing a PK parameter. Inhibitor can also be combined with a prodrug that is susceptible to degradation by a GI enzyme and has a site of action outside the GI tract. In this composition, the inhibitor protects ingested prodrug in the GI tract prior to its distribution outside the GI tract and cleavage at a desired site of action.

Methods Used to Define Relative Amounts of Prodrug and Inhibitor in a Dose Unit

Dose units that provide for a desired PK profile, such as a desired concentration-time PK profile and/or a desired concentration-dose PK profile, can be made by combining a prodrug and an inhibitor in a dose unit in relative amounts effective to provide for release of drug that provides for a desired drug PK profile following ingestion by a patient.

Prodrugs can be selected as suitable for use in a dose unit by determining the GI enzyme-mediated drug release competency of the prodrug. This can be accomplished in vitro, in vivo or ex vivo.

In vitro assays can be conducted by combining a prodrug with a GI enzyme (e.g., trypsin) in a reaction mixture. The GI enzyme can be provided in the reaction mixture in an amount sufficient to catalyze cleavage of the prodrug. Assays are conducted under suitable conditions, and optionally may be under conditions that mimic those found in a GI tract of a subject, e.g., human. "Prodrug conversion" refers to release of drug from prodrug. Prodrug conversion can be assessed by detecting a level of a product of prodrug conversion (e.g., released drug) and/or by detecting a level of prodrug that is maintained in the presence of the GI enzyme. Prodrug conversion can also be assessed by detecting the rate at which a product of prodrug conversion occurs or the rate at which prodrug disappears. An increase in released drug, or a decrease in prodrug, indicate prodrug conversion has occurred. Prodrugs that exhibit an acceptable level of prodrug conversion in the presence of the GI enzyme within an acceptable period of time are suitable for use in a dose unit in combination with an inhibitor of the GI enzyme that is shown to mediate prodrug conversion.

In vivo assays can assess the suitability of a prodrug for use in a dose unit by administration of the prodrug to an animal (e.g., a human or non-human animal, e.g., rat, dog, pig, etc.). Such administration can be enteral (e.g., oral administration). Prodrug conversion can be detected by, for example, detecting a product of prodrug conversion (e.g., released drug or a metabolite of released drug) or detecting prodrug in blood or plasma of the animal at a desired time point(s) following administration.

Ex vivo assays, such as a gut loop or inverted gut loop assay, can assess the suitability of a prodrug for use in a dose unit by, for example, administration of the prodrug to a ligated section of the intestine of an animal. Prodrug conversion can be detected by, for example, detecting a product of prodrug conversion (e.g., released drug or a metabolite of released drug) or detecting prodrug in the ligated gut loop of the animal at a desired time point(s) following administration.

Inhibitors are generally selected based on, for example, activity in interacting with the GI enzyme(s) that mediate release of drug from a prodrug with which the inhibitor is to be co-dosed. Such assays can be conducted in the presence of enzyme either with or without prodrug. Inhibitors can also be selected according to properties such as half-life in the GI system, potency, avidity, affinity, molecular size and/or enzyme inhibition profile (e.g., steepness of inhibition curve in an enzyme activity assay, inhibition initiation rate). Inhibitors for use in prodrug-inhibitor combinations can be selected through use of in vitro, in vivo and/or ex vivo assays.

One embodiment is a method for identifying a prodrug and a GI enzyme inhibitor suitable for formulation in a dose unit wherein the method comprises combining a prodrug (e.g., a ketone-modified opioid prodrug), a GI enzyme inhibitor (e.g., a trypsin inhibitor), and a GI enzyme (e.g., trypsin) in a reaction mixture and detecting prodrug conversion. Such a combination is tested for an interaction between the prodrug, inhibitor and enzyme, i.e., tested to determine how the inhibitor will interact with the enzyme that mediates enzymatically-controlled release of the drug from the prodrug. In one embodiment, a decrease in prodrug conversion in the presence of the GI enzyme inhibitor as compared to prodrug conversion in the absence of the GI enzyme inhibitor indicates the prodrug and GI enzyme inhibitor are suitable for formulation in a dose unit. Such a method can be an in vitro assay.

One embodiment is a method for identifying a prodrug and a GI enzyme inhibitor suitable for formulation in a dose unit wherein the method comprises administering to an animal a prodrug and a GI enzyme inhibitor and detecting prodrug conversion. In one embodiment, a decrease in prodrug conversion in the presence of the GI enzyme inhibitor as compared to prodrug conversion in the absence of the GI enzyme inhibitor indicates the prodrug and GI enzyme inhibitor are suitable for formulation in a dose unit. Such a method can be an in vivo assay; for example, the prodrug and GI enzyme inhibitor can be administered orally. Such a method can also be an ex vivo assay; for example, the prodrug and GI enzyme inhibitor can be administered orally or to a tissue, such as an intestine, that is at least temporarily exposed. Detection can occur in the blood or plasma or respective tissue. As used herein, tissue refers to the tissue itself and can also refer to contents within the tissue.

One embodiment is a method for identifying a prodrug and a GI enzyme inhibitor suitable for formulation in a dose unit wherein the method comprises administering a prodrug and a gastrointestinal (GI) enzyme inhibitor to an animal tissue that has removed from an animal and detecting prodrug conversion. In one embodiment, a decrease in prodrug conversion in the presence of the GI enzyme inhibitor as compared to prodrug conversion in the absence of the GI enzyme inhibitor indicates the prodrug and GI enzyme inhibitor are suitable for formulation in a dose unit.

In vitro assays can be conducted by combining a prodrug, an inhibitor and a GI enzyme in a reaction mixture. The GI enzyme can be provided in the reaction mixture in an amount sufficient to catalyze cleavage of the prodrug, and assays conducted under suitable conditions, optionally under conditions that mimic those found in a GI tract of a subject, e.g., human. Prodrug conversion can be assessed by detecting a level of a product of prodrug conversion (e.g., released drug) and/or by detecting a level of prodrug maintained in the presence of the GI enzyme. Prodrug conversion can also be assessed by detecting the rate at which a product of prodrug conversion occurs or the rate at which prodrug disappears. Prodrug conversion that is modified in the presence of inhibitor as compared to a level of prodrug conversion in the absence of inhibitor indicates the inhibitor is suitable for attenuation of prodrug conversion and for use in a dose unit. Reaction mixtures having a fixed amount of prodrug and increasing amounts of inhibitor, or a fixed amount of inhibitor and increasing amounts of prodrug, can be used to identify relative amounts of prodrug and inhibitor which provide for a desired modification of prodrug conversion.

In vivo assays can assess combinations of prodrugs and inhibitors by co-dosing of prodrug and inhibitor to an animal. Such co-dosing can be enteral. "Co-dosing" refers to administration of prodrug and inhibitor as separate doses or a combined dose (i.e., in the same formulation). Prodrug conversion can be detected by, for example, detecting a product of prodrug conversion (e.g., released drug or drug metabolite) or detecting prodrug in blood or plasma of the animal at a desired time point(s) following administration. Combinations of prodrug and inhibitor can be identified that provide for a prodrug conversion level that yields a desired PK profile as compared to, for example, prodrug without inhibitor.

Combinations of relative amounts of prodrug and inhibitor that provide for a desired PK profile can be identified by dosing animals with a fixed amount of prodrug and increasing amounts of inhibitor, or with a fixed amount of inhibitor and increasing amounts of prodrug. One or more PK parameters can then be assessed, e.g., drug Cmax, drug Tmax, and drug exposure. Relative amounts of prodrug and inhibitor that provide for a desired PK profile are identified as amounts of prodrug and inhibitor for use in a dose unit. The PK profile of the prodrug and inhibitor combination can be, for example, characterized by a decreased PK parameter value relative to prodrug without inhibitor. A decrease in the PK parameter value of an inhibitor-to-prodrug combination (e.g., a decrease in drug Cmax, a decrease in 1/drug Tmax (i.e., a delay in drug Tmax) or a decrease in drug exposure) relative to a corresponding PK parameter value following administration of prodrug without inhibitor can be indicative of an inhibitor-to-prodrug combination that can provide a desired PK profile. Assays can be conducted with different relative amounts of inhibitor and prodrug.

In vivo assays can be used to identify combinations of prodrug and inhibitor that provide for dose units that provide for a desired concentration-dose PK profile following ingestion of multiples of the dose unit (e.g., at least 2, at least 3, at least 4 or more). Ex vivo assays can be conducted by direct administration of prodrug and inhibitor into a tissue and/or its contents of an animal, such as the intestine, including by introduction by injection into the lumen of a ligated intestine (e.g., a gut loop, or intestinal loop, assay, or an inverted gut assay). An ex vivo assay can also be conducted by excising a tissue and/or its contents from an animal and introducing prodrug and inhibitor into such tissues and/or contents.

For example, a dose of prodrug that is desired for a single dose unit is selected (e.g., an amount that provides an efficacious plasma drug level). A multiple of single dose units for which a relationship between that multiple and a PK parameter to be tested is then selected. For example, if a concentration-dose PK profile is to be designed for ingestion of 2, 3, 4, 5, 6, 7, 8, 9 or 10 dose units, then the amount of prodrug equivalent to ingestion of that same number of dose units is determined (referred to as the "high dose"). The multiple of dose units can be selected based on the number of ingested pills at which drug Cmax is modified relative to ingestion of the single dose unit. If, for example, the profile is to provide for abuse deterrence, then a multiple of 10 can be selected, for example. A variety of different inhibitors (e.g., from a panel of inhibitors) can be tested using different relative amounts of inhibitor and prodrug. Assays can be used to identify suitable combination(s) of inhibitor and prodrug to obtain a single dose unit that is therapeutically effective, wherein such a combination, when ingested as a multiple of dose units, provides a modified PK parameter compared to ingestion of the same multiple of drug or prodrug alone (wherein a single dose of either drug or prodrug alone releases into blood or plasma the same amount of drug as is released by a single dose unit).

Increasing amounts of inhibitor are then co-dosed to animals with the high dose of prodrug. The dose level of inhibitor that provides a desired drug Cmax following ingestion of the high dose of prodrug is identified and the resultant inhibitor-to-prodrug ratio determined.

Prodrug and inhibitor are then co-dosed in amounts equivalent to the inhibitor-to-prodrug ratio that provided the desired result at the high dose of prodrug. The PK parameter value of interest (e.g., drug Cmax) is then assessed. If a desired PK parameter value results following ingestion of the single dose unit equivalent, then single dose units that provide for a desired concentration-dose PK profile are identified. For example, where a zero dose linear profile is desired, the drug Cmax following ingestion of a single dose unit does not increase significantly following ingestion of a multiple number of the single dose units.

Methods for Manufacturing, Formulating, and Packaging Dose Units

Dose units of the present disclosure can be made using manufacturing methods available in the art and can be of a variety of forms suitable for enteral (including oral, buccal and sublingual) administration, for example as a tablet, capsule, thin film, powder, suspension, solution, syrup, dispersion or emulsion. The dose unit can contain components conventional in pharmaceutical preparations, e.g. one or more carriers, binders, lubricants, excipients (e.g., to impart controlled release characteristics), pH modifiers, flavoring agents (e.g., sweeteners), bulking agents, coloring agents or further active agents. Dose units of the present disclosure can include can include an enteric coating or other component(s) to facilitate protection from stomach acid, where desired.

Dose units can be of any suitable size or shape. The dose unit can be of any shape suitable for enteral administration, e.g., ellipsoid, lenticular, circular, rectangular, cylindrical, and the like.

Dose units provided as dry dose units can have a total weight of from about 1 microgram to about 1 gram, and can be from about 5 micrograms to 1.5 grams, from about 50 micrograms to 1 gram, from about 100 micrograms to 1 gram, from 50 micrograms to 750 milligrams, and may be from about 1 microgram to 2 grams.

Dose units can comprise components in any relative amounts. For example, dose units can be from about 0.1% to 99% by weight of active ingredients (i.e., prodrug and inhibitor) per total weight of dose unit (0.1% to 99% total combined weight of prodrug and inhibitor per total weight of single dose unit). In some embodiments, dose units can be from 10% to 50%, from 20% to 40%, or about 30% by weight of active ingredients per total weight dose unit.

Dose units can be provided in a variety of different forms and optionally provided in a manner suitable for storage. For example, dose units can be disposed within a container suitable for containing a pharmaceutical composition. The container can be, for example, a bottle (e.g., with a closure device, such as a cap), a blister pack (e.g., which can provide for enclosure of one or more dose units per blister), a vial, flexible packaging (e.g., sealed Mylar or plastic bags), an ampule (for single dose units in solution), a dropper, thin film, a tube and the like.

Containers can include a cap (e.g., screw cap) that is removably connected to the container over an opening through which the dose units disposed within the container can be accessed.

Containers can include a seal which can serve as a tamper-evident and/or tamper-resistant element, which seal is disrupted upon access to a dose unit disposed within the container. Such seal elements can be, for example, a frangible element that is broken or otherwise modified upon access to a dose unit disposed within the container. Examples of such frangible seal elements include a seal positioned over a container opening such that access to a dose unit within the container requires disruption of the seal (e.g., by peeling and/or piercing the seal). Examples of frangible seal elements include a frangible ring disposed around a container opening and in connection with a cap such that the ring is broken upon opening of the cap to access the dose units in the container.

Dry and liquid dose units can be placed in a container (e.g., bottle or package, e.g., a flexible bag) of a size and configuration adapted to maintain stability of dose units over a period during which the dose units are dispensed into a prescription. For example, containers can be sized and configured to contain 10, 20, 30, 40, 50, 60, 70, 80, 90, 100 or more single dry or liquid dose units. The containers can be sealed or resealable. The containers can packaged in a carton (e.g., for shipment from a manufacturer to a pharmacy or other dispensary). Such cartons can be boxes, tubes, or of other configuration, and may be made of any material (e.g., cardboard, plastic, and the like). The packaging system and/or containers disposed therein can have one or more affixed labels (e.g., to provide information such as lot number, dose unit type, manufacturer, and the like).

The container can include a moisture barrier and/or light barrier, e.g., to facilitate maintenance of stability of the active ingredients in the dose units contained therein. Where the dose unit is a dry dose unit, the container can include a desiccant pack which is disposed within the container. The container can be adapted to contain a single dose unit or multiples of a dose unit. The container can include a dispensing control mechanism, such as a lock out mechanism that facilitates maintenance of dosing regimen.

The dose units can be provided in solid or semi-solid form, and can be a dry dose unit. "Dry dose unit" refers to a dose unit that is in other than in a completely liquid form. Examples of dry dose units include, for example, tablets, capsules (e.g., solid capsules, capsules containing liquid), thin film, microparticles, granules, powder and the like. Dose units can be provided as liquid dose units, where the dose units can be provided as single or multiple doses of a formulation containing prodrug and inhibitor in liquid form. Single doses of a dry or liquid dose unit can be disposed within a sealed container, and sealed containers optionally provided in a packaging system, e.g., to provide for a prescribed number of doses, to provide for shipment of dose units, and the like.

Dose units can be formulated such that the prodrug and inhibitor are present in the same carrier, e.g., solubilized or suspended within the same matrix. Alternatively, dose units can be composed of two or more portions, where the prodrug and inhibitor can be provided in the same or different portions, and can be provided in adjacent or non-adjacent portions.

Dose units can be provided in a container in which they are disposed, and may be provided as part of a packaging system (optionally with instructions for use). For example, dose units containing different amounts of prodrug can be provided in separate containers, which containers can be disposed with in a larger container (e.g., to facilitate protection of dose units for shipment). For example, one or more dose units as described herein can be provided in separate containers, where dose units of different composition are provided in separate containers, and the separate containers disposed within package for dispensing.

In another example, dose units can be provided in a double-chambered dispenser where a first chamber contains a prodrug formulation and a second chamber contains an inhibitor formulation. The dispenser can be adapted to provide for mixing of a prodrug formulation and an inhibitor formulation prior to ingestion. For example, the two chambers of the dispenser can be separated by a removable wall (e.g., frangible wall) that is broken or removed prior to administration to allow mixing of the formulations of the two chambers. The first and second chambers can terminate into a dispensing outlet, optionally through a common chamber. The formulations can be provided in dry or liquid form, or a combination thereof. For example, the formulation in the first chamber can be liquid and the formulation in the second chamber can be dry, both can be dry, or both can be liquid.

Dose units that provide for controlled release of prodrug, of inhibitor, or of both prodrug and inhibitor are contemplated by the present disclosure, where "controlled release" refers to release of one or both of prodrug and inhibitor from the dose unit over a selected period of time and/or in a pre-selected manner.

Methods of Use of Dose Units

Dose units are advantageous because they find use in methods to reduce side effects and/or improve tolerability of drugs to patients in need thereof by, for example, limiting a PK parameter as disclosed herein. The present disclosure thus provides methods to reduce side effects by administering a dose unit of the present disclosure to a patient in need so as to provide for a reduction of side effects as compared to those associated with administration of drug and/or as compared to administration of prodrug without inhibitor. The present disclosure also provides methods to improve tolerability of drugs by administering a dose unit of the present disclosure to a patient in need so as to provide for improvement in tolerability as compared to administration of drug and/or as compared to administration of prodrug without inhibitor.

Dose units find use in methods for increasing patient compliance of a patient with a therapy prescribed by a clinician, where such methods involve directing administration of a dose unit described herein to a patient in need of therapy so as to provide for increased patient compliance as compared to a therapy involving administration of drug and/or as compared to administrations of prodrug without inhibitor. Such methods can help increase the likelihood that a clinician-specified therapy occurs as prescribed.

Dose units can provide for enhanced patient compliance and clinician control. For example, by limiting a PK parameter (e.g., such as drug Cmax or drug exposure) when multiples (e.g., two or more, three or more, or four or more) dose units are ingested, a patient requiring a higher dose of drug must seek the assistance of a clinician. The dose units can provide for control of the degree to which a patient can readily "self-medicate", and further can provide for the patient to adjust dose to a dose within a permissible range. Dose units can provide for reduced side effects, by for example, providing for delivery of drug at an efficacious dose but with a modified PK profile over a period of treatment, e.g., as defined by a decreased PK parameter (e.g., decreased drug Cmax, decreased drug exposure).

Dose units find use in methods to reduce the risk of unintended overdose of drug that can follow ingestion of multiple doses taken at the same time or over a short period of time. Such methods of the present disclosure can provide for reduction of risk of unintended overdose as compared to risk of unintended overdose of drug and/or as compared to risk of unintended overdose of prodrug without inhibitor. Such methods involve directing administration of a dosage described herein to a patient in need of drug released by conversion of the prodrug. Such methods can help avoid unintended overdosing due to intentional or unintentional misuse of the dose unit.

The present disclosure provides methods to reduce misuse and abuse of a drug, as well as to reduce risk of overdose, that can accompany ingestion of multiples of doses of a drug, e.g., ingested at the same time. Such methods generally involve combining in a dose unit a prodrug and an inhibitor of a GI enzyme that mediates release of drug from the prodrug, where the inhibitor is present in the dose unit in an amount effective to attenuate release of drug from the prodrug, e.g., following ingestion of multiples of dose units by a patient. Such methods provide for a modified concentration-dose PK profile while providing therapeutically effective levels from a single dose unit, as directed by the prescribing clinician. Such methods can provide for, for example, reduction of risks that can accompany misuse and/or abuse of a prodrug, particularly where conversion of the prodrug provides for release of a narcotic or other drug of abuse (e.g., opioid). For example, when the prodrug provides for release of a drug of abuse, dose units can provide for reduction of reward that can follow ingestion of multiples of dose units of a drug of abuse.

Dose units can provide clinicians with enhanced flexibility in prescribing drug. For example, a clinician can prescribe a dosage regimen involving different dose strengths, which can involve two or more different dose units of prodrug and inhibitor having different relative amounts of prodrug, different amounts of inhibitor, or different amounts of both prodrug and inhibitor. Such different strength dose units can provide for delivery of drug according to different PK parameters (e.g., drug exposure, drug Cmax, and the like as described herein). For example, a first dose unit can provide for delivery of a first dose of drug following ingestion, and a second dose unit can provide for delivery of a second dose of drug following ingestion. The first and second prodrug doses of the dose units can be different strengths, e.g., the second dose can be greater than the first dose. A clinician can thus prescribe a collection of two or more, or three or more dose units of different strengths, which can be accompanied by instructions to facilitate a degree of self-medication, e.g., to increase delivery of an opioid drug according to a patient's needs to treat pain.

Thwarting Tampering by Trypsin Mediated Release of Ketone-Containing Opioid from Prodrugs The disclosure provides for a composition comprising a compound disclosed herein and a trypsin inhibitor that reduces drug abuse potential. A trypsin inhibitor can thwart the ability of a user to apply trypsin to effect the release of a ketone-containing opioid from the ketone-containing opioid prodrug in vitro. For example, if an abuser attempts to incubate trypsin with a composition of the embodiments that includes a ketone-containing opioid prodrug and a trypsin inhibitor, the trypsin inhibitor can reduce the action of the added trypsin, thereby thwarting attempts to release ketone-containing opioid for purposes of abuse.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used.

Synthesis of Small Molecule Trypsin Inhibitors

Example 1

Synthesis of (S)-ethyl 4-(5-guanidino-2-(naphthalene-2-sulfonamido)pentanoyl)piperazine-1-carboxylate (Compound 101)

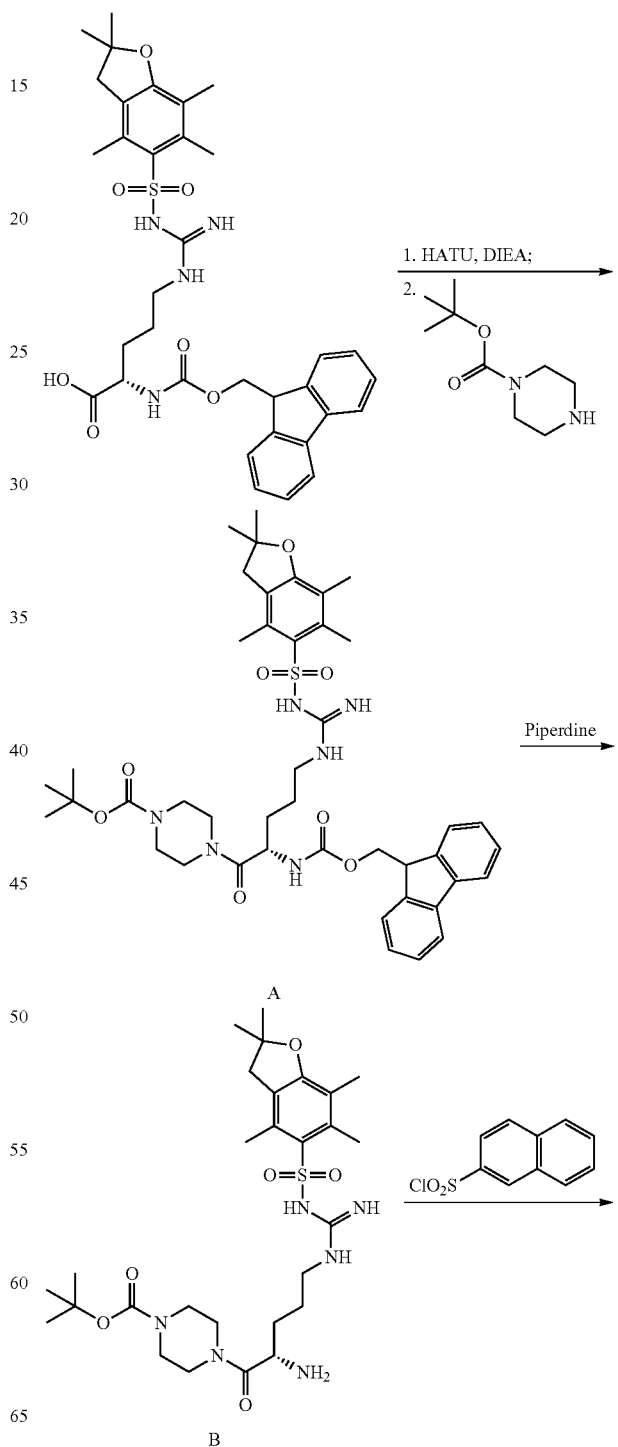

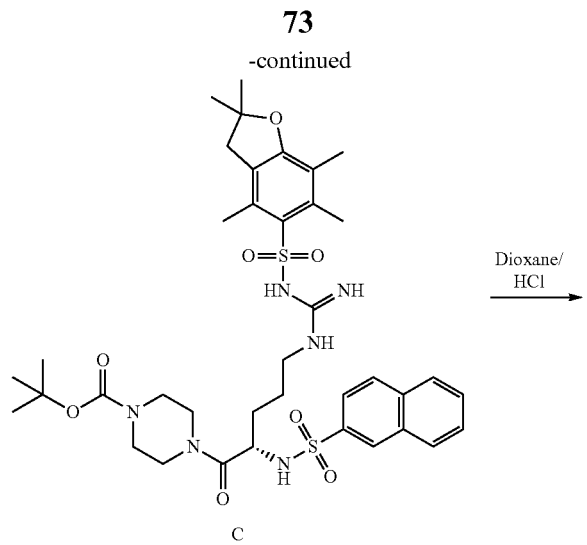

C

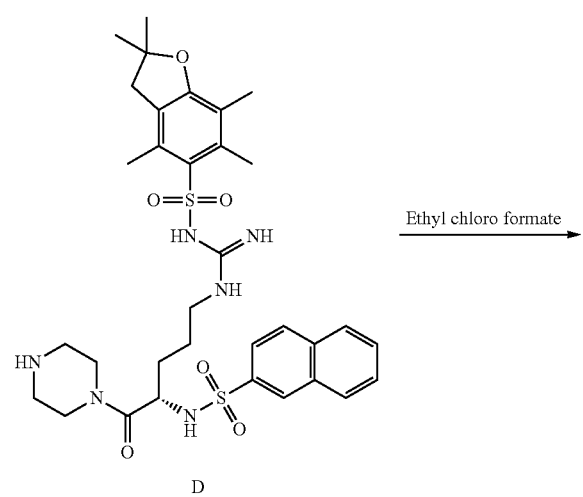

D

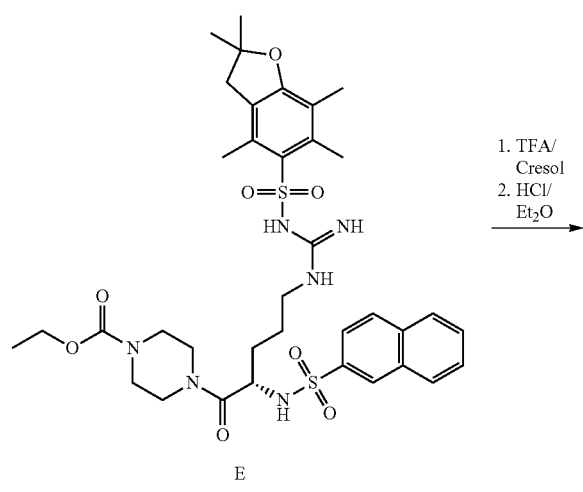

E

Dioxane/ HCl →

Ethyl chloro formate →

1. TFA/ Cresol
2. HCl/ Et₂O
→

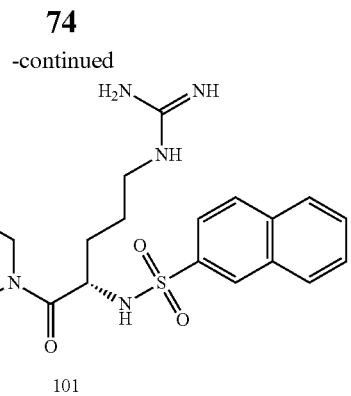

101

Preparation 1

Synthesis of 4-[(S)-5-({Amino-[(E)-2,2,4,6,7-pentamethyl-2,3-dihydro-benzofuran-5-sulfonylimino]-methyl}-amino)-2-(9H-fluoren-9-ylmethoxycarbonylamino)-pentanoyl]-piperazine-1-carboxylic acid tert-butyl ester (A)

To a solution of Fmoc-Arg(Pbf)-OH 1 (25.0 g, 38.5 mmol) in DMF (200 mL) at room temperature was added DIEA (13.41 mL, 77.1 mmol). After stirring at room temperature for 10 min, the reaction mixture was cooled to ~5° C. To the reaction mixture was added HATU (16.11 g, 42.4 mmol) in portions and stirred for 20 min and a solution of tert-butyl-1-piperazine carboxylate (7.18 g, 38.5 mmol) in DMF (50 mL) was added dropwise. The reaction mixture was stirred at ~5° C. for 5 min. The mixture reaction was then allowed to warm to room temperature and stirred for 2 h. Solvent was removed in vacuo and the residue was dissolved in EtOAc (500 mL), washed with water (2×750 mL), 1% $H_2SO_4$ (300 mL) and brine (750 mL). The organic layer was separated, dried over $Na_2SO_4$ and solvent removed in vacuo to a total volume of 100 mL. Compound A was taken to the next step as EtOAc solution (100 mL). LC-MS [M+H] 817.5 ($C_{43}H_{56}N_6O_8S$+H, calc: 817.4).

Preparation 2

Synthesis of 4-[(S)-2-Amino-5-({amino-[(E)-2,2,4,6,7-pentamethyl-2,3-dihydro-benzofuran-5-sulfonylimino]-methyl}-amino)-pentanoyl]-piperazine-1-carboxylic acid tert-butyl ester (B)

To a solution of compound A (46.2 mmol) in EtOAc (175 mL) at room temperature was added piperidine (4.57 mL, 46.2 mmol) and the reaction mixture was stirred for 18 h at room temperature. Next the solvent was removed in vacuo and the resulting residue dissolved in minimum amount of EtOAc (~50 mL) and hexane (~1 L) was added. The precipitated crude product was filtered off and recrystallised again with EtOAc (~30 mL) and hexane (~750 mL). The precipitate was filtered off, washed with hexane and dried in vacuo to afford compound B (28.0 g, 46.2 mmol). LC-MS [M+H] 595.4 ($C_{28}H_{46}N_6O_6S$+H, calc: 595.3). Compound B was used without further purification.

Preparation 3

Synthesis of 4-[(S)-5-({Amino-[(E)-2,2,4,6,7-pentamethyl-2,3-dihydro-benzofuran-5-sulfonylimino]-methyl}-amino)-2-(naphthalene-2-sulfonylamino)-pentanoyl]-piperazine-1-carboxylic acid tert-butyl ester (C)

To a solution of compound B (28.0 g, 46.2 mmol) in THF (250 mL) was added aqueous 1N NaOH (171 mL). The reaction mixture was cooled to ~5° C., a solution of 2-naphthalene sulfonylchloride (26.19 g, 115.6 mmol) in THF (125 mL) was added dropwise. The reaction mixture was stirred at ~5° C. for 10 min, with stirring continued at room temperature for 2 h. The reaction mixture was diluted with EtOAc (1 L), washed with aqueous 1N NaOH (1 L), water (1 L) and brine (1 L). The organic layer was separated, dried over $Na_2SO_4$ and removal of the solvent in vacuo to afford compound C (36.6 g, 46.2 mmol). LC-MS [M+H] 785.5 ($C_{38}H_{52}N_6O_8S_2$+H, calc: 785.9). Compound C was used without further purification.

Preparation 4

Synthesis of 2,2,4,6,7-Pentamethyl-2,3-dihydro-benzofuran-5-sulfonic acid 1-amino-1-[(S)-4-(naphthalene-2-sulfonylamino)-5-oxo-5-piperazin-1-yl-pentylamino]-meth-(E)-ylideneamide (D)

To a solution of compound C (36.6 g, 46.2 mmol) in dioxane (60 mL) was added 4M HCl in dioxane (58 mL) dropwise. The reaction mixture was stirred at room temperature for 1.5 h. $Et_2O$ (600 mL) was added to the reaction mixture, the precipitated product was filtered off, washed with $Et_2O$ and finally dried in vacuo to afford compound D (34.5 g, 46.2 mmol). LC-MS [M+H] 685.4 ($C_{33}H_{44}N_6O_6S_2$+H, calc: 685.9). Compound D was used without further purification.

Preparation 5

Synthesis of 4-[(S)-5-({Amino-[(E)-2,2,4,6,7-pentamethyl-2,3-dihydro-benzofuran-5-sulfonylimino]-methyl}-amino)-2-(naphthalene-2-sulfonylamino)-pentanoyl]-piperazine-1-carboxylic acid ethyl ester (E)

To a solution of compound D (8.0 g, 11.1 mmol) in $CHCl_3$ (50 mL) was added DIEA (4.1 mL, 23.3 mmol) at room temperature and stirred for 15 min. The mixture was cooled to ~5° C., ethyl chloroformate (1.06 mL, 11.1 mmol) was added dropwise. After stirring at room temperature overnight (~18 h), solvent removed in vacuo. The residue was dissolved in MeOH (~25 mL) and $Et_2O$ (~500 mL) was added. The precipitated crude product was filtered off, washed with $Et_2O$ and dried in vacuo to afford compound E (8.5 g, 11.1 mmol). LC-MS [M+H] 757.6 ($C_{36}H_{48}N_6O_8S_2$+H, calc: 757.9). Compound E was used without further purification.

Synthesis of (S)-ethyl 4-(5-guanidino-2-(naphthalene-2-sulfonamido)pentanoyl)piperazine-1-carboxylate (Compound 101)

A solution of 5% m-cresol/TFA (50 mL) was added to compound E (8.5 g, 11.1 mmol) at room temperature. After stirring for 1 h, the reaction mixture was precipitated with $Et_2O$ (500 mL). The precipitate was filtered and washed with $Et_2O$ and dried in vacuo to afford the crude product. The crude product was purified by preparative reverse phase HPLC. [Column: VARIAN, LOAD & LOCK, L&L 4002-2, Packing: Microsorb 100-10 C18, Injection, Volume: ~15 mL×2, Injection flow rate: 20 mL/min, 100% A, (water/0.1% TFA), Flow rate: 100 mL/min, Fraction: 30 Sec (50 mL), Method: 0% B (MeCN/0.1% TFA)-60% B/60 min/100 mL/min/254 nm]. Solvents were removed from pure fractions in vacuo. Trace of water was removed by co-evaporation with 2×i-PrOH (50 mL). The residue was dissolved in a minimum amount of i-PrOH and product was precipitated with 2 M HCl in $Et_2O$. Product was filtered off and washed with $Et_2O$ and dried in vacuo to afford Compound 101 as HCl salt 7 (3.78 g, 63% yield, 99.4% purity). LC-MS [M+H] 505.4 ($C_{38}H_{52}N_6O_8S_2$+H, calc: 505.6).

Example 2

Synthesis of (S)-ethyl 4-(5-guanidino-2-(2,4,6-triisopropylphenylsulfonamido)pentanoyl)piperazine-1-carboxylate (Compound 102)

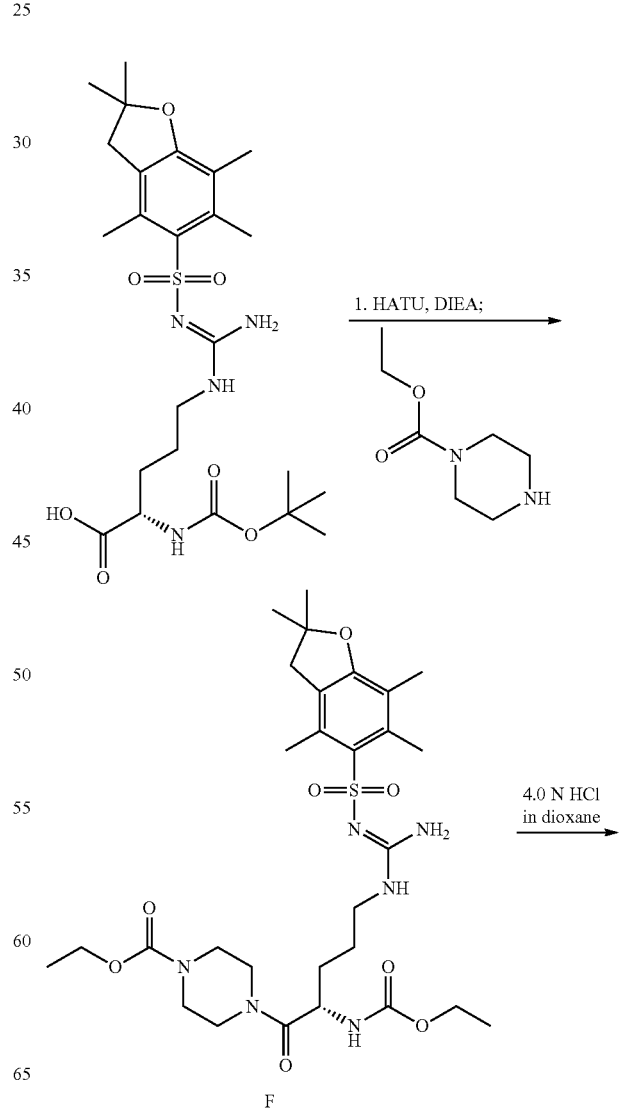

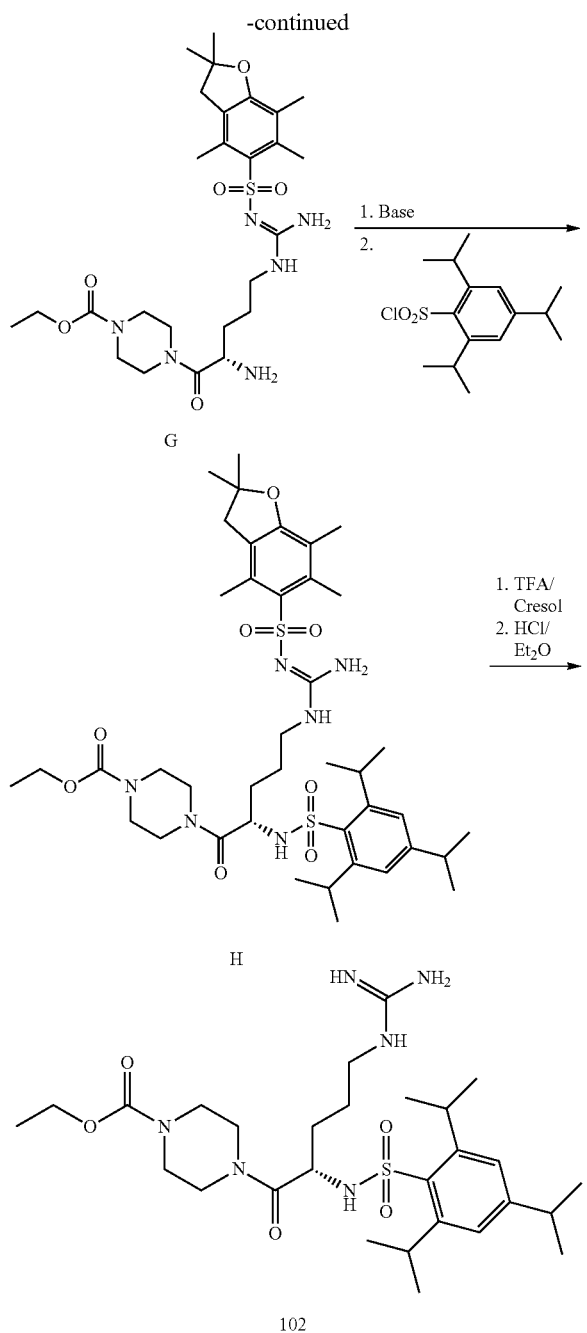

Preparation 6

Synthesis of 4-[(S)-5-({Amino-[(E)-2,2,4,6,7-pentamethyl-2,3-dihydro-benzofuran-5-sulfonylimino]-methyl}-amino)-2-tert-butoxycarbonylamino-pentanoyl]-piperazine-1-carboxylic acid ethyl ester (F)

To a solution of Boc-Arg(Pbf)-OH (13.3 g, 25.3 mmol) in DMF (10 mL) was added DIEA (22.0 mL, 126.5 mmol) at room temperature and stirred for 15 min. The reaction mixture was then cooled to ~5° C. and HATU (11.5 g, 30.3 mmol) was added in portions and stirred for 30 min, followed by the dropwise addition of ethyl-1-piperazine carboxylate (4.0 g, 25.3 mmol) in DMF (30 mL). After 40 min, the reaction mixture was diluted with EtOAc (400 mL) and poured into $H_2O$ (1 L). Extracted with EtOAc (2×400 mL) and washed with $H_2O$ (800 mL), 2% $H_2SO_4$ (500 mL), $H_2O$ (2×800 mL) and brine (800 mL). Organic layer was separated, dried over $MgSO_4$ and solvent removed in vacuo. The resultant oily residue was dried in vacuo to afford compound F (16.4 g, 24.5 mmol) as foamy solid. LC-MS [M+H] 667.2 ($C_{31}H_{50}N_6O_8S$+H, calc: 667.8). Compound F was used without further purification.

Preparation 7

Synthesis of 4-[(S)-2-Amino-5-({amino-[(E)-2,2,4,6,7-pentamethyl-2,3-dihydro-benzofuran-5 sulfonylimino]-methyl}-amino)-pentanoyl]-piperazine-1-carboxylic acid ethyl ester (G)

A solution of compound F (20.2 g, 30.2 mmol) in dichloromethane (90 mL) was treated with 4.0 N HCl in 1,4-dioxane (90 mL, 363.3 mmol) and stirred at room temperature for 2 h. Next most of the dichloromethane (~90%) was removed in vacuo and $Et_2O$ (~1 L) was added. The resultant precipitate was filtered off and washed with $Et_2O$ and dried in vacuo to afford compound G (17.8 g, 30.2 mmol). LC-MS [M+H] 567.8 ($C_{26}H_{42}N_6O_6S$+H, calc: 567.8). Compound G was used without further purification.

Preparation 8

Synthesis of 4-[(S)-5-({Amino-[(E)-2,2,4,6,7-pentamethyl-2,3-dihydro-benzofuran-5-sulfonylimino]-methyl}-amino)-2-(2,4,6-triisopropyl-benzenesulfonylamino)-pentanoyl]-piperazine-1-carboxylic acid ethyl ester (H)

To a solution of compound G (1.0 g, 1.8 mmol) in THF (7 mL) was added 3.1N aqueous NaOH (4.0 mL) and stirred for 5 min. The reaction mixture was cooled to ~5° C., and then a solution of tripsyl chloride added dropwise (2.2 g, 7.3 mmol) in THF (5 mL) and stirred at room temperature overnight (~18 h). The reaction mixture was diluted with $H_2O$ (130 mL), acidified with 2% $H_2SO_4$ (15 mL) and extracted with EtOAc (3×80 mL). Organic layer were combined and washed with $H_2O$ (2×400 mL), saturated $NaHCO_3$ (100 mL), $H_2O$ (200 mL) and brine (200 mL). The organic layer was separated, dried over $MgSO_4$ and solvent removed in vacuo to afford (2.9 g) of crude product. This was purified by normal phase flash chromatography (5-10% MeOH/DCM) to afford compound H (0.52 g, 1.0 mmol). LC-MS [M+H] 833.8 ($C_{41}H_{64}N_6O_8S_2$+H, calc: 834.1).

Synthesis of (S)-ethyl 4-(5-guanidino-2-(2,4,6-triisopropylphenylsulfonamido)pentanoyl)piperazine-1-carboxylate (Compound 102)

A solution of 5% m-cresol/TFA (40 mL) was added to compound H (3.73 g, 3.32 mmol) at room temperature. After stirring for 45 min, solvents were removed in vacuo. Residue was dissolved in dichloromethane (100 mL), washed with $H_2O$ (3×200 mL) and brine (200 mL). The organic layer was separated, dried over $MgSO_4$ and then the solvent removed in vacuo. The residue was dissolved in dichloromethane (~5 mL) and then hexane (250 mL) was added and a precipitate was formed. This was washed with hexane and dried in vacuo to afford the crude product (1.95 g). The crude product was purified by reverse phase HPLC [Column: VARIAN, LOAD & LOCK, L&L 4002-2, Packing:

Microsorb 100-10 C18, Injection Volume: ~15 mL, Injection flow rate: 20 mL/min, 100% A, (water/0.1% TFA), Flow rate: 100 mL/min, Fraction: 30 Sec (50 mL), Method: 25% B (MeCN/0.1% TFA)/70% B/98 min/100 mL/min/254 nm]. Solvents were removed from pure fractions in vacuo. Trace of water was removed by co-evaporation with 2×i-PrOH (50 mL). The residue was dissolved in a minimum amount of i-PrOH and product was precipitated with 2 M HCl in Et$_2$O. Product was filtered off and washed with Et$_2$O and dried in vacuo to afford the product as HCl salt of Compound 102 (0.72 g, 35% yield, 99.8% purity). LC-MS [M+H] 581.6 ($C_{28}H_{48}N_6O_5S$+H, calc: 581.7).

Example 3

Synthesis of (S)-ethyl 1-(5-guanidino-2-(naphthalene-2-sulfonamido)pentanoyl)piperidine-4-carboxylate HCl salt (Compound 103)

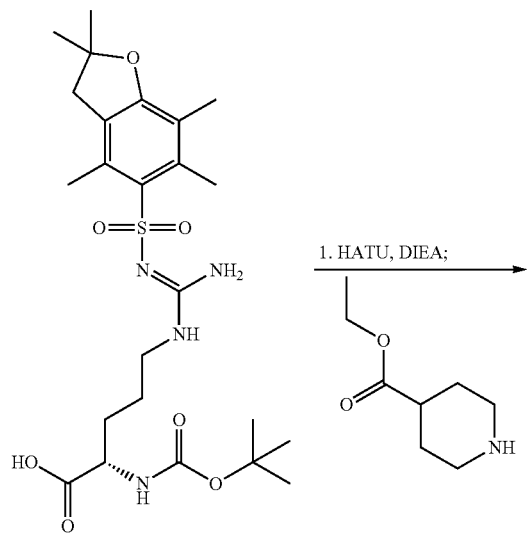

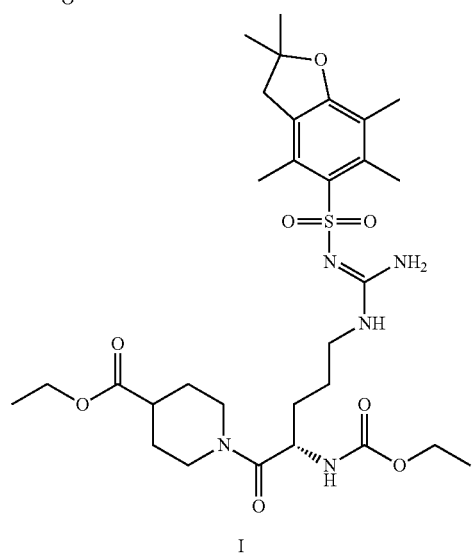

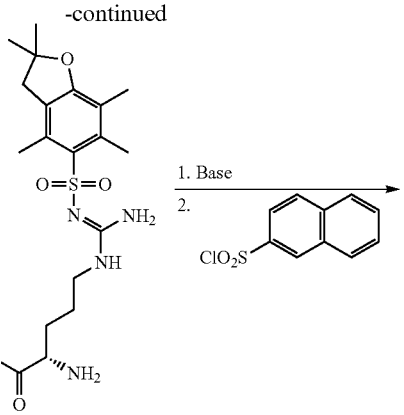

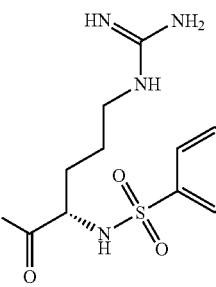

Preparation 9

Synthesis of 1-[boc-Arg(Pbf)]-piperidine-4-carboxylic acid ethyl ester (I)

To a solution of Boc-Arg(Pbf)-OH (3.4 g, 6.36 mmol) and HATU (2.9 g, 7.63 mmol) in DMF (15 mL) was added DIEA (7.4 mL, 42.4 mmol) and the reaction mixture was stirred for 10 min at room temperature. A solution of ethyl isonipecotate (1.0 g, 6.36 mmol) in DMF (6 mL) was added to the reaction mixture dropwise. The reaction mixture was stirred at room temperature for 1 h, then diluted with EtOAc (150 mL) and poured into water (500 mL). The product was extracted with EtOAc (2×100 mL). The organic layer was washed with aqueous 0.1 N HCl (200 mL), 2% aqueous sodium bicarbonate (200 mL), water (200 mL) and brine (200 mL). The organic layer was then dried over sodium sulfate, filtered, and then evaporated in vacuo. The resultant oily product was dried in vacuo overnight to give compound I (3.7 g, 5.57 mmol) as a viscous solid. LC-MS [M+H] 666.5 ($C_{32}H_{51}N_5O_8S$+H, calc: 666.7). Compound I was used without further purification.

Preparation 10

Synthesis of 1-[Arg(Pbf)]-piperidine-4-carboxylic acid ethyl ester HCl salt (J)

To a solution of compound I (4.7 g, 7.07 mmol) in dichloromethane (25 mL) was added 4N HCl in dioxane (25.0 mL, 84.84 mmol), and the reaction mixture was stirred at room temperature for 2 h. The reaction mixture was concentrated in vacuo to ~20 mL of solvent, and then diluted with diethyl ether (250 mL) to produce a white fine precipitate. The reaction mixture was stirred for 1 h and the solid was washed with ether (50 mL) and dried in vacuo overnight to give compound J (4.3 g, 7.07 mmol) as a fine powder. LC-MS [M+H] 566.5 ($C_{27}H_{43}N_5O_6S$+H, calc: 566.7). Compound J was used without further purification.

Preparation 11

Synthesis of 1-[5(S)—(N'-Pbf-guanidino)-2-(naphthalene-2-sulfonylamino)-pentanoyl]-piperidine-4-carboxylic acid ethyl ester (K)

To a solution of compound J (1.1 g, 1.6 mmol) and NaOH (260 mg, 5.9 mmol) in a mixture of THF (5 mL) and water (3 mL) was added a solution of 2-naphthalosulfonyl chloride (0.91 g, 2.5 mmol) in THF (10 mL) dropwise with stirring at ~5° C. The reaction mixture was stirred at room temperature for 1 h, then diluted with water (5 mL). Aqueous 1N HCl (5 mL) was added to obtain pH~3. Additional water was added (20 mL), and the product was extracted with ethyl acetate (3×50 mL). The organic layer was removed and then washed with 2% aqueous sodium bicarbonate (50 mL), water (50 mL) and brine (50 mL). The extract was dried over anhydrous sodium sulfate, filtered, and was evaporated in vacuo. The formed oily product was dried in vacuo overnight to give compound K (1.3 g, 1.6 mmol) as an oily foaming solid. LC-MS [M+H] 756.5 ($C_{37}H_{49}N_5O_8S_2$+H, calc: 756.7). Compound K was used without further purification.

Synthesis of (S)-ethyl 1-(5-guanidino-2-(naphthalene-2-sulfonamido)pentanoyl)piperidine-4-carboxylate HCl salt (Compound 103)

To a flask, was added compound K (1.3 g, 1.6 mmol) and then treated with 5% m-cresol/TFA (10 mL). The reaction mixture was stirred at room temperature for 1 h. Next, the reaction mixture was concentrated in vacuo to a volume ~5 mL. Diethyl ether (200 mL) was then added to the residue, and formed fine white precipitate. The precipitate was filtered off and washed with ether (2×25 mL). The resultant solid was dried in vacuo overnight to give a crude material, which was purified by preparative reverse phase HPLC. [Nanosyn-Pack Microsorb (100-10)C-18 column (50×300 mm); flow rate: 100 mL/min; injection volume 12 mL (DMSO-water, 1:1, v/v); mobile phase A: 100% water, 0.1% TFA; mobile phase B: 100% ACN, 0.1% TFA; gradient elution from 25% B to 55% B in 90 min, detection at 254 nm]. Fractions containing desired compound were combined and concentrated in vacuo. The residue was dissolved in i-PrOH (50 mL) and evaporated in vacuo (repeated twice). The residue was next dissolved in i-PrOH (5 mL) and treated with 2 N HCl/ether (100 mL, 200 mmol) to give a white precipitate. It was dried in vacuo overnight to give Compound 103 (306 mg, 31% yield, 95.7% purity) as a white solid. LC-MS [M+H] 504.5 ($C_{24}H_{33}N_5O_5S$+H, calc: 504.6).

Example 4

Synthesis of (S)-ethyl 1-(5-guanidino-2-(2,4,6-triisopropylphenylsulfonamido)pentanoyl)piperidine-4-carboxylate HCl salt (Compound 104)

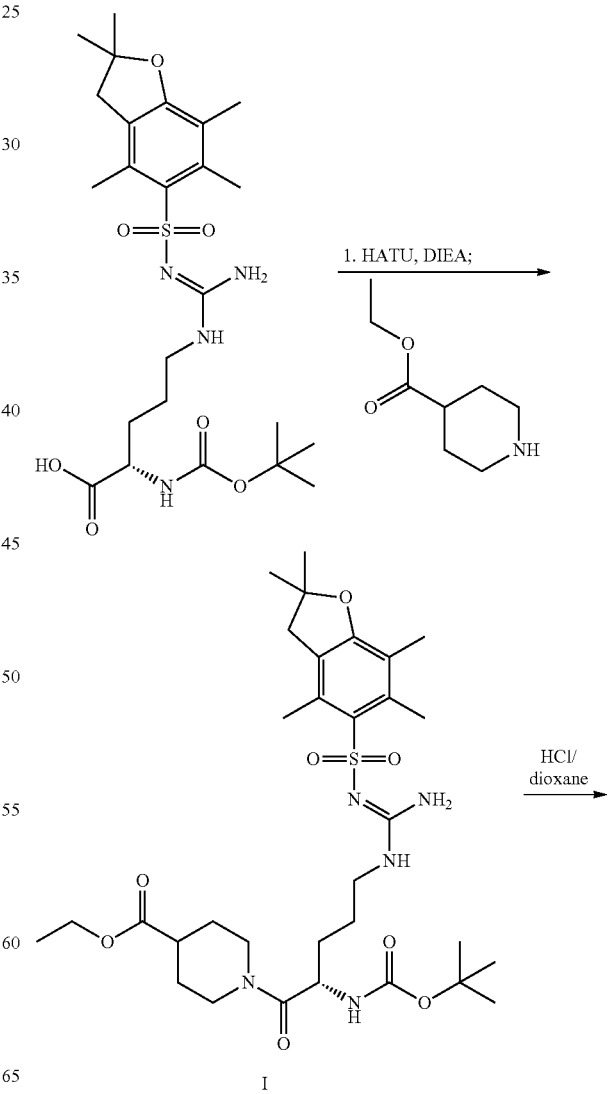

-continued

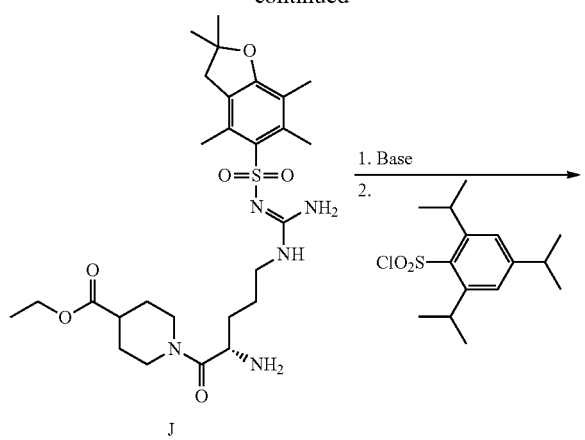

J

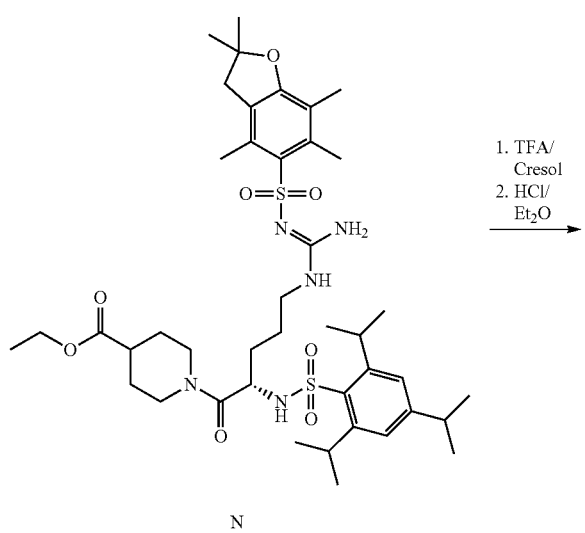

N

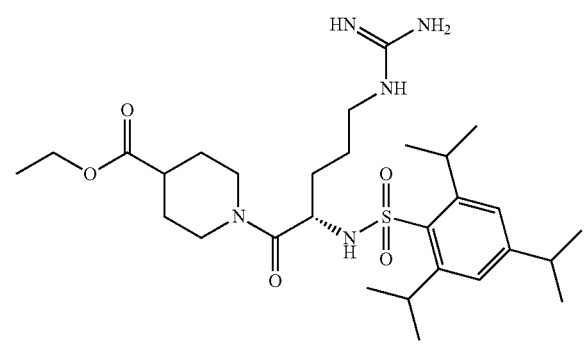

104

Preparation 12

Synthesis of 1-[5(S)—(N'-Pbf-guanidino)-2-(2,4,6-triisopropyl-benzenesulfonylamino)-pentanoyl]-piperidine-4-carboxylic acid ethyl ester (N)

To a solution of compound J (1.0 g, 1.6 mmol) and NaOH (420.0 mg, 10.4 mmol) in a mixture of THF (5 mL) and water (4 mL) was added a solution of 2,4,6-triisopropyl-benzenesulfonyl chloride (2.4 g, 8.0 mmol) dropwise with stirring and maintained at ~5° C. The reaction mixture was then stirred at room temperature for 1 h, monitoring the reaction progress, then diluted with water (20 mL), and acidified with aqueous 1 N HCl (5 mL) to pH ~3. Additional water was added (30 mL), and the product was extracted with EtOAc (3×50 mL). The organic layer was washed with 2% aqueous sodium bicarbonate (50 mL), water (50 mL) and brine (50 mL). The organic layer was dried over anhydrous sodium sulfate, filtered, and was evaporated in vacuo. Formed oily residue was dried in a vacuo overnight to give compound N (1.0 g, 1.2 mmol) as an oily material. LC-MS [M+H] 832.8 ($C_{42}H_{65}N_5O_8S_2$+H, calc: 832.7). Compound N was used without further purification.

Synthesis of (S)-ethyl 1-(5-guanidino-2-(2,4,6-tri-isopropylphenylsulfonamido)pentanoyl)piperidine-4-carboxylate HCl salt (Compound 104)

To a flask was added compound N (2.3 g, 2.8 mmol) and then treated with 5% m-cresol/TFA (16 mL). The reaction mixture was stirred at room temperature for 1 h. The reaction mixture was then concentrated in vacuo to a volume of 5 mL. Hexane (200 mL) was added to the residue and decanted off to give an oily precipitate. The product was purified by preparative reverse phase HPLC. [Nanosyn-Pack Microsorb (100-10)C-18 column (50×300 mm); flow rate: 100 mL/min; injection volume 15 mL (DMSO-water, 1:1, v/v); mobile phase A: 100% water, 0.1% TFA; mobile phase B: 100% ACN, 0.1% TFA; gradient elution from 35% B to 70% B in 90 min, detection at 254 nm]. Fractions containing desired compound were combined and concentrated in vacuo. The residue was dissolved in i-PrOH (100 mL) and evaporated in vacuo (repeated twice). The residue was dissolved in i-PrOH (5 mL) and treated with 2 N HCl/ether (100 mL, 200 mmol) to give an oily residue. It was dried in vacuo overnight to give Compound 104 (1.08 g, 62.8%) as a viscous solid. LC-MS [M+H] 580.6 ($C_{29}H_{49}N_5O_5S$+H, calc: 580.8).

Example 5
Synthesis of (S)-6-(4-(5-guanidino-2-(naphthalene-2-sulfonamido)pentanoyl)piperazin-1-yl)-6-oxo-hexanoic acid (Compound 105)
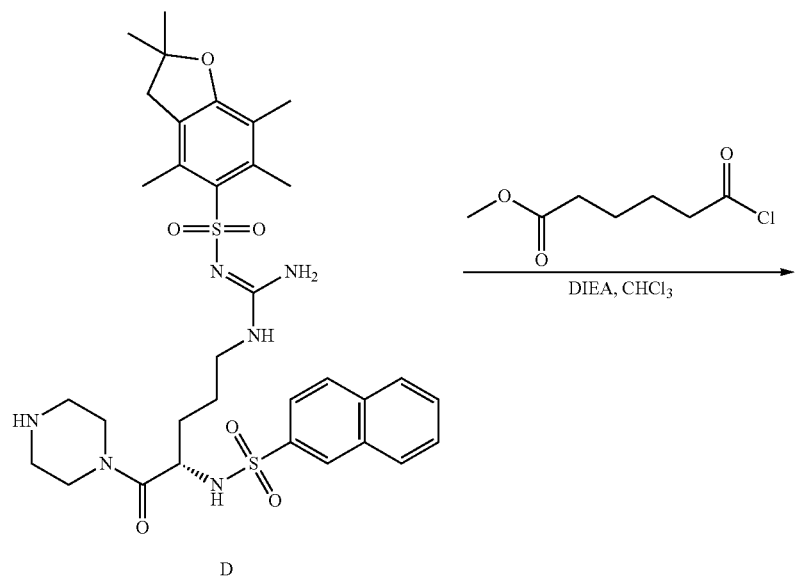
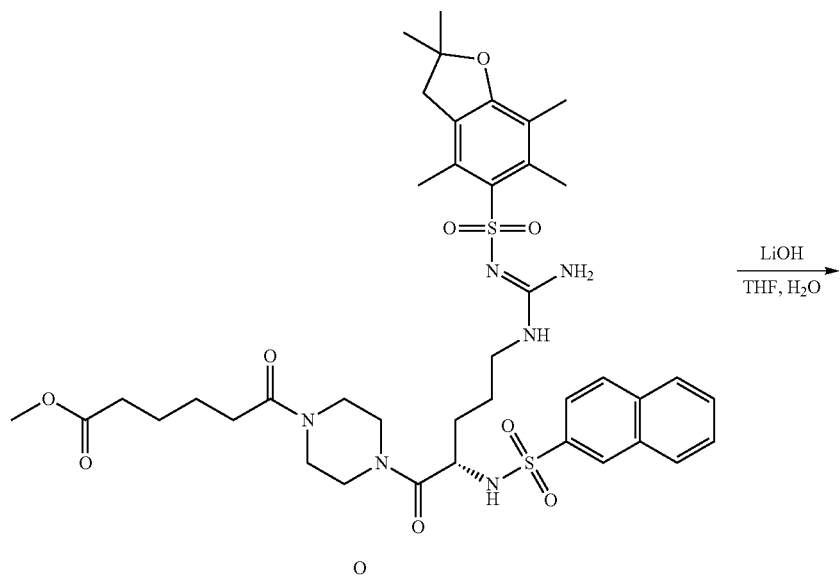

-continued

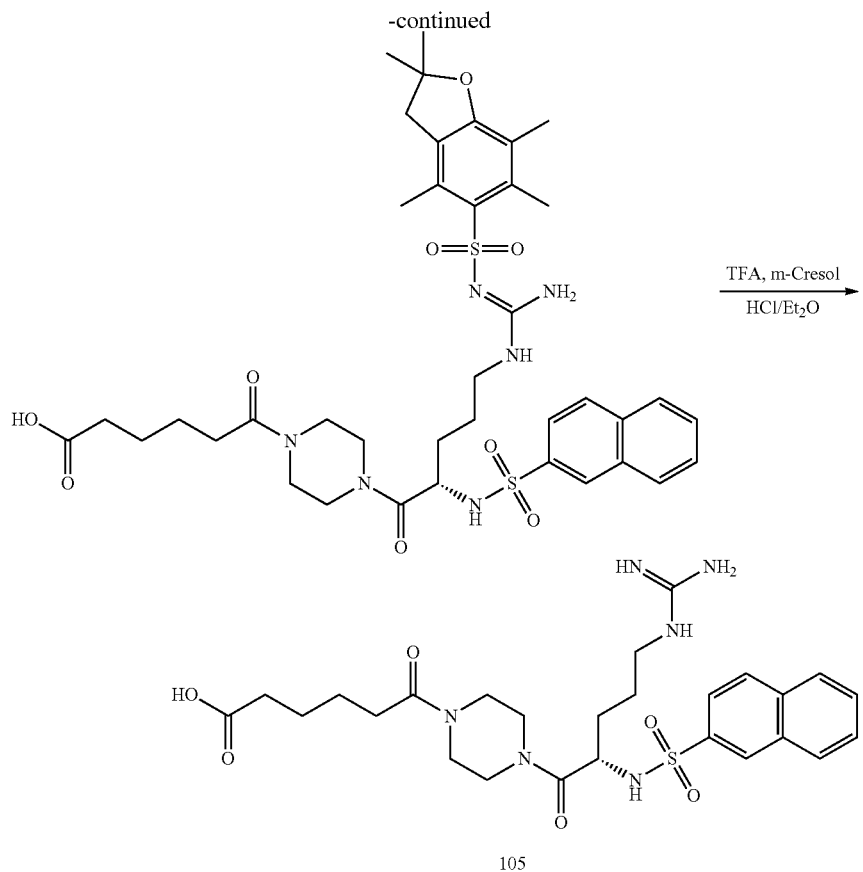

105

Preparation 13

Synthesis of 6-{4-[(S)-5-({Amino-[(E)-2,2,4,6,7-pentamethyl-2,3-dihydro-benzofuran-5-sulfonylimino]-methyl}-amino)-2-(naphthalene-2-sulfonylamino)-pentanoyl]-piperazin-1-yl}-6-oxo-hexanoic acid methyl ester (O)

To a solution of compound D (1.5 g, 2.08 mmol) in CHCl$_3$ (50 mL) was added DIEA (1.21 mL, 4.16 mmol) followed by adipoyl chloride (0.83 mL, 6.93 mmol) dropwise. The reaction mixture was stirred at room temperature overnight (~18 h). Solvents were removed in vacuo and the residue was dried in vacuo to afford the compound O (2.1 g, amount exceeded quantitative). LC-MS [M+H] 827.5 ($C_{40}H_{54}N_6O_9S_2$+H, calc: 827.3). Compound O was used without further purification.

Preparation 14

Synthesis of 6-{4-[(S)-5-({Amino-[(E)-2,2,4,6,7-pentamethyl-2,3-dihydro-benzofuran-5-sulfonylimino]-methyl}-amino)-2-(naphthalene-2-sulfonylamino)-pentanoyl]-piperazin-1-yl}-6-oxohexanoic acid (P)

To a solution of compound O (2.1 g, 2.08 mmol) in THF (5 mL), H$_2$O (5 mL) was added 2 M aq LiOH (6 mL). The reaction mixture was stirred at room temperature for 2 h. Solvents were removed in vacuo, then the residue was dissolved in water (~50 mL), acidified with saturated aqueous NaHSO$_4$ (~100 mL) and extracted with EtOAc (2×100 mL). The organic layer was dried over Na$_2$SO$_4$ and removal of the solvent gave compound P (1.72 g, 2.08 mmol). LC-MS [M+H] 813.5 ($C_{39}H_{52}N_6O_9S_2$+H, calc: 813.3). Compound P was used without further purification.

Synthesis of (S)-6-(4-(5-guanidino-2-(naphthalene-2-sulfonamido)pentanoyl)piperazin-1-yl)-6-oxohexanoic acid (Compound 105)

A solution of 5% m-cresol/TFA (25 mL) was added to compound P (1.72 g, 2.08 mmol) at room temperature. After stirring for 30 min, the reaction mixture was precipitated with addition of Et$_2$O (~200 mL). The precipitate was filtered and washed with Et$_2$O and dried in vacuo to afford the crude product. The crude product was purified by preparative reverse phase HPLC [Column: VARIAN, LOAD & LOCK, L&L 4002-2, Packing: Microsorb 100-10 C18, Injection Volume: ~25 mL, Injection flow rate: 20 mL/min, 95% A, (water/0.1% TFA), Flow rate: 100 mL/min, Fraction: 30 Sec (50 mL), Method: 5% B (MeCN/0.1% TFA)/5 min/25% B/20 min/25% B/15 min/50% B/25 min/100 mL/min/254 nm]. Solvents were removed from pure fractions in vacuo. Trace amounts of water was removed by co-evaporation with i-PrOH (25 mL) (repeated twice). The residue was dissolved in a minimum amount of i-PrOH, then 2 M HCl in Et$_2$O (~50 mL) was added and diluted with Et$_2$O (~250 mL). Precipitate formed was filtered off and washed with Et$_2$O and dried in vacuo to afford the product as HCl salt Compound 105 (0.74 g, 59% yield, 98.9% purity). LC-MS [M+H] 561.4 ($C_{26}H_{36}N_6O_6S$+H, calc: 561.2).

Example 6

Synthesis of 3-(4-carbamimidoylphenyl)-2-oxopropanoic acid (Compound 107)

Compound 107, i.e., 3-(4-carbamimidoylphenyl)-2-oxopropanoic acid can be produced using methods known to those skilled in the art, such as that described by Richter P et al, Pharmazie, 1977, 32, 216-220 and references contained within. The purity of Compound 107 used herein was estimated to be 76%, an estimate due low UV absorbance of this compound via HPLC. Mass spec data: LC-MS [M+H] 207.0 ($C_{10}H_{10}N_2O_3$+H, calc: 207.1).

Example 7

Synthesis of (S)-5-(4-carbamimidoylbenzylamino)-5-oxo-4-((R)-4-phenyl-2-(phenylmethylsulfonamido)butanamido)pentanoic acid (Compound 108)

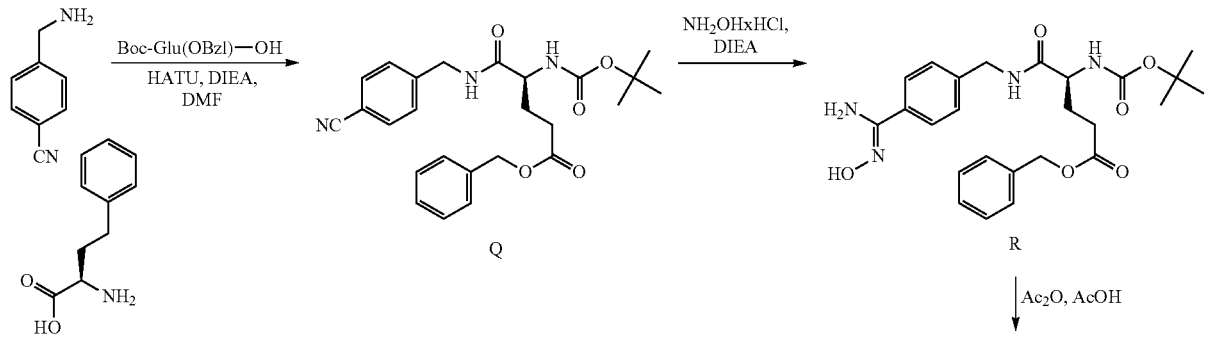

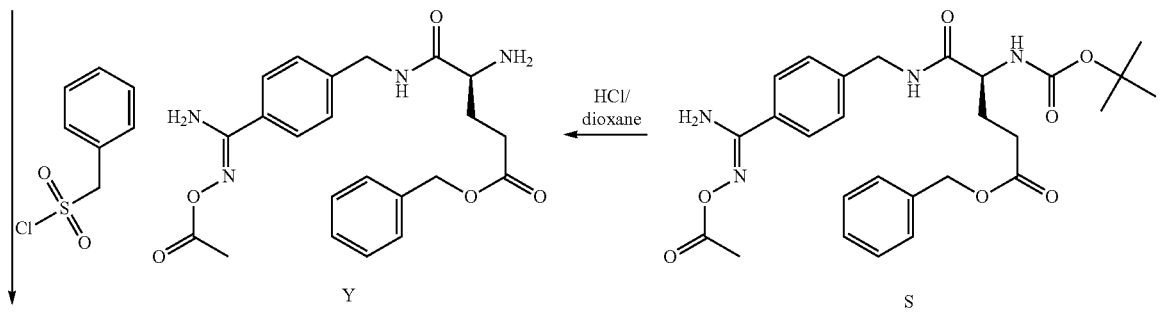

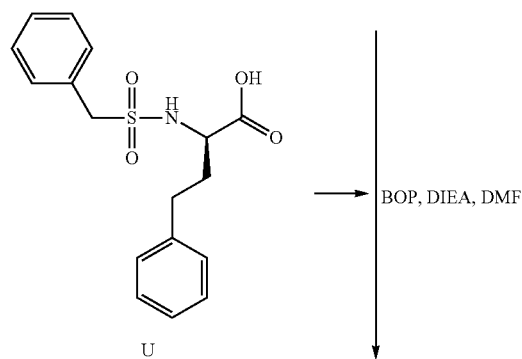

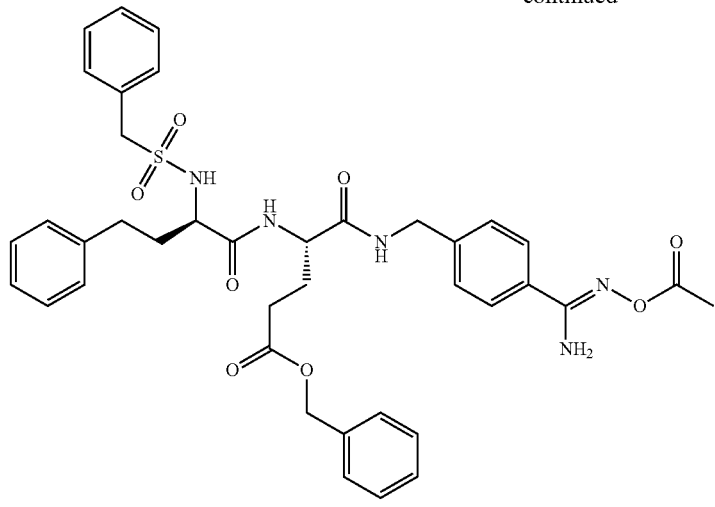

V

↓ H₂/Pd/C, AcOH/water

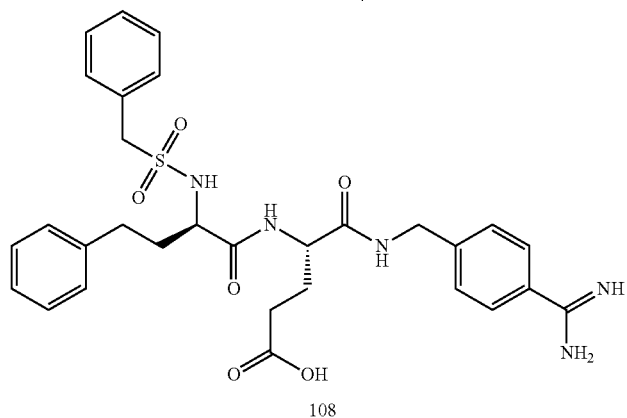

108

Preparation 15

Synthesis of (S)-4-tert-butoxycarbonylamino-4-(4-cyano-benzylcarbamoyl)-butyric acid benzyl ester (Q)

A solution of Boc-Glu(OBzl)-OH (7.08 g, 21.0 mmol), BOP (9.72 g, 22.0 mmol) and DIEA (12.18 mL, 70.0 mmol) in DMF (50 mL) was maintained at room temperature for 20 min, followed by the addition of 4-(aminomethyl)benzonitrile hydrochloride (3.38 g, 20.0 mmol). The reaction mixture was stirred at room temperature for an additional 1 h and diluted with EtOAc (500 mL). The obtained solution was extracted with water (100 mL), 5% aq. NaHCO₃ (100 mL) and water (2×100 mL). The organic layer was dried over MgSO₄, evaporated and dried in vacuo to provide compound Q (9.65 g, yield exceeded quantitative) as yellowish oil. LC-MS [M+H] 452.0 ($C_{25}H_{29}N_3O_5$+H, calc: 452.4). Compound Q was used without further purification.

Preparation 16

Synthesis of (S)-4-tert-butoxycarbonylamino-4-[4-(N-hydroxycarbamimidoyl)-benzyl carbamoyl]-butyric acid benzyl ester (R)

A solution of compound Q (9.65 g, 20.0 mmol), hydroxylamine hydrochloride (2.10 g, 30.0 mmol) and DIEA (5.22 mL, 30.0 mmol) in ethanol (abs., 150 mL) was refluxed for 6 h. The reaction mixture was allowed to cool to room temperature and stirred for additional 16 h. The solvents were evaporated in vacuo. The resultant residue was dried in vacuo to provide compound R (14.8 g, yield exceeded quantitative) as yellowish oil. LC-MS [M+H] 485.5 ($C_{25}H_{32}N_4O_6$+H, calc: 485.8). Compound R was used without further purification.

Preparation 17

Synthesis of (S)-4-tert-butoxycarbonylamino-4-[4-(N-acetylhydroxycarbamimidoyl)-benzyl carbamoyl]-butyric acid benzyl ester (S)

A solution of compound R (14.8 g, 20.0 mmol) and acetic anhydride (5.7 mL, 60.0 mmol) in acetic acid (100 mL) was stirred at room temperature for 45 min, and then solvent was evaporated in vacuo. The resultant residue was dissolved in EtOAc (300 mL) and extracted with water (2×75 mL) and brine (75 mL). The organic layer was then dried over $MgSO_4$, evaporated and dried in vacuo to provide compound S (9.58 g, 18.2 mmol) as yellowish solid. LC-MS [M+H] 527.6 ($C_{27}H_{34}N_4O_7$+H, calc: 527.9). Compound S was used without further purification.

Preparation 18

Synthesis of (S)-4-[4-(N-acetylhydroxycarbamimidoyl)-benzyl carbamoyl]-butyric acid benzyl ester (T)

Compound S (9.58 g, 18.2 mmol) was dissolved in 1,4-dioxane (50 mL) and treated with 4 N HCl/dioxane (50 mL, 200 mmol) at room temperature for 1 h. Next, the solvent was evaporated in vacuo. The resultant residue was triturated with ether (200 mL). The obtained precipitate was filtered, washed with ether (100 mL) and hexane (50 mL) and dried in vacuo to provide compound T (9.64 g, yield exceeded quantitative) as off-white solid. LC-MS [M+H] 426.9 ($C_{22}H_{26}N_4O_5$+H, calc: 427.3). Compound T was used without further purification.

Preparation 19

Synthesis of (R)-4-phenyl-2-phenylmethanesulfonylamino-butyric acid (U)

A solution of D-homo-phenylalanine (10.0 g, 55.9 mmol) and NaOH (3.35 g, 83.8 mmol) in a mixture of 1,4-dioxane (80 mL) and water (50 mL) was cooled to ~5° C., followed by alternate addition of α-toluenesulfonyl chloride (16.0 g, 83.8 mmol; 5 portions by 3.2 g) and 1.12 M NaOH (50 mL, 55.9 mmol; 5 portions by 10 mL) maintaining pH>10. The reaction mixture was then acidified with 2% aq. $H_2SO_4$ to a pH of about pH 2. The obtained solution was extracted with EtOAc (2×200 mL). The obtained organic layer was washed with water (3×75 mL), dried over $MgSO_4$ and then the solvent was evaporated in vacuo. The resultant residue was dried in vacuo to provide compound U (12.6 g, 37.5 mmol) as white solid. LC-MS [M+H] 334.2 ($C_{17}H_{19}NO_4S$+H, calc: 333.4). Compound U was used without further purification.

Preparation 20

Synthesis of (S)-4-[4-(N-acetylhydroxycarbamimidoyl)-benzylcarbamoyl]-4-((R)-4-phenyl-2-phenylmethanesulfonylamino-butyrylamino)-butyric acid benzyl ester (V)

A solution of compound U (5.9 g, 17.8 mmol), compound T di-hydrochloride (18.0 mmol), BOP (8.65 g, 19.6 mmol) and DIEA (10.96 mL, 19.6 mmol) in DMF (250 mL) was stirred at room temperature for 2 h. The reaction mixture was then diluted with EtOAc (750 mL) and extracted with water (200 mL). The formed precipitate was filtered, washed with EtOAc (200 mL) and water (200 mL) and dried at room temperature overnight (~18 h) to provide compound V (8.2 g, 11.0 mmol) as off-white solid. LC-MS [M+H] 743.6 ($C_{39}H_{43}N_5O_8S$+H, calc: 743.9). Compound V was used without further purification.

Synthesis of (S)-5-(4-carbamimidoylbenzylamino)-5-oxo-4-((R)-4-phenyl-2-(phenylmethylsulfonamido)butanamido)pentanoic acid (Compound 108)

Compound V (8.0 g, 10.77 mmol) was dissolved in acetic acid (700 mL) followed by the addition of Pd/C (5% wt, 3.0 g) as a suspension in water (50 mL). Reaction mixture was subjected to hydrogenation (Parr apparatus, 50 psi $H_2$) at room temperature for 3 h. The catalyst was filtered over a pad of Celite on sintered glass filter and washed with methanol. Filtrate was evaporated in vacuo to provide Compound 108 as colorless oil. LC-MS [M+H] 594.2 ($C_{30}H_{35}N_5O_6S$+H, calc: 594). Obtained oil was dissolved in water (150 mL) and subjected to HPLC purification. [Nanosyn-Pack YMC-ODS-A (100-10)C-18 column (75×300 mm); flow rate: 250 mL/min; injection volume 150 mL; mobile phase A: 100% water, 0.1% TFA; mobile phase B: 100% acetonitrile, 0.1% TFA; isocratic elution at 10% B in 4 min., gradient elution to 24% B in 18 min, isocratic elution at 24% B in 20 min, gradient elution from 24% B to 58% B in 68 min; detection at 254 nm]. Fractions containing desired compound were combined and concentrated in vacuo. Residue was dissolved in i-PrOH (75 mL) and evaporated in vacuo (procedure was repeated twice) to provide Compound 108 (4.5 g, 70% yield, 98.0% purity) as white solid. LC-MS [M+H] 594.2 ($C_{30}H_{35}N_5O_6S$+H, calc: 594). Retention time*: 3.55 min. *—[Chromolith SpeedRod RP-18e C18 column (4.6×50 mm); flow rate 1.5 mL/min; mobile phase A: 0.1% TFA/water; mobile phase B 0.1% TFA/acetonitrile; gradient elution from 5% B to 100% B over 9.6 min, detection 254 nm]

Synthesis of Ketone-Modified Opioid Prodrugs

Example 8: Synthesis of N,N-Bis(tert-butyl) N'-2-(chlorocarbonyl(methyl)amino)ethylcarbamate

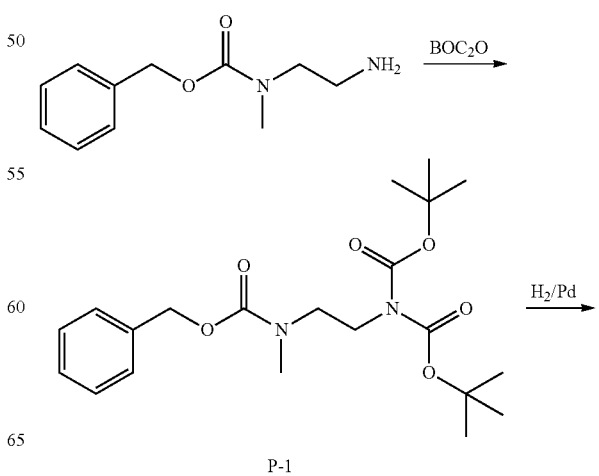

P-1

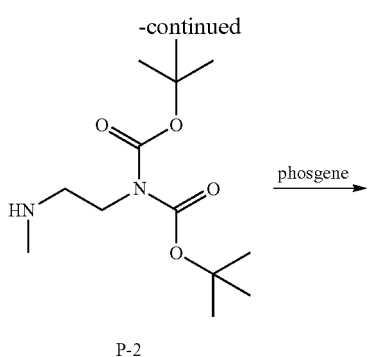

P-2

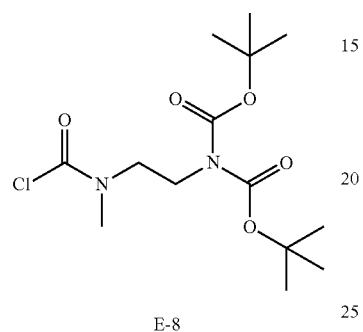

E-8

Preparation 21: Synthesis of [2-(Benzyloxycarbonyl-methyl-amino)-ethyl]-dicarbamic acid tert-butyl ester (P-1)

2-(Aminoethyl)-methyl-carbamic acid benzyl ester (2.0 g, 9.6 mmol) was dissolved in dichloroethene (DCE) (20 mL) at room temperature. Triethyl amine (NEt$_3$) (1.40 mL, 11.5 mmol) was added, followed by di-tert-butyl dicarbonate (BOC$_2$O) (10.5 g, 48 mmol) and dimethylaminopyridine (DMAP) (120 mg). The reaction mixture was stirred at room temperature under nitrogen (N$_2$) for 2 h and then heated at 60° C. for 16 h. The reaction mixture was then concentrated. The residue was purified by silica gel chromatography, using 4/1 hexanes/EtOAc, to give P-1 in 86% yield (3.4 g, 8.3 mmol). MS: (m/z) calc: 408.2, observed (M+Na$^+$) 431.9.

Preparation 22: Synthesis of N1,N1-bis-BOC-N2-methylethane-1,2-diamine (P-2)

P-1 (1.3 g, 3.18 mmol) was dissolved in methanol/EtOAc (10 mL/3 mL respectively). The mixture was degassed and saturated with N$_2$. Palladium on carbon (Pd/C) (330 mg, 5% on carbon) was added. The mixture was shaken in a Parr hydrogenator flask (50 psi H$_2$) for 4 h. The mixture was then filtered through a celite pad and the filtrate was concentrated to give P-2 (1.08 g, yield exceeded quantative). P-2 was used without further purification.

Synthesis of N,N-Bis(tert-butyl) N'-2-(chlorocarbonyl(methyl)amino)ethylcarbamate (E-8)

P-2 (500 mg, 1.82 mmol) and NEt$_3$ (0.4 mL, 2.74 mmol) was mixed together in dichloromethane (4 mL). The mixture was added to a pre-chilled to 0° C. solution of phosgene (5.5 mL, 0.5 M in toluene). The reaction mixture was stirred at 0° C. for 1 h, followed by dilution with ether (20 mL) and filtered through filter paper. The filtrate was concentrated and passed through a short silica gel column (10 cm×3 cm), eluted with 3/1 hexanes/EtOAc. The fractions were concentrated to give N,N-Bis(tert-butyl) N'-2-(chlorocarbonyl(methyl)amino)ethylcarbamate (E-8) as a colorless solid in quantative yield (615 mg, 1.82 mmol). MS: (m/z) calc: 336.1, observed (M+Na$^+$) 359.8.

Example 9: Synthesis of Oxycodone 6-(N-methyl-N-(2-amino)ethylcarbamate-2TFA

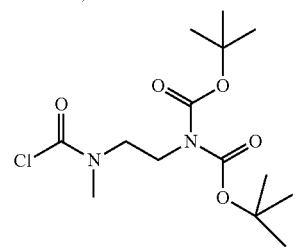

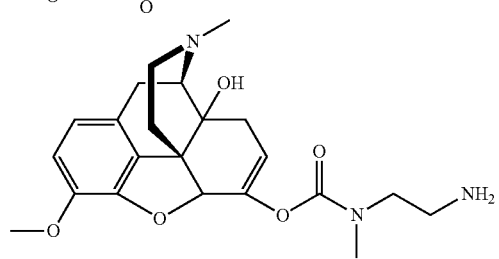

E-9

Synthesis of oxycodone 6-(N-methyl-N-(2-amino)ethylcarbamate-2TFA

Oxycodone free base (6.5 g, 20.6 mmol) was dissolved in dry, degassed tetrahydrofuran (120 mL), and the mixture was cooled to ~-10° C. using dry ice/acetone bath. Potassium bis(trimethylsilyl)amide (KHMDS) (103.0 mL, 51.6 mmol, 0.5 M in toluene) was added via cannula. The mixture was stirred under N$_2$ at below -5° C. for 30 min. N,N-Bis(tert-butyl) N'-2-(chlorocarbonyl(methyl)amino)ethylcarbamate (8.0 g, 23.7 mmol), (E-8) prepared as described in Example 8, in THF (30 mL) was then added via cannula over 15 min. The mixture was stirred at -5° C. for 30 min. Another portion of carbamoyl chloride (4.0 g, 11.9 mmol) in THF (10 mL) was added. The reaction was stirred at room temperature for 2 h. Sodium bicarbonate (10 mL, sat. aq.) was added. The mixture was concentrated in vacuo to half of its initial volume. EtOAc (50 mL) was added and layers were separated. The organic phase was further washed with water (3×20 mL), brine (40 mL) and then was concentrated. The residue was purified by silica gel chromatography, using DCM/MeOH (gradient 100/1 to 100/15) to afford a white foam in 55% yield (7.0 g, 13.4 mmol). This material was dissolved in a 1:1 mixture of DCM/trifluoroacetic acid (TFA) (20 mL/20 mL) at room temperature and stirred for 1 h. The solution was then concentrated in vacuo to afford oxycodone 6-(N-methyl-N-(2-amino)ethylcarbamate-2TFA as a thick oil (7.3 g, 11.4 mmol, 99% purity). MS: (m/z) calc: 415.2, observed (M+H⁺) 416.5. The oxycodone 6-(N-methyl-N-(2-amino)ethylcarbamate-2TFA (E-9) was used without further purification.

Example 10: Synthesis of Oxycodone 6-(N-methyl-N-(2-N'-acetylarginylamino)) ethylcarbamate (Compound KC-2)

9, was dissolved in dimethylformamide (DMF) (60 mL). Boc-Arg(Pbf)-OH (6.0 g, 11.4 mmol), HATU (4.75 g, 12.5 mmol) and diisopropylethylamine (DIPEA) (6.0 mL, 34.4 mmol) were added in this order. The reaction was stirred at room temperature for 2 h. The mixture was then concentrated in vacuo and the residue was partitioned between

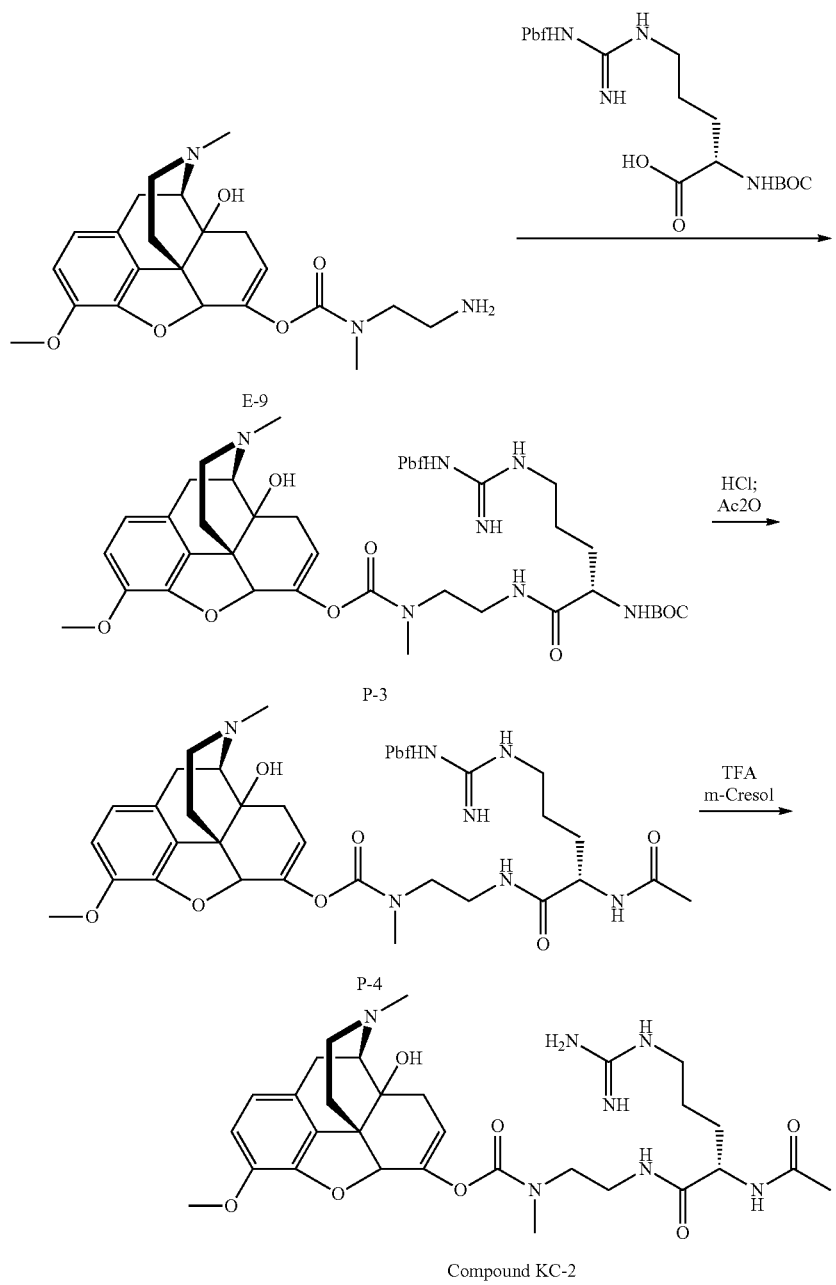

Preparation 23: Synthesis of oxycodone 6-(N-methyl-N-(2-N'—Boc-arginyl(Pbf)amino))ethylcarbamate (P-3)

Oxycodone 6-(N-methyl-N-(2-amino)ethylcarbamate-2TFA (7.3 g, 11.4 mmol), prepared as described in Example EtOAc/water (100 mL/60 mL). The organic layer was washed with water (60 mL), brine (50 mL), dried over Na₂SO₄ and concentrated to afford crude P-3 (11.0 g). P-3 was used without further purification.

Preparation 24: Synthesis of oxycodone 6-(N-methyl-N-(2-N'-acetylarginyl(Pbf)amino))ethylcarbamate (P-4)

P-3 (11.0 g), prepared as described above, was dissolved into dioxane (10 mL) and cooled to 0° C. A hydrochloric acid (HCl) solution in dioxane (4 N, 30 mL) was added. The mixture was stirred at room temperature for 3 h and then concentrated in vacuo. 10 g of the crude mixture was dissolved in a mixture of DIPEA (5.0 mL 28.5 mmol) in DCM (60 mL). Acetic anhydride (1.4 mL, 14.3 mmol) was added drop wise. The reaction mixture was stirred at room temperature for 2 h. NaHCO$_3$ (30 mL, sat. aq.) was then added. The layers were separated and the DCM layer was dried over Na$_2$SO$_4$, filtered and concentrated to afford P-4 (8.5 g). P-4 was used without further purification.

Synthesis of oxycodone 6-(N-methyl-N-(2-N'-acetylarginylamino))ethylcarbamate, as the bis-TFA salt (Compound KC-2)

P-4 (8.5 g) was dissolved in a mixture of m-cresol (3 mL) in TFA (30 mL). The mixture was stirred at room temperature for 3 h. TFA was then removed in vacuo. The residue was dissolved into MeOH (10 mL) and added drop wise to a stirred HCl solution in ether (40 mL, 2 M). The white solid was filtered and washed with ethyl ether (4×30 mL). The white solid was further purified by prep HPLC (*RP-18e C18 column (4.6×50 mm); flow rate 1.5 mL/min; mobile phase A: 0.1% TFA/water; mobile phase B 0.1% TFA/acetonitrile (CH$_3$CN); gradient elution), yielding Compound KC-2 (3.5 g, 4.1 mmol, 96.6% purity). MS: (m/z) calc: 613.7, observed (M+H$^+$) 614.5.

Example 11: Synthesis of N—{(S)-4-guanidino-1-[2-(methyl-[(5R,9R,13S,14S)-4,5a-epoxy-6,7-didehydro-14-hydroxy-3-methoxy-17-methylmorphinan-6-oxy]carbonyl-amino)-ethylcarbamoyl]-butyl}-malonamic acid (Compound KC-3)

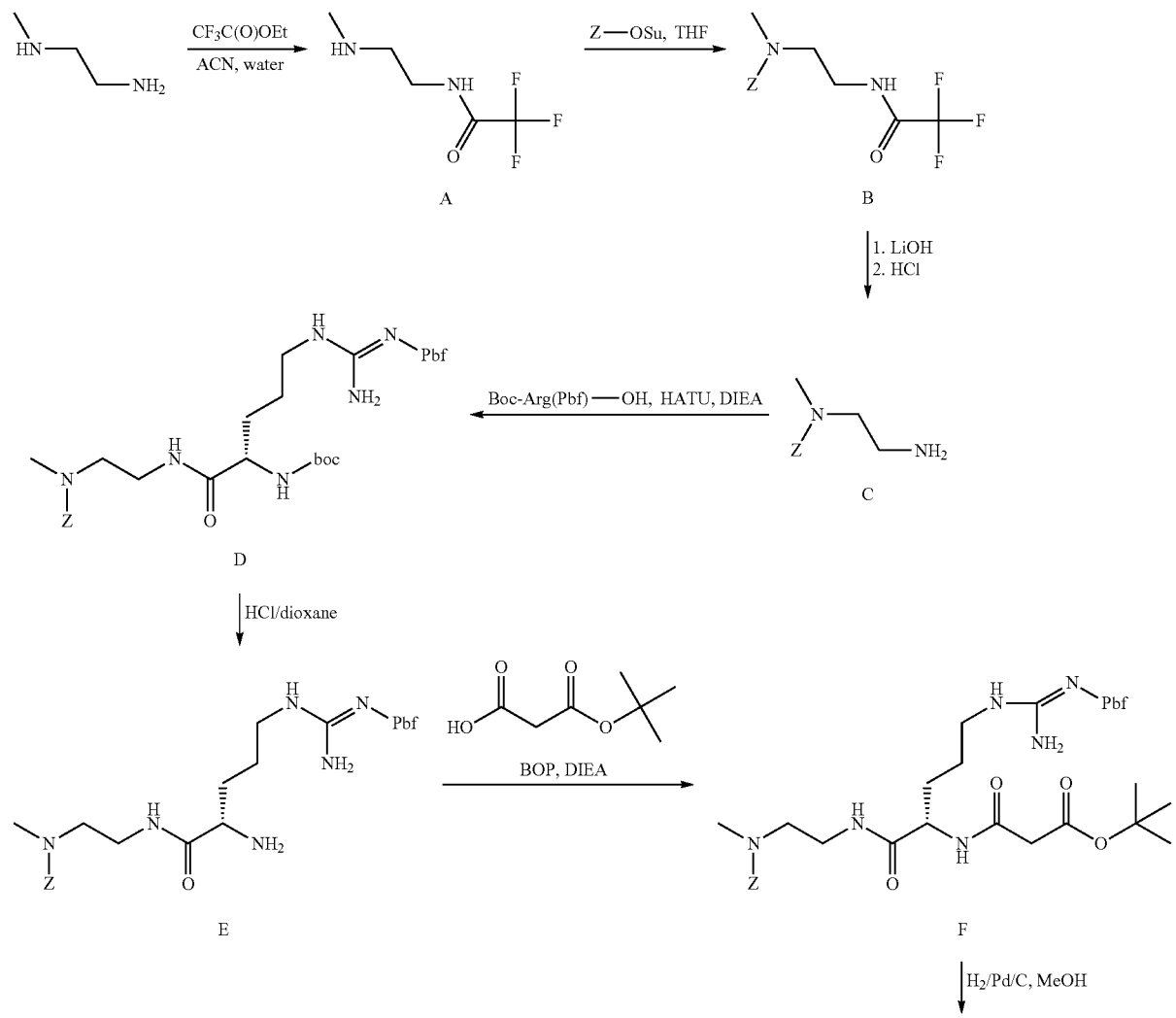

-continued

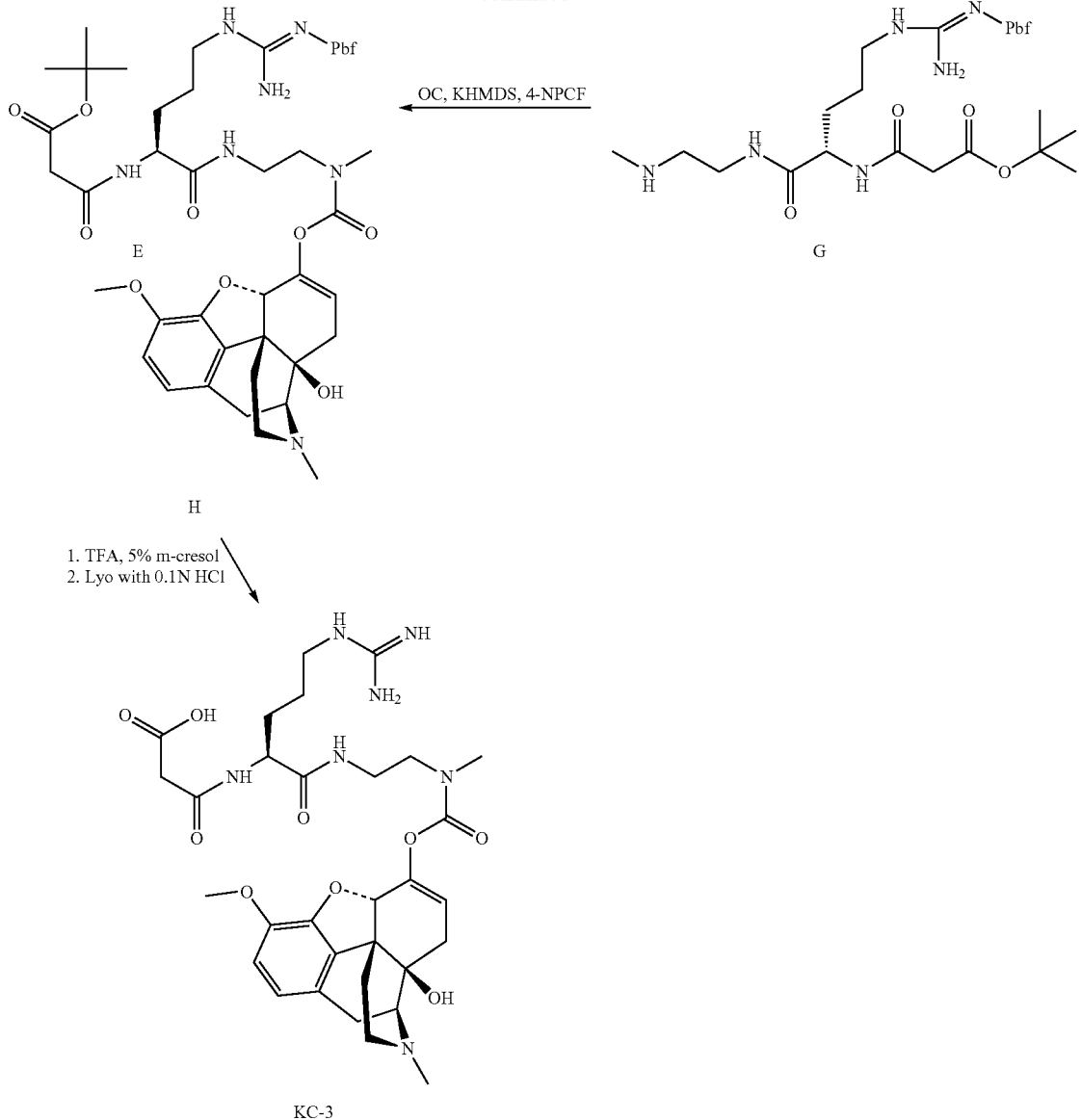

Preparation 25: Synthesis of 2,2,2-trifluoro-N-(2-methylamino-ethyl)-acetamide (A)

A solution of N-methylethylenediamine (27.0 g, 364 mmol) and ethyl trifluoroacetate (96.6 mL, 812 mmol) in a mixture of ACN (350 mL) and water (7.8 mL, 436 mmol) was refluxed with stirring overnight. Solvents were evaporated in vacuo. The residue was re-evaporated with i-PrOH (3×100 mL), followed by heat-cool crystallization from DCM (500 mL). Formed crystals were filtered, washed with DCM and dried in vacuo to provide compound A (88.3 g, 85%) as white solid powder.

Preparation 26: Synthesis of methyl-[2-(2,2,2-trifluoro-acetylamino)-ethyl]-carbamic acid benzyl ester (B)

A solution of compound A (88.2 g, 311 mmol) and DIEA (54.1 mL, 311 mmol) in THF (350 mL) was cooled in an ice bath, followed by the addition of a solution of N-(benzyloxycarbonyl)succinimide (76.6 g, 307 mmol) in THF (150 mL) drop wise over the period of 20 min. The temperature of the reaction mixture was raised to ambient temperature and stirring was continued for an additional 30 min. Solvents were then evaporated and the resulting residue was dissolved in EtOAc (600 mL). The organic layer was extracted with 5% aq. NaHCO$_3$ (2×150 mL) and brine (150 mL). The organic layer was evaporated to provide compound B as yellowish oil. LC-MS [M+H] 305.1 ($C_{13}H_{15}F_3N_2O_3$+H, calc: 305.3). Compound B was used directly in the next reaction without purification as a MeOH solution.

Preparation 27: Synthesis of (2-amino-ethyl)-methyl-carbamic acid benzyl ester (C)

To a solution of compound B (~311 mmol) in MeOH (1.2 L) was added a solution of LiOH (14.9 g, 622 mmol) in water (120 mL). The reaction mixture was stirred at ambient temperature for 3 h. Solvents were evaporated to 75% of the initial volume followed by dilution with water (400 mL). The solution was extracted with EtOAc (2×300 mL). The organic layer was washed with brine (200 mL), dried over $MgSO_4$ and evaporated in vacuo. The residue was dissolved in ether (300 mL) and treated with 2 N HCl/ether (200 mL). Formed precipitate was filtrated, washed with ether and dried in vacuo to provide the hydrochloric salt of compound C (67.8 g, 89%) as a white solid. LC-MS [M+H] 209.0 ($C_{11}H_{16}N_2O_2$+H, calc: 209.3). Compound C was used directly in the next reaction without purification as a DMF solution.

Preparation 28: Synthesis of {2-[boc-Arg(Pbf)]-aminoethyl}-methyl-carbamic acid benzyl ester (D)

A solution of Boc-Arg(Pbf)-OH (16.0 g, ~30.4 mmol), compound C hydrochloride (8.2 g, 33.4 mmol) and DIEA (16.9 mL, 97.2 mmol) in DMF (150 mL) was cooled in an ice bath followed by the addition of a solution of HATU (13.8 g, 36.4 mmol) drop wise over 20 min. The temperature of the reaction mixture was raised to ambient temperature and stirring was continued for an additional 1 h. The reaction mixture was diluted with EtOAc (1 L) and extracted with water (3×200 mL) and brine (200 mL). The organic layer was dried over $MgSO_4$ and evaporated to provide compound D (24.4 g, yield exceeded quantitative) as a yellowish oil. LC-MS [M+H] 717.4 ($C_{35}H_{52}N_6O_8S$+H, calc: 717.9). Compound D was used directly in the next reaction without purification as a dioxane solution.

Preparation 29: Synthesis of {2-[H-Arg(Pbf)]-aminoethyl}-methyl-carbamic acid benzyl ester (E)

Compound D (24.4 g, ~30.4 mmol) was dissolved in dioxane (150 mL) and treated with 4 N HCl/dioxane (150 mL, 600 mmol) at ambient temperature for 1 h. The solvent was then evaporated. The residue was suspended in i-PrOH (100 mL) and the mixture was evaporated (procedure was repeated twice). The residue was then dried in vacuo to provide compound E (21.1 g, yield exceeded quantitative) as a yellowish solid. LC-MS [M+H] 617.5 ($C_{30}H_{44}N_6O_6S$+H, calc: 617.8). Compound E was used directly in the next reaction without purification as a DMF solution.

Preparation 30: Synthesis of {2-[2-tert-butylmalonyl-Arg(Pbf)]-aminoethyl}-methyl-carbamic acid benzyl ester (F)

A solution of compound E (21.1 g, ~30.4 mmol), mono-tert-butyl malonate (5.9 mL, 36.7 mmol), BOP (16.2 g, 36.7 mmol) and DIEA (14.9 mL, 83.5 mmol) in DMF (100 mL) was maintained at ambient temperature for 1 h. The reaction mixture was diluted with EtOAc (1 L) and extracted with water (500 mL), 5% aq. $NaHCO_3$ (500 mL), water (3×500 mL) and brine (500 mL). The organic layer was dried over $MgSO_4$, filtered, and then evaporated to provide compound F (24.5 g, 97%) as a yellowish amorphous solid. LC-MS [M+H] 759.6 ($C_{37}H_{54}N_6O_9S$+H, calc: 759.9). Compound F was used without further purification.

Preparation 31: Synthesis of N-{2-[2-tert-butylmalonyl-Arg(Pfb)]}-N'-methyl-ethane-1,2-diamine (G)

Compound F (12.3 g, 16.7 mmol) was dissolved in methanol (100 mL) followed by the addition of a Pd/C (5% wt, 2.0 g) suspension in water (2 mL). The reaction mixture was subjected to hydrogenation (Parr apparatus, 70 psi $H_2$) at ambient temperature for 1 h. The catalyst was then filtered and washed with methanol. The filtrate was evaporated in vacuo to provide compound G (10.0 g, 99%) as a colorless amorphous solid. LC-MS [M+H] 625.5 ($C_{29}H_{48}N_6O_7S$+H, calc: 625.8). Compound G was used without further purification.

Preparation 32: Oxycodone Free Base

Oxycodone hydrochloride (10.0 g, 28.5 mmol) was dissolved in chloroform (150 mL) and washed with 5% aq. $NaHCO_3$ (50 mL). The organic layer was dried over $MgSO_4$ and evaporated. The residue was dried in vacuo overnight to provide oxycodone free base (8.3 g, 93%) as a white solid.

Preparation 33: Synthesis of N—{(S)-4-(2,2,4,6,7-pentamethyldihydrobenzofuran-5-sulfonyl-guanidino)-1-[2-(methyl-[(5R,9R,13S,14S)-4,5a-epoxy-6,7-didehydro-14-hydroxy-3-methoxy-17-methylmorphinan-6-oxy]carbonyl-amino)-ethylcarbamoyl]-butyl}-malonamic acid tert-butyl ester (H)

A solution of oxycodone free base (6.6 g, 21.0 mmol) in THF (400 mL) was cooled to −20° C., followed by addition of a 0.5 M solution of KHMDS in toluene (46.3 mL, 23.1 mmol). The obtained solution was then added to a solution of 4-nitro-phenyl chloroformate (4.3 g, 21.0 mmol) in THF (100 mL) drop wise over the period of 20 min at ~20° C. The reaction was maintained at −20° C. for an additional 1 h, followed by addition of a solution of compound G (10.0 g, 16.1 mmol) in THF (200 mL) at ~20° C. The reaction mixture was allowed to warm to ambient temperature and stirred overnight. Solvents were evaporated in vacuo. The resulting residue was dissolved in EtOAc (20 mL) and precipitated with ether (1 L). The formed precipitate was filtrated, washed with ether and dried in vacuo to provide compound H (13.6 g, 87%) as an off-white solid. LC-MS [M+H] 966.9 ($C_{48}H_{67}N_7O_{12}S$+H, calc: 966.2).

Synthesis of N—{(S)-4-guanidino-1-[2-(methyl-[(5R,9R,13S,14S)-4,5a-epoxy-6,7-didehydro-14-hydroxy-3-methoxy-17-methylmorphinan-6-oxy]carbonyl-amino)-ethylcarbamoyl]-butyl}-malonamic acid (Compound KC-3)

Compound H (13.6 g, 14.1 mmol) was dissolved in a mixture of 5% m-cresol/TFA (100 mL). The reaction mixture was maintained at ambient temperature for 1 h, followed by dilution with ethyl ether (1 L). The formed precipitate was filtered, washed with ether and hexane, and dried in vacuo to provide a TFA salt of Compound KC-3 (11.4 g, 81%) as an off-white solid. LC-MS [M+H] 658.6 ($C_{31}H_{43}N_7O_9$+H, calc: 658.7).

The TFA salt of crude Compound KC-3 (11.4 g, 11.4 mmol) was dissolved in water (50 mL). The obtained solution was subjected to HPLC purification. [Nanosyn-Pack YMC-GEL-ODS A (100-10)C-18 column (75×500 mm); flow rate: 250 mL/min; injection volume 50 mL; mobile phase A: 100% water, 0.1% TFA; mobile phase B: 100% ACN, 0.1% TFA; isocratic elution at 0% B in 4 min, gradient elution from 0% to 10% B in 20 min, isocratic elution at 10% B in 30 min, gradient elution from 10% B to 30% B in 41 min; detection at 254 nm]. Fractions containing Compound KC-3 were combined and concentrated in vacuo. The TFA counterion of the latter was replaced with an HCl counterion via lyophilization using 0.1N HCl to provide a HCl salt of Compound KC-3 (4.2 g, 41% yield) as a white solid. LC-MS [M+H] 658.6 ($C_{31}H_{43}N_7O_9$+H, calc: 658.7).

Example 12: Synthesis of N—((S)-1-{2-[(Dihydro-codein-6-enyloxycarbonyl)-methylamino]-ethylcarbamoyl-4-guanidino}-butyl)-malonamic acid (Compound KC-4)
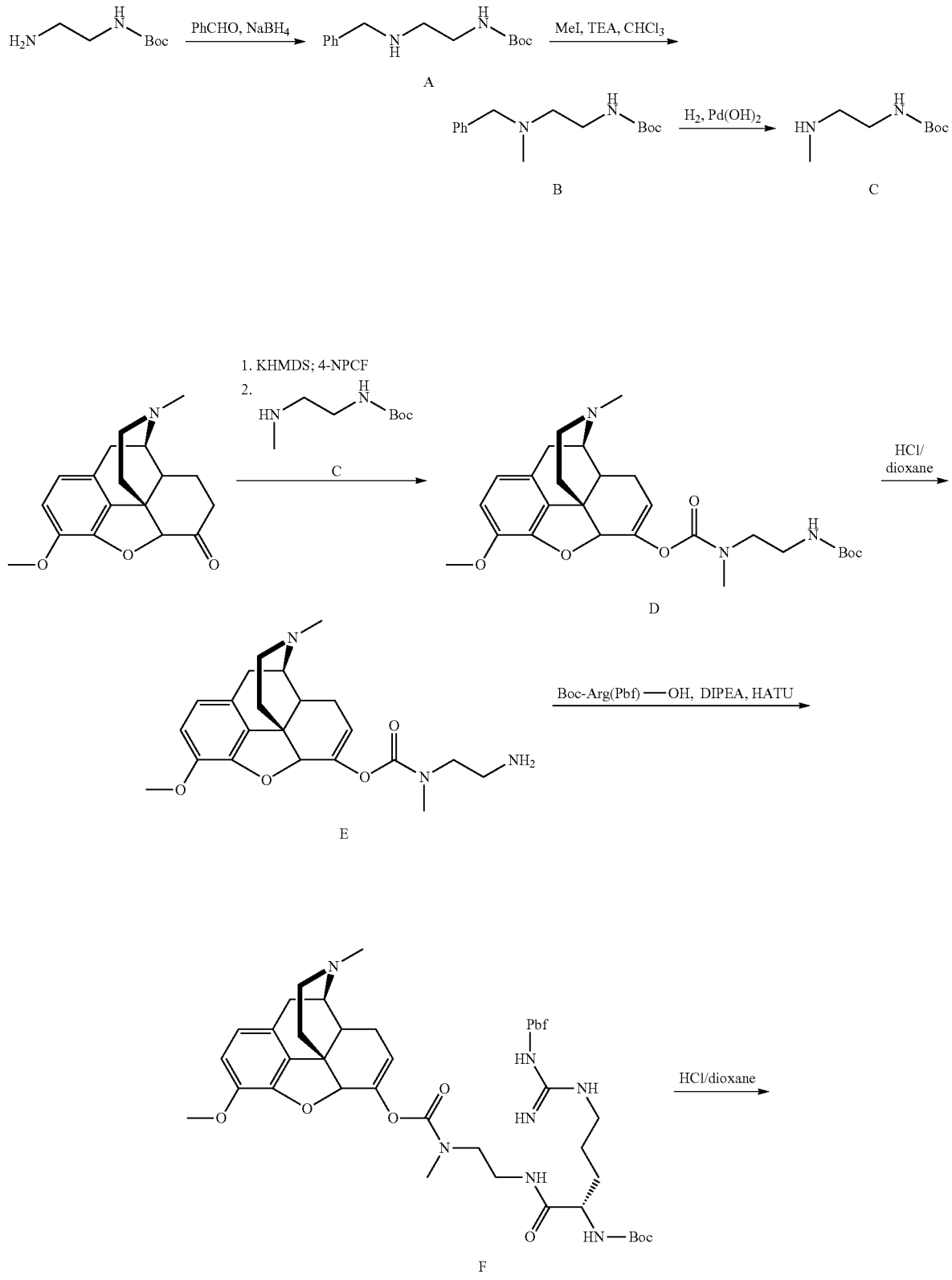

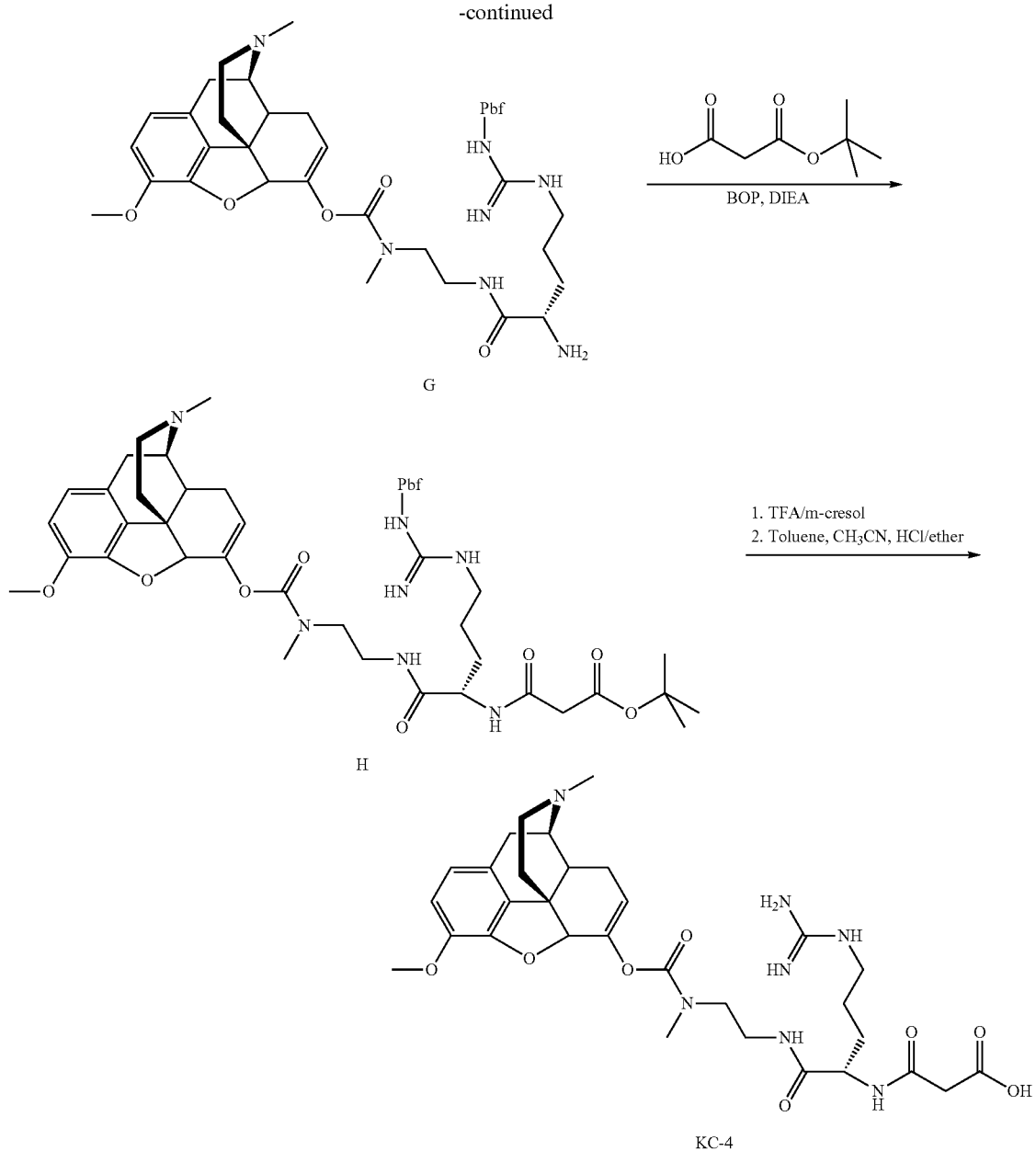

Preparation 34: Synthesis of tert-butyl 2-(benzylamino)ethylcarbamate (A)

To a solution of tert-butyl 2-aminoethylcarbamate (6.4 g, 40.0 mmol) in methanol (60 mL) was added benzaldehyde (4.7 g, 44.0 mmol) and molecular sieve 3 Å. After stirring at ambient temperature overnight, the mixture was cooled down to ca. −10° C. (ice/salt bath) and treated portion wise with NaBH$_4$ (9.1 g, 240.0 mmol) over 30 min. After complete addition, the bath was removed and the reaction mixture stirred at ambient temperature for 16 h. The solvent was evaporated and the residue taken into EtOAc (150 mL) and poured into water (100 mL). The organic layer was extracted with 0.5 N HCl (3×100 mL). The combined aqueous solution was cooled to 0° C., basified with sat. NaHCO$_3$ and extracted with CHCl$_3$ (3×100 mL). The combined organic layers were washed with brine (200 mL). After drying over MgSO$_4$ and filtering, the solvent was evaporated in vacuo to give compound A (9.2 g, 36.8 mmol, 92%) as a colorless oil. LC-MS [M+H] 251.2 (C$_{14}$H$_{22}$N$_2$O$_2$+H, calc: 251.3). TLC R$_f$(DCM/MeOH 9:1): 0.30. Compound A was used without further purification.

Preparation 35: Synthesis of tert-butyl 2-(N-benzyl-N-methylamino)ethylcarbamate (B)

To a cooled (~5° C.) solution of compound A (6.2 g, 25.0 mmol) and TEA (3.0 g, 29.7 mmol, 4.13 mL) in chloroform (50 mL) was added iodomethane (4.2 g, 29.7 mmol, 1.85 mL). The pressure tube was sealed, and the mixture stirred at ambient temperature for 20 h. The mixture was then precipitated with ether (300 mL); the white solid was filtered off and washed with ether (50 mL). The filtrate was concentrated and the residual yellow oil (5.2 g) was purified by silica gel column chromatography (2-10% MeOH gradient in DCM) to give compound B (3.3 g, 12.5 mmol, 50%) as a colorless oil. TLC $R_f$ (DCM/MeOH 9:1): 0.55. LC-MS [M+H] 264.3 ($C_{15}H_{24}N_2O_2$+H, calc: 264.4).

Preparation 36: Synthesis of tert-butyl 2-(methylamino)ethylcarbamate (C)

To a flask was added 20% Pd(OH)$_2$ on carbon (3.1 g), compound B (3.3 g, 12.5 mmol) in MeOH (200 mL) and water (10 mL), while being exposed to H$_2$ (40 psi). After 2.5 h, the reaction mixture was filtered through celite and concentrated in vacuo. Water was then added (50 mL) and the mixture brought to pH 12 (by addition of 1 N NaOH) and extracted with DCM (3×50 mL). The combined organic layers were dried over MgSO$_4$, filtered, and concentrated in vacuo to give compound C (2.0 g, 11.7 mmol, 94%) as a colorless oil. LC-MS [M+H] 686.5 ($C_{35}H_{51}N_5O_7S$+H, calc: 685.9). Compound C was used without further purification.

Preparation 37: Synthesis of [2-(N-dihydrocodein-6-enyloxycarbonyl-N-methylamino)ethyl]carbamic acid tert-butyl ester (D)

To a cooled (−5° C.) solution of hydrocodone (2.9 g, 9.8 mmol, free base) in anhydrous THF (150 mL) was added drop wise, a 0.5 M solution of KHMDS in toluene (11.6 mmol, 23.3 mL) over 20 min. The yellow solution was stirred at this temperature for 30 min. The solution was added through a cannula to a cooled solution (−30° C.) of 4-nitrophenyl chloroformate (1.9 g, 9.5 mmol) in anhydrous THF (40 mL) over 15 min. The bath was removed and the mixture stirred at ambient temperature for 15 min until treated drop wise with a solution of compound C (2.3 g, 11.6 mmol) in anhydrous THF (15 mL) over 10 min. After stirring at ambient temperature for 18 h, the reaction mixture was quenched with sat. NaHCO$_3$ solution (7 mL). The resulting precipitate was filtered, washed with EtOAc (30 mL) and the filtrate concentrated in vacuo. The residue was taken into EtOAc (300 mL) and washed with a mixture of water (100 mL) and 2% aq. H$_2$SO$_4$ (30 mL). The aqueous layer was basified with 2 N NaOH to pH 12 and extracted with EtOAc (2×200 mL). The combined organic layers were washed with water (2×400 mL) and brine (300 mL), dried over MgSO$_4$, filtered and concentrated in vacuo to give a yellowish foamy solid (5.9 g), which was purified by HPLC. [Nanosyn-Pack Microsorb (100-10)C-18 column (50×300 mm); flow rate: 100 mL/min; injection volume: 65 mL; mobile phase A: 100% water, 0.1% TFA; mobile phase B: 100% acetonitrile, 0.1% TFA; isocratic elution at 10% B in 5 min, gradient elution to 18% B in 8 min, isocratic elution at 18% B in 20 min, gradient elution from 18% B to 40% B in 44 min; detection at UV 254 nm]. Fractions containing the desired compound were combined and concentrated in vacuo. Traces of water were removed by treating the residue with toluene (30 mL) followed by evaporation in vacuo (procedure was repeated twice). The isolated fractions are a 1:1 mixture of compound D and the boc deprotected compound E (4.37 g, 7.85 mmol, 83%). LC-MS [M+H] 500.2 ($C_{27}H_{37}N_3O_6$+H, calc: 500.6). Retention time [Chromolith SpeedRod RP-18e C18 column (4.6×50 mm); flow rate: 1.5 ml/min; mobile phase A: 0.1% TFA/water; mobile phase B 0.1% TFA/ACN; gradient elution from 5% B to 100% B over 9.6 min, detection 254 nm]: 3.52 min (compound D), 1.82 (compound E).

Preparation 38: Synthesis of dihydrocodein-6-enyl-2-aminoethylmethylcarbamate (E)

A solution of compound D (4.4 g, 8.8 mmol) in DCM (40 mL) was treated with 4 M HCl in dioxane (105 mmol, 26 mL), leading to some precipitate formation. The mixture was homogenized by addition of acetonitrile (20 mL) and stirred at ambient temperature for 45 min. Ether (400 mL) was added and the resulting white precipitate filtered, washed with ether (50 mL) and hexane (50 mL) and then dried in vacuo to give compound E as an off-white solid (2.4 g, 4.7 mmol, 58%). LC-MS [M+H] 400.3 ($C_{22}H_{29}N_3O_4$+H, calc: 400.5). Compound E was used without further purification.

Preparation 39: Synthesis of {2-[boc-Arg(Pbf)]-aminomethyl}-ethyl carbamic acid hydrocodone ester (F)

Compound E (2.0 g, 4.0 mmol), Boc-Arg(Pbf)-OH (2.0 g, 3.8 mmol) and HATU (1.7 g, 4.3 mmol) were dissolved in DMF (40 mL), brought to ~5° C. and treated drop wise with DIPEA (3.2 mL, 18.1 mmol) over 10 min. The reaction mixture was stirred at ~5° C. for an additional 10 min and then warmed to ambient temperature, followed by stirring for 30 min. The reaction was then diluted with EtOAc (200 mL) and poured into water (250 mL). The layers were separated, the aqueous extracted with EtOAc (2×150 mL) and the combined organic layers washed with 2% aq. H$_2$SO$_4$ (30 mL), water (2×250 mL) and brine (250 mL). The organic layer was dried over MgSO$_4$, filtered and concentrated in vacuo to give compound F (3.0 g, 3.2 mmol, 83%) as a yellowish foamy solid. LC-MS [M+H] 908.7 ($C_{46}H_{65}N_7O_{10}S$+H, calc: 909.1). Compound F was used without further purification.

Preparation 40: Synthesis of {2-[H-Arg(Pbf)]-aminomethyl}-ethyl carbamic acid hydrocodone ester (G)

A solution of compound F (3.0 g, 3.3 mmol) in DCM (20 mL) was treated with 4 M HCl in dioxane (39 mmol, 9.8 mL) and stirred at ambient temperature for 30 min. Ether (500 mL) was added and the resulting white precipitate was filtered, washed with ether (50 mL) and hexane (50 mL) and then dried in vacuo to give compound G as an off-white solid (2.7 g, 3.0 mmol, 93%). LC-MS [M+H] 808.7 ($C_{41}H_{57}N_7O_8S$+H, calc: 809.0). Compound G was used without further purification.

Preparation 41: Synthesis of N—((S)-1-{2-[(Dihydrocodein-6-enyloxycarbonyl)-methylamino]-ethylcarbamoyl-4-guanidino(Pbf))-butyl}-malonamic acid tert-butyl ester (H)

To a cooled solution (~5° C.) of compound G (2.7 g, 3.0 mmol) was added mono tert-Butyl malonate (474 mg, 3.0 mmol, 438 µL) in DMF (25 mL) followed by BOP (1.4 g, 3.2 mmol) over 5 min and finally by DIEA (1.6 g, 12.1 mmol, 2.1 mL) drop wise over 10 min. After an additional 15 min, the ice bath was removed and the mixture stirred at ambient temperature. After 45 min, the reaction mixture was diluted with EtOAc (300 mL) and poured into water (200 mL). The layers were separated and the aqueous layer extracted with EtOAc (2×250 mL). The combined organic layers were washed with water (500 mL), 2% aq. H$_2$SO$_4$ (100 mL), water (3×500 mL) and brine (2×500 mL). After drying over MgSO$_4$, the solvent was evaporated in vacuo and the residue dried under high vacuum to give H (1.7 g, 1.8 mmol, 58%) as a yellowish solid. LC-MS [M+H] 950.8 (C$_{48}$H$_{67}$N$_7$O$_{11}$S+H, calc: 951.2). Compound H was used without further purification.

Synthesis of N—((S)-1-{2-[(Dihydrocodein-6-enyloxycarbonyl)-methylamino]-ethylcarbamoyl-4-guanidino-butyl)-malonamic acid (Compound KC-4)

A solution of compound H (1.7 g, 1.8 mmol) in 5% m-cresol/TFA (45 mL) was stirred at ambient temperature. After 1 h, the mixture was diluted with ether (300 mL). The resulting fine suspension was filtered, the solid washed with ether (30 mL) and hexane (30 mL) and dried in vacuo for 15 min. The crude material was dissolved in water (35 mL) and purified by HPLC [Nanosyn-Pack Microsorb (100-10)C-18 column (50×300 mm); flow rate: 100 mL/min; injection volume: 35 mL; mobile phase A: 100% water, 0.1% TFA; mobile phase B: 100% acetonitrile, 0.1% TFA; gradient elution 0 to 10% B in 10 min, isocratic elution at 10% B in 20 min, gradient elution from 10% B to 42% B in 60 min; detection at UV 254 nm]. Fractions containing the desired compound were combined and concentrated in vacuo. The residue was treated with toluene (50 mL) to remove traces of water and co-evaporated in vacuo (procedure repeated twice). The residue was dissolved in acetonitrile (5 mL), treated with 2.0 M HCl in ether (20 mL), followed by dilution with ether (100 mL). The resulting solid was filtered, washed with ether (20 mL) and hexane (20 mL) and dried in vacuo overnight to provide Compound KC-4 (1.1 g, 86% yield) as a white solid, hydrochloride salt. LC-MS [M+H] 642.5 (C$_{31}$H$_{43}$N$_7$O$_8$+H, calc: 642.7). Purity >95% (UV/254 nm). Retention time [Chromolith SpeedRod RP-18e C18 column (4.6×50 mm); flow rate: 1.5 ml/min; mobile phase A: 0.1% TFA/water; mobile phase B 0.1% TFA/ACN; gradient elution from 5% B to 100% B over 9.6 min, detection 254 nm]: 2.24 min.

Example 13: Synthesis of 6-{[2-(2-Acetylamino-5-guanidino-pentanoylamino)-ethyl]-[(5R,9R,13S,14S)-4,5a-epoxy-6,7-didehydro-14-hydroxy-3-methoxy-17-methylmorphinan-6-oxy]-1-enyloxycarbonyl-amino}-hexanoic acid (Compound KC-5)

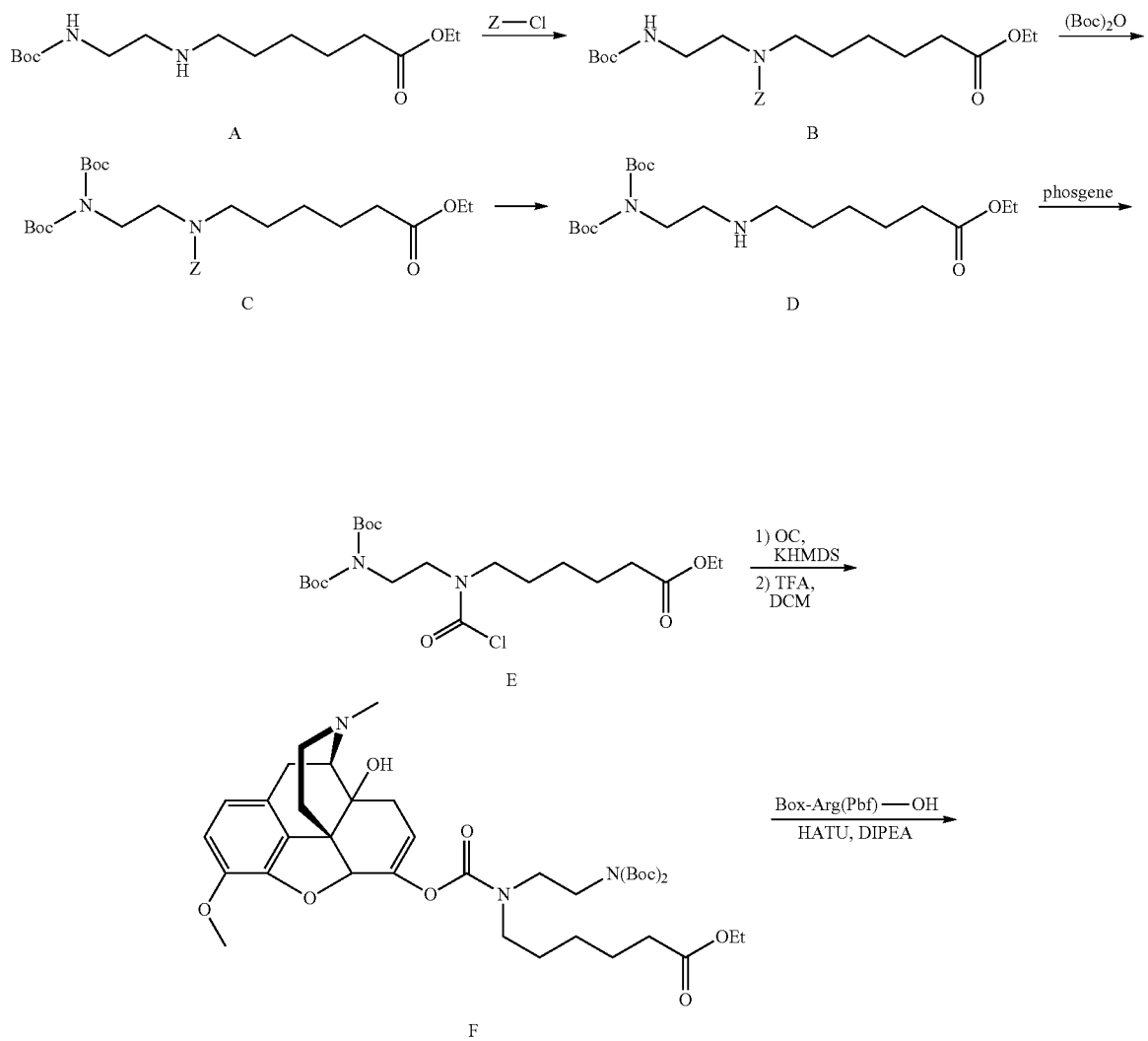

-continued
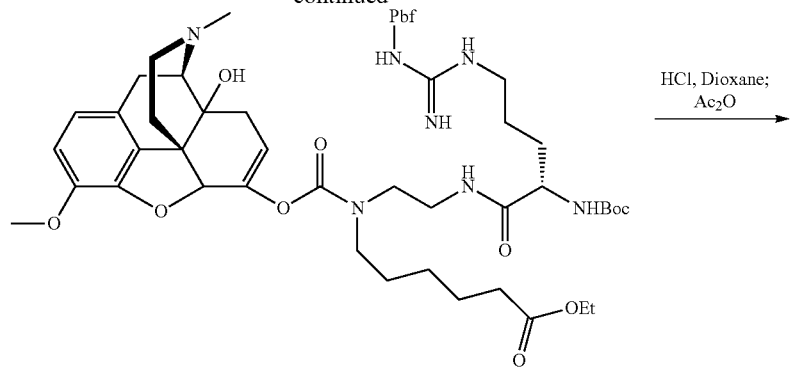
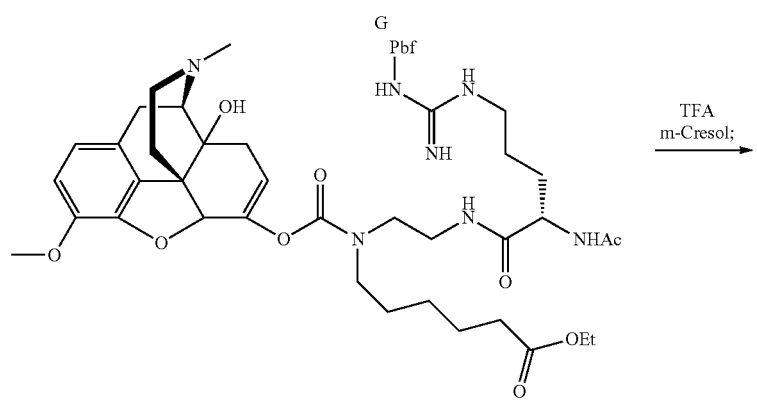
G
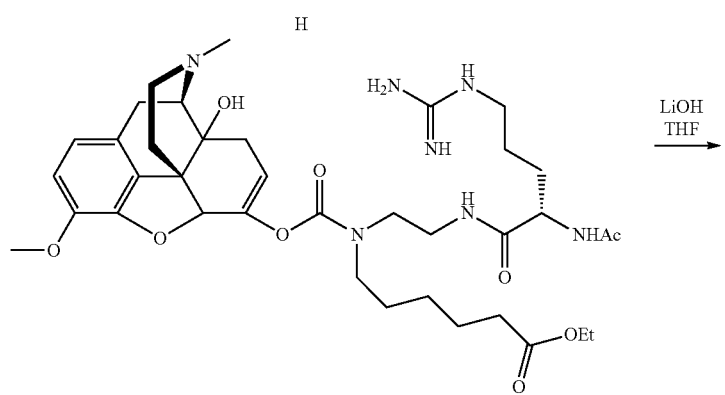
H
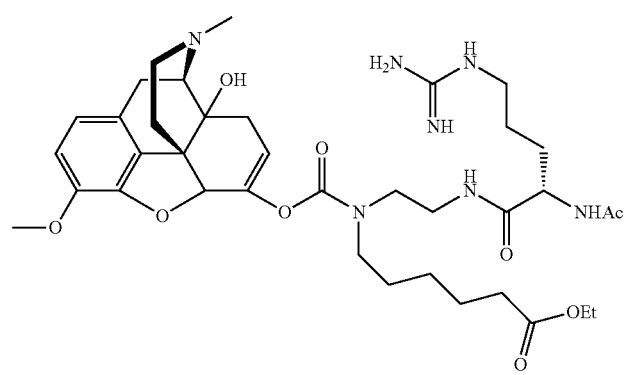
I
KC-5

Preparation 42: Synthesis of 6-[Benzyloxycarbonyl-(2-tert-Butoxycarbonylamino-ethyl)-amino]-hexanoic acid ethyl ester (B)

Compound A (26.8 g, 88.6 mmol) was dissolved in DCM (200 mL) at ambient temperature. $NEt_3$ (12.5 mL, 88.6 mmol) was added, followed by Cbz-Cl (Z-Cl) (12.5 mL, 88.6 mmol). The reaction mixture was stirred at ambient temperature under $N_2$ for 2 h. The reaction mixture was treated with $NaHCO_3$ (30 mL, aq. sat.). The layers were separated and the organic layer was dried over $MgSO_4$, filtered and concentrated. The residue was purified by silica gel chromatography, using 4/1 hexanes/EtOAc, to give compound B as a colorless oil (22.5 g, 66.5 mmol, 75%).

Preparation 43: Synthesis of Intermediate (C)

Compound B (22.0 g, 50.4 mmol) was dissolved in DCE (100 mL) at ambient temperature. $NEt_3$ (8.5 mL, 61 mmol) was added, followed by $(Boc)_2O$ (33.0 g, 151.2 mmol) and DMAP (615 mg, 5.0 mmol). The reaction mixture was stirred at ambient temperature under $N_2$ for 2 h and then heated at 60° C. for 16 h. The reaction mixture was concentrated, and the residue was purified by silica gel chromatography, using 4/1 hexanes/EtOAc, to give compound C as a colorless oil (23.2 g, 41.9 mmol, 86%). MS: (m/z) calc: 536.6, observed (M+Na$^+$) 560.1.

Preparation 44: Synthesis of Intermediate (D)

Compound C (22.5 g, 41.9 mmol) was dissolved in EtOH (50 mL). The mixture was degassed and saturated with $N_2$. Pd/C (500 mg, 5% on carbon) was added. The mixture was shaken in a Parr hydrogenator flask under 2 atm $H_2$ for 2 h. The mixture was then filtered through a celite pad and the filtrate was concentrated to give crude compound D as a colorless oil (21.0 g, 52.2 mmol, crude). This material was used without further purification.

Preparation 45: Synthesis of Intermediate (E)

Compound D (21.0 g, 52.2 mmol, crude) and $NEt_3$ (11.0 mL, 78.3 mmol) were mixed together with DCM (150 mL). The mixture was added to a pre-chilled (ice/water bath) phosgene solution in toluene (41.2 mL, 20% wt in toluene, ~83.3 mmol). The reaction mixture was stirred at 0° C. for 2 h. It was then concentrated to one-third of its original volume and diluted with ether (50 mL). The mixture was filtered through filter paper. The filtrate was concentrated to give compound E as a white solid (20.0 g, 43.1 mmol, 82%) MS: (m/z) calc: 464.2, observed (M+Na$^+$) 487.7. Compound E was used without further purification.

Preparation 46: Synthesis of Intermediate (F)

Oxycodone free base (1.0 g, 3.2 mmol) was dissolved in dry THF (degassed) (15 mL) and the mixture was cooled to ~10° C. using a dry ice/acetone bath. KHMDS (7.6 mL, 3.8 mmol, 0.5 M in toluene) was added via syringe. The mixture was stirred under $N_2$ at a temperature below −5° C. for 30 min. Compound E (1.5 g, 3.2 mmol) in THF (10 mL) was then added via syringe over 5 min. The mixture was stirred at ~5° C. for 30 min. The reaction was continued at ambient temperature for 2 h. $NaHCO_3$ (10 mL, sat. aq.) was added. The mixture was concentrated in vacuo to half of its initial volume. EtOAc (20 mL) was added and the layers were separated. The organic phase was further washed with water (20 mL) and brine (20 mL), followed by concentration with the resulting residue purified by silica gel chromatography (DCM/MeOH (gradient 100/1 to 100/15)) to afford a colorless oil (~1.7 g, 3.1 mmol, 97%). This material was dissolved in a mixture of DCM/TFA (5 mL/5 mL) at ambient temperature and stirred for 1 h. It was then concentrated in vacuo to afford compound F as its TFA salt (1.8 g, 2.7 mmol, 88%). MS: (m/z) calc: 543.7, observed (M+H$^+$) 545.2. Compound F was used without further purification.

Preparation 47: Synthesis of Intermediate (G)

Compound F (1.8 g, 2.6 mmol) was dissolved in DMF (20 mL) with stirring. Boc-Arg(Pbf)-OH (1.4 g, 2.7 mmol), HATU (1.1 g, 2.9 mmol) and DIPEA (1.4 mL, 8.0 mmol) were added with stirring. The reaction was continued at ambient temperature for 2 h. The mixture was then concentrated, and the residue was partitioned between EtOAc and water (30 mL/20 mL). The organic layer was separated, washed with water (20 mL), brine (20 mL), dried over $Na_2SO_4$ and concentrated to afford crude compound G (1.5 g, 1.4 mmol, 54%). MS: (m/z) calc: 1052.3, observed (M+H$^+$) 1053.9. Compound G was used without further purification.

Preparation 48: Synthesis of Intermediate (H)

Crude compound G (1.5 g, 1.4 mmol)) was taken into dioxane (3 mL) and cooled in an ice/water bath. An HCl solution in dioxane (4 N, 10 mL, 40 mmol) was added and the mixture was stirred at ambient temperature for 3 h and then concentrated in vacuo to afford a white foam. This material was dissolved in a mixture of DIPEA (0.8 mL 4.3 mmol) in DCM (20 mL). Acetic anhydride (0.2 mL, 2.1 mmol) was added. The reaction mixture was stirred at ambient temperature for 2 h. $NaHCO_3$ (20 mL, sat. aq.) was added. The layers were separated and the DCM layer was dried over $Na_2SO_4$, filtered and concentrated to afford intermediate compound H (0.85 g, crude). Compound H was used without further purification.

Synthesis of 6-{[2-(2-Acetylamino-5-guanidino-pentanoylamino)-ethyl]-[(5R,9R,13S,14S)-4,5a-epoxy-6,7-didehydro-14-hydroxy-3-methoxy-17-methylmorphinan-6-oxy]-1-enyloxycarbonyl-amino}-hexanoic acid (Compound KC-5)

Compound H (0.85 g, crude) was dissolved in a mixture of m-Cresol (0.5 mL) in TFA (20 mL). The mixture was stirred at ambient temperature for 2 h. The mixture was concentrated in vacuo. The residue was taken into MeOH (3 mL) and added drop wise to a stirred HCl solution in ether (20 mL, 2 M, 40 mmol). The resulting white solid (compound I) was filtered and washed with ether (3×10 mL). Compound I was then dissolved in a mixture of THF/$H_2O$ (2 mL/2 mL) at ambient temperature. LiOH (41 mg, 1.7 mmol) was added in one portion. The mixture was stirred for 4 h. The mixture was then acidified by adding AcOH until pH ~6. The mixture was then concentrated and the residue was purified by prep HPLC, using RP-18e C18 column (4.6×50 mm); flow rate: 1.5 ml/min; mobile phase A: 0.1% TFA/water; mobile phase B 0.1% TFA/$CH_3CN$; gradient elution. Lyophilization of the collected fractions afforded Compound KC-5 (TFA salt) as a white solid. The solid was treated with 0.1 N HCl (aq.) and lyophilized to give the corresponding HCl salt of Compound KC-5 as a white foam (406 mg, 38% from compound E, 100% purity). MS: (m/z) calc: 713.8, observed (M+H⁺) 714.5.
Example 14: ({(S)-2-((S)-2-Acetylamino-5-guanidino-pentanoylamino)-3-[(oxycodone-enyloxycarbonyl)-methyl-amino]-propionyl}-methyl-amino)-acetic acid (Compound KC-6)
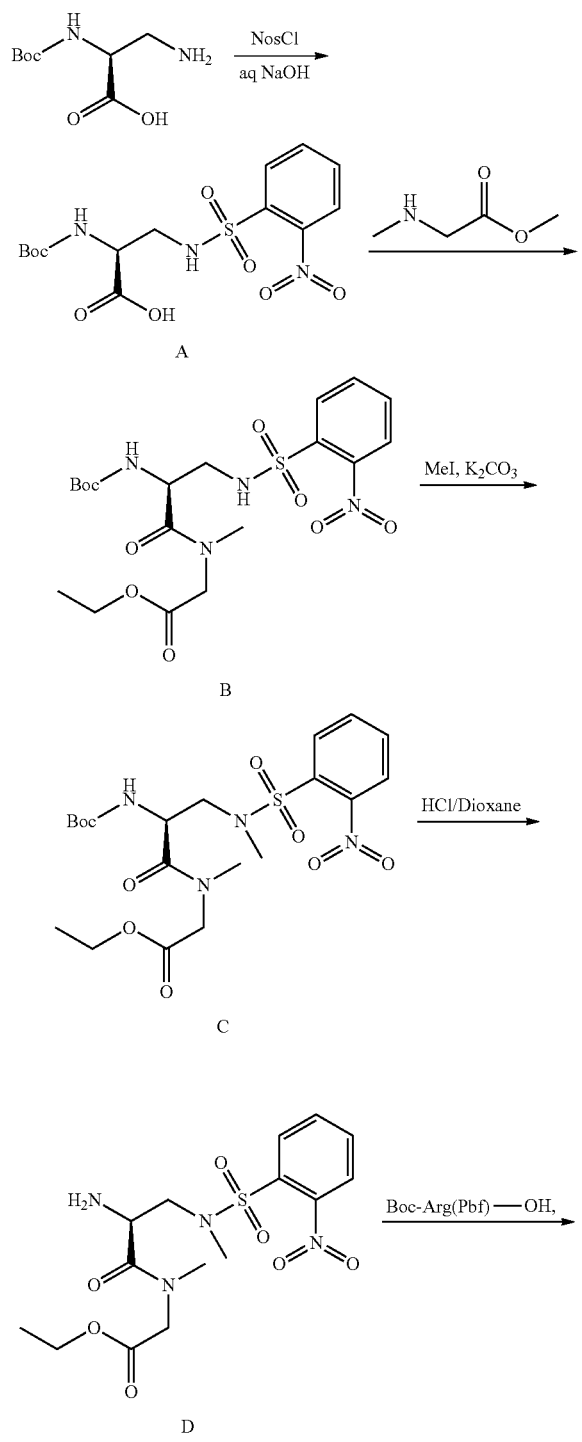
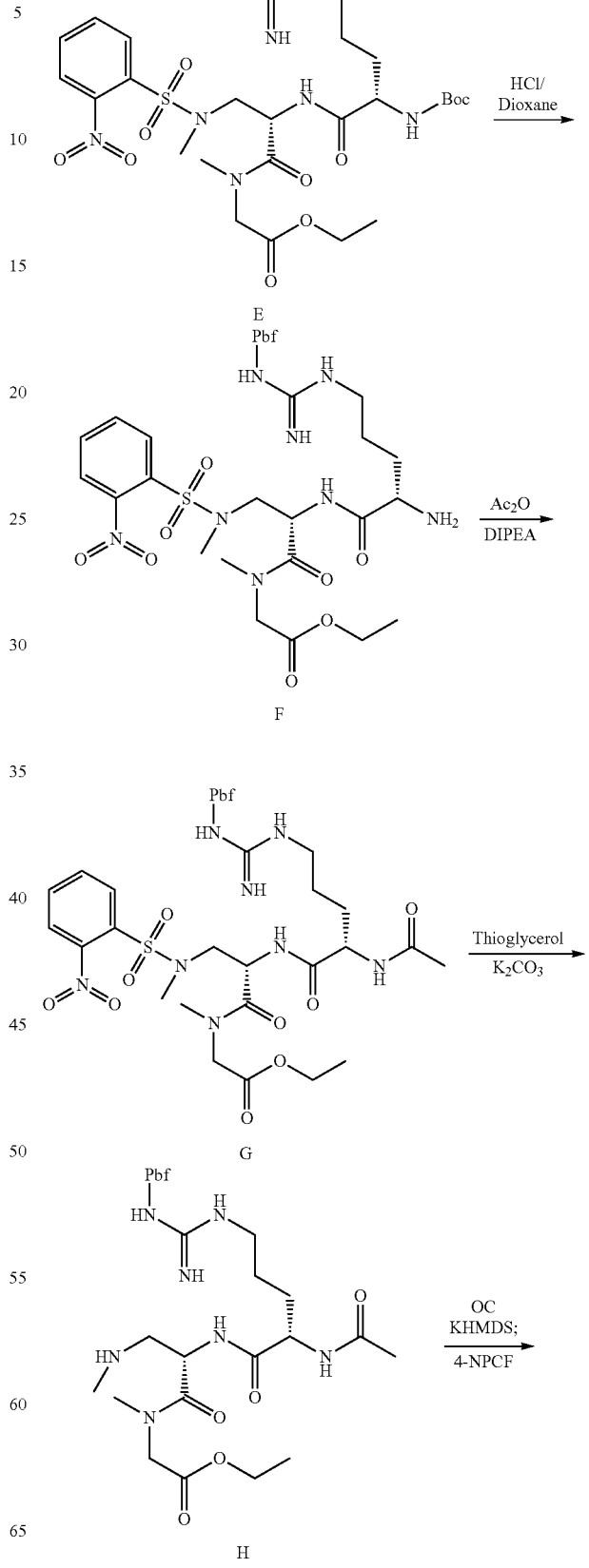

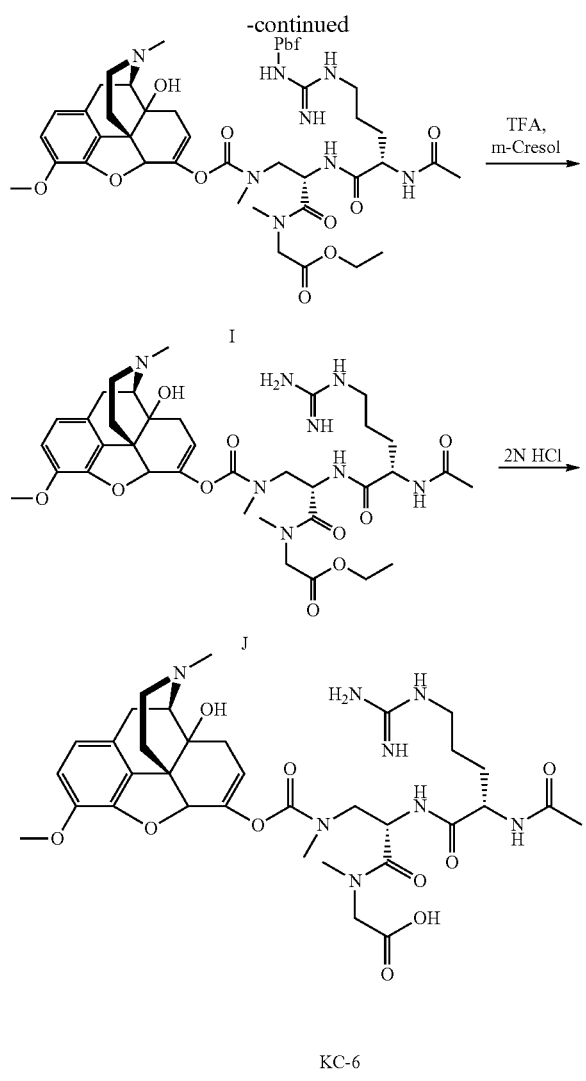

KC-6

Preparation 49: (S)-2-tert-Butoxycarbonylamino-3-(2-nitro-benzenesulfonylamino)-propionic acid (A)

(S)-2-tert-Butoxycarbonylamino-3-amino-propionic acid (14.9 g, 73.2 mmol) was dissolved in a mixture of THF (45 mL) and 3 N aq. NaOH (45 mL). The reaction mixture was cooled to ~10° C. and nosyl chloride (17.9 g, 80.5 mmol) was added as a THF solution (75 mL) drop wise over 30 min. The reaction mixture was stirred at ~10° C. for 45 min followed by stirring at ambient temperature for 30 min. The reaction mixture was diluted with water (150 mL), acidified with 2% aqueous $H_2SO_4$ (to pH ~2) and diluted with additional water (450 mL). The product was extracted with EtOAc (600 mL total) and washed with water (3×400 mL) and brine (100 mL). The organic layer was separated, dried over $Na_2SO_4$, filtered and condensed in vacuo to afford compound A (20.0 g, 70% yield) as a cream solid. LC-MS [M+H-Boc] 290.3 ($C_{14}H_{19}N_3O_8S$+H, calc: 390.4). Purity >95% (UV/254 nm). Compound A was used without further purification.

Preparation 50: {[(S)-2-tert-Butoxycarbonylamino-3-(2-nitro-benzenesulfonylamino)-propionyl]-methyl-amino}-acetic acid ethyl ester (B)

Free basing procedure of Sarcosine ethyl ester: Sarcosine ethyl ester hydrochloride (39.3 g, 256.8 mmol) was dissolved in water (300 mL), washed with $Et_2O$ (2×100 mL), pH adjusted to ~pH 8, extracted with $CHCl_3$ (3×100 mL) and dried over $Na_2SO_4$ and finally filtered.

To a solution of compound A (10.0 g, 25.7 mmol) in DMF (100 mL) was added HOBt (5.2 g, 38.5 mmol) and the reaction mixture was cooled to ~10° C. To this reaction mixture, EDC-HCl (5.4 g, 28.2 mmol) was added in portions over 10 min and stirred at ~10° C. for 20 min. To the reaction mixture, Sarcosine ethyl ester (256.8 mmol) in $CHCl_3$ (300 mL) was added drop wise over 30 min. The reaction mixture was stirred at this temperature for 30 min followed by stirring at ambient temperature overnight. Solvents were then removed in vacuo, and the residue was dissolved in EtOAc (500 mL), washed with water (3×300 mL), saturated aqueous $NaHCO_3$ (2×300 mL) and brine (100 mL). The organic layer was separated, dried over $Na_2SO_4$ and concentrated in vacuo to afford compound B (11.5 g, 91%) as a cream solid. LC-MS [M+H]489.5 ($C_{19}H_{28}N_4O_9S$+H, calc: 489.3). Purity >95% (UV/254 nm). Compound B was used without further purification.

Preparation 51: ({(S)-2-tert-Butoxycarbonylamino-3-[methyl-(2-nitro-benzenesulfonyl)-amino]-propionyl}-methyl-amino)-acetic acid ethyl ester (C)

Compound B (8.0 g, 16.3 mmol) was dissolved in DMF (40 mL) and the reaction mixture was cooled to ~10° C. To the reaction mixture was added $K_2CO_3$ (6.8 g, 49.1 mmol) followed by addition of MeI (5.1 mL, 81.9 mmol) drop wise and stirred at 0° C. for 1 h. The reaction mixture was filtered and washed with EtOAc. Solvents removed in vacuo and the residue was dissolved in EtOAc (250 mL) and poured into water (500 mL), extracted with EtOAc (2×250 mL), and washed with water (250 mL) and brine (100 mL). The organic layer was dried over $Na_2SO_4$, filtered, and then concentrated in vacuo, to afford compound C (8.1 g, 98% yield) as a cream solid. LC-MS [M+H] 503.1 ($C_{20}H_{30}N_4O_9S$+H, calc: 503.5). Purity >95% (UV/254 nm). Compound C was used without further purification.

Preparation 52: ({(S)-2-Amino-3-[methyl-(2-nitro-benzenesulfonyl)-amino]-propionyl}-methyl-amino)-acetic acid ethyl ester (D)

Compound C (6.9 g, 13.8 mmol) was dissolved in DCM (45 mL) and then treated with 4 M HCl in dioxane (40 mL) at ambient temperature. The reaction mixture was stirred at ambient temperature for 90 min. The mixture was concentrated in vacuo to a total volume of ~25 mL, and $Et_2O$ (400 mL) was added. The precipitated product was filtered off, washed with $Et_2O$ (250 mL), and hexane (250 mL) and finally dried in vacuo to afford compound D (6.3 g, 100% yield) as a cream solid. LC-MS [M+H] 403.3 ($C_{15}H_{22}N_4O_7S$+H, calc: 403.4). Purity >95% (UV/254 nm). Compound D was used without further purification.

Preparation 53: ({(S)-2-[(S)-5-({Amino-[(Z)-2,2,4,6,7-pentamethyl-2,3-dihydro-benzofuran-5-sulfonylimino]-methyl}-amino)-2-tert-butoxycarbonylamino-pentanoylamino]-3-[methyl-(2-nitro-benzenesulfonyl)-amino]-propionyl}-methyl-amino)-acetic acid ethyl ester (E)

To a solution of Boc-Arg(Pbf)-OH (7.3 g, 13.8 mmol), DIPEA (7.7 mL, 44.2 mmol) in DMF (35 mL) was added HATU (5.8 g, 15.2 mmol) and stirred at 5° C. for 15 min. To this reaction mixture, compound D (6.3 g, 13.8 mmol) was added and stirred at ambient temperature for 1 h. DMF was then removed in vacuo to a total volume of ~15 mL. The reaction mixture was diluted with EtOAc (250 mL) and poured into water (500 mL), extracted with EtOAc (2×250 mL), and washed with 2% aqueous $H_2SO_4$ (150 mL), water (150 mL) and brine (150 mL). The organic layer was dried over anhydrous $Na_2SO_4$, filtered and then evaporated to give an oily residue, which was dried overnight under high vacuum to give compound E (7.4 g, 59%) as an off-white solid. LC-MS [M+H] 911.5 ($C_{39}H_{58}N_8O_{13}S$+H, calc: 912.05). Purity >95% (UV/254 nm). Compound E was used without further purification.

Preparation 54: ({(S)-2-[(S)-2-Amino-5-({amino-[(Z)-2,2,4,6,7-pentamethyl-2,3-dihydro-benzofuran-5-sulfonylimino]-methyl}-amino)-pentanoylamino]-3-[methyl-(2-nitro-benzenesulfonyl)-amino]-propionyl}-methyl-amino)-acetic acid ethyl ester (F)

Compound E (7.4 g, 8.2 mmol) in DCM (24 mL) was treated with 4 M HCl in dioxane (24 mL) at ambient temperature. The reaction mixture was stirred at ambient temperature for 1 h. DCM and most of the dioxane were removed in vacuo to a total volume of ~15 mL, and $Et_2O$ (300 mL) was added. Precipitated product was filtered off, washed with $Et_2O$ (150 mL) and hexane and finally dried in vacuo to afford compound F (6.34 g, 100% yield) as a cream solid. LC-MS [M+H] 811.4 ($C_{34}H_{50}N_8O_{11}S_2$+H, calc: 811.94). Purity >95% (UV/254 nm). Compound F was used without further purification.

Preparation 55: ({(S)-2-[(S)-2-Acetylamino-5-({amino-[(Z)-2,2,4,6,7-pentamethyl-2,3-dihydro-benzofuran-5-sulfonylimino]-methyl}-amino)-pentanoylamino]-3-[methyl-(2-nitro-benzenesulfonyl)-amino]-propionyl}-methyl-amino)-acetic acid ethyl ester (G)

To a solution of compound F (6.6 g, 7.8 mmol) in $CHCl_3$ (50 mL) at 5° C. was added DIPEA (4.8 mL, 27.4 mmol) followed by $Ac_2O$ (0.9 mL, 9.4 mmol). The reaction mixture was stirred at ambient temperature for 30 min. Solvents were removed in vacuo, and then the residue was diluted with water (500 mL) and EtOAc (500 mL). The organic layer was separated and washed with water (300 mL), 2% aqueous $H_2SO_4$ (200 mL), water (2×300 mL) and brine (100 mL). The organic layer was separated, dried over $Na_2SO_4$ and solvent removed in vacuo to afford compound G (5.5 g, 82%). LC-MS [M+H] 853.4 ($C_{36}H_{52}N_8O_{12}S_2$+H, calc: 853.9). Purity >95% (UV/254 nm). Compound G was used without further purification.

Preparation 56: ({(S)-2-[(S)-2-Acetylamino-5-({amino-[(Z)-2,2,4,6,7-pentamethyl-2,3-dihydro-benzofuran-5-sulfonylimino]-methyl}-amino)-pentanoylamino]-3-methylamino-propionyl}-methyl-amino)-acetic acid ethyl ester (H)

To a solution of compound G (5.5 g, 6.5 mmol) in DMF (21 mL) at ambient temperature was added $K_2CO_3$ (8.9 g, 64.5 mmol) followed by thioglycerol (5.6 mL, 64.5 mmol). The reaction mixture was stirred at ambient temperature for 1 h, filtered off and DMF was removed in vacuo. The residue was diluted with water (500 mL) and extracted with EtOAc (2×300 mL) and $CHCl_3$ (2×300 mL). Combined organic layers were dried and removal of the solvents in vacuo afforded the crude product. The crude product was purified by flash chromatography eluting with EtOAc followed by 10% MeOH in $CHCl_3$ to afford compound H (1.3 g, 30%). LC-MS [M+H] 668.3 ($C_{30}H_{49}N_7O_8S$+H, calc: 667.8). Purity >95% (UV/254 nm).

Preparation 57: ({(S)-2-[(S)-2-Acetylamino-5-({amino-[(Z)-2,2,4,6,7-pentamethyl-2,3-dihydro-benzofuran-5-sulfonylimino]-methyl}-amino)-pentanoylamino]-3-[(oxycodone-enyloxycarbonyl)-methyl-amino]-propionyl}-methyl-amino)-acetic acid ethyl ester (I)

To a solution of oxycodone free base (2.0 g, 6.3 mmol) in THF (100 mL) at ~60° C. was added 0.5 M KHMDS (13.9 mL, 7.0 mmol) drop wise. The reaction mixture was stirred for 30 min and then transferred to a solution of 4-nitrophenyl chloroformate (1.3 g) in THF (100 mL) at −60° C. and stirred for 30 min. A solution of amine compound H (3.2 g, 4.9 mmol) was added as a THF (20 mL) solution to the reaction mixture. After stirring at ~60° C. for 15 min, the cooling bath was removed and the reaction was stirred at ambient temperature overnight. Another portion (1.0 g, 3.2 mmol) of oxycodone free base was activated using the above procedure and added to the reaction mixture as above, and stirring continued overnight. The reaction was determined to be complete by LC-MS. The solvents were removed, and the residue was dissolved in MeOH (~25 mL) and precipitated with $Et_2O$ (400 mL). The precipitate was washed with $Et_2O$ and hexane and dried in vacuo. The product was dissolved in water and DMSO and purified by HPLC. [Nanosyn-Pack Microsorb (100-10)C-18 column (50×300 mm); flow rate: 100 mL/min; injection volume 15 mL; mobile phase A: 100% water, 0.1% TFA; mobile phase B: 100% ACN, 0.1% TFA; gradient elution from 0% to 33% B in 33 min, isocratic elution at 33% B in 30 min, gradient elution from 33% B to 50% B in 33 min; detection at 254 nm]. Desired fractions were combined and dried in vacuo to afford compound I (5 g, 92% yield)). LC-MS [M+H] 979.6 ($C_{48}H_{66}N_8O_{12}S$+H, calc: 980.15). Purity >95% (UV/254 nm).

Preparation 58: ({(S)-2-((S)-2-Acetylamino-5-guanidino-pentanoylamino)-3-[(oxycodone-enyloxycarbonyl)-methyl-amino]-propionyl}-methyl-amino)-acetic acid ethyl ester (J)

Compound I (5 g, 4.5 mmol) was treated with 5% m-cresol in TFA (25 mL). After 1 h, ether (400 mL) was added to the reaction mixture. The precipitated product was filtered off, washed with $Et_2O$ and hexane and dried in vacuo to afford compound J (3.2 g, 65% yield). LC-MS [M+H] 757.7 ($C_{36}H_{52}N_8O_{10}$+H, calc: 757.9). Purity >95% (UV/254 nm). Compound J was used without further purification.

({(S)-2-((S)-2-Acetylamino-5-guanidino-pentanoylamino)-3-[(oxycodone-enyloxycarbonyl)-methyl-amino]-propionyl}-methyl-amino)-acetic acid (Compound KC-6)

Compound J was treated with 2 N aq. HCl (75 mL) and heated at 55° C. for 6.5 h. Heating was removed and the reaction mixture was cooled to ~5° C. and pH was adjusted to ~pH 6 with aqueous saturated $NaHCO_3$. Most of the water was removed in vacuo to a total volume of ~50 mL. This solution was subjected to HPLC purification. [Nanosyn- Pack Microsorb (100-10)C-18 column (50×300 mm); flow rate: 100 mL/min; injection volume 15 mL; mobile phase A: 100% water, 0.1% TFA; mobile phase B: 100% ACN, 0.1% TFA; isocratic elution at 0% B in 2 min, gradient elution from 0% to 8% B in 14 min, isocratic elution at 8% B in 30 min, gradient elution from 8% B to 33% B in 55 min; detection at 254 nm]. Desired fractions were combined and dried in vacuo, followed by lyophilization using 0.1 N HCl to afford Compound KC-6 as a HCl salt (1.5 g, 48% yield). LC-MS [M+H] 729.6 ($C_{34}H_{48}N_8O_{10}$+H, calc: 729.8). Purity >95% (UV/254 nm).

Biological Data

Example 15: Pharmacokinetics of Oxycodone Prodrug Following PO Administration to Rats This Example compares the plasma concentrations of oxycodone in rats following oral (PO) administration of oxycodone 6-(N-methyl-N-(2-N'-acetylarginylamino)) ethylcarbamate (produced as described in Example 10 and herein also referred to as Compound KC-2) or oxycodone.

Compound KC-2 and oxycodone were each dissolved in saline and dosed at equimolar doses (20 mg/kg and 10 mg/kg, respectively) via oral gavage into jugular vein-cannulated male Sprague Dawley rats; four rats were dosed per group. At specified time points, blood samples were drawn, harvested for plasma via centrifugation at 5,400 rpm at 4° C. for 5 min, and 100 microliters (μl) plasma transferred from each sample into a fresh tube containing 1 μl of formic acid. The tubes were vortexed for 5-10 seconds, immediately placed in dry ice and then stored until analysis by high performance liquid chromatography/mass spectrometry (HPLC/MS).

Table 1 indicates plasma $C_{max}$ (maximum plasma concentration) and $T_{max}$ (time after administration when the maximum plasma concentration was reached) values of oxycodone (average±standard deviation) for each group of 4 rats. Also indicated are the $C_{max}$ and $T_{max}$ values for oxymorphone, a metabolite of oxycodone.

TABLE 1

Plasma $C_{max}$ and $T_{max}$ values of oxycodone (OC) and oxymorphone (OM) in rats dosed PO with oxycodone or Compound KC-2

| Compound administered | $C_{max}$ OC (ng/mL OC) | $T_{max}$ OC (hr) | $C_{max}$ OM (ng/mL OM) | $T_{max}$ OM (hr) |
|---|---|---|---|---|
| Oxycodone | 14.7 ± 6.5 | 0.63 ± 0.43 | 18.4 ± 10.0 | 0.50 ± 0.35 |
| Compound KC-2 | 3.8 ± 1.1 | 3.8 ± 1.5 | 3.9 ± 1.6 | 3.8 ± 1.5 |

Figure 4:
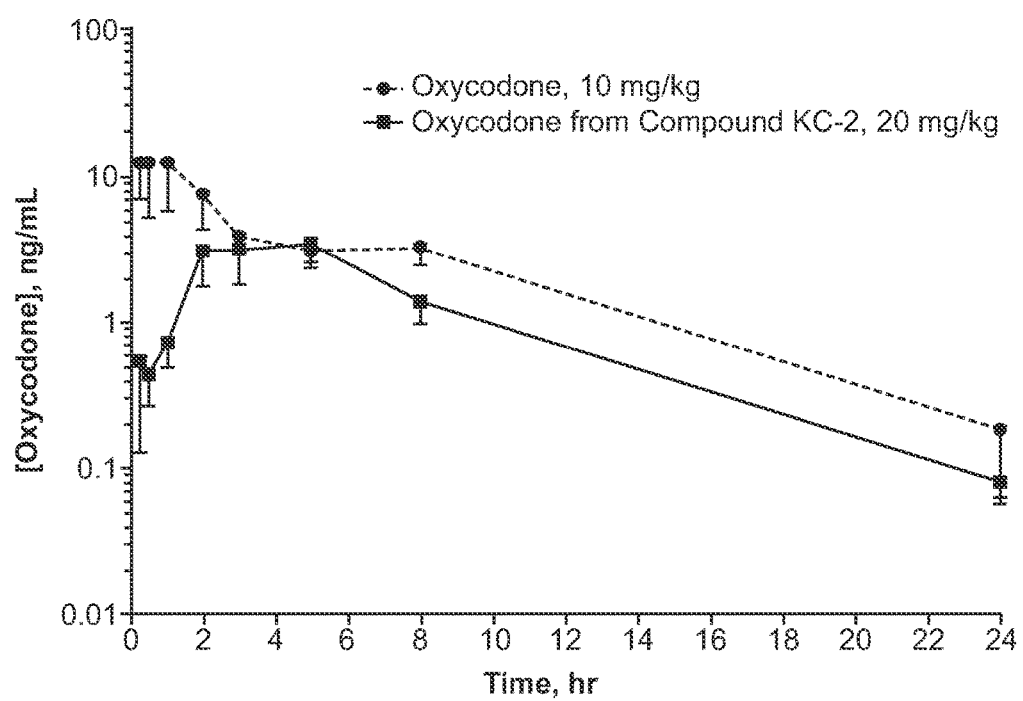
FIG. 4 shows a plasma concentration time course of the production of oxycodone following oral (PO) dosing of an oxycodone prodrug in rats.

FIG. 4 compares mean plasma concentrations (±standard deviations) over time of oxycodone following PO administration of 20 mg/kg Compound KC-2 (solid line) or 10 mg/kg oxycodone (dashed line) to rats.

The results in Table 1 and FIG. 4 indicate that administration of Compound KC-2 yields oxycodone plasma concentrations that exhibit a suppressed $C_{max}$ and delayed $T_{max}$ compared to administration of oxycodone.

Example 16: Pharmacokinetics of Oxycodone Prodrug Following IV Administration to Rats This Example compares the plasma concentrations of prodrug and oxycodone in rats following intravenous (IV) administration of oxycodone 6-(N-methyl-N-(2-N'-acetylarginylamino)) ethylcarbamate (produced as described in Example 10 and herein also referred to as Compound KC-2).

Compound KC-2 was dissolved in saline and injected into the tail vein of 4 jugular vein-cannulated male Sprague Dawley rats at a dose of 2 mg/kg. At specified time points, blood samples were drawn, harvested for plasma via centrifugation at 5,400 rpm at 4° C. for 5 min, and 100 microliters (μl) plasma transferred from each sample into a fresh tube containing 1 μl of formic acid. The tubes were vortexed for 5-10 seconds, immediately placed in dry ice and then stored until analysis by high performance liquid chromatography/mass spectrometry (HPLC/MS).

Table 2 indicates plasma $C_{max}$ values (average±standard deviation) of Compound KC-2, oxycodone and oxymorphone (a metabolite of oxycodone).

TABLE 2

Plasma $C_{max}$ values of Compound KC-2, oxycodone and oxymorphone in rats dosed IV with Compound KC-2

| Compound in plasma measured | Cmax (ng/mL) |
|---|---|
| Compound KC-2 | 2680 ± 755 |
| Oxycodone | 0.798 ± 0.1 |
| Oxymorphone | 0.118 ± 0.1 |

Figure 5:
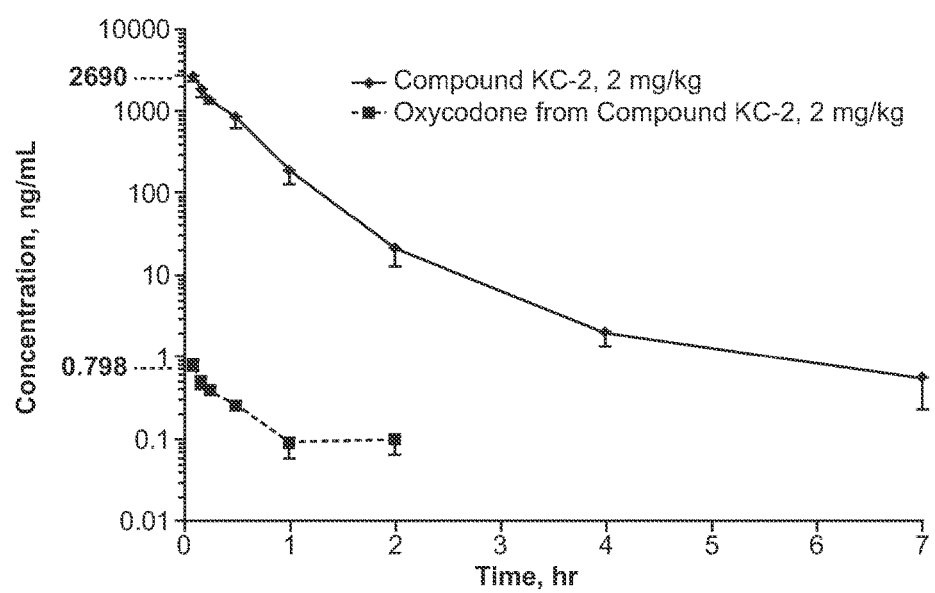
FIG. 5 shows a plasma concentration time course of the production of oxycodone following intravenous (IV) dosing of an oxycodone prodrug in rats.

FIG. 5 compares mean plasma concentrations (±standard deviations) over time of Compound KC-2 (solid line) and oxycodone (dashed line) following IV administration of 2 mg/kg Compound KC-2 to rats. Numbers on the Y-axis also depict the Cmax values of Compound KC-2 and oxycodone, respectively.

Table 2 and FIG. 5 demonstrate that the plasma concentration of oxycodone in rats administered Compound KC-2 IV is only 0.03% of the plasma concentration of Compound KC-2, indicating that IV administration of Compound KC-2 does not lead to significant release of oxycodone.

Example 17: In Vitro Stability of Oxycodone Prodrug

This Example demonstrates the stability of oxycodone 6-(N-methyl-N-(2-N'-acetylarginylamino)) ethylcarbamate (produced as described in Example 10 and herein also referred to as Compound KC-2) to a variety of readily available household chemicals and enzyme preparations.

Compound KC-2 was exposed at room temperature (RT) or 80° C. for either 1 or 24 hours (hr) to the following household chemicals: vodka (40% alcohol), baking soda (saturated sodium bicarbonate solution, pH 9), WINDEX® with Ammonia-D (pH11) and vinegar (5% acetic acid). Compound KC-2 was also exposed to the following enzyme-containing compositions at RT for 1 or 24 hr: GNC® Super Digestive (2 capsules of GNC Super Digestive Enzymes dissolved in 5 mL of water), tenderizer (Adolf's meat tenderizer, primarily papain, dissolved in water to a concentration of 0.123 g/mL to approximate the concentration of a marinade given on the bottle label), and subtilisn (8 tablets of ULTRAZYME® contact lens cleaner (Advanced Medical Optics) dissolved in 4 mL water). Samples were incubated as described and aliquots removed at 1 hr and 24 hr and stabilized by adding each to a solution of 50% or 100% of 85% phosphoric acid solution to achieve a final pH of less than or equal to pH 4. The stabilized aliquots were then diluted 4- to 6-fold with water, vortex-mixed and applied to HPLC.

Figure 6:
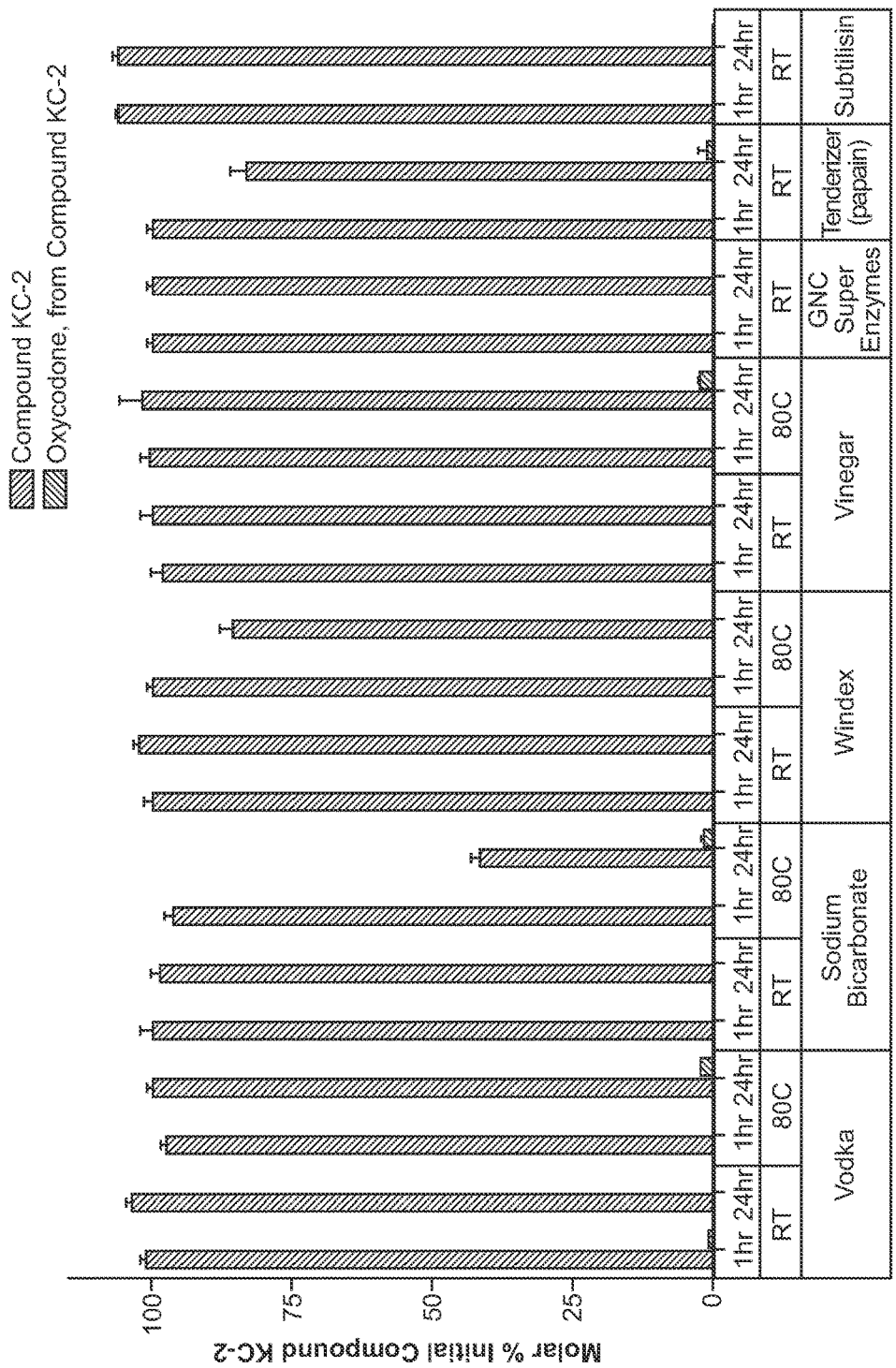
FIG. 6 shows release of oxycodone from an oxycodone prodrug exposed to a variety of readily availably household chemicals or enzyme preparations.

FIG. 6 demonstrates the release of oxycodone when Compound KC-2 was exposed to the various household chemicals and enzyme-containing compositions described above. The percentage of Compound KC-2 remaining after exposure is indicated by the solid black bars and percentage conversion of Compound KC-2 to oxycodone is indicated by the lightly shaded bars with a black outline. These results indicate that exposure of Compound KC-2 to these various conditions leads to substantially less than 10% conversion to oxycodone.

Example 18: In Vitro IC50 Data of Several Candidate Trypsin Inhibitors

Several candidate trypsin inhibitors, namely Compounds 101-105, 107 and 108 were produced as described in the Examples herein. Compound 106 (also known as 4-aminobenzamidine), Compound 109 and Compound 110 are available from Sigma-Aldrich (St. Louis, Mo.).

The half maximal inhibitory concentration (IC50 or $IC_{50}$) values of each of Compounds 101-110 as well as of SBTI and BBSI were determined using a modified trypsin assay as described by Bergmeyer, H U et al, 1974, Methods of Enzymatic Analysis Volume 1, $2^{nd}$ edition, 515-516, Bergmeyer, HU, ed., Academic Press, Inc. New York, N.Y.

Table 3 indicates the IC50 values for each of the designated trypsin inhibitors.

TABLE 3

IC50 values of certain trypsin inhibitors

| Compound | IC50 value |
| --- | --- |
| 101 | 2.0E−5 |
| 102 | 7.5E−5 |
| 103 | 2.3E−5 |
| 104 | 2.7E−5 |
| 105 | 4.1E−5 |
| 106 | 2.4E−5 |
| 107 | 1.9E−6 |
| 108 | 8.8E−7 |
| 109 | 9.1E−7 |
| 110 | 1.8E−5 |
| SBTI | 2.7E−7 |
| BBSI | 3.8E−7 |

The results of Table 3 indicate that each of Compounds 101-110 exhibits trypsin inhibition activity.

Example 19: Effect of Trypsin Inhibition on In Vitro Trypsin-Mediated Trypsin Release of Oxycodone from Compound KC-2

Compound KC-2 (which can be prepared as described in Example 10) was incubated with trypsin from bovine pancreas (Catalog No. T8003, Type I, ~10,000 BAEE units/mg protein, Sigma-Aldrich), in the absence or presence of Compound 109 (Catalog No. N0289, Sigma-Aldrich). When Compound 109 was part of the incubation mixture, Compound KC-2 was added 5 min after the other incubation components. Specifically, the reactions included 0.523 mg/mL (0.761 mM) Compound KC-2.2HCl, 0.0228 mg/mL trypsin, 22.5 mM calcium chloride, 172 mM Tris pH 8 and 0.00108 mg/mL (2 µM) Compound 109 or 0.25% DMSO depending on whether inhibitor was included in the incubation. The reactions were conducted at 37° C. for 24 hr. Samples were collected at specified time points, transferred into 0.5% formic acid in acetonitrile to stop trypsin activity and stored at less than −70° C. until analysis by LC-MS/MS.

Figure 7:
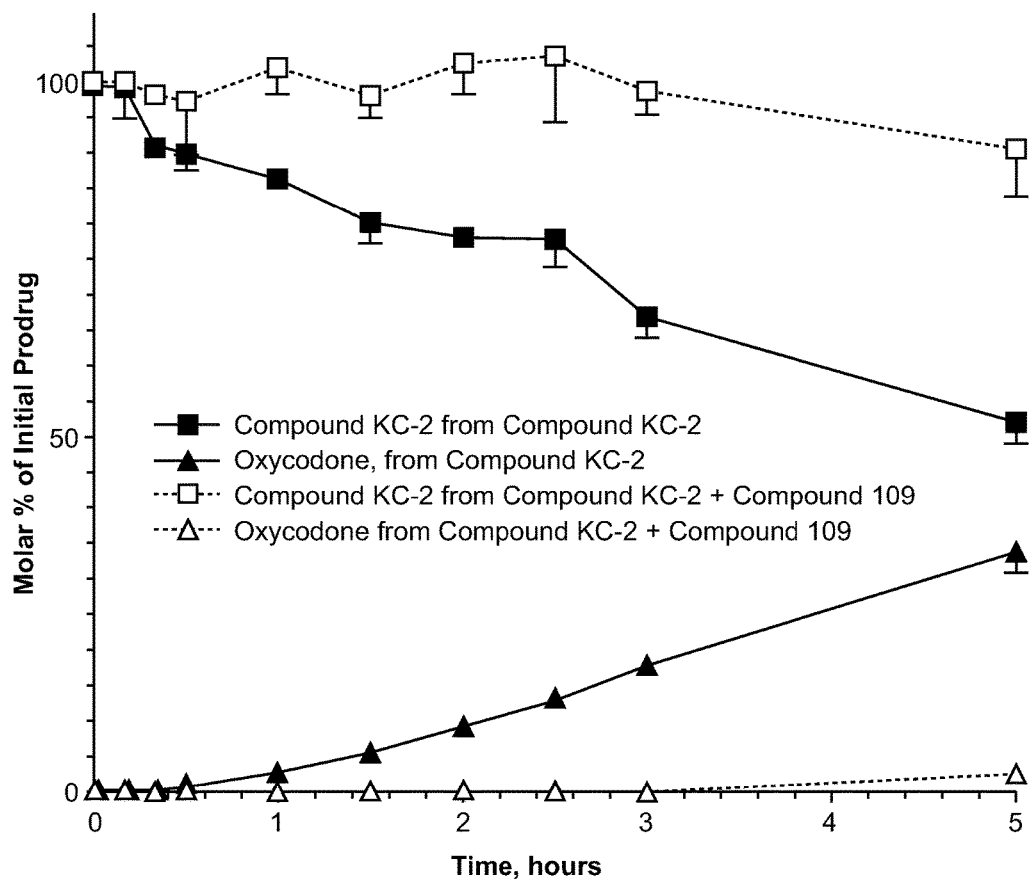
FIG. 7 shows disappearance of an oxycodone prodrug and appearance of oxycodone following in vitro incubation of the prodrug and trypsin, in the absence or presence of a trypsin inhibitor.

FIG. 7 indicates the results of exposure of Compound KC-2 to trypsin in the absence of any trypsin inhibitor (solid symbols) or in the presence of Compound 109 (open symbols). The square symbols indicate the disappearance of Compound KC-2, and the triangle symbols depict the appearance of oxycodone, over time under the conditions described in this Example.

The results in FIG. 7 indicate that a trypsin inhibitor of the embodiments can attenuate trypsin-mediated release of oxycodone from Compound KC-2. In addition, such a trypsin inhibitor can thwart the ability of a user to apply trypsin to effect the release of oxycodone from Compound KC-2.

Table 4 indicates the results of exposure of Compound KC-2 to trypsin in the absence and presence of Compound 109. The results are expressed as half-life of prodrug when exposed to trypsin (i.e., Prodrug trypsin half-life) in hours and rate of formation of oxycodone per unit to trypsin.

TABLE 4

In Vitro Trypsin Conversion of Compound KC-2 to Oxycodone

| | No trypsin inhibitor | | With trypsin inhibitor | |
| --- | --- | --- | --- | --- |
| Pro-drug | Pro-drug trypsin half-life, h Average ± sd | Rate of oxycodone formation, umols/h/ umol trypsin Average ± sd | Compound 109 | Pro-drug trypsin half-life, h Average ± sd | Rate of oxycodone formation, umols/h/ umol trypsin Average ± sd |
| KC-2 | 5.64 ± 0.26 | 37.4 ± 0.9 | 2 uM | 116 ± 118 | nd* |

*nd = not detectable

The results in Table 4 indicate that trypsin can effect release of oxycodone from a prodrug of the embodiments and that a trypsin inhibitor of the embodiments can attenuate trypsin-mediated release of oxycodone.

Example 20: Oral Administration of Compound KC-2 and Trypsin Inhibitor Compound 109 to Rats Saline solutions of Compound KC-2 (which can be prepared as described in Example 10) were dosed at 8.7 µmol/kg (6 mg/kg) with or without a co-dose of 55 µmol/kg (30 mg/kg) Compound 109 (Catalog No. 3081, Tocris Bioscience, Ellisville, Mo., USA or Catalog No. WS38665, Waterstone Technology, Carmel, Ind., USA) as indicated in Table 5 via oral gavage into jugular vein-cannulated male Sprague Dawley rats (4 per groups) that had been fasted for 16-18 hr prior to oral dosing. At specified time points, blood samples were drawn, harvested for plasma via centrifugation at 5,400 rpm at 4° C. for 5 min, and 100 microliters (µl) plasma transferred from each sample into a fresh tube containing 2 µl of 50% formic acid. The tubes were vortexed for 5-10 seconds, immediately placed in dry ice and then stored in −80° C. freezer until analysis by HPLC/MS.

Figure 8:
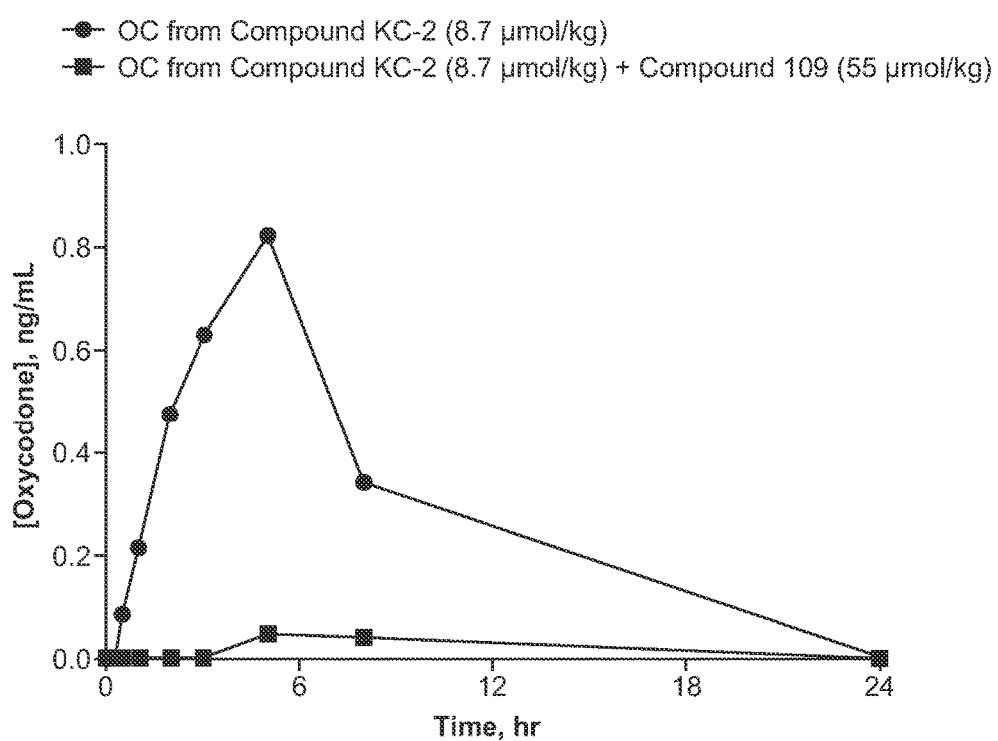
FIG. 8 compares mean plasma concentrations over time of oxycodone release following PO administration of prodrug Compound KC-2 alone and Compound KC-2 with trypsin inhibitor Compound 109 to rats.

Table 5 and FIG. 8 provide oxycodone exposure results for rats administered with Compound KC-2 in the absence or presence of trypsin inhibitor. Results in Table 5 are reported as (a) maximum plasma concentration (Cmax) of oxycodone (OC) (average±standard deviation) and (b) time after administration of Compound KC-2 to reach maximum oxycodone concentration (Tmax) (average±standard deviation).

TABLE 5

Cmax and Tmax values of oxycodone in rat plasma

| KC-2 Dose, mg/kg | KC-2 Dose, µmol/kg | Compound 109 Dose, mg/kg | Compound 109 Dose, µmol/kg | OC Cmax ± sd, ng/mL | Tmax ± sd, hr |
|---|---|---|---|---|---|
| 6 | 8.7 | 0 | 0 | 0.863 ± 0.69 | 3.00 ± 1.4 |
| 6 | 8.7 | 30 | 55 | 0.0468 ± 0.094 | 5.00 ± nc |

Lower limit of quantitation was 0.100 ng/mL;
nc = not calculated

FIG. 8 compares mean plasma concentrations over time of oxycodone release following PO administration of Compound KC-2 with or without a co-dose of trypsin inhibitor.

The results in Table 5 and FIG. 8 indicate that Compound 109 attenuates Compound KC-2's ability to release oxycodone, both by suppressing Cmax and by delaying Tmax.

Example 21: Pharmacokinetics of Compound KC-2 Following PO Administration to Rats Saline solutions of Compound KC-2 (which can be prepared as described in Example 10) were dosed as indicated in Table 6 via oral gavage into jugular vein-cannulated male Sprague Dawley rats (4 per group) that had been fasted for 16-18 hr prior to oral dosing. At specified time points, blood samples were drawn, harvested for plasma via centrifugation at 5,400 rpm at 4° C. for 5 min, and 100 microliters (µl) plasma transferred from each sample into a fresh tube containing 2 µl of 50% formic acid. The tubes were vortexed for 5-10 seconds, immediately placed in dry ice and then stored in −80° C. freezer until analysis by HPLC/MS.

Figure 9:
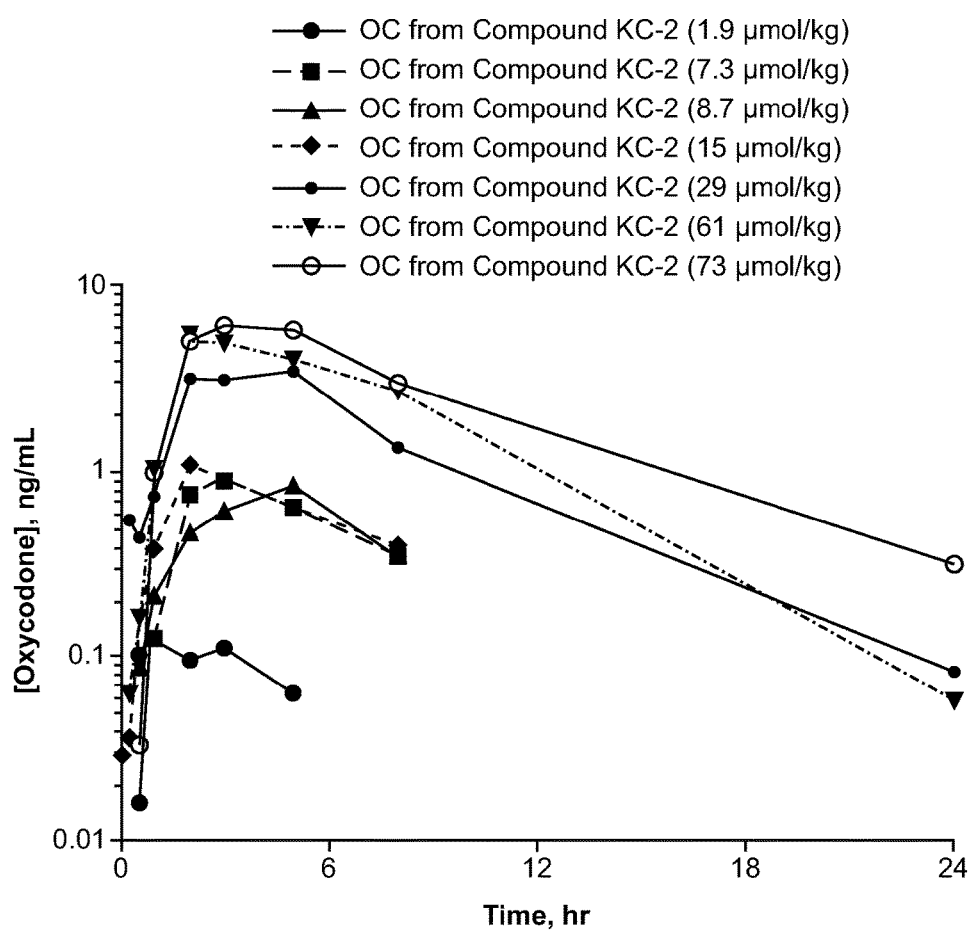
FIG. 9 compares mean plasma concentrations over time of oxycodone release following PO administration of increasing doses of prodrug Compound KC-2 to rats.

Table 6 and FIG. 9 provide oxycodone exposure results for rats administered with different doses of Compound KC-2. Results in Table 6 are reported, for each group of rats, as (a) maximum plasma concentration (Cmax) of oxycodone (OC) (average+standard deviation), (b) time after administration of Compound KC-2 to reach maximum oxycodone concentration (Tmax) (average±standard deviation) and (c) area under the curve (AUC) from 0 to 24 hr (average±standard deviation).

TABLE 6

Rat dosing PO with Compound KC-2

| Dose, mg/kg | Dose µmol/kg | OC Cmax ± sd, ng/mL | Tmax ± sd, hr | AUC ± sd, ng*hr/mL |
|---|---|---|---|---|
| 1.3 | 1.9 | 0.144 ± 0.018 | 1.50 ± 0.58 | 0.445 ± 0.13 |
| 5 | 7.3 | 0.918 ± 0.30 | 2.75 ± 0.5 | 4.30 ± 1.1 |

TABLE 6-continued

Rat dosing PO with Compound KC-2

| Dose, mg/kg | Dose µmol/kg | OC Cmax ± sd, ng/mL | Tmax ± sd, hr | AUC ± sd, ng*hr/mL |
|---|---|---|---|---|
| 6 | 8.7 | 0.863 ± 0.69 | 3.00 ± 1.4 | 4.29 ± 2.6 |
| 10 | 15 | 1.13 ± 0.75 | 3.75 ± 2.9 | 4.94 ± 2.2 |
| 20 | 29 | 3.84 ± 1.1 | 3.75 ± 1.5 | 30.9 ± 6.3 |
| 42 | 61 | 6.00 ± 2.4 | 3.00 ± 1.4 | 39.6 ± 18 |
| 50 | 73 | 7.03 ± 2.3 | 3.75 ± 1.5 | 59.9 ± 14 |

Lower limit of concentration was 0.0500 ng/mL except 20 mg/kg dose was 0.0250 ng/mL FIG. 9 compares mean plasma concentrations over time of oxycodone release following PO administration of increasing doses of Compound KC-2.

The results in Figure Table 6 and 9 indicate that plasma concentrations of oxycodone increase proportionally with Compound KC-2 dose.

Example 22: Oral Administration of Compound KC-2 Co-Dosed with Trypsin Inhibitor Compound 109 to Rats Saline solutions of Compound KC-2 were dosed at 7.3 µmol/kg (5 mg/kg) and 73 µmol/kg (50 mg/kg). The higher dose was co-dosed with increasing concentrations of Compound 109 (Catalog No. 3081, Tocris Bioscience or Catalog No. WS38665, Waterstone Technology) as indicated in Table 7 via oral gavage into jugular vein-cannulated male Sprague Dawley rats (4 per group) that had been fasted for 16-18 hr prior to oral dosing. At specified time points, blood samples were drawn, harvested for plasma via centrifugation at 5,400 rpm at 4° C. for 5 min, and 100 microliters (µl) plasma transferred from each sample into a fresh tube containing 2 µl of 50% formic acid. The tubes were vortexed for 5-10 seconds, immediately placed in dry ice and then stored in −80° C. freezer until analysis by HPLC/MS.

Figure 10:
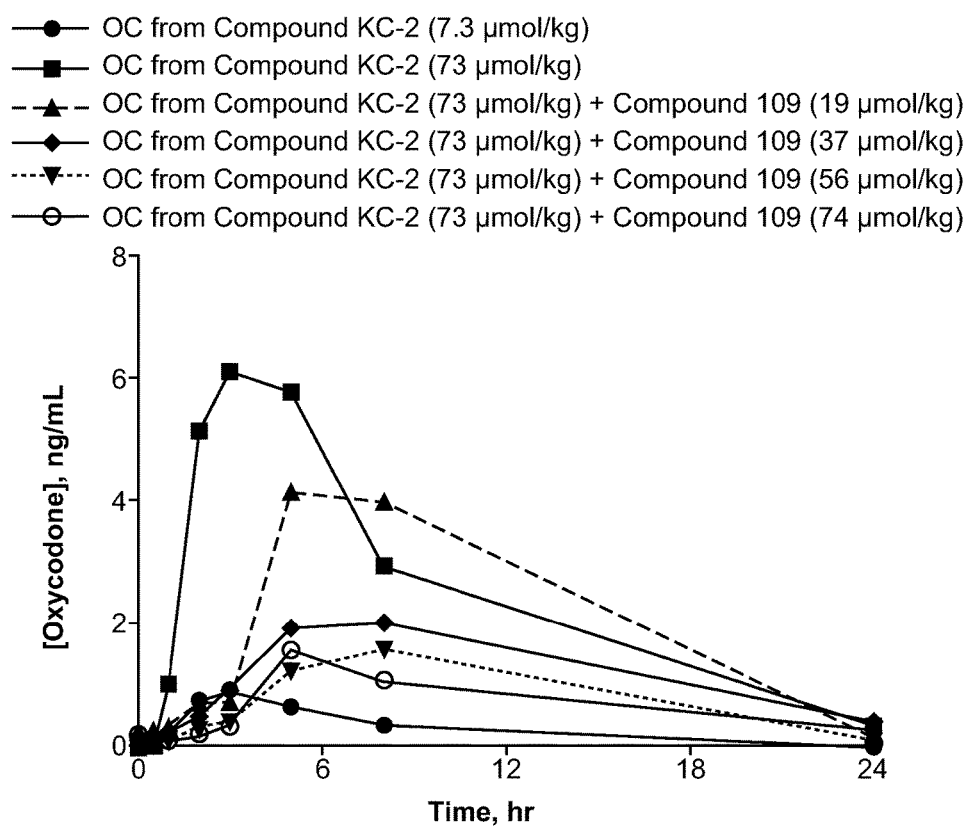
FIG. 10 compares mean plasma concentrations over time of oxycodone release following PO administration of prodrug Compound KC-2 with increasing amounts of co-dosed trypsin inhibitor Compound 109 to rats.

Table 7 and FIG. 10 provide oxycodone exposure results for rats administered with different doses of Compound KC-2. Results in Table 7 are reported, for each group of rats, as (a) maximum plasma concentration (Cmax) of oxycodone (OC) (average+standard deviation), (b) time after administration of Compound KC-2 to reach maximum oxycodone concentration (Tmax) (average±standard deviation) and (c) area under the curve (AUC) from 0 to 24 hr (average±standard deviation).

TABLE 7

Rat dosing PO with Compound KC-2 in the absence or presence of Compound 109

| KC-2 Dose, mg/kg | KC-2 Dose, µmol/kg | Compound 109 Dose, mg/kg | Compound 109 Dose, µmol/kg | OC Cmax ± sd, ng/mL | Tmax ± sd, hr | AUC ± sd, ng*hr/mL |
|---|---|---|---|---|---|---|
| 5 | 7.3 | 0 | 0 | 0.918 ± 0.30 | 2.75 ± 0.5 | 4.30 ± 1.1 |
| 50 | 73 | 0 | 0 | 7.03 ± 2.3 | 3.75 ± 1.5 | 59.9 ± 14 |
| 50 | 73 | 10 | 19 | 4.44 ± 1.5 | 6.50 ± 1.7 | 51.0 ± 16 |
| 50 | 73 | 20 | 37 | 2.25 ± 0.89 | 7.25 ± 1.5 | 29.2 ± 8.9 |
| 50 | 73 | 30 | 56 | 1.77 ± 0.57 | 6.50 ± 1.7 | 19.8 ± 7.6 |
| 50 | 73 | 40 | 74 | 1.64 ± 0.96 | 5.75 ± 1.5 | 16.5 ± 5.9 |

Lower limit of quantitations were 0.0250 ng/ml

FIG. 10 compares mean plasma concentrations over time of oxycodone release following PO administration of Compound KC-2 with increasing amounts of co-dosed trypsin inhibitor Compound 109.

The results in Table 7 and FIG. 10 indicate Compound 109's ability to attenuate Compound KC-2's ability to release oxycodone in a dose dependent manner, both by suppressing Cmax and AUC and by delaying Tmax.

Example 23: In Vitro Human μ-Opioid Receptor Binding Assay

This example measures the affinity of compound KC-2 for the mu (μ)-opioid receptor expressed in recombinant HEK-293 cells.

The general procedure follows the protocol described by Wang, J.-B., Johnson, P. S., Perscio, A. M., Hawkins, A. L., Griffin, C. A. and Uhl, G. R. (1994). FEBS Lett., 338: 217-222. More specifically, the assays included, as appropriate, oxycodone or Compound KC-2 (which can be prepared as described in Example 10) as well as recombinant HEK-293 cells expressing the human μ-opioid receptor on their cell surfaces, reference compound [d-Ala$^2$,N-Me-Phe$^4$, Gly$^5$-ol]-enkephalin (DAMGO), radioligand [$^3$H]DAMGO (0.5 nM) and non-specific ligand naloxone (10 uM). The reaction mixtures were incubated at 22° C. for 2 hr. The samples were then submitted to scintillation counting.

In these assays, the specific binding of a test compound to the receptors is defined as the difference between the total binding and the non-specific binding determined in the presence of an excess of unlabelled ligand. Results are expressed as a percent of control of specific binding and as a percent inhibition of control specific binding obtained in the presence of test compounds. The $IC_{50}$ values (concentration of competing ligand required for 50% inhibition of [$^3$H]DAMGO binding), and Hill coefficients (nH) were determined by non-linear regression analysis of competition curves using Hill equation curve fitting.

Table 8 shows the $IC_{50}$ values for oxycodone and Compound KC-2.

TABLE 8

$IC_{50}$ values

| Compound | $IC_{50}$ Human μ-opioid receptor |
|---|---|
| Oxycodone | 1.2E−08 |
| Compound KC-2 | 2.2E−08 |

These data demonstrate that Compound KC-2 binds to the μ-opioid receptor with an affinity about 2-fold less than that of oxycodone.

Example 24: In Vitro Human μ-Opioid Receptor Agonist Cellular Functional Assay This Example measures the ability of certain compounds of the present disclosure to effect an agonist response when exposed to recombinant human μ-opioid receptor expressed in CHO cells.

The general procedure follows the protocol described by Wang, J.-B., Johnson, P. S., Perscio, A. M., Hawkins, A. L., Griffin, C. A. and Uhl, G. R. (1994). FEBS Lett., 338: 217-222. More specifically, the assays included each of the compounds indicated in Table 9 and recombinant Chinese hamster ovary (CHO) cells expressing the human μ-opioid receptor on their cell surfaces. The control reaction included 1 M DAMGO. The reaction mixtures were incubated at 37° C. for 10 min, and the reaction product was cyclic AMP (cAMP). The samples were submitted to homogeneous time resolved fluorescence (HTRF®). $EC_{50}$ values (concentration producing a half-maximal specific response) were determined by non-linear regression fit using the Hillplot software.

Table 9 shows results from three separate experiments. $EC_{50}$ values are provided for Compound KC-2, Compound KC-3, Compound KC-5, and Compound KC-6 (each of which can be prepared as described in Examples, 10, 11, 13 and 14, respectively) and compared to the $EC_{50}$ value for oxycodone, measured in the same respective experiments. Also shown are the $EC_{50}$ values for Compound KC-4 (which can be prepared as described in Example 12) and hydrocodone, measured in the same experiment. Table 9 also provides the drug-to-prodrug (drug/prodrug) relative potency (i.e., $EC_{50}$ at the human μ-opioid receptor) of oxycodone or hydrocodone to a prodrug of that respective drug.

TABLE 9

$EC_{50}$ values

| Experiment # | Compound | $EC_{50}$ Human μ-opioid receptor | Drug/prodrug relative potency |
|---|---|---|---|
| 1 | Oxycodone | 1.2E−7 | |
| 1 | Compound KC-2 | 4.9E−7 | 4.1 |
| 2 | Oxycodone | 4.0E−8 | |
| 2 | Compound KC-3 | 1.6E−6 | 40 |
| 2 | Compound KC-5 | 2.0E−6 | 50 |
| 3 | Hydrocodone | 8.8E−8 | |
| 3 | Compound KC-4 | 1.3E−6 | 15 |
| 3 | Oxycodone | 7.8E−8 | |
| 3 | Compound KC-6 | 1.8E−6 | 23 |

The results of Table 9 show that prodrugs of the embodiments exhibit a drug/prodrug relative potency greater than 1; thus, prodrugs of the embodiments are less potent at the human t-opioid receptor than are the respective drugs they release.

Example 25: Pharmacokinetics Following IV Administration of Compound KC-2 or Oxycodone to Rats: Plasma and Cerebrospinal Fluid Penetration This Example compares the plasma and cerebrospinal fluid (CSF) concentrations of prodrug Compound KC-2 and oxycodone following intravenous (IV) administration of the respective compounds to rats. Plasma/CSF partitioning coefficients are predictive of the ability of a compound to penetrate the blood-brain barrier.

Compound KC-2 (which can be prepared as described in Example 10), at a dose of 10 mg/kg, or an equimolar dose of oxycodone each was dissolved in saline and injected into the tail vein of 4 male Sprague Dawley rats. After 15 minutes, the rats were anesthetized by carbon dioxide asphyxiation and blood samples were drawn, harvested for plasma via centrifugation at 5,400 rpm at 4° C. for 5 min, and 100 microliters (μl) plasma transferred from each sample into a fresh tube containing 2 μl of 50% formic acid. The CSF fluid was collected using a 22×1 inch gauge needle connected to polyurethane catheter type MRE-040 tubing (Braintree Scientific, Inc., Braintree, Mass.). The needle was inserted just below the nuchal crest at the area of the foramen magnum; clear CSF fluid was collected into the catheter and transferred into a collection tube. The CSF samples were centrifuged at 5,400 rpm at 4° C. for 5 min, and 100 μl CSF fluid transferred from each sample into a fresh tube. The plasma and CSF samples were immediately placed in dry ice and then stored in a −80° C. freezer until analysis by high performance liquid chromatography/mass spectrometry (HPLC/MS).

Results in Table 10 are reported, for each group of 4 rats as mean concentrations of the indicated compounds in plasma or CSF. Table 10 also provides the plasma-to-CSF (plasma/CSF) partitioning coefficient, i.e., the ratio of concentration in the plasma to concentration in the CSF of the indicated compounds.

TABLE 10

Mean plasma and CSF concentration values and partitioning coefficients of Compound KC-2 and oxycodone

| Compound | Compound conc. in Plasma, ng/mL | Compound conc. in CSF, ng/mL | Plasma/CSF partitioning coefficient |
|---|---|---|---|
| Compound KC-2 | 27,200 | 61.9 | 439 |
| OC | 3,257 | 863 | 3.8 |

The results in Table 10 indicate that the relative plasma/CSF partitioning coefficient of Compound KC-2 to oxycodone is about 116 (i.e., 439/3.8); that is, Compound KC-2 is about 116-fold less CSF penetrant than oxycodone. In addition, as shown in Example 24, the drug/prodrug relative potency of Compound KC-2 is about 4.1. Thus, Compound KC-2, when administered intravenously in equimolar amounts would be expected to be about 475-fold (i.e., 116×4.1) less effective at CNS mu-opioid receptors than oxycodone.

Example 26: Pharmacokinetics of Compound KC-3 Following PO Administration to Rats This Example compares the pharmacokinetics of several concentrations of Compound KC-3 administered orally (PO) to rats.

Saline solutions of Compound KC-3 (which can be prepared as described in Example 11) were dosed as indicated in Table 11 via oral gavage into jugular vein-cannulated male Sprague Dawley rats (4 per group, except dose 46 mg/kg KC-3 where 3 rats were used) that had been fasted for 16-18 hr prior to oral dosing. At specified time points, blood samples were drawn, harvested for plasma via centrifugation at 5,400 rpm at 4° C. for 5 min, and 100 µl plasma transferred from each sample into a fresh tube containing 2 µl of 50% formic acid. The tubes were vortexed for 5-10 seconds, immediately placed in dry ice and then stored in −80° C. freezer until analysis by HPLC/MS.

Figure 11:
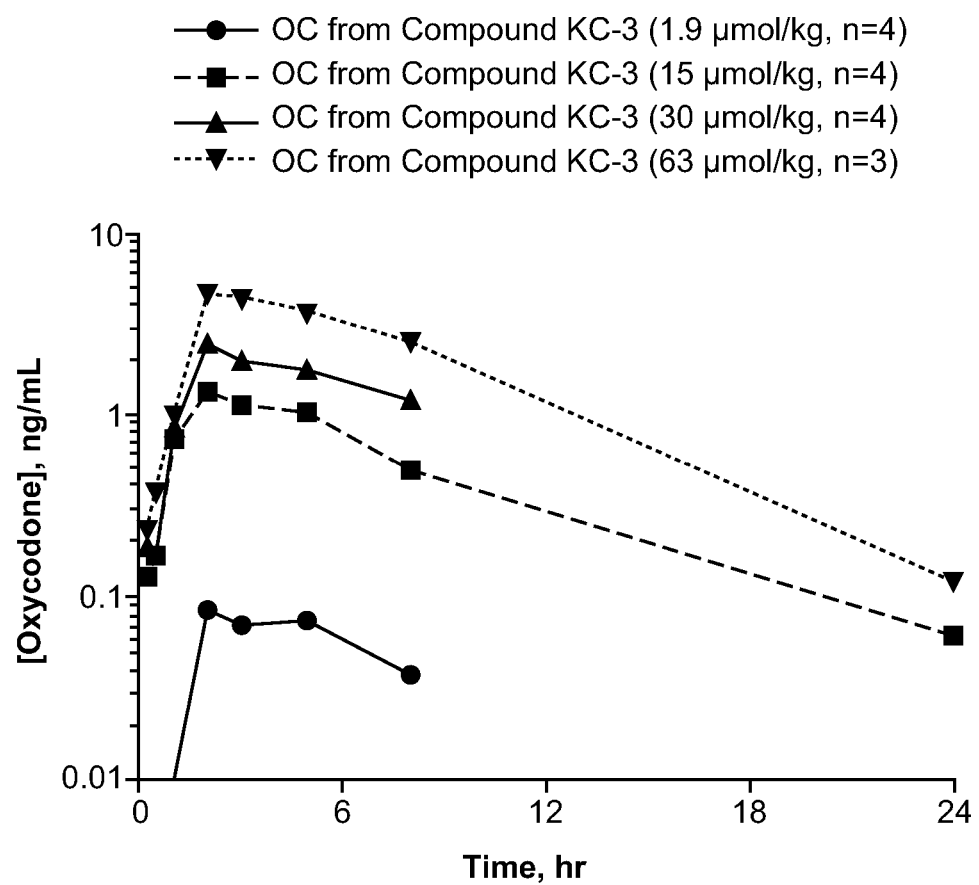
FIG. 11 compares mean plasma concentrations over time of oxycodone release following PO administration of increasing doses of Compound KC-3 to rats.

Table 11 and FIG. 11 provide oxycodone exposure results for rats administered with different doses of Compound KC-3. Results in Table 11 are reported, for each group of rats, as (a) maximum plasma concentration (Cmax) of oxycodone (OC) (average+standard deviation), (b) time after administration of Compound KC-3 to reach maximum oxycodone concentration (Tmax) (average±standard deviation) and (c) area under the curve (AUC) from 0 to 24 hr for all doses except for the 1.4 mg/kg and 22 mg/kg doses where the AUC values were calculated from 0 to 8 hr (average±standard deviation).

TABLE 11

Cmax, Tmax and AUC values of oxycodone in rat plasma

| Compound | Dose, mg/kg | Dose µmol/kg | OC Cmax ± sd, ng/mL | Tmax ± sd, hr | AUC ± sd (ng × hr)/mL |
|---|---|---|---|---|---|
| KC-3 | 1.4 | 1.9 | 0.0992 ± 0.0084 | 2.25 ± 0.5 | 0.376 ± 0.14 |
| KC-3 | 11 | 15 | 1.34 ± 0.31 | 2.00 ± 0.0 | 8.96 ± 4.9 |
| KC-3 | 22 | 30 | 2.54 ± 0.34 | 2.00 ± 0.0 | 12.6 ± 1.9 |
| KC-3 | 46 | 63 | 5.19 ± 0.76 | 3.33 ± 1.5 | 40.5 ± 17 |

Lower limit of quantitation was 0.05 ng/mL

FIG. 11 compares mean plasma concentrations over time of oxycodone release following PO administration of increasing doses of Compound KC-3.

The results in Table 11 and FIG. 11 indicate that plasma concentrations of oxycodone increase proportionally with Compound KC-3 dose.

Example 27: Pharmacokinetics of Compound KC-3 Following IV Administration to Rats This Example compares the plasma concentrations of prodrug and oxycodone in rats following intravenous (IV) administration of Compound KC-3.

Compound KC-3 (which can be prepared as described in Example 11) was dissolved in saline and injected into the tail vein of 4 jugular vein-cannulated male Sprague Dawley rats at a dose of 2 mg/kg. At specified time points, blood samples were drawn, harvested for plasma via centrifugation at 5,400 rpm at 4° C. for 5 min, and 100 µl plasma transferred from each sample into a fresh tube containing 2 µl of 50% formic acid. The tubes were vortexed for 5-10 seconds, immediately placed in dry ice and then stored in −80° C. freezer until analysis by high performance liquid chromatography/mass spectrometry (HPLC/MS).

Figure 12:
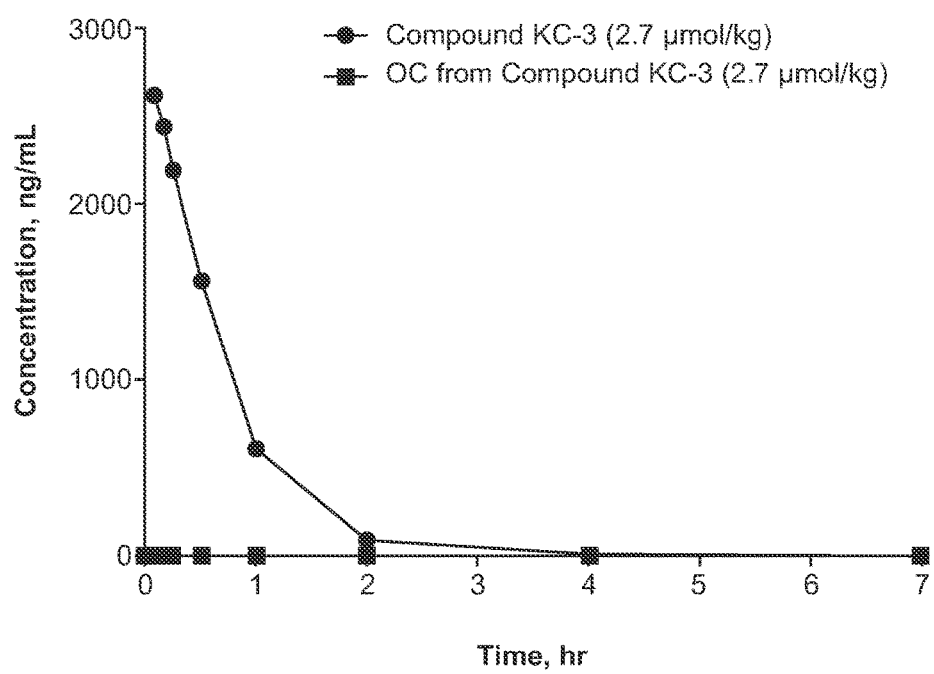
FIG. 12 shows a plasma concentration time course of the production of oxycodone following intravenous (IV) dosing of prodrug Compound KC-3 in rats.

Table 12 and FIG. 12 provide Compound KC-3 and oxycodone exposure results for the group of rats administered Compound KC-3 intravenously. Results in Table 12 are reported as maximum plasma concentration (Cmax) of Compound KC-3 and oxycodone (OC), respectively (average±standard deviation).

TABLE 12

Cmax values of Compound KC-3 and oxycodone in rat plasma

| KC-3 Dose, mg/kg | KC-3 Dose, µmol/kg | KC-3 Cmax ± sd, ng/mL | OC Cmax ± sd, ng/mL |
|---|---|---|---|
| 2 | 2.7 | 2620 ± 85 | 1.14 ± 0.48 |

Lower limit of quantitation was 0.05 ng/mL

Table 12 and FIG. 12 demonstrate that the plasma concentration of oxycodone in rats administered Compound KC-3 intravenously is only 0.04% of the plasma concentration of Compound KC-3, indicating that IV administration of Compound KC-3 does not lead to significant release of oxycodone into plasma.

Example 28: Effect of Trypsin Inhibition on In Vitro Trypsin-Mediated Trypsin Release of Drug from Ketone-Modified Opioid Prodrugs This Example demonstrates the ability of trypsin to cleave a prodrug of the embodiments and the effect of trypsin inhibitors on such cleavage.

Compound KC-3, Compound KC-4, Compound KC-5, or Compound KC-6 was each incubated with trypsin from bovine pancreas (Catalog No. T8003, Type I, ~10,000 BAEE units/mg protein, Sigma-Aldrich). Specifically, the reactions included 0.761 mM of Compound KC-3.2HCl, Compound KC-5.2HCl, Compound KC-4.2HCl, or Compound KC-6.2HCl, 22.5 mM calcium chloride, 40 to 172 mM Tris pH 8 and 0.25% DMSO with variable activities of trypsin as indicated in Table 13A. The reactions were conducted at 37° C. for 24 hr. Samples were collected at specified time points, transferred into 0.5% formic acid in acetonitrile to stop trypsin activity and stored at less than −70° C. until analysis by LC-MS/MS.

Compound KC-3 was also incubated in the presence of 2 micromolar (µM) trypsin inhibitor Compound 109. In that case, Compound KC-3 was added 5 min after the other incubation components. Other reaction and sample treatment conditions were as described above.

Tables 13A and 13B indicate the results of exposure of the tested compounds to trypsin in the absence or presence of trypsin inhibitor. The results are expressed as half-life of prodrug when exposed to trypsin (i.e., Prodrug trypsin half-life) in hours and rate of oxycodone or hydrocodone formation in umoles per hour per BAEE unit (umol/h/BAEE U) trypsin.

TABLE 13A

In vitro trypsin conversion of prodrugs to oxycodone or hydrocodone

| Pro-drug | BAEE U trypsin/mL | Pro-drug trypsin half-life, h Average ± sd | Rate of oxycodone formation, umol/h/BAEE U Average ± sd | Rate of hydrocodone formation, umol/h/BAEE U Average ± sd |
|---|---|---|---|---|
| KC-3 | 241 | 8.92 ± 1.91 | 0.0684 ± 0.0009 | na |
| KC-5 | 241 | 1.2 ± 0.04 | 0.135 ± 0.005 | na |
| KC-4 | 241 | 6.35 ± 0.13 | na | 0.0911 ± 0.015 |
| KC-4 | 4815 | 0.315 ± 0.004 | na | 0.0137 ± 0.0014 |
| KC-6 | 241 | nc | 0.0118 ± 0.0042 | na |
| KC-6 | 4815 | nc | 0.00571 ± 0.0002 | na | nc = not calculable;
na = not applicable

TABLE 13B

Inhibition of in vitro trypsin conversion of Compound KC-3 to oxycodone by Compound 109

| | | With trypsin inhibitor | |
|---|---|---|---|
| Prodrug | Compound 109 | Pro-drug trypsin half-life, h Average ± sd | Rate of oxycodone formation, umol/h/BAEE U Average ± sd |
| KC-3 | 2 uM | 43.338 ± 40.637 | nc | nc = not calculable

The results in Table 13A indicate that trypsin can mediate release of oxycodone or hydrocodone from a prodrug of the embodiments. The results in Table 13B indicate that a trypsin inhibitor of the embodiments can attenuate trypsin-mediated release of drug from a ketone-modified opioid prodrug of the embodiments.

Example 29: Oral Administration of Compound KC-3 and Trypsin Inhibitor Compound 109 to Rats This Example demonstrates the ability of a trypsin inhibitor of the embodiments to affect drug release into plasma from Compound KC-3 administered orally.

Saline solutions of Compound KC-3 (which can be prepared as described in Example 11) were dosed at 6.8 µmol/kg (5 mg/kg) and 68 µmol/kg (50 mg/kg) Compound KC-3 with or without a co-dose of increasing concentrations of Compound 109 (Catalog No. 3081, Tocris Bioscience or Catalog No. WS38665, Waterstone Technology) as indicated in Table 14 via oral gavage into jugular vein-cannulated male Sprague Dawley rats (4 per groups) that had been fasted for 16-18 hr prior to oral dosing. At specified time points, blood samples were drawn, harvested for plasma via centrifugation at 5,400 rpm at 4° C. for 5 min, and 100 µl plasma transferred from each sample into a fresh tube containing 2 µl of 50% formic acid. The tubes were vortexed for 5-10 seconds, immediately placed in dry ice and then stored in −80° C. freezer until analysis by HPLC/MS.

Figure 13:
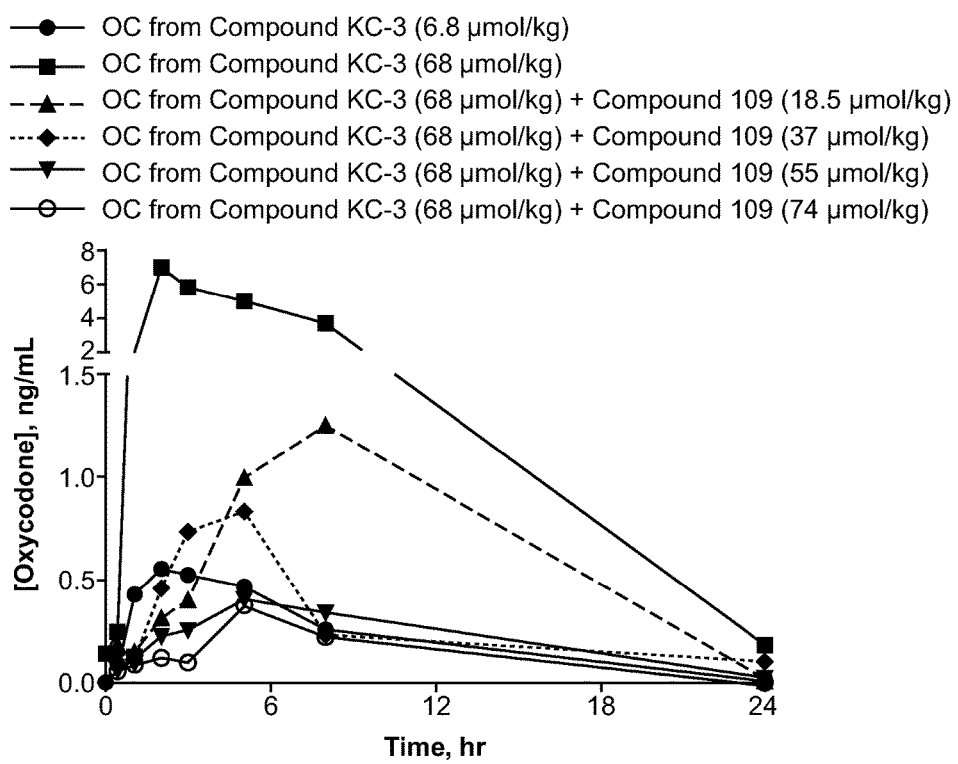
FIG. 13 compares mean plasma concentrations over time of oxycodone release following PO administration of prodrug Compound KC-3 with increasing amounts of co-dosed trypsin inhibitor Compound 109 to rats.

Table 14 and FIG. 13 provide oxycodone exposure results for rats administered with Compound KC-3 in the absence or presence of trypsin inhibitor. Results in Table 14 are reported as (a) maximum plasma concentration (Cmax) of oxycodone (OC) (average±standard deviation), (b) time after administration of Compound KC-3 to reach maximum oxycodone concentration (Tmax) (average±standard deviation) and (c) area under the curve (AUC) from 0 to 24 hr (average±standard deviation).

TABLE 14

Cmax, Tmax and AUC values of oxycodone in rat plasma

| KC-3 Dose, mg/kg | KC-3 Dose, µmol/kg | Compound 109 Dose, mg/kg | Compound 109 Dose, µmol/kg | OC Cmax ± sd, ng/mL | Tmax ± sd, hr | AUC ± sd (ng × hr)/mL |
|---|---|---|---|---|---|---|
| 5 | 6.8 | 0 | 0 | 0.611 ± 0.10 | 3.00 ± 1.4 | 3.95 ± 1.6 |
| 50 | 68 | 0 | 0 | 7.08 ± 2.6 | 3.00 ± 1.4 | 59.1 ± 23 |
| 50 | 68 | 10 | 18.5 | 1.26 ± 0.34 | 8.00 ± 0.0 | 12.3 ± 2.9 |
| 50 | 68 | 20 | 37 | 1.05 ± 0.61 | 3.75 ± 1.5 | 10.5 ± 5.4 |
| 50 | 68 | 30 | 55 | 0.49 ± 0.19 | 4.50 ± 2.6 | 2.82 ± 1.3 |
| 50 | 68 | 40 | 74 | 0.47 ± 0.36 | 4.63 ± 3.1 | 2.71 ± 3.7 |

Lower limit of quantitation was 0.025 ng/mL

FIG. 13 compares mean plasma concentrations over time of oxycodone release following PO administration of Compound KC-3 with or without a co-dose of trypsin inhibitor.

The results in Table 14 and FIG. 13 indicate that Compound 109 attenuates Compound KC-3's ability to release oxycodone, both by suppressing Cmax and AUC and by delaying Tmax.

Example 30: Pharmacokinetics Following IV Administration of Compound KC-3 or Oxycodone to Rats: Plasma and Cerebrospinal Fluid Penetration This Example compares the plasma and cerebrospinal fluid (CSF) concentrations of prodrug Compound KC-3 and oxycodone following intravenous (IV) administration of the respective compounds to rats. Plasma/CSF partitioning coefficients are predictive of the ability of a compound to penetrate the blood-brain barrier.

Compound KC-3 (which can be prepared as described in Example 11), at a dose of 10 mg/kg, or an equimolar dose of oxycodone each was dissolved in saline and injected into the tail vein of 4 male Sprague Dawley rats. After 2 minutes, the rats were anesthetized by carbon dioxide asphyxiation and blood samples were drawn, harvested for plasma via centrifugation at 5,400 rpm at 4° C. for 5 min, and 100 µl plasma transferred from each sample into a fresh tube containing 2 µl of 50% formic acid. The CSF fluid was collected using a 22×1 inch gauge needle connected to polyurethane catheter type MRE-040 tubing (Braintree Scientific, Inc.). The needle was inserted just below the nuchal crest at the area of the foramen magnum; clear CSF fluid was collected into the catheter and transferred into a collection tube. The CSF samples were centrifuged at 5,400 rpm at 4° C. for 5 min, and 100 µl CSF fluid transferred from each sample into a fresh tube. The plasma and CSF samples were immediately placed in dry ice and then stored in a −80° C. freezer until analysis by high performance liquid chromatography/mass spectrometry (HPLC/MS). In order to study Compound KC-3 and oxycodone plasma and CSF penetration over time, additional groups of 4 rats were administered compounds as described above and anesthetized at specified time points. Plasma and CSF were collected and analyzed as described above. Results from these rats indicated that equilibrium was quickly reached in the plasma and CSF compartments after dosing and that the extent of partitioning between CSF and plasma was consistent across time points. Thus, only the 2-minute time point data are reported in Table 15.

Results in Table 15 are reported, for each group of 4 rats as mean concentrations of the indicated compounds in plasma or CSF. Table 15 also provides the plasma-to-CSF (plasma/CSF) partitioning coefficient, i.e., the ratio of concentration in the plasma to concentration in the CSF of the indicated compounds.

TABLE 15

Mean plasma and CSF concentration values and partitioning coefficients of Compound KC-3 and oxycodone

| Compound | Compound conc. in Plasma, ng/mL | Compound conc. in CSF, ng/mL | Plasma/CSF partitioning coefficient |
|---|---|---|---|
| Compound KC-3 | 59,225 | 34.1 | 1,737 |
| OC | 10,300 | 2158 | 4.8 |

The results in Table 15 indicate that the relative plasma/CSF partitioning coefficient of Compound KC-3 to oxycodone is about 364 (i.e., 1,737/4.8); that is, Compound KC-3 is about 364-fold less CSF penetrant than oxycodone. In addition, as shown in Example 24, the drug/prodrug relative potency of Compound KC-3 is about 40. Thus, Compound KC-3, when administered intravenously in equimolar amounts would be expected to be about 14,500-fold (i.e., 364×40) less effective at CNS mu-opioid receptors than oxycodone.

Example 31: In Vivo Tolerability of Compound KC-3 in Rats

This Example demonstrates that Compound KC-3 was tolerated when administered intravenously to rats.

Male naïve Sprague-Dawley rats, 4 per dose, were used in the study. Rats were weighed, and then placed under a heat lamp for 15-20 minutes to dilate the lateral tail veins. Dose volumes were based on the body weights (1 mL/kg); dosing of Compound KC-3 (which can be prepared as described in Example 11) was as indicated in Table 16. Before dosing, rats were placed in Broome restrainers and the drug was introduced into one of the tail veins using a syringe and needle. After dosing, the timer was set and rats were observed for clinical signs. Blood samples were collected 5 minutes post-dose via the saphenous vein. The rats were observed up to 24 hours. Results are shown in Table 16.

TABLE 16

In vivo tolerability of Compound KC-3 in rats

| Compound | Dose, mg/kg | Dose, µmol/kg | Number of Rats dosed | Clinical observations |
|---|---|---|---|---|
| KC-3 | 71 | 97 | 4 | 2 normal and 2 with ataxia which resolved by 2 minutes |

The results in Table 16 indicate that rats tolerate a dose of 97 µmol/kg of Compound KC-3 and recover to normal activity within 2 minutes.

Example 32: In Vitro Stability of Oxycodone Prodrug Compound KC-3

This Example demonstrates the stability of Compound KC-3 to a variety of readily available household chemicals and enzyme preparations.

Compound KC-3 (which can be prepared as described in Example 11) was exposed at room temperature (RT) or 80° C. for either 1 or 24 hours (hr) to the following household chemicals: vodka (40% alcohol), baking soda (saturated sodium bicarbonate solution, pH 9), WINDEX® with Ammonia-D (pH11) and vinegar (5% acetic acid). Compound KC-3 was also exposed to the following enzyme-containing compositions at RT for 1 or 24 hr: GNC® Super Digestive (2 capsules of GNC Super Digestive Enzymes dissolved in 5 mL of water), tenderizer (Adolf's meat tenderizer, primarily papain, dissolved in water to a concentration of 0.123 g/mL to approximate the concentration of a marinade given on the bottle label), and subtilisn (8 tablets of ULTRAZYME® contact lens cleaner (Advanced Medical Optics) dissolved in 4 mL water).

Samples were incubated as described. Aliquots were removed at 1 hr and 24 hr and stabilized by adding each to a solution of 50% or 100% of 85% phosphoric acid solution to achieve a final pH of less than or equal to pH 4. The stabilized aliquots were then diluted 4- to 6-fold with water, vortex-mixed and applied to HPLC.

Figure 14:
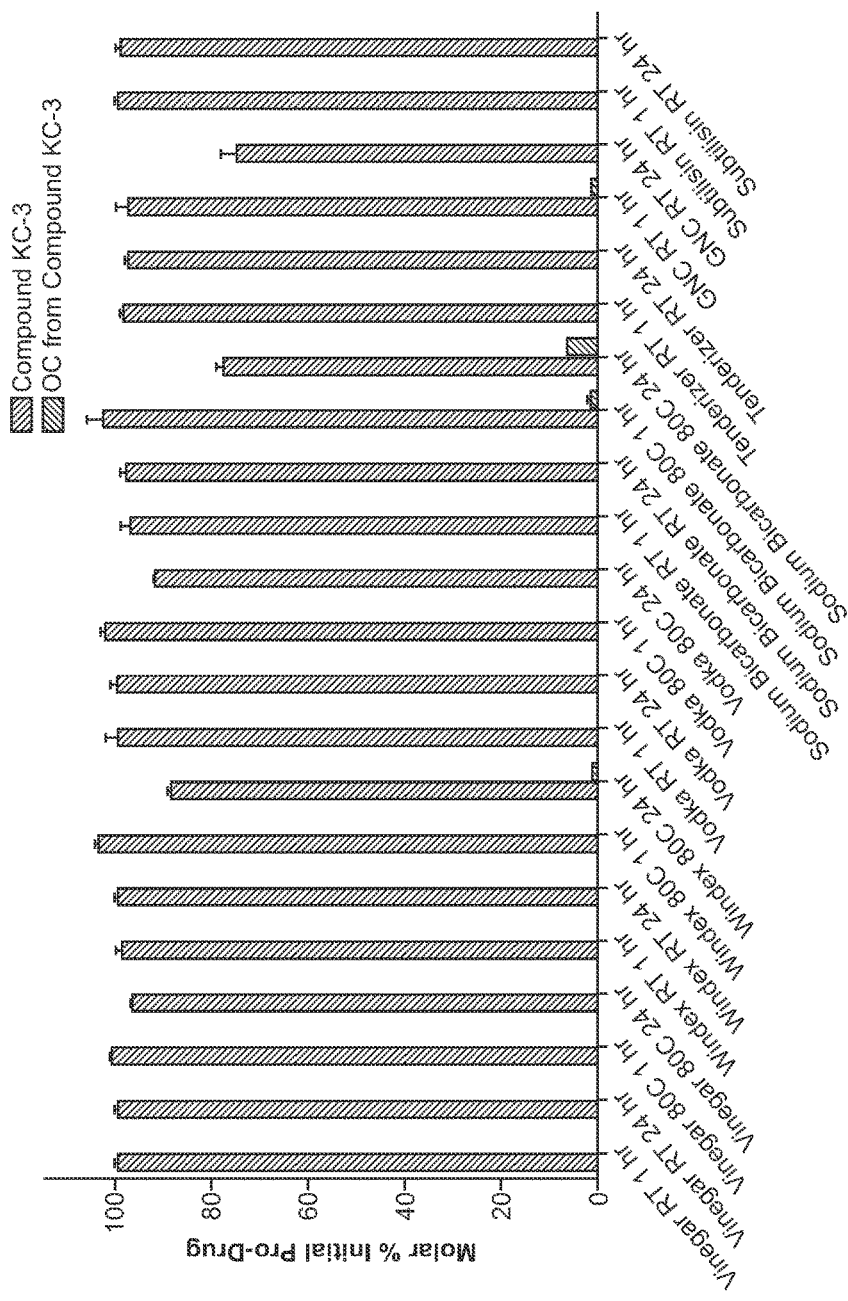
FIG. 14 demonstrates the release of oxycodone from prodrug Compound KC-3 exposed to a variety of household chemicals and enzyme preparations.

FIG. 14 demonstrates the release of oxycodone when Compound KC-3 was exposed to the various household chemicals and enzyme-containing compositions described above. The percentage of Compound KC-3 remaining after exposure is indicated by the solid black bars and percentage conversion of Compound KC-3 to oxycodone is indicated by the lightly shaded bars with a black outline. These results indicate that exposure of Compound KC-3 to these various conditions leads to substantially less than 10% conversion to oxycodone.

Example 33: Pharmacokinetics of Compound KC-4 Following PO Administration to Rats This Example demonstrates the release of hydrocodone into plasma when Compound KC-4 is administered orally (PO) to rats.

Saline solutions of Compound KC-4 (which can be prepared as described in Example 12) were dosed as indicated in Table 17) via oral gavage into jugular vein-cannulated male Sprague Dawley rats (4 per group) that had been fasted for 16-18 hr prior to oral dosing. At specified time points, blood samples were drawn, harvested for plasma via centrifugation at 5,400 rpm at 4° C. for 5 min, and 100 µl plasma transferred from each sample into a fresh tube containing 2 µl of 50% formic acid. The tubes were vortexed for 5-10 seconds, immediately placed in dry ice and then stored in −80° C. freezer until analysis by HPLC/MS.

Table 17 provides hydrocodone exposure results for rats administered Compound KC-4 orally. Results in Table 17 are reported as (a) maximum plasma concentration (Cmax) of hydrocodone (OC) (average±standard deviation), (b) time after administration of Compound KC-4 to reach maximum hydrocodone concentration (Tmax) (average±standard deviation) and (c) area under the curve (AUC) from 0 to 24 hr (average±standard deviation).

TABLE 17

Cmax, Tmax and AUC values of hydrocodone in rat plasma

| Compound | Dose, mg/kg | Dose µmol/kg | HC Cmax ± sd ng/mL | Tmax ± sd, hr | AUC ± sd (ng × hr)/mL |
|---|---|---|---|---|---|
| KC-4 | 6 | 8.4 | 0.0667 ± 0.019 | 4.5 ± 2.6 | 0.315 ± 0.063 |

Lower limit of quantitation was 0.025 ng/mL

The results in Table 17 indicate that oral administration of Compound KC-4 leads to release of hydrocodone by a hydrocodone prodrug of the embodiments.

Example 34: Pharmacokinetics of Compound KC-4 Following IV Administration to Rats This Example compares the plasma concentrations of prodrug and hydrocodone in rats following intravenous (IV) administration of Compound KC-4.

Compound KC-4 (which can be prepared as described in Example 14) was dissolved in saline and injected into the tail vein of 4 jugular vein-cannulated male Sprague Dawley rats at a dose of 2 mg/kg. At specified time points, blood samples were drawn, harvested for plasma via centrifugation at 5,400 rpm at 4° C. for 5 min, and 100 µl plasma transferred from each sample into a fresh tube containing 2 µl of 50% formic acid. The tubes were vortexed for 5-10 seconds, immediately placed in dry ice and then stored in −80° C. freezer until analysis by high performance liquid chromatography/mass spectrometry (HPLC/MS).

Figure 15:
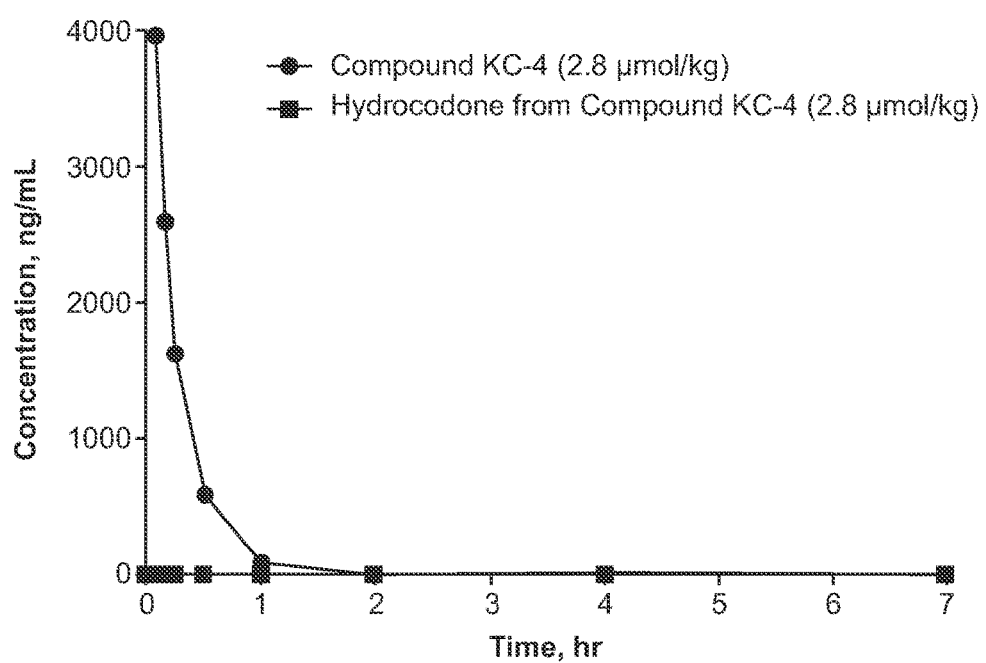
FIG. 15 shows a plasma concentration time course of the production of oxycodone following intravenous (IV) dosing of prodrug Compound KC-4 in rats.

Table 18 and FIG. 15 provide Compound KC-4 and hydrocodone exposure results for rats administered Compound KC-4 intravenously. Results in Table 18 are reported as maximum plasma concentration (Cmax) of Compound KC-4 and hydrocodone (HC), respectively, (average±standard deviation).

TABLE 18

Cmax values of Compound KC-4 and hydrocodone in rat plasma

| KC-4 Dose, mg/kg | KC-4 Dose, µmol/kg | KC-4 Cmax ± sd, ng/mL* | HC Cmax ± sd, ng/mL^ |
|---|---|---|---|
| 2 | 2.8 | 3960 ± 570 | 0.224 ± 0.020 |

*Lower limit of quantitation was 0.05 ng/mL
^Lower limit of quantitation was 0.025 ng/mL Table 18 and FIG. 15 demonstrate that the plasma concentration of hydrocodone in rats administered Compound KC-4 intravenously is only 0.006% of the plasma concentration of Compound KC-4, indicating that IV administration of Compound KC-4 does not lead to significant release of hydrocodone into plasma.

Example 35: Oral Administration of Compound KC-4 and Trypsin Inhibitor Compound 109 to Rats This Example demonstrates the ability of a trypsin inhibitor of the embodiments to affect drug release into plasma from Compound KC-4 administered orally.

Saline solutions of Compound KC-4 (which can be prepared as described in Example 12) were dosed at 8.4 µmol/kg (6 mg/kg) with or without a co-dose of 55 µmol/kg (30 mg/kg) Compound 109 (Catalog No. 3081, Tocris Bioscience or Catalog No. WS38665, Waterstone Technology) as indicated in Table 19 via oral gavage into jugular vein-cannulated male Sprague Dawley rats (4 per groups) that had been fasted for 16-18 hr prior to oral dosing. At specified time points, blood samples were drawn, harvested for plasma via centrifugation at 5,400 rpm at 4° C. for 5 min, and 100 µl plasma transferred from each sample into a fresh tube containing 2 µl of 50% formic acid. The tubes were vortexed for 5-10 seconds, immediately placed in dry ice and then stored in −80° C. freezer until analysis by HPLC/MS.

Figure 16:
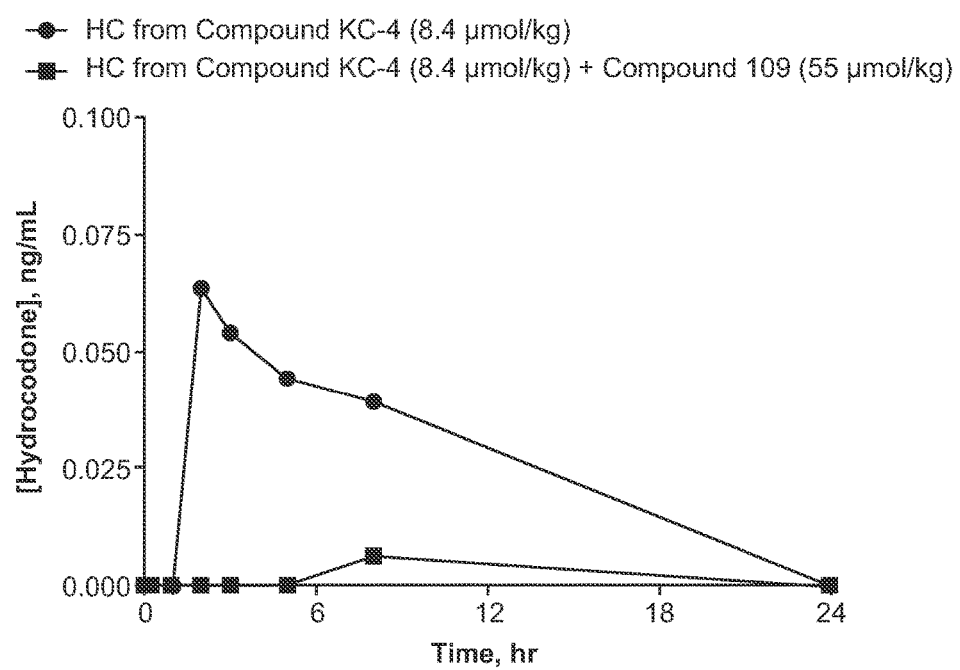
FIG. 16 compares mean plasma concentrations over time of hydrocodone release following PO administration of prodrug Compound KC-4 with or without a co-dose of trypsin inhibitor to rats.

Table 19 and FIG. 16 provide hydrocodone exposure results for rats administered with Compound KC-4 in the absence or presence of trypsin inhibitor. Results in Table 19 are reported as (a) maximum plasma concentration (Cmax) of hydrocodone (HC) (average±standard deviation), (b) time after administration of Compound KC-4 to reach maximum hydrocodone concentration (Tmax) (average±standard deviation) and (c) area under the curve from 0 to 24 hr (average±standard deviation).

TABLE 19

Cmax, Tmax and AUC values of hydrocodone in rat plasma

| KC-4 Dose, mg/kg | KC-4 Dose, μmol/kg | Compound 109 Dose, mg/kg | Compound 109 Dose, μmol/kg | HC Cmax ± sd, ng/mL | Tmax ± sd, hr | AUC ± sd (ng × hr)/mL |
|---|---|---|---|---|---|---|
| 6 | 8.4 | 0 | 0 | 0.0667 ± 0.019 | 4.5 ± 2.6 | 0.315 ± 0.063 |
| 6 | 8.4 | 30 | 55 | 0.0064 ± 0.013 | 8.0 ± 0.0 | 0.016 ± 0.032 |

Lower limit of quantitation was 0.025 ng/mL

FIG. 16 compares mean plasma concentrations over time of hydrocodone release following PO administration of Compound KC-4 with or without a co-dose of trypsin inhibitor.

The results in Table 19 and FIG. 16 indicate that Compound 109 attenuates Compound KC-4's ability to release hydrocodone, both by suppressing Cmax and AUC and by delaying Tmax.

Example 36: Pharmacokinetics of Compound KC-5 Following PO Administration to Rats This Example demonstrates the release of oxycodone into plasma when Compound KC-5 is administered orally (PO) to rats.

Saline solutions of Compound KC-5 (which can be prepared as described in Example 13) were dosed as indicated in Table 20 via oral gavage into jugular vein-cannulated male Sprague Dawley rats (4 per group) that had been fasted for 16-18 hr prior to oral dosing. At specified time points, blood samples were drawn, harvested for plasma via centrifugation at 5,400 rpm at 4° C. for 5 min, and 100 μl plasma transferred from each sample into a fresh tube containing 2 μl of 50% formic acid. The tubes were vortexed for 5-10 seconds, immediately placed in dry ice and then stored in −80° C. freezer until analysis by HPLC/MS.

Figure 17:
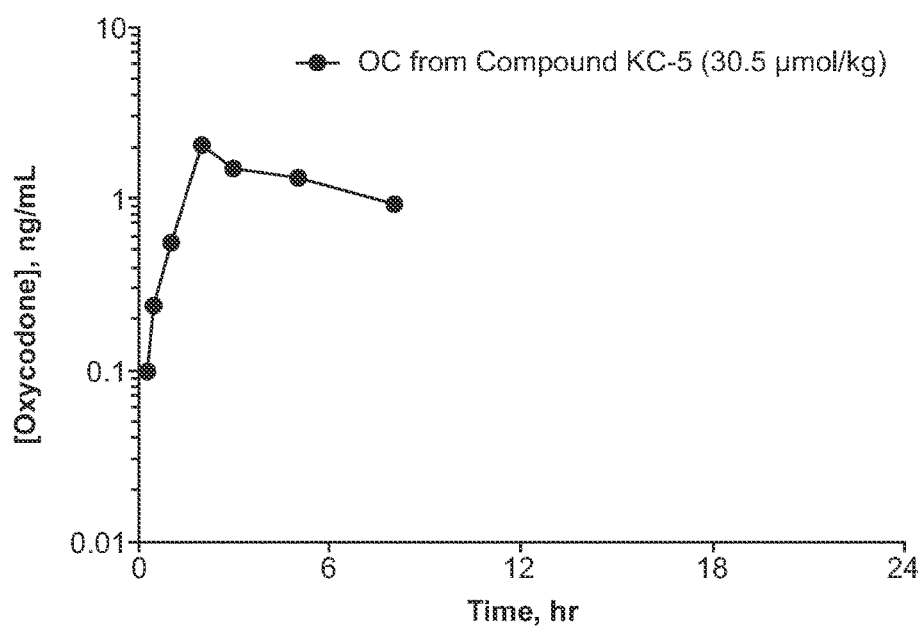
FIG. 17 demonstrates mean plasma concentrations over time of oxycodone release following PO administration of Compound KC-5 to rats.

Table 20 and FIG. 17 provide oxycodone exposure results for rats administered Compound KC-5 orally. Results in Table 20 are reported as (a) maximum plasma concentration (Cmax) of oxycodone (OC) (average±standard deviation), (b) time after administration of Compound KC-5 to reach maximum oxycodone concentration (Tmax) (average±standard deviation) and (c) area under the curve (AUC) (ng×hr)/mL from 0 to 8 hr (average±standard deviation).

TABLE 20

Cmax, Tmax and AUC values of oxycodone (OC) in rat plasma

| Compound | Dose, mg/kg | Dose μmol/kg | OC Cmax ± sd, ng/mL | Tmax ± sd, hr | AUC ± sd (ng × hr)/mL |
|---|---|---|---|---|---|
| KC-5 | 24 | 30.5 | 2.06 ± 0.45 | 2.0 ± 0.0 | 9.61 ± 1.4 |

Lower limit of quantitation was 0.025 ng/mL

FIG. 17 demonstrates mean plasma concentrations over time of oxycodone release following PO administration of Compound KC-5.

The results in Table 20 and FIG. 17 indicate that oral administration of Compound KC-5 yields oxycodone plasma concentrations that exhibit a suppressed Cmax and AUC and delayed Tmax compared to administration of oxycodone (see Example 15).

Example 37

Pharmacokinetics of Compound KC-5 Following IV Administration to Rats

This Example compares the plasma concentrations of prodrug and oxycodone in rats following intravenous (IV) administration of Compound KC-5.

Compound KC-5 (which can be prepared as described in Example 13) was dissolved in saline and injected into the tail vein of 4 jugular vein-cannulated male Sprague Dawley rats at a dose of 2 mg/kg. At specified time points, blood samples were drawn, harvested for plasma via centrifugation at 5,400 rpm at 4° C. for 5 min, and 100 μl plasma transferred from each sample into a fresh tube containing 2 μl of 50% formic acid. The tubes were vortexed for 5-10 seconds, immediately placed in dry ice and then stored in −80° C. freezer until analysis by high performance liquid chromatography/mass spectrometry (HPLC/MS).

Figure 18:
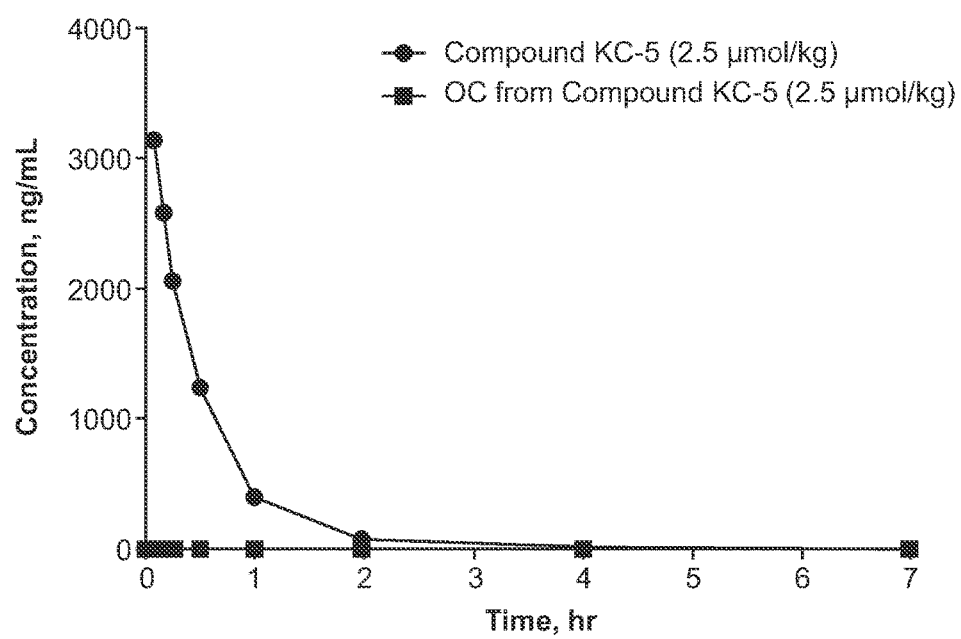
FIG. 18 shows a plasma concentration time course of the production of oxycodone following intravenous (IV) dosing of prodrug Compound KC-5 in rats.

Table 21 and FIG. 18 provide Compound KC-5 and oxycodone exposure results for rats administered Compound KC-5 intravenously. Results in Table 21 are reported as maximum plasma concentration (Cmax) of Compound KC-5 and oxycodone (OC), respectively (average±standard deviation).

TABLE 21

Cmax values of Compound KC-5 and oxycodone in rat plasma

| KC-5 Dose, mg/kg | KC-5 Dose, μmol/kg | KC-5 Cmax ± sd, ng/mL* | OC Cmax ± sd, ng/mL^ |
|---|---|---|---|
| 2 | 2.5 | 3140 ± 270 | 0.878 ± 0.78 |

*Lower limit of quantitation was 0.100 ng/mL
^Lower limit of quantitation was 0.0125 ng/mL Table 21 and FIG. 18 demonstrate that the plasma concentration of oxycodone in rats administered Compound KC-5 IV is only 0.028% of the plasma concentration of Compound KC-5, indicating that IV administration of Compound KC-5 does not lead to significant release of oxycodone into plasma.

Example 38: Pharmacokinetics Following IV Administration of Compound KC-5 or Oxycodone to Rats: Plasma and Cerebrospinal Fluid Penetration This Example compares the plasma and cerebrospinal fluid (CSF) concentrations of prodrug Compound KC-5 and oxycodone following intravenous (IV) administration of the respective compounds to rats. Plasma/CSF partitioning coefficients are predictive of the ability of a compound to penetrate the blood-brain barrier.

Compound KC-5 (which can be prepared as described in Example 13), at a dose of 10 mg/kg, or an equimolar dose of oxycodone each was dissolved in saline and injected into the tail vein of 4 male Sprague Dawley rats. After 2 minutes, the rats were anesthetized by carbon dioxide asphyxiation and blood samples were drawn, harvested for plasma via centrifugation at 5,400 rpm at 4° C. for 5 min, and 100 µl plasma transferred from each sample into a fresh tube containing 2 µl of 50% formic acid. The CSF fluid was collected using a 22×1 inch gauge needle connected to polyurethane catheter type MRE-040 tubing (Braintree Scientific, Inc.). The needle was inserted just below the nuchal crest at the area of the foramen magnum and clear CSF fluid was collected into the catheter and transferred into a collection tube. The CSF samples were centrifuged at 5,400 rpm at 4° C. for 5 min, and 100 µl CSF fluid transferred from each sample into a fresh tube. The plasma and CSF samples were immediately placed in dry ice and then stored in a −80° C. freezer until analysis by high performance liquid chromatography/mass spectrometry (HPLC/MS). In order to study Compound KC-5 and oxycodone plasma and CSF penetration over time, additional groups of 4 rats were administered compounds as described above and anesthetized at specified time points. Plasma and CSF were collected and analyzed as described above. Results from these rats indicated that equilibrium was quickly reached in the plasma and CSF compartments after dosing and that the extent of partitioning between CSF and plasma was consistent across time points. Thus, only the 2-minute time point data are reported in Table 22.

Results in Table 22 are reported, for each group of 4 rats as mean concentrations of the indicated compounds in plasma or CSF. Table 22 also provides the plasma-to-CSF (plasma/CSF) partitioning coefficient, i.e., the ratio of concentration in the plasma to concentration in the CSF of the indicated compounds.

TABLE 22

Mean plasma and CSF concentration values and partitioning coefficients of Compound KC-5 and oxycodone

| Compound | Compound conc. in Plasma, ng/mL | Compound conc. in CSF, ng/mL | Plasma/CSF partitioning coefficient |
|---|---|---|---|
| Compound KC-5 | 54,900 | 36.4 | 1,508 |
| OC | 10,300 | 2,158 | 4.8 |

The results in Table 22 indicate that the relative plasma/CSF partitioning coefficient of Compound KC-5 to oxycodone is about 316 (i.e., 1,508/4.8); that is, Compound KC-5 is about 316-fold less CSF penetrant than oxycodone. In addition, as shown in Example 24, the drug/prodrug relative potency of Compound KC-5 is about 50. Thus, Compound KC-5, when administered intravenously in equimolar amounts would be expected to be about 15,800-fold (i.e., 316×50) less effective at CNS mu-opioid receptors than oxycodone.

Example 39: Pharmacokinetics of Compound KC-6 Following PO Administration to Rats This Example demonstrates the release of oxycodone into plasma when Compound KC-6 is administered orally (PO) to rats.

Saline solutions of Compound KC-6 (which can be prepared as described in Example 14) were dosed as indicated in Table 23 via oral gavage into jugular vein-cannulated male Sprague Dawley rats (4 per group) that had been fasted for 16-18 hr prior to oral dosing. At specified time points, blood samples were drawn, harvested for plasma via centrifugation at 5,400 rpm at 4° C. for 5 min, and 100 µl plasma transferred from each sample into a fresh tube containing 2 µl of 50% formic acid. The tubes were vortexed for 5-10 seconds, immediately placed in dry ice and then stored in −80° C. freezer until analysis by HPLC/MS.

Figure 19:
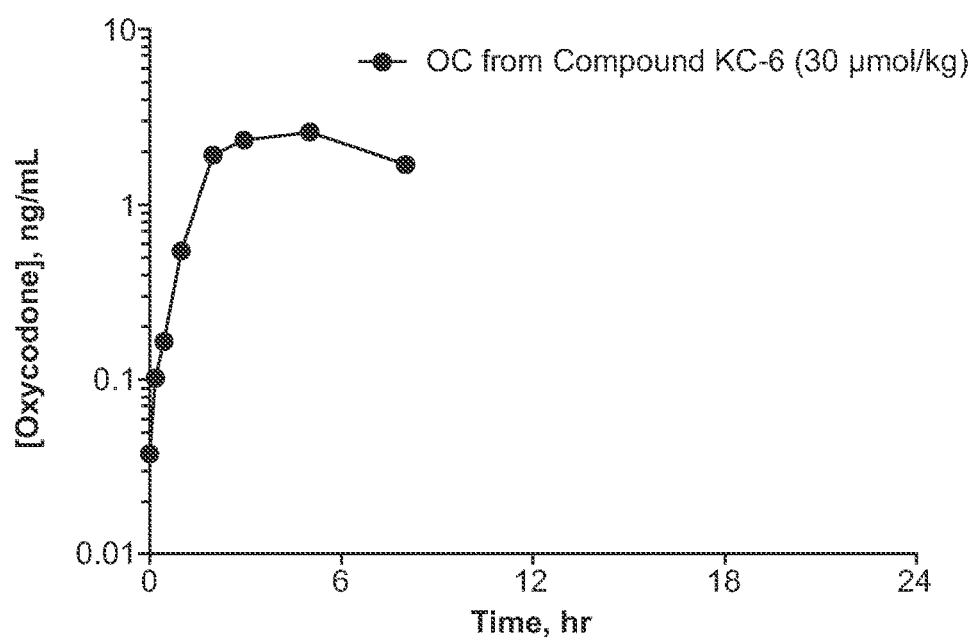
FIG. 19 demonstrates mean plasma concentrations over time of oxycodone release following PO administration of Compound KC-6 to rats.

Table 23 and FIG. 19 provide oxycodone exposure results for rats administered Compound KC-6 orally. Results in Table 23 are reported as (a) maximum plasma concentration (Cmax) of oxycodone (OC) (average±standard deviation), (b) time after administration of Compound KC-6 to reach maximum oxycodone concentration (Tmax) (average±standard deviation) and (c) area under the curve (AUC) (ng×hr)/mL from 0 to 8 hr (average±standard deviation).

TABLE 23

Cmax, Tmax and AUC values of oxycodone in rat plasma

| Compound | Dose, mg/kg | Dose µmol/kg | OC Cmax ± sd, ng/mL | Tmax ± sd, hr | AUC ± sd (ng × hr)/mL |
|---|---|---|---|---|---|
| KC-6 | 24 | 30 | 2.72 ± 0.18 | 4.25 ± 1.5 | 15.1 ± 0.75 |

Lower limit of quantitation was 0.025 ng/mL

FIG. 19 demonstrates mean plasma concentrations over time of oxycodone release following PO administration of Compound KC-6.

The results in Table 23 and FIG. 19 indicate that oral administration of Compound KC-6 yields oxycodone plasma concentrations that exhibit a suppressed Cmax and AUC and delayed Tmax compared to administration of oxycodone (see Example 15).

Example 40: Pharmacokinetics of Compound KC-6 Following IV Administration to Rats This Example compares the plasma concentrations of prodrug and oxycodone in rats following intravenous (IV) administration of Compound KC-6.

Compound KC-6 (which can be prepared as described in Example 14) was dissolved in saline and injected into the tail vein of 4 jugular vein-cannulated male Sprague Dawley rats at a dose of 2 mg/kg. At specified time points, blood samples were drawn, harvested for plasma via centrifugation at 5,400 rpm at 4° C. for 5 min, and 100 µl plasma transferred from each sample into a fresh tube containing 2 µl of 50% formic acid. The tubes were vortexed for 5-10 seconds, immediately placed in dry ice and then stored in −80° C. freezer until analysis by high performance liquid chromatography/mass spectrometry (HPLC/MS).

Figure 20:
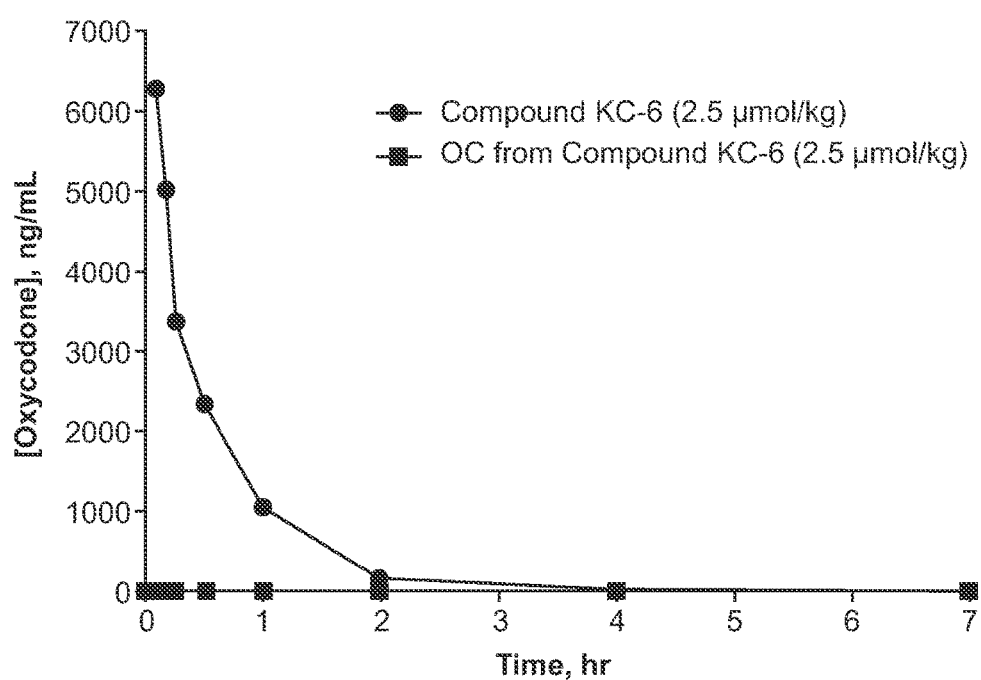
FIG. 20 shows a plasma concentration time course of the production of oxycodone following intravenous (IV) dosing of prodrug Compound KC-6 in rats.

Table 24 and FIG. 20 provide Compound KC-6 and oxycodone exposure results for rats administered Compound KC-6 intravenously. Results in Table 24 are reported as maximum plasma concentration (Cmax) of Compound KC-6 and oxycodone (OC), respectively, (average±standard deviation).

143

TABLE 24

Cmax values of Compound KC-6 and oxycodone in rat plasma

| KC-6 Dose, mg/kg | KC-6 Dose, µmol/kg | KC-6 Cmax ± sd, ng/mL | OC Cmax ± sd, ng/mL |
|---|---|---|---|
| 2 | 2.5 | 6360 ± 2300* | 0.960 ± 0.22^ |

*Lower limit of quantitation was 0.05 ng/mL
^Lower limit of quantitation was 0.1 ng/mL Table 24 and FIG. 20 demonstrate that the plasma concentration of oxycodone in rats administered Compound KC-6 intravenously is only 0.015% of the plasma concentration of Compound KC-6, indicating that IV administration of Compound KC-6 does not lead to significant release of oxycodone into plasma.

Example 41: Pharmacokinetics Following IV Administration of Compound KC-6 to Rats: Plasma and Cerebrospinal Fluid Penetration This Example compares the plasma and cerebrospinal fluid (CSF) concentrations of prodrug Compound KC-6 and oxycodone following intravenous (IV) administration of the respective compounds to rats. Plasma/CSF partitioning coefficients are predictive of the ability of a compound to penetrate the blood-brain barrier.

Compound KC-6 (which can be prepared as described in Example 14), at a dose of 7.5 mg/kg, and oxycodone at a dose of 7.5 mg/kg, each was dissolved in saline and injected into the tail vein of 4 male Sprague Dawley rats. After 2 minutes, the rats were anesthetized by carbon dioxide asphyxiation and blood samples were drawn, harvested for plasma via centrifugation at 5,400 rpm at 4° C. for 5 min, and 100 µl plasma transferred from each sample into a fresh tube containing 2 µl of 50% formic acid. The CSF fluid was collected using a 22×1 inch gauge needle connected to polyurethane catheter type MRE-040 tubing (Braintree Scientific, Inc.). The needle was inserted just below the nuchal crest at the area of the foramen magnum and clear CSF fluid was collected into the catheter and transferred into a collection tube. The CSF samples were centrifuged at 5,400 rpm at 4° C. for 5 min, and 100 µl CSF fluid transferred from each sample into a fresh tube. The plasma and CSF samples were immediately placed in dry ice and then stored in a −80° C. freezer until analysis by high performance liquid chromatography/mass spectrometry (HPLC/MS). In order to study Compound KC-6 and oxycodone plasma and CSF penetration over time, additional groups of 4 rats were administered compounds as described above and anesthetized at specified time points. Plasma and CSF were collected and analyzed as described above. Results from these rats indicated that equilibrium was quickly reached in the plasma and CSF compartments after dosing and that the extent of partitioning between CSF and plasma was consistent across time points. Thus, only the 2-minute time point data are reported in Table 25.

Results in Table 25 are reported, for each group of 4 rats as mean concentrations of the indicated compounds in plasma or CSF. Table 25 also provides the plasma-to-CSF (plasma/CSF) partitioning coefficient, i.e., the ratio of concentration in the plasma to concentration in the CSF of the indicated compounds.

144

TABLE 25

Mean plasma and CSF concentration values and partitioning coefficients of Compound KC-6 and oxycodone

| Compound | Compound conc. in Plasma, ng/mL | Compound conc. in CSF, ng/mL | Plasma/CSF partitioning coefficient |
|---|---|---|---|
| Compound KC-6 | 60,400 | 74.1 | 815 |
| OC | 10,300 | 2,158 | 4.8 |

The results in Table 25 indicate that the relative plasma/CSF partitioning coefficient of Compound KC-6 to oxycodone is about 171 (i.e., 815/4.8); that is, Compound KC-6 is about 171-fold less CSF penetrant than oxycodone. In addition, as shown in Example 24, the drug/prodrug relative potency of Compound KC-6 is about 23. Thus, Compound KC-6, when administered intravenously in equimolar amounts would be expected to be about 3,940-fold (i.e., 171×23) less effective at CNS mu-opioid receptors than oxycodone.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:
1. A composition comprising:
(i) a trypsin inhibitor; and
(ii) a compound of formula KC-(IIIa):

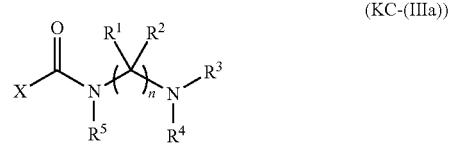

(KC-(IIIa))

wherein:
X represents a residue of a ketone-containing opioid, wherein the hydrogen atom of the corresponding enolic group of the ketone is replaced by a covalent bond to —C(O)—NR$^5$—(C(R$^1$)(R$^2$))$_n$—NR$^3$R$^4$;
R$^5$ is selected from alkyl, substituted alkyl, arylalkyl, substituted arylalkyl, aryl and substituted aryl;
each R$^1$ is independently selected from hydrogen, alkyl, substituted alkyl, aryl, substituted aryl, acyl, and aminoacyl;
each R$^2$ is independently selected from hydrogen, alkyl, substituted alkyl, aryl, substituted aryl, acyl, and aminoacyl;
or R$^1$ and R$^2$ together with the carbon to which they are attached form a cycloalkyl, substituted cycloalkyl, aryl, or substituted aryl group, or two R$^1$ and R$^2$ groups on adjacent carbon atoms, together with the carbon atoms to which they are attached, form a cycloalkyl, substituted cycloalkyl, aryl, or substituted aryl group;
n is an integer from 2 to 4;
R$^3$ is hydrogen;

$R^4$ is

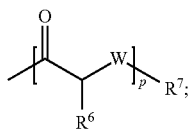

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently —$NR^8$—, —O— or —S—;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof; or (i) a trypsin inhibitor; and (ii) a compound of formula KC-(IIIb):

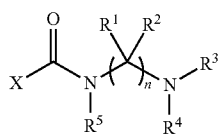

(KC-(IIIb))

wherein:

X represents a residue of a ketone-containing opioid, wherein the hydrogen atom of the corresponding enolic group of the ketone is replaced by a covalent bond to —C(O)—$NR^5$—(C($R^1$)($R^2$))$_n$—$NR^3R^4$;

$R^5$ is selected from alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl or substituted cycloalkyl group, or two $R^1$ or $R^2$ groups on adjacent carbon atoms, together with the carbon atoms to which they are attached, form a cycloalkyl or substituted cycloalkyl group;

n is an integer from 2 to 4;

$R^3$ is hydrogen;

$R^4$ is

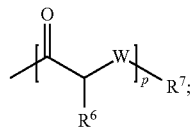

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently —$NR^8$—, —O— or —S—;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

2. The composition of claim 1, wherein the ketone-containing opioid is selected from acetylmorphine, hydrocodone, hydromorphone, ketobemidone, methadone, naloxone, N-methylnaloxone, naltrexone, N-methylnaltrexone, oxycodone, oxymorphone, and pentamorphine.

3. The composition of claim 1, wherein the ketone-containing opioid is hydrocodone or oxycodone.

4. The composition of claim 1, wherein $R^5$ is (1-4C)alkyl.

5. The composition of claim 4, wherein $R^5$ is methyl or ethyl.

6. The composition of claim 1, wherein $R^1$ and $R^2$ are hydrogen.

7. The composition of claim 1, wherein $R^1$ and $R^2$ which are on the same carbon are methyl.

8. The composition of claim 1, wherein one of $R^1$ and $R^2$ is aminoacyl.

9. The composition of claim 1, wherein one of $R^1$ and $R^2$ is —C(O)$NR^{10a}R^{10b}$, wherein each $R^{10a}$ and $R^{10b}$ is independently selected from hydrogen, alkyl, substituted alkyl, and acyl.

10. The composition of claim 1, wherein one of $R^1$ and $R^2$ is —C(O)$NR^{10a}R^{10b}$, wherein $R^{10a}$ is an alkyl and $R^{10b}$ is substituted alkyl.

11. The composition of claim 1, wherein n is 2 or 3.

12. The composition of claim 1, wherein $R^4$ is a residue of an L-amino acid selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine, or a residue of an N-acyl derivative of any of said amino acids; or a residue of a peptide composed of at least two L-amino acid residues selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine or a residue of an N-acyl derivative thereof.

13. The composition of claim 12, wherein the N-acyl derivative is an acetyl, benzoyl, malonyl, piperonyl or succinyl derivative.

14. The composition of claim 1, wherein $R^4$ is a residue of L-arginine or L-lysine, or a residue of an N-acyl derivative of L-arginine or L-lysine.

15. The composition of claim 1, wherein $R^6$ is a side chain of an amino acid.

16. The composition of claim 1, wherein $R^6$ is —H, —CH$_2$CH$_2$CH$_2$NH(C=NH)NH$_2$ or —CH$_2$CH$_2$CH$_2$CH$_2$NH$_2$.

17. The composition of claim 1, wherein $R^7$ is selected from hydrogen, acetyl, benzoyl, malonyl, piperonyl and succinyl.

18. The composition of claim 1, wherein the compound is selected from the following formulae:

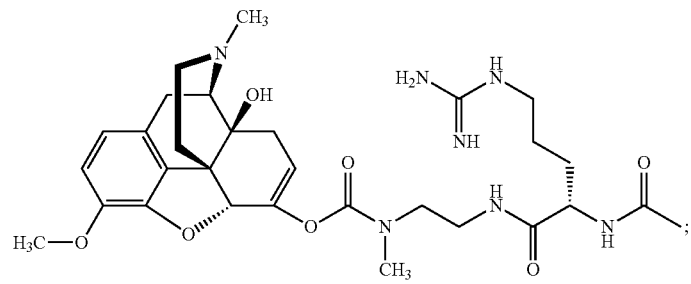

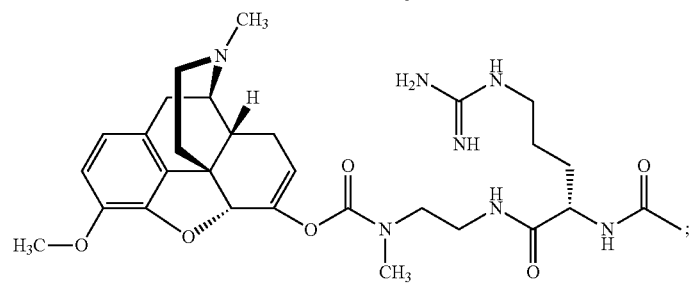

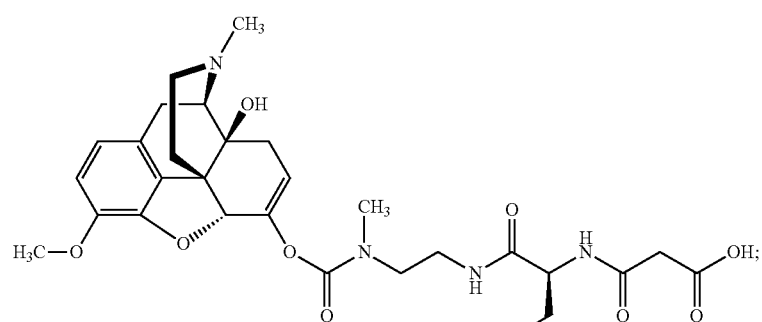

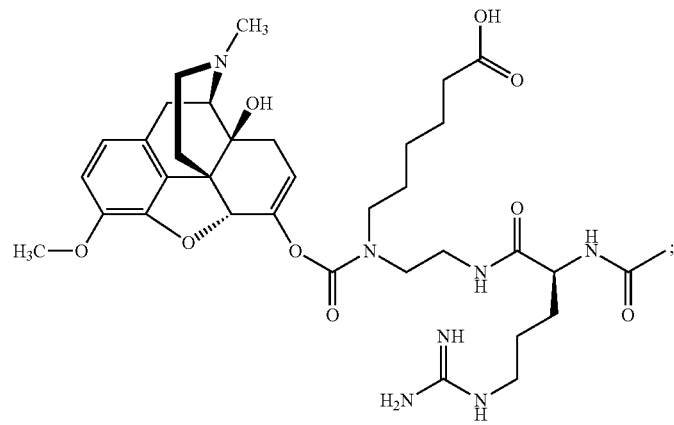

-continued
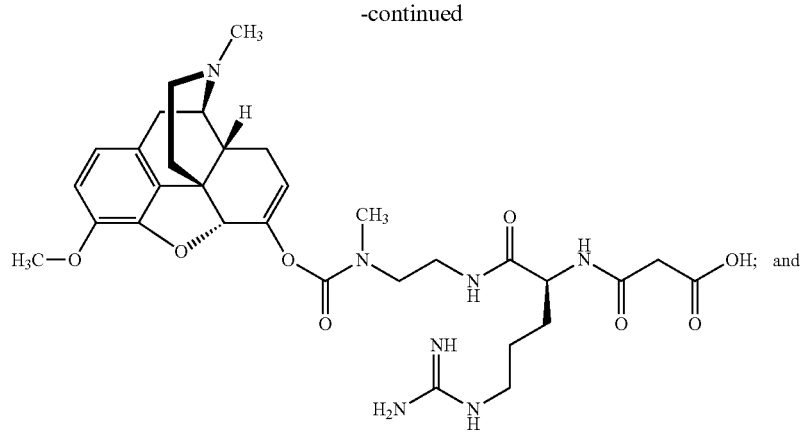
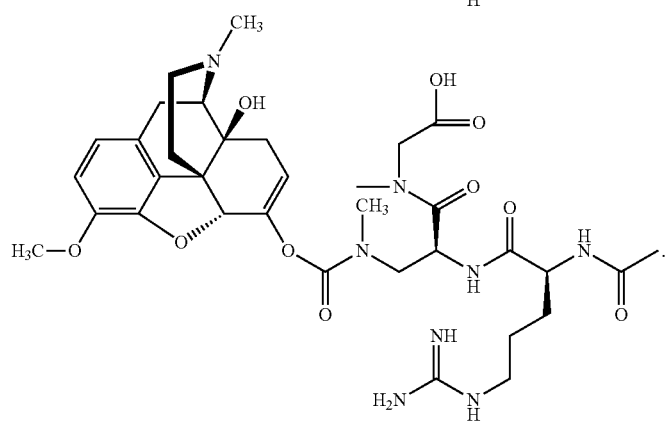
19. The composition of claim 1, wherein the trypsin inhibitor is an arginine mimic or a lysine mimic.
20. A method of treating or preventing pain comprising administering an effective amount of a composition of claim 1 to a patient in need thereof.
* * * * *